(12) United States Patent
Tilson et al.

(10) Patent No.: US 11,554,248 B1
(45) Date of Patent: *Jan. 17, 2023

(54) RIGIDIZING DEVICES

(71) Applicant: Neptune Medical Inc., Burlingame, CA (US)

(72) Inventors: Alexander Q. Tilson, Burlingame, CA (US); Stephen J. Morris, Sunnyvale, CA (US); Garrett J. Gomes, San Mateo, CA (US); Adam S. Wigginton, Sunnyvale, CA (US); Mark C. Scheeff, Oakland, CA (US); Charles S. Love, Santa Barbara, CA (US)

(73) Assignee: Neptune Medical Inc., Burlingame, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/903,879

(22) Filed: Sep. 6, 2022

Related U.S. Application Data

(63) Continuation of application No. 17/493,785, filed on Oct. 4, 2021, now Pat. No. 11,478,608, which is a
(Continued)

(51) Int. Cl.
*A61M 25/00* (2006.01)
*A61M 25/01* (2006.01)
*A61M 25/09* (2006.01)

(52) U.S. Cl.
CPC ...... *A61M 25/005* (2013.01); *A61M 25/0102* (2013.01); *A61M 25/0147* (2013.01);
(Continued)

(58) Field of Classification Search
CPC ............ A61M 25/005; A61M 25/0102; A61M 25/0147; A61M 2025/0063;
(Continued)

(56) References Cited

U.S. PATENT DOCUMENTS 2,268,321 A 12/1941 Flynn
2,767,705 A 10/1956 Moore
(Continued)

FOREIGN PATENT DOCUMENTS

AU 2013207571 B1 8/2013
CN 2613655 Y 4/2004
(Continued)

OTHER PUBLICATIONS

Entrada® colonic overtube broduct brochure downloaded from internet http://www.usendoscopy.com/~/media/Files/Documents/Spec-Sheet-International/760358c_entrada_intl_ss_web.pdf Accessed Date: Jun. 5, 2017 (the year of publication is sufficiently earlier than the effective U.S. filing date and any foreign priority date so that the particular month of publication is not in issue) 2009.
(Continued)

*Primary Examiner* — Katherine H Schwiker
*Assistant Examiner* — Hong-Van N Trinh
(74) *Attorney, Agent, or Firm* — Shay Glenn LLP

(57) ABSTRACT

A rigidizing device includes an elongate flexible tube, a braid layer positioned over the elongate flexible tube, an outer layer over the flexible tube and the braid layer, and an inlet between the elongate flexible tube and the outer layer and configured to attach to a source of vacuum or pressure. The braid layer has a plurality of strands braided together at a braid angle of 5-40 degrees relative to a longitudinal axis of the elongate flexible tube when the elongate flexible tube is straight. The rigidizing device is configured to have a rigid configuration when vacuum or pressure is applied through the inlet and a flexible configuration when vacuum or pressure is not applied through the inlet. The braid angle is configured to change as the rigidizing device bends when the rigidizing device is in the flexible configuration.

22 Claims, 100 Drawing Sheets

Related U.S. Application Data continuation of application No. 17/152,706, filed on Jan. 19, 2021, now Pat. No. 11,135,398, which is a continuation of application No. PCT/US2019/042650, filed on Jul. 19, 2019.

(60) Provisional application No. 62/854,199, filed on May 29, 2019, provisional application No. 62/835,101, filed on Apr. 17, 2019, provisional application No. 62/780,820, filed on Dec. 17, 2018, provisional application No. 62/700,760, filed on Jul. 19, 2018.

(52) U.S. Cl.
CPC ............ *A61M 2025/0063* (2013.01); *A61M 2025/015* (2013.01); *A61M 2025/0915* (2013.01)

(58) Field of Classification Search
CPC .... A61M 2025/015; A61M 2025/0915; A61B 1/00135; A61B 1/00078
See application file for complete search history.

(56) References Cited

U.S. PATENT DOCUMENTS

| | | | |
|---|---|---|---|
| 3,859,986 A | 1/1975 | Okada et al. | |
| 3,998,216 A | 12/1976 | Hosono | |
| 4,066,071 A | 1/1978 | Nagel | |
| 4,141,364 A | 2/1979 | Schultze | |
| 4,176,662 A | 12/1979 | Frazer | |
| 4,425,919 A | 1/1984 | Alston, Jr | |
| 4,551,140 A | 11/1985 | Shinohara | |
| 4,690,131 A | 9/1987 | Lyddy, Jr. et al. | |
| 4,696,544 A | 9/1987 | Costella | |
| 4,717,379 A | 1/1988 | Ekholmer | |
| 4,794,412 A | 12/1988 | Casey et al. | |
| 4,794,912 A | 1/1989 | Lia | |
| 4,815,450 A * | 3/1989 | Patel ................ | A61M 25/0054 600/152 |
| 4,817,613 A | 4/1989 | Jaraczewski et al. | |
| 4,893,613 A * | 1/1990 | Hake .................... | A61B 1/0053 600/152 |
| 4,959,058 A | 9/1990 | Michelson | |
| 4,961,738 A | 10/1990 | Mackin | |
| 5,018,436 A | 5/1991 | Evangelista et al. | |
| 5,019,121 A | 5/1991 | Krauter | |
| 5,025,778 A * | 6/1991 | Silverstein ......... | A61B 1/00078 600/117 |
| 5,037,386 A | 8/1991 | Marcus | |
| 5,105,819 A | 4/1992 | Wollsdiiager et al. | |
| 5,123,421 A | 6/1992 | Sinofsky | |
| 5,174,276 A | 12/1992 | Crockard | |
| 5,188,595 A | 2/1993 | Jacobi | |
| 5,251,611 A | 10/1993 | Zehel et al. | |
| 5,337,733 A * | 8/1994 | Bauerfeind ......... | A61B 1/00078 604/524 |
| 5,496,292 A | 3/1996 | Burnham | |
| 5,531,685 A | 7/1996 | Hemmer et al. | |
| 5,531,719 A | 7/1996 | Takahashi | |
| 5,577,992 A | 11/1996 | Chiba et al. | |
| 5,601,588 A | 2/1997 | Tonomura et al. | |
| 5,607,435 A | 3/1997 | Sachdeva et al. | |
| 5,624,381 A | 4/1997 | Kieturakis | |
| 5,632,734 A | 5/1997 | Galel et al. | |
| 5,662,587 A | 9/1997 | Grundfest et al. | |
| 5,662,621 A | 9/1997 | Lafontaine | |
| 5,746,692 A | 5/1998 | Bacich et al. | |
| 5,749,828 A | 5/1998 | Solomon et al. | |
| 5,759,151 A | 6/1998 | Sturges | |
| 5,779,624 A | 7/1998 | Chang | |
| 5,782,811 A | 7/1998 | Samson | |
| 5,823,961 A | 10/1998 | Fields et al. | |
| 5,882,347 A | 3/1999 | Laan et al. | |
| 5,891,112 A | 4/1999 | Samson | |
| 5,906,591 A | 5/1999 | Dario et al. | |
| 5,916,145 A | 6/1999 | Chu et al. | |
| 5,916,147 A | 6/1999 | Boury | |
| 5,951,539 A | 9/1999 | Nita et al. | |
| 5,976,074 A | 11/1999 | Moriyama | |
| 6,090,099 A | 7/2000 | Samson et al. | |
| 6,159,187 A | 12/2000 | Park et al. | |
| 6,162,171 A | 12/2000 | Ng et al. | |
| 6,179,776 B1 | 1/2001 | Adams et al. | |
| 6,190,357 B1 | 2/2001 | Ferrari et al. | |
| 6,217,565 B1 | 4/2001 | Cohen | |
| 6,296,644 B1 | 10/2001 | Surat et al. | |
| 6,309,346 B1 | 10/2001 | Farhadi | |
| 6,364,878 B1 | 4/2002 | Hall | |
| 6,468,203 B2 | 10/2002 | Belson | |
| 6,485,409 B1 | 11/2002 | Voloshin et al. | |
| 6,503,225 B1 | 1/2003 | Kirsch | |
| 6,517,477 B1 | 2/2003 | Wendlandt | |
| 6,547,724 B1 | 4/2003 | Soble et al. | |
| 6,572,538 B2 | 6/2003 | Takase | |
| 6,572,590 B1 | 6/2003 | Stevens et al. | |
| 6,579,277 B1 | 6/2003 | Rabiner et al. | |
| 6,610,007 B2 | 8/2003 | Belson et al. | |
| 6,612,982 B1 | 9/2003 | Ouchi | |
| 6,616,628 B2 | 9/2003 | Hayzelden | |
| 6,620,126 B2 | 9/2003 | Unsworth et al. | |
| 6,623,424 B2 | 9/2003 | Hayakawa et al. | |
| 6,712,832 B2 | 3/2004 | Shah | |
| 6,726,677 B1 | 4/2004 | Flaherty | |
| 6,730,020 B2 | 5/2004 | Peng et al. | |
| 6,780,151 B2 | 8/2004 | Grabover et al. | |
| 6,783,491 B2 | 8/2004 | Saadat et al. | |
| 6,790,173 B2 | 9/2004 | Saadat et al. | |
| 6,793,621 B2 | 9/2004 | Butler et al. | |
| 6,793,661 B2 | 9/2004 | Hamilton et al. | |
| 6,800,056 B2 | 10/2004 | Tartaglia et al. | |
| 6,869,393 B2 | 3/2005 | Butler | |
| 6,899,673 B2 | 5/2005 | Ogura et al. | |
| 6,911,004 B2 | 6/2005 | Kim et al. | |
| 6,923,754 B2 | 8/2005 | Lubock | |
| 6,960,162 B2 | 11/2005 | Saadat et al. | |
| 6,974,411 B2 | 12/2005 | Belson | |
| 6,984,203 B2 | 1/2006 | Tartaglia | |
| 7,060,199 B2 | 6/2006 | Woydt | |
| 7,172,552 B2 | 2/2007 | Wendlandt | |
| 7,214,230 B2 | 5/2007 | Brock | |
| 7,288,101 B2 | 10/2007 | Deem et al. | |
| 7,291,127 B2 | 11/2007 | Eldenschink | |
| 7,365,509 B2 | 4/2008 | Park et al. | |
| 7,438,712 B2 | 10/2008 | Chouinard | |
| 7,511,733 B2 | 3/2009 | Takizawa et al. | |
| 7,537,562 B2 | 5/2009 | Takano | |
| 7,559,916 B2 * | 7/2009 | Smith ................. | A61M 25/005 604/95.04 |
| 7,591,782 B2 | 9/2009 | Fujikura | |
| 7,598,652 B2 | 10/2009 | Kornbluh et al. | |
| 7,695,428 B2 | 4/2010 | Machida | |
| 7,736,323 B2 | 6/2010 | Von Weymarn-Scharli | |
| 7,837,615 B2 | 11/2010 | Le et al. | |
| 7,850,725 B2 | 12/2010 | Vardi et al. | |
| 7,901,347 B2 | 3/2011 | Sekiguchi et al. | |
| 7,909,755 B2 | 3/2011 | Itoi | |
| 7,918,819 B2 | 4/2011 | Karmarkar et al. | |
| 7,918,845 B2 | 4/2011 | Saadat et al. | |
| 7,931,661 B2 | 4/2011 | Saadat et al. | |
| 7,935,047 B2 | 5/2011 | Yoshida et al. | |
| 7,947,000 B2 * | 5/2011 | Vargas .............. | A61M 25/0158 600/587 |
| 7,957,790 B2 | 6/2011 | Kleen | |
| 7,970,455 B2 | 6/2011 | Zilberstein et al. | |
| 7,988,621 B2 | 8/2011 | Smith et al. | |
| 8,047,236 B2 | 11/2011 | Perry | |
| 8,075,476 B2 | 12/2011 | Vargas | |
| 8,092,374 B2 | 1/2012 | Smith et al. | |
| 8,109,953 B1 | 2/2012 | King, III et al. | |
| 8,125,755 B2 * | 2/2012 | Garcia .................... | B25J 18/06 361/233 |
| 8,192,422 B2 | 6/2012 | Zublate et al. | |
| 8,206,287 B2 | 6/2012 | Matsuo | |

(56) References Cited

U.S. PATENT DOCUMENTS

| | | |
|---|---|---|
| 8,226,548 B2 | 7/2012 | Kucklick |
| 8,241,299 B2 | 8/2012 | Hibner |
| 8,246,575 B2 | 8/2012 | Viola |
| 8,257,257 B2 | 9/2012 | Takizawa et al. |
| 8,298,161 B2 | 10/2012 | Vargas |
| 8,361,090 B2 | 1/2013 | Befson |
| 8,366,606 B2 | 2/2013 | Watanabe et al. |
| 8,388,519 B2 | 3/2013 | Garcia et al. |
| 8,439,825 B2 | 5/2013 | Sekiguchi |
| 8,460,179 B2 | 6/2013 | Ikeda |
| 8,485,968 B2 | 7/2013 | Weimer et al. |
| 8,496,648 B2 | 7/2013 | Rogers |
| 8,506,479 B2 | 8/2013 | Piskun et al. |
| 8,517,923 B2 | 8/2013 | Belson et al. |
| 8,545,491 B2 | 10/2013 | Abboud et al. |
| 8,550,989 B2 | 10/2013 | Dohi et al. |
| 8,556,804 B2 | 10/2013 | Smith |
| 8,663,096 B2 | 3/2014 | Viola |
| 8,663,196 B2 | 3/2014 | Kassab et al. |
| 8,708,894 B2 | 4/2014 | Smith et al. |
| 8,721,530 B2 | 5/2014 | Ohline et al. |
| 8,753,312 B2 | 6/2014 | Bowe et al. |
| 8,920,369 B2 | 12/2014 | Salahieh et al. |
| 8,969,639 B2 | 3/2015 | Xu et al. |
| 9,011,318 B2 | 4/2015 | Choset et al. |
| 9,066,655 B2 | 6/2015 | Stefanchik et al. |
| 9,125,653 B2 | 9/2015 | Kovach |
| 9,155,451 B2 | 10/2015 | Smith et al. |
| 9,192,284 B2 | 11/2015 | Hirsch et al. |
| 9,192,288 B2 | 11/2015 | Okaniwa |
| 9,211,140 B2 | 12/2015 | Lauryssen et al. |
| 9,220,398 B2 | 12/2015 | Woodley et al. |
| 9,226,825 B2 | 1/2016 | Starksen et al. |
| 9,241,611 B2 | 1/2016 | Konno |
| 9,254,123 B2 | 2/2016 | Alvarez et al. |
| 9,295,511 B2 | 3/2016 | Smith |
| 9,358,073 B2 | 6/2016 | Piligian et al. |
| 9,364,955 B2 | 6/2016 | Oyola et al. |
| 9,386,910 B2 | 7/2016 | West |
| 9,498,108 B1 | 11/2016 | Lombardi |
| 9,498,198 B2 | 11/2016 | Hu et al. |
| 9,505,125 B2 | 11/2016 | Zubiate et al. |
| 9,585,546 B2 | 3/2017 | Surti et al. |
| 9,610,068 B2 | 4/2017 | Kappel et al. |
| 9,649,473 B2 | 5/2017 | Gregorich et al. |
| 9,763,562 B2 | 9/2017 | Avitsian et al. |
| 9,814,372 B2 | 11/2017 | Smith et al. |
| 9,913,570 B2 | 3/2018 | Kucharski et al. |
| 9,937,324 B2 | 4/2018 | Kim et al. |
| 10,092,291 B2 | 10/2018 | Voegele et al. |
| 10,307,042 B2 | 6/2019 | Lombardi |
| 10,463,495 B2 | 11/2019 | Rogers et al. |
| 11,122,971 B2 | 9/2021 | Tilson et al. |
| 11,135,398 B2 | 10/2021 | Tilson et al. |
| 11,219,351 B2 | 1/2022 | Tilson et al. |
| 11,478,608 B2 | 10/2022 | Tilson et al. |
| 2002/0107478 A1 | 8/2002 | Wendlandt |
| 2002/0120178 A1* | 8/2002 | Tartaglia ............ A61B 5/065 600/114 |
| 2002/0161355 A1 | 10/2002 | Wollschlager |
| 2003/0023259 A1 | 1/2003 | Dubrul et al. |
| 2003/0083546 A1 | 5/2003 | Butler et al. |
| 2003/0153866 A1 | 8/2003 | Long et al. |
| 2003/0208220 A1 | 11/2003 | Worley et al. |
| 2003/0216691 A1 | 11/2003 | Jacobson |
| 2003/0225379 A1 | 12/2003 | Schaffer et al. |
| 2004/0019252 A1 | 1/2004 | Hirata |
| 2004/0044350 A1 | 3/2004 | Martin et al. |
| 2004/0092960 A1 | 5/2004 | Abrams et al. |
| 2004/0186349 A1 | 9/2004 | Ewers et al. |
| 2004/0186350 A1 | 9/2004 | Brenneman et al. |
| 2004/0243227 A1 | 12/2004 | Starksen et al. |
| 2004/0260236 A1 | 12/2004 | Manning et al. |
| 2005/0085829 A1 | 4/2005 | Kraemer et al. |
| 2005/0165275 A1 | 7/2005 | Von Felten et al. |
| 2005/0203340 A1 | 9/2005 | Butler et al. |
| 2005/0272974 A1 | 12/2005 | Iddan |
| 2005/0277966 A1 | 12/2005 | Ewers et al. |
| 2006/0041188 A1 | 2/2006 | Dirusso et al. |
| 2006/0047183 A1 | 3/2006 | Park |
| 2006/0058582 A1 | 3/2006 | Maahs et al. |
| 2006/0129130 A1 | 6/2006 | Tal et al. |
| 2006/0192465 A1 | 8/2006 | Kornbluh et al. |
| 2006/0258906 A1 | 11/2006 | Binmoeller |
| 2006/0264707 A1 | 11/2006 | Kinney |
| 2006/0287666 A1 | 12/2006 | Saadat et al. |
| 2007/0015965 A1 | 1/2007 | Cox et al. |
| 2007/0038025 A1 | 2/2007 | Yoshida |
| 2007/0045504 A1 | 3/2007 | Wollschlaeger |
| 2007/0060880 A1* | 3/2007 | Gregorich ........ A61M 25/0097 604/95.04 |
| 2007/0088367 A1 | 4/2007 | Von Weymarn-Scharli |
| 2007/0100414 A1 | 5/2007 | Licata et al. |
| 2007/0106302 A1 | 5/2007 | Ortiz |
| 2007/0118015 A1 | 5/2007 | Wendlandt |
| 2007/0208364 A1* | 9/2007 | Smith ................. A61B 1/005 606/191 |
| 2007/0219411 A1 | 9/2007 | Dejima et al. |
| 2007/0239252 A1 | 10/2007 | Hopkins et al. |
| 2007/0250149 A1 | 10/2007 | Oepen et al. |
| 2007/0260121 A1 | 11/2007 | Bakos et al. |
| 2007/0270648 A1* | 11/2007 | Smith ................. A61B 1/31 600/139 |
| 2008/0051635 A1 | 2/2008 | Tanaka et al. |
| 2008/0058722 A1 | 3/2008 | Oepen et al. |
| 2008/0091073 A1 | 4/2008 | Park |
| 2008/0103440 A1 | 5/2008 | Ferren et al. |
| 2008/0139887 A1 | 6/2008 | Fitzpatrick |
| 2008/0172037 A1 | 7/2008 | Huang et al. |
| 2008/0188928 A1 | 8/2008 | Salahieh et al. |
| 2008/0200762 A1 | 8/2008 | Stokes et al. |
| 2008/0214893 A1 | 9/2008 | Tartaglia et al. |
| 2008/0234546 A1 | 9/2008 | Kawano et al. |
| 2008/0242928 A1 | 10/2008 | Kawano et al. |
| 2008/0262300 A1 | 10/2008 | Ewers et al. |
| 2008/0275299 A1 | 11/2008 | Park |
| 2009/0048483 A1 | 2/2009 | Yamamoto |
| 2009/0062611 A1 | 3/2009 | Toyama |
| 2009/0062837 A1 | 3/2009 | Gasche et al. |
| 2009/0112063 A1 | 4/2009 | Bakos et al. |
| 2009/0131752 A1 | 5/2009 | Park |
| 2009/0157068 A1 | 6/2009 | Kallel et al. |
| 2009/0187163 A1* | 7/2009 | Uihlein ................. A61M 25/09 604/528 |
| 2009/0240202 A1 | 9/2009 | Drasler et al. |
| 2009/0259200 A1 | 10/2009 | Lampropoulos et al. |
| 2009/0264704 A1 | 10/2009 | Shtul |
| 2010/0010308 A1 | 1/2010 | Braun et al. |
| 2010/0016663 A1 | 1/2010 | Maisch et al. |
| 2010/0069712 A1 | 3/2010 | Yamaya |
| 2010/0076451 A1 | 3/2010 | Zwolinski et al. |
| 2010/0087711 A1 | 4/2010 | Edwards |
| 2010/0137686 A1 | 6/2010 | Meron et al. |
| 2010/0145151 A1 | 6/2010 | Fukunaga et al. |
| 2010/0160735 A1 | 6/2010 | Bakos |
| 2010/0204546 A1 | 8/2010 | Hassidov et al. |
| 2010/0268025 A1 | 10/2010 | Belson |
| 2010/0331625 A1 | 12/2010 | Rosemurgy et al. |
| 2010/0331820 A1 | 12/2010 | Prisco et al. |
| 2011/0015729 A1 | 1/2011 | Jimenez et al. |
| 2011/0040282 A1* | 2/2011 | Uihlein ............ A61M 25/0043 604/525 |
| 2011/0046442 A1 | 2/2011 | Matsushita |
| 2011/0049282 A1 | 3/2011 | Danielsson |
| 2011/0054253 A1 | 3/2011 | Jordá Albiñana et al. |
| 2011/0237888 A1 | 9/2011 | Matsushita |
| 2011/0245611 A1 | 10/2011 | Yeh et al. |
| 2011/0282149 A1 | 11/2011 | Vargas et al. |
| 2011/0306950 A1 | 12/2011 | Cucin |
| 2012/0022329 A1 | 1/2012 | Wagh et al. |
| 2012/0041291 A1 | 2/2012 | Ferren et al. |
| 2012/0108902 A1 | 5/2012 | Frassica et al. |
| 2012/0130173 A1 | 5/2012 | Lutze et al. |
| 2012/0143005 A1 | 6/2012 | Yeh et al. |

(56) References Cited

U.S. PATENT DOCUMENTS

| | | | |
|---|---|---|---|
| 2012/0165607 A1 | 6/2012 | Ashida et al. | |
| 2012/0165792 A1 | 6/2012 | Ortiz et al. | |
| 2012/0172651 A1 | 7/2012 | Cutrer | |
| 2012/0209062 A1 | 8/2012 | Qiao | |
| 2012/0277528 A1 | 11/2012 | Qiao | |
| 2012/0277729 A1* | 11/2012 | Melsheimer | A61M 25/01 604/525 |
| 2013/0131641 A1 | 5/2013 | Jimenez et al. | |
| 2013/0190565 A1 | 7/2013 | Gora et al. | |
| 2013/0338440 A1 | 12/2013 | Sinai et al. | |
| 2014/0005683 A1 | 1/2014 | Stand et al. | |
| 2014/0081169 A1 | 3/2014 | Gerding et al. | |
| 2014/0088459 A1 | 3/2014 | Roush et al. | |
| 2014/0142393 A1 | 5/2014 | Piskun et al. | |
| 2014/0155702 A1 | 6/2014 | Tilson et al. | |
| 2014/0155783 A1 | 6/2014 | Starksen et al. | |
| 2014/0188054 A1 | 7/2014 | Iijima et al. | |
| 2014/0243873 A1 | 8/2014 | Franklin | |
| 2014/0275860 A1 | 9/2014 | Rottenberg et al. | |
| 2014/0276642 A1 | 9/2014 | Cully et al. | |
| 2014/0343358 A1 | 11/2014 | Hameed et al. | |
| 2014/0371764 A1 | 12/2014 | Oyola et al. | |
| 2015/0018616 A1 | 1/2015 | Kumoyama | |
| 2015/0038919 A1 | 2/2015 | Bramwell et al. | |
| 2015/0073216 A1 | 3/2015 | Papay | |
| 2015/0073409 A1 | 3/2015 | Watson et al. | |
| 2015/0094656 A1 | 4/2015 | Salahieh et al. | |
| 2015/0119640 A1 | 4/2015 | Reydel | |
| 2015/0133729 A1 | 5/2015 | Reydel | |
| 2015/0148602 A1 | 5/2015 | Hill et al. | |
| 2015/0148606 A1 | 5/2015 | Rottenberg et al. | |
| 2015/0164314 A1 | 6/2015 | Peterson | |
| 2015/0216589 A1 | 8/2015 | Wittenberger et al. | |
| 2015/0342608 A1 | 12/2015 | Hernandez | |
| 2016/0007832 A1 | 1/2016 | Shimada | |
| 2016/0066773 A1 | 3/2016 | Cooper et al. | |
| 2016/0096004 A1 | 4/2016 | Gerrans et al. | |
| 2016/0129547 A1 | 5/2016 | Duescher et al. | |
| 2016/0136393 A1 | 5/2016 | Tsai et al. | |
| 2016/0174829 A1 | 6/2016 | Reydel | |
| 2016/0198935 A1 | 7/2016 | Choi et al. | |
| 2016/0270870 A1 | 9/2016 | Kowshik | |
| 2016/0287059 A1 | 10/2016 | Ha et al. | |
| 2016/0324412 A1 | 11/2016 | Hassidov et al. | |
| 2017/0156567 A1 | 6/2017 | Kaneko | |
| 2017/0157363 A1 | 6/2017 | Barrish et al. | |
| 2018/0015257 A1 | 1/2018 | Krolik et al. | |
| 2018/0064366 A1 | 3/2018 | Sweeney et al. | |
| 2018/0184885 A1 | 7/2018 | St. George | |
| 2018/0249893 A1 | 9/2018 | Yeung et al. | |
| 2018/0263469 A1 | 9/2018 | Okaniwa et al. | |
| 2018/0289925 A1 | 10/2018 | Palmer et al. | |
| 2018/0326197 A1 | 11/2018 | McArthur et al. | |
| 2018/0361116 A1 | 12/2018 | Quick et al. | |
| 2020/0030575 A1 | 1/2020 | Bogusky et al. | |
| 2020/0178763 A1 | 6/2020 | Tilson et al. | |
| 2021/0137366 A1 | 5/2021 | Tilson et al. | |
| 2022/0000355 A1 | 1/2022 | Tilson et al. | |
| 2022/0104690 A1 | 4/2022 | Tilson et al. | |
| 2022/0323166 A1 | 10/2022 | Tilson et al. | |

FOREIGN PATENT DOCUMENTS

| | | |
|---|---|---|
| CN | 1706349 A | 12/2005 |
| CN | 1732855 A | 2/2006 |
| CN | 1806770 A | 7/2006 |
| CN | 1861011 A | 11/2006 |
| CN | 101119765 A | 2/2008 |
| CN | 101129255 A | 2/2008 |
| CN | 102137628 A | 7/2011 |
| CN | 201899767 U | 7/2011 |
| CN | 102711585 A | 10/2012 |
| CN | 102872519 A | 1/2013 |
| CN | 103384500 A | 11/2013 |
| CN | 104168860 A | 11/2014 |
| CN | 104287684 B | 3/2016 |
| CN | 105759418 A | 7/2016 |
| CN | 105832279 A | 8/2016 |
| CN | 106137397 A | 11/2016 |
| CN | 106455929 A | 2/2017 |
| CN | 106488744 A | 3/2017 |
| CN | 106659367 A | 5/2017 |
| CN | 107296584 A | 10/2017 |
| DE | 102005039601 A1 | 2/2007 |
| EP | 401129 A1 | 12/1990 |
| EP | 0941743 A2 | 9/1999 |
| EP | 1662972 A2 | 6/2006 |
| EP | 1695657 A1 | 8/2006 |
| EP | 1487318 B1 | 3/2008 |
| EP | 2016914 A2 | 1/2009 |
| EP | 1499227 B1 | 10/2010 |
| EP | 2258322 A | 12/2010 |
| EP | 2364637 A1 | 9/2011 |
| EP | 2368481 A1 | 9/2011 |
| EP | 2368483 A1 | 9/2011 |
| EP | 3256052 A1 | 12/2017 |
| GB | 2482355 A | 10/2010 |
| GB | 2497544 A | 6/2013 |
| JP | H05293077 A | 11/1993 |
| JP | 2002125921 A | 5/2002 |
| JP | 2005152300 A | 6/2005 |
| JP | 03965108 B2 | 8/2007 |
| JP | 2009507617 A | 2/2009 |
| JP | 2013176465 A | 9/2013 |
| JP | 2014124475 A | 7/2014 |
| KR | 10-2015-0131502 A | 11/2015 |
| WO | WO97/43941 A1 | 11/1997 |
| WO | WO99/053827 A1 | 10/1999 |
| WO | WO03/013348 A1 | 2/2003 |
| WO | WO2007/035931 A2 | 3/2007 |
| WO | WO2008/041809 A1 | 4/2008 |
| WO | WO2008/122997 A1 | 10/2008 |
| WO | WO2011/013147 A1 | 2/2011 |
| WO | WO2011/018157 A1 | 2/2011 |
| WO | WO2011/148172 A2 | 12/2011 |
| WO | WO2012/054480 A2 | 4/2012 |
| WO | WO2012/080947 A1 | 6/2012 |
| WO | WO2012/122288 A2 | 9/2012 |
| WO | WO2017/041052 A1 | 3/2017 |
| WO | WO2018/035452 A1 | 8/2017 |
| WO | WO2019/054867 A1 | 3/2019 |
| WO | WO2020/018934 A1 | 1/2020 |
| WO | WO2020/214221 A1 | 10/2020 |

OTHER PUBLICATIONS

Filip et al.; Design, Implementation, and Testing of a miniature self-stabilizing capsule endoscope with wireless image transmission capabilities; Intl. Journal "Information Technologies & Knowledge", 5(1), downloaded from http://www.foibg.com/jitk/ijitk-vol05/ijitk05-1-p01.pdf on Jul. 28, 2016, (the year of publicalion is sufficiently earlier than the effective U.S. filing date and any foreign priority date so that the particular month of publication is not in issue) 2011.

Loeve et al.; Endoscope Shaft-Rigidity Control Mechanism: "FORGUIDE"; IEEE Trans. On Biomed. Eng.; 59(2); pp. 542-551; Feb. 2012.

Loeve et al.; Vacuum packed particles as flexible endoscope guides with controllable rigidity; Granular Matter; 12(6); pp. 543-554; Jun. 24, 2010.

Shah et al.; Magnetic Imaging of Colonoscopy: An Audit of Looping, Accuracy and Ancillary maneuvers; Gastrointest. Endosc.; 52(1); pp. 1-8; Jul. 1, 2000.

Simi et al.; Design, Fabrication, and Testing of a Capsule With Hybrid Locomotion for Gastrointestinal Tract Exploration; IEEE/ASME Trans on Mechatronics; 15(2); p. 170-x; Apr. 2010.

Valdastri et al.; Advanced Technologies for Gastrointestinal Endoscopy; Annu. Rev. Biomed. Eng.; 14; pp. 397-429; May 2012.

Zhao et al.; Development of a variable stiffness over tube based on low-melting-point-alloy for endoscopic surgery; J. Med. Devices; 10(2); 8 pages; May 12, 2016.

(56) References Cited

OTHER PUBLICATIONS

Tilson et al.; U.S. Appl. No. 17/902,770 entitled "Nested rigidizing devices," filed Sep. 2, 2022.
Tilson et al.; U.S. Appl. No. 17/940,906 entitled "External working channels," filed Sep. 8, 2022.
Lopez et al.; U.S. Appl. No. 17/995,294 entitled "Layered walls for rigidizing devices," filed Sep. 30, 2022.

* cited by examiner

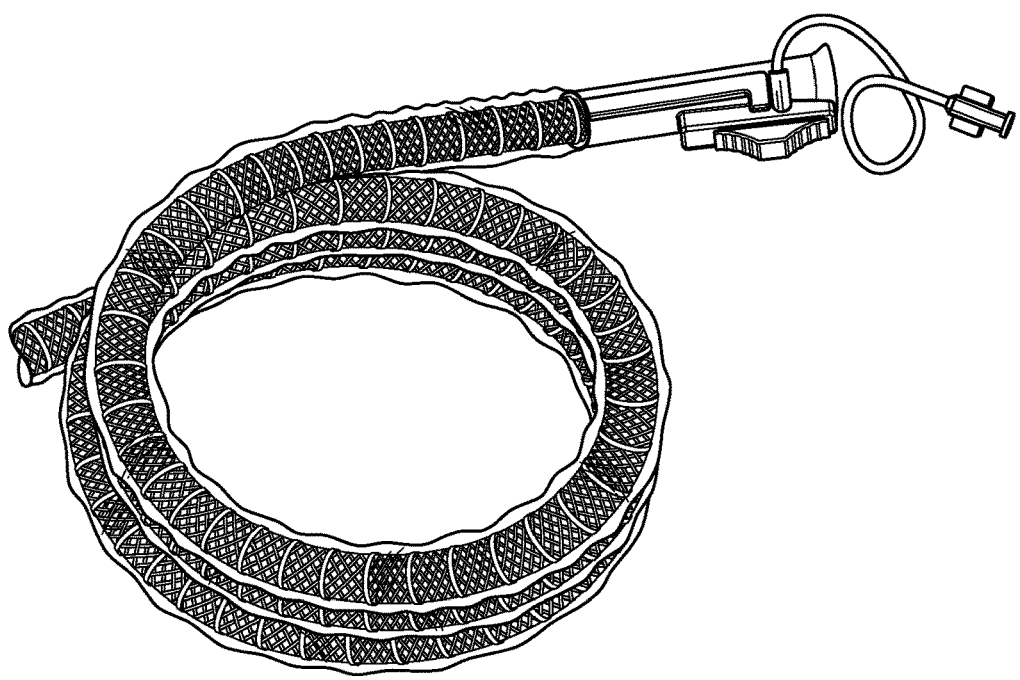
FIG. 12A
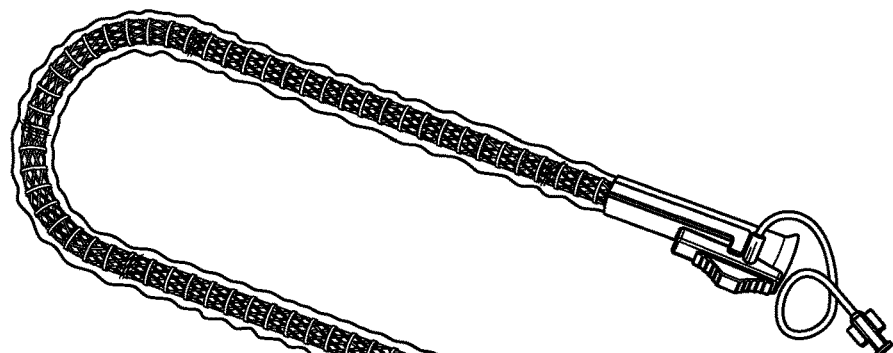
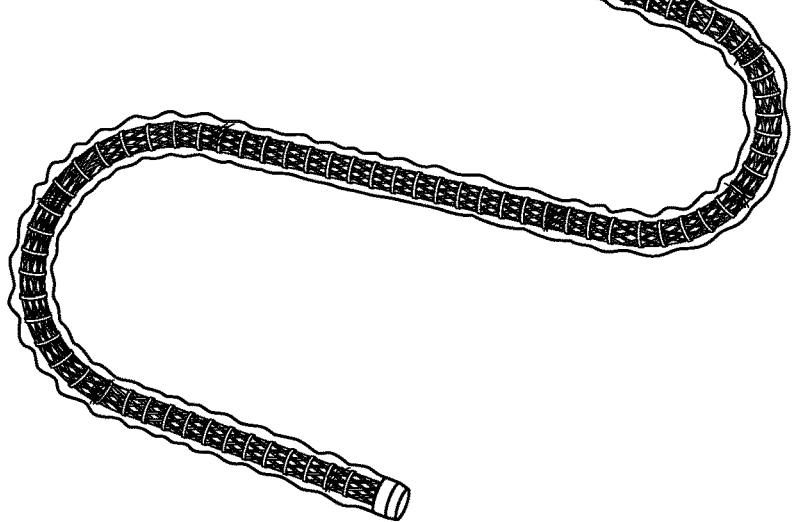
FIG. 12B

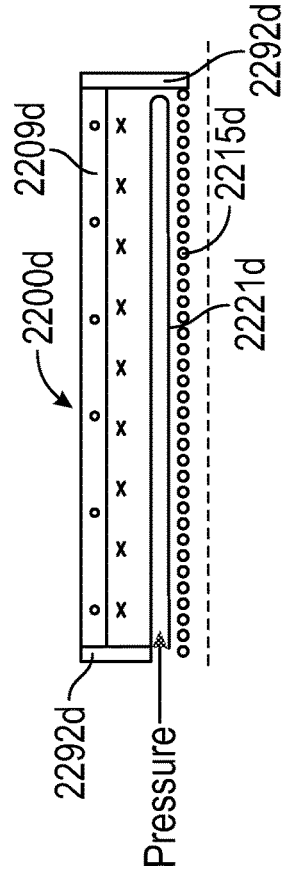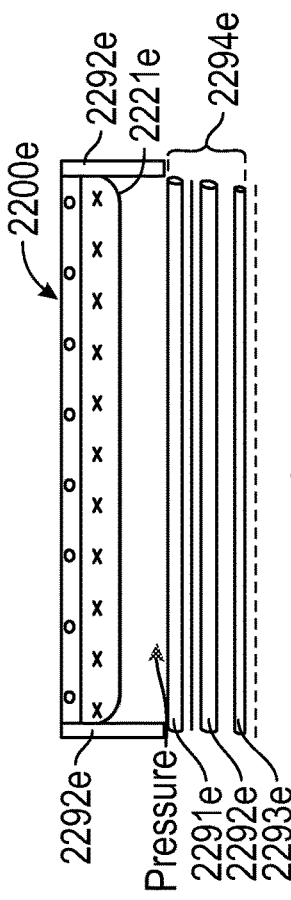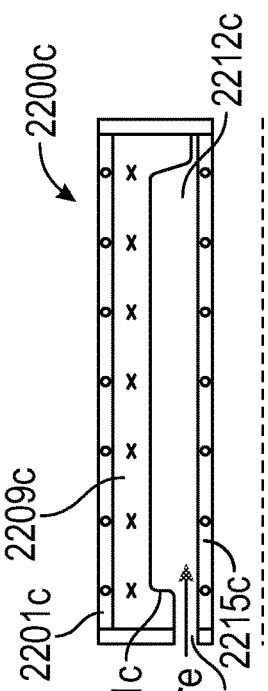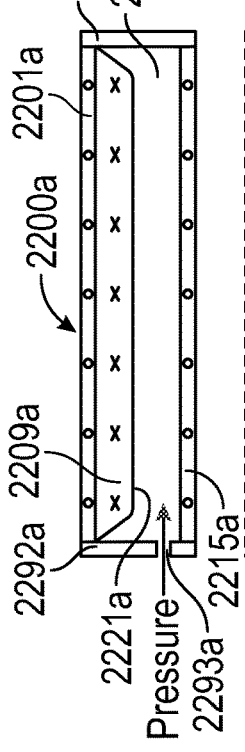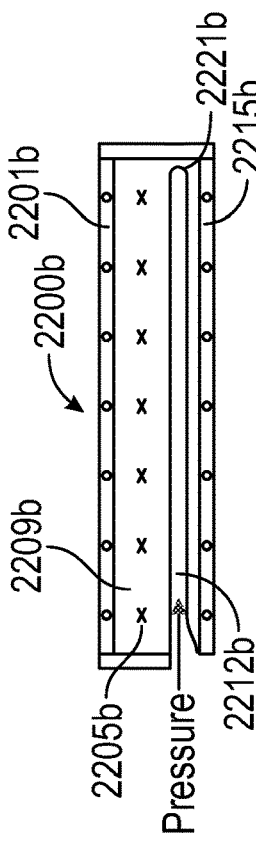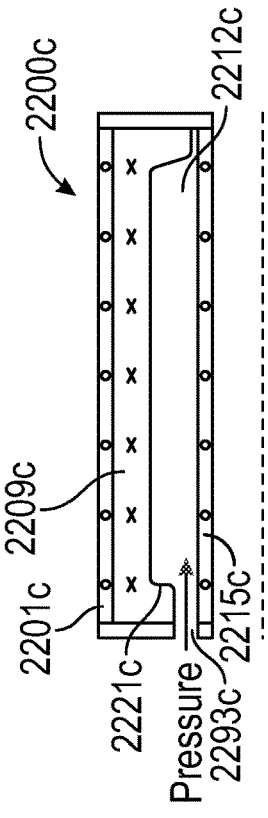

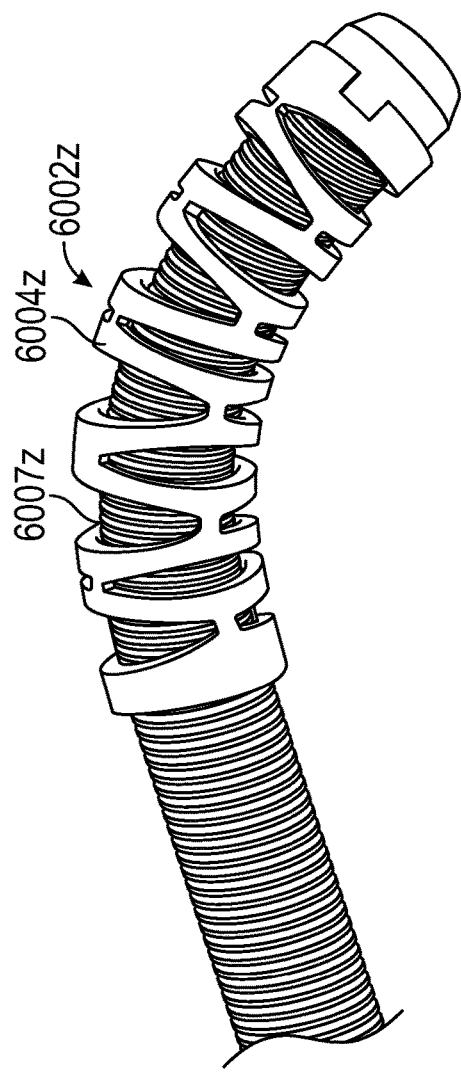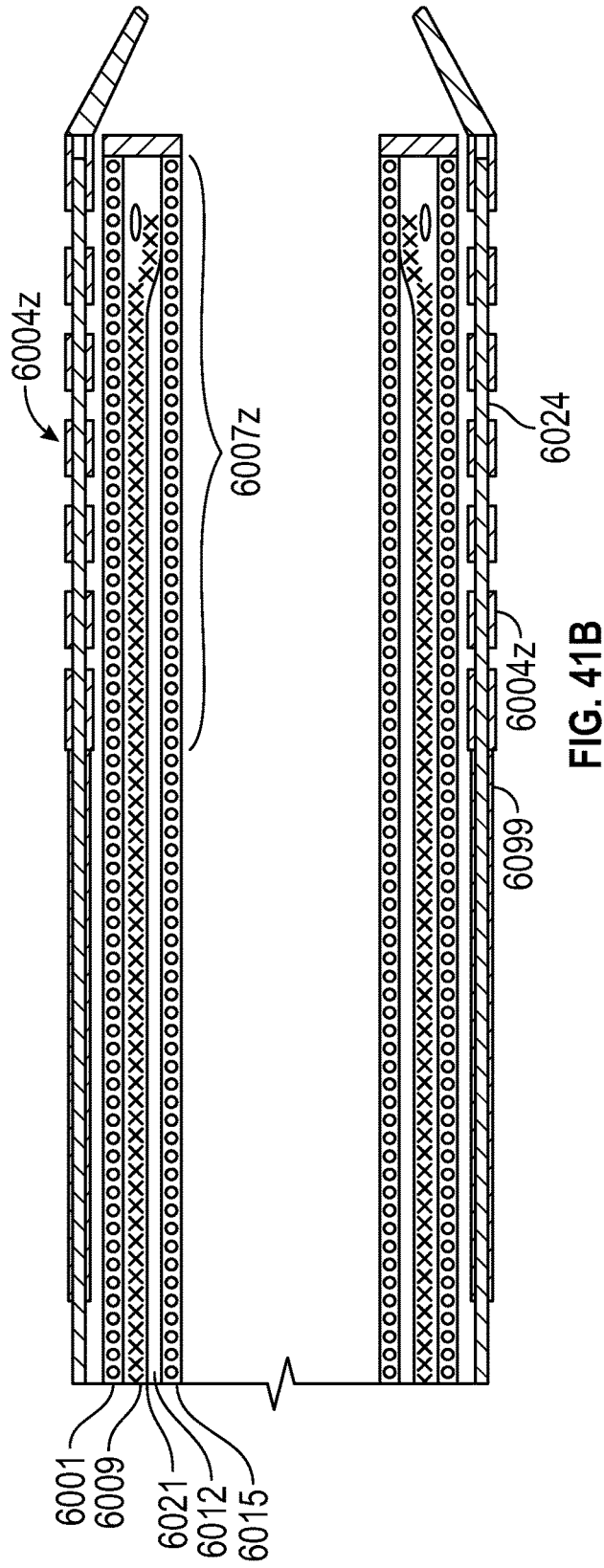
FIG. 41A
FIG. 41B

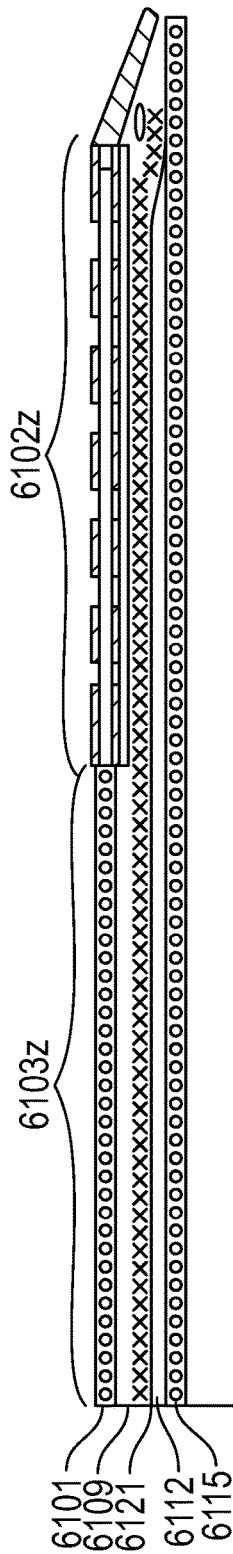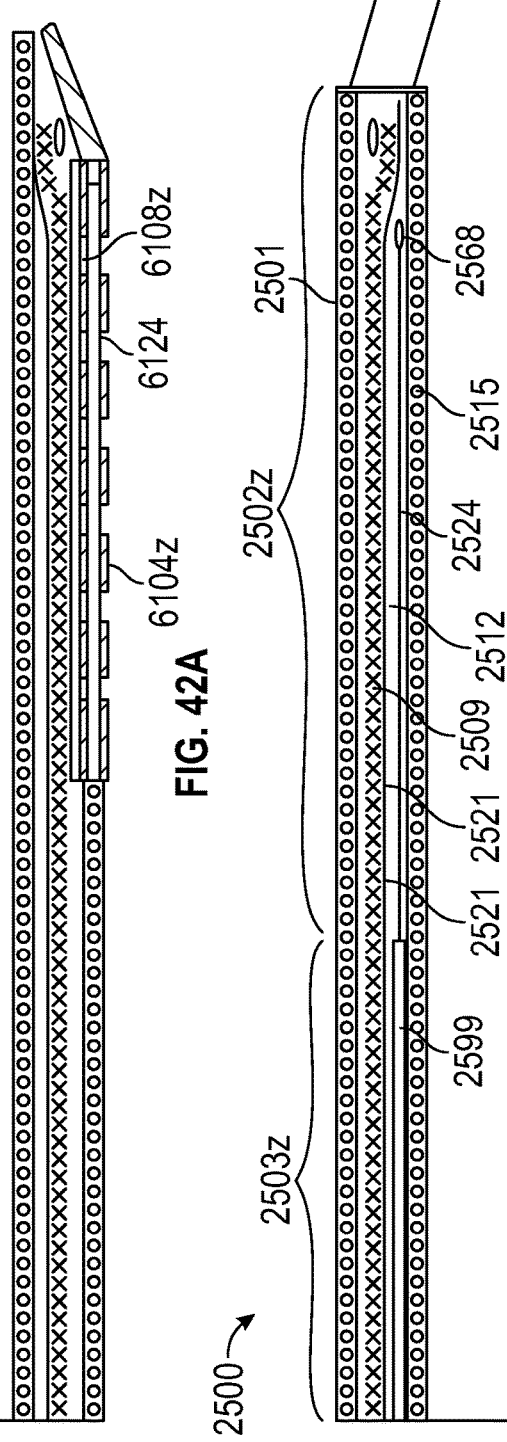
FIG. 42A
FIG. 42B

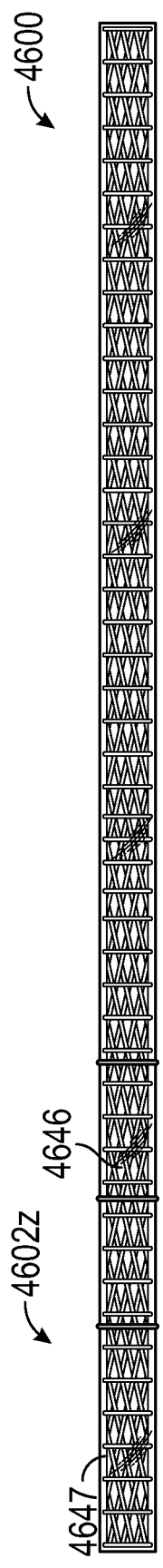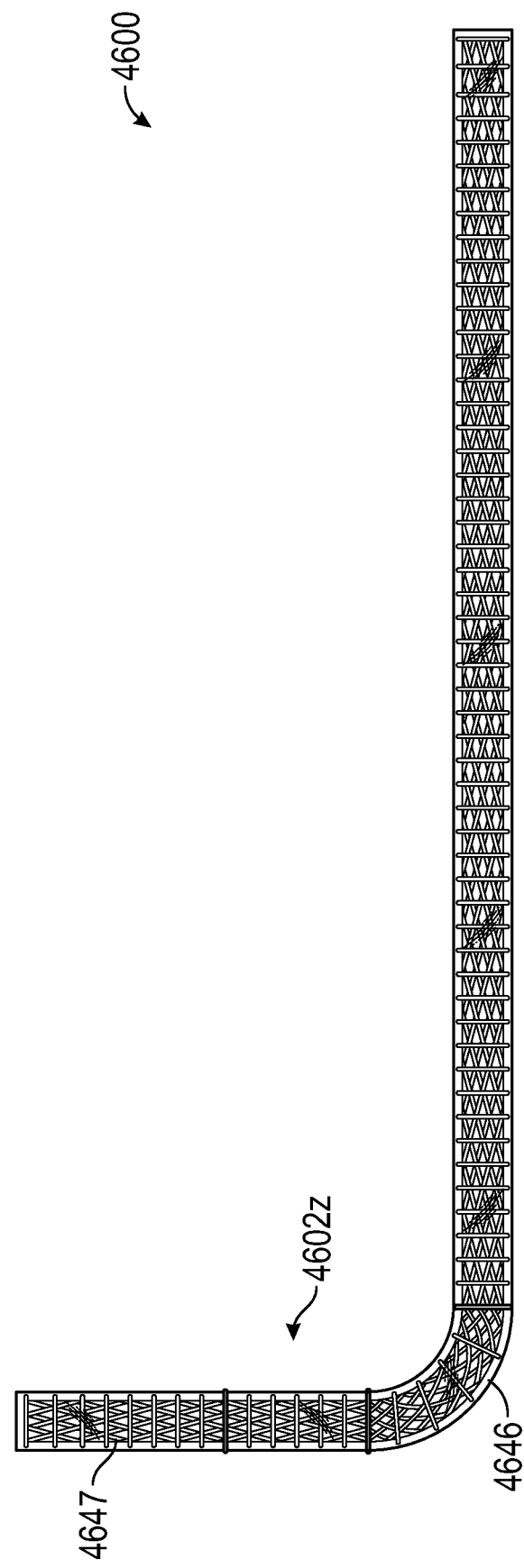
FIG. 43A
FIG. 43B

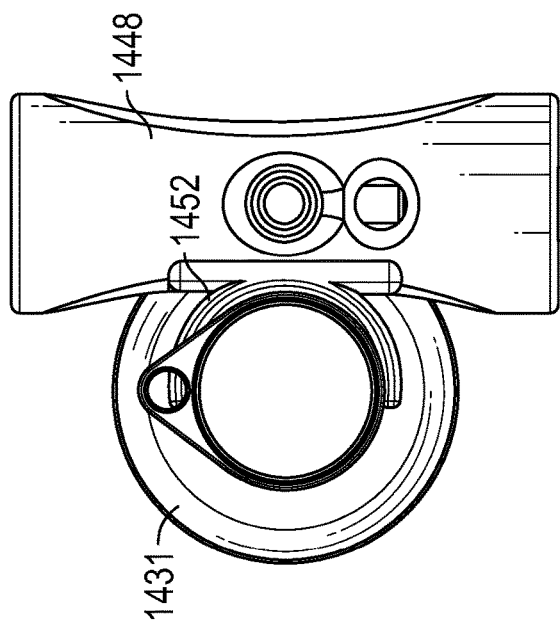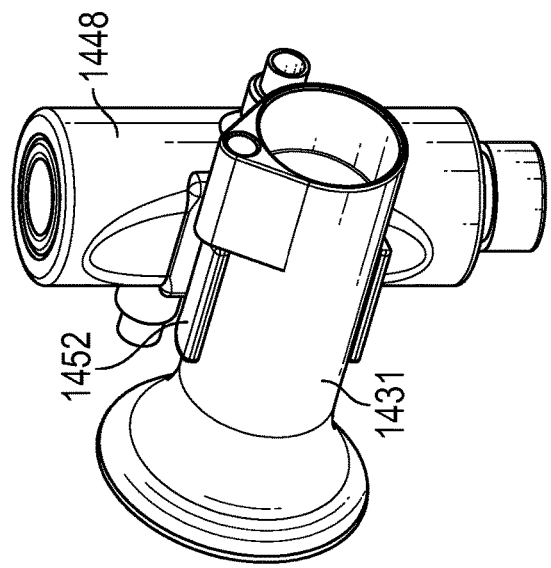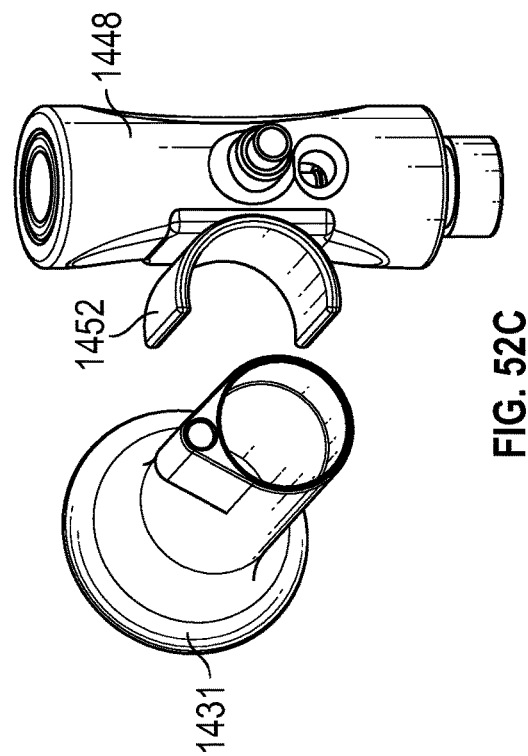

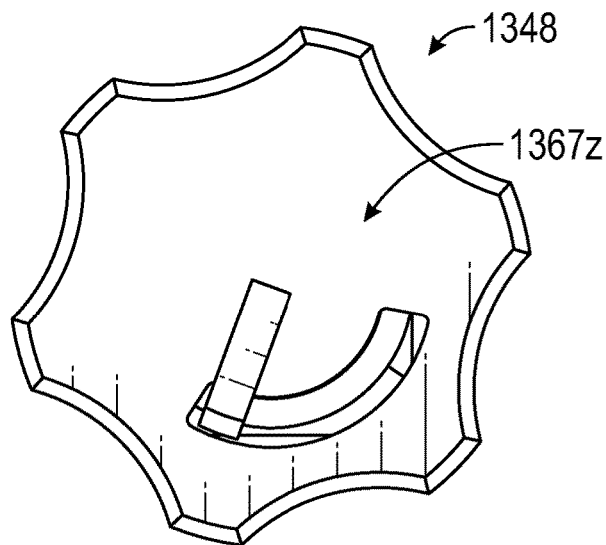 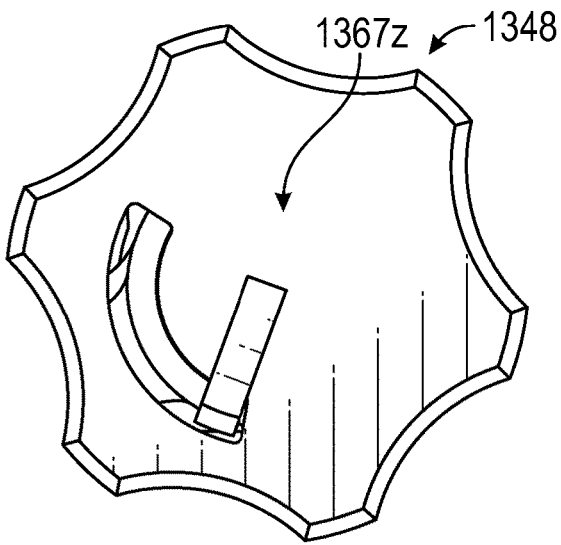
FIG. 55A  FIG. 55B
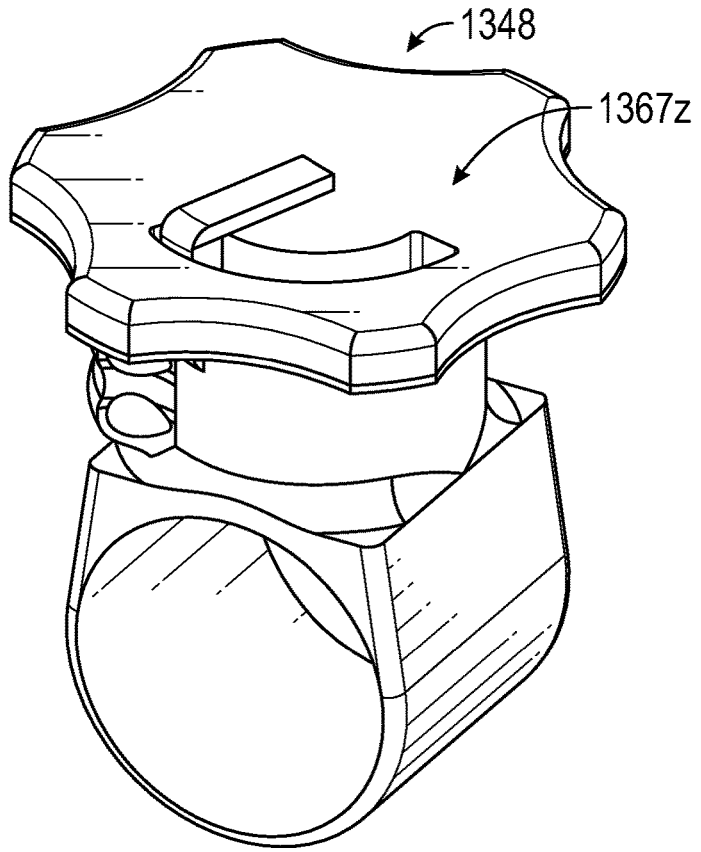
FIG. 55C

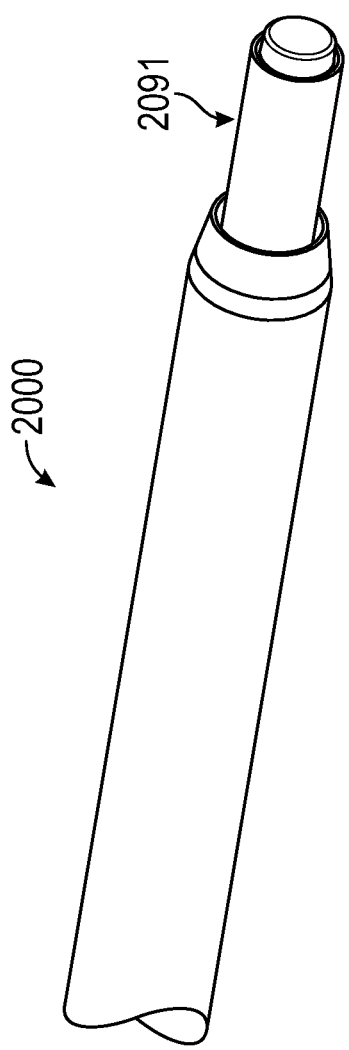
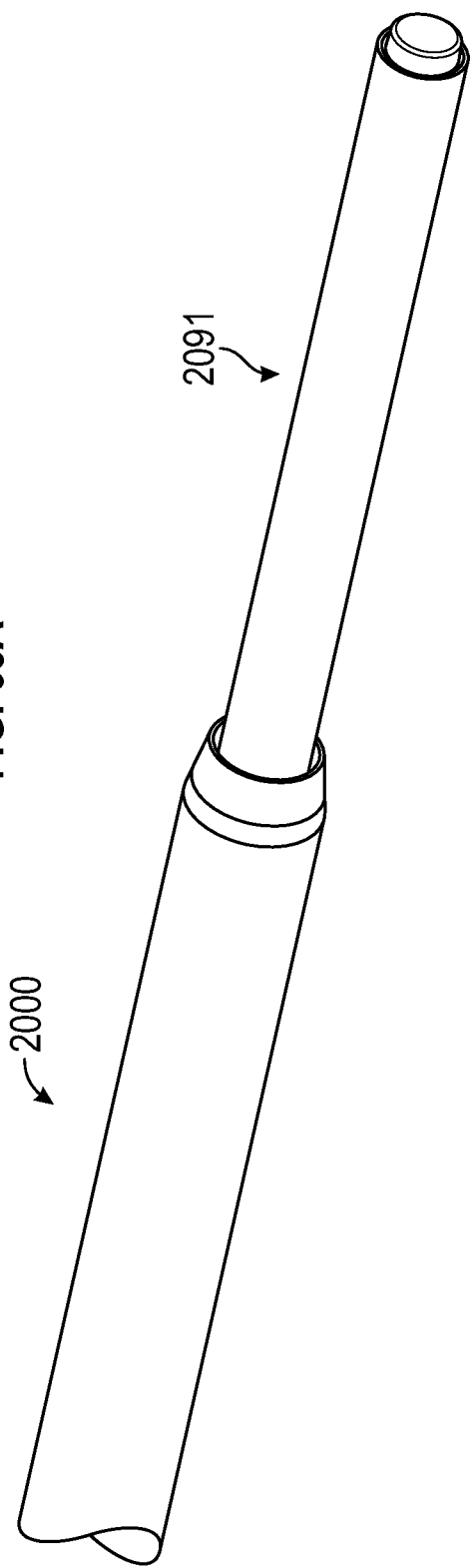

RIGIDIZING DEVICES

CROSS REFERENCE TO RELATED APPLICATIONS

This application is a continuation of U.S. patent application Ser. No. 17/493,785, filed Oct. 4, 2021, titled "DYNAMICALLY RIGIDIZING COMPOSITE MEDICAL STRUCTURES," now U.S. Patent Application Publication No. 2022/0023586, which is a continuation of U.S. patent application Ser. No. 17/152,706, filed Jan. 19, 2021, titled "DYNAMICALLY RIGIDIZING COMPOSITE MEDICAL STRUCTURES," now U.S. Pat. No. 11,135,398, which is a continuation of International Application No. PCT/US2019/042650, filed Jul. 19, 2019, titled "DYNAMICALLY RIGIDIZING COMPOSITE MEDICAL STRUCTURES," which claims priority to U.S. Provisional Application No. 62/835,101, filed Apr. 17, 2019, titled "DYNAMICALLY RIGIDIZING COMPOSITE MEDICAL STRUCTURES," U.S. Provisional Application No. 62/854,199, filed May 29, 2019, titled "DYNAMICALLY RIGIDIZING COMPOSITE MEDICAL STRUCTURES," U.S. Provisional Application No. 62/780,820, filed Dec. 17, 2018, titled "DYNAMICALLY RIGIDIZING COMPOSITE MEDICAL STRUCTURES," and U.S. Provisional Patent Application No. 62/700,760, filed Jul. 19, 2018, titled "BRAIDED DYNAMICALLY RIGIDIZING OVERTUBE," the entireties of which are incorporated by reference herein.

This application may also be related to International Patent Application No. PCT/US2018/042946, filed Jul. 19, 2018, titled "DYNAMICALLY RIGIDIZING OVERTUBE," which claims priority to U.S. Provisional Patent Application No. 62/672,444, filed May 16, 2018, titled "DYNAMICALLY RIGIDIZING OVERTUBE," and U.S. Provisional Patent Application No. 62/535,134, filed Jul. 20, 2017, titled "DYNAMICALLY RIGIDIZING OVERTUBE," the entireties of which are incorporated by reference herein.

This application may also be related to U.S. patent application Ser. No. 15/757,230, filed Mar. 2, 2018, titled "DEVICE FOR ENDOSCOPIC ADVANCEMENT THROUGH THE SMALL INTESTINE," now U.S. Patent Application Publication No. US2018/0271354, which national phase application under 35 USC 371 of International Patent Application No. PCT/US2016/050290, filed Sep. 2, 2016, titled "DEVICE FOR ENDOSCOPIC ADVANCEMENT THROUGH THE SMALL INTESTINE," now International Publication No. WO 2017/041052, which claims priority to U.S. Provisional Patent Application No. 62/339,593, filed May 20, 2016, titled "DEVICE FOR ENDOSCOPIS ADVANCEMENT THROUGH THE SMALL INTESTINE," and U.S. Provisional Patent Application No. 62/213,908, filed Sep. 3, 2015, and titled "DEVICE FOR ENDOSCOPIC ADVANCEMENT THROUGH THE SMALL INTESTINE," the entireties of which are incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

BACKGROUND

During medical procedures, the interventional medical device can curve or loop through the anatomy, making advancement of the medical device difficult.

Gastrointestinal looping, caused when the endoscope can no longer advance due to excessive curving or looping of the gastrointestinal tract, is a particularly well-known clinical challenge for endoscopy. Indeed, one study found that looping occurred in 91 of 100 patients undergoing colonoscopy [Shah et al, "Magnetic Imaging of Colonoscopy: An Audit of Looping, Accuracy and Ancillary maneuvers." Gastrointest Endosc 2000; 52:1-8]. Gastrointestinal looping prolongs the procedure and can cause pain to the patient because it can stretch the vessel wall and the mesentery. Furthermore, gastrointestinal looping leads to an increased incidence of perforations. In severe cases of gastrointestinal looping, complete colonoscopies are impossible since looping stretches the length of the colon and the colonoscope is not long enough to reach the end. Gastrointestinal looping is an impediment to precise tip control, denying the user the coveted one-to-one motion relationship between the handle and the endoscope tip. Such problems commonly occur across a wide range of endoscopic procedures, including colonoscopy, esophagogastroduodenoscopy (EGD), enteroscopy, endoscopic retrograde cholangiopancreatography (ERCP), interventional endoscopy procedures (including ESD (Endoscopic Submucosal Dissection) and EMR (Endoscopic Mucosal Resection)), robotic flexible endoscopy, trans-oral robotic surgery (TORS), altered anatomy cases (including Roux-en-Y), and during NOTES (Natural Orifice Transluminal Endoscopic Surgery) procedures. Accordingly, there is a need for device that helps prevent gastrointestinal looping to provide more successful access to the gastrointestinal tract.

Similar difficulties in advancing medical instruments can arise, for example, during interventional procedures in the lungs, kidneys, brain, cardiac space, and other anatomical locations. Accordingly, there is a need for a device that can provide safe, efficient, and precise access to otherwise difficult to reach anatomical locations.

SUMMARY OF THE DISCLOSURE

In general, in one embodiment, a rigidizing device includes an elongate flexible tube, a braid layer positioned over the elongate flexible tube, an outer layer over the flexible tube and the braid layer, and an inlet between the elongate flexible tube and the outer layer and configured to attach to a source of vacuum or pressure. The braid layer has a plurality of strands braided together at a braid angle of 5-40 degrees relative to a longitudinal axis of the elongate flexible tube when the elongate flexible tube is straight. The rigidizing device is configured to have a rigid configuration when vacuum or pressure is applied through the inlet and a flexible configuration when vacuum or pressure is not applied through the inlet. The braid angle is configured to change as the rigidizing device bends when the rigidizing device is in the flexible configuration.

This and other embodiments can include one or more of the following features. The braid angle can be between 10 and 35 degrees. The braid angle can be between 15 and 25 degrees. The rigidizing device in the rigid configuration can be at least two times stiffer than the rigidizing device in the flexible configuration. The rigidizing device in the rigid configuration can be at least 5 times stiffer than the rigidizing device in the flexible configuration. The rigidizing can further include a slip layer adjacent to the braid layer and having a lower coefficient of friction than the braid layer. The elongate flexible tube can include a reinforcement element extending therein. The reinforcement element can include a coil or plurality of hoop elements. The plurality of strands can be braided together at 4-60 picks per inch. The strands can include polyethylene terephthalate or stainless steel. The braid layer can provide a coverage of 30-70% relative to the elongate flexible tube. The plurality of strands can include 96 strands or more. The inlet can be configured to attach to a source of pressure, and the rigidizing device can further include a bladder layer therein. The bladder layer can be configured to be pushed against the braid layer when pressure is supplied through the inlet. The outer layer can further include a plurality of reinforcement elements therein. The inlet can be configured to attach to a source of vacuum, and the outer layer can be a thin flexible sheath. The rigidizing device can further include a radial gap between the braid layer and the outer layer. The gap can have a thickness of 0.00002"-0.04". The rigidizing device can further include a steerable distal end. The rigidizing device can further include a sealed channel between the elongate flexible tube and the outer layer. The sealed channel can include a working channel, a cable guide, or an inflation lumen.

In general, in one embodiment, a method of advancing a rigidizing device through a body lumen includes: (1) inserting a rigidizing device into the body lumen while the rigidizing device is in a flexible configuration, where the rigidizing device includes an elongate flexible tube, a braid layer having a plurality of strands braided together at a braid angle of 5-40 degrees when the rigidizing device is straight, and an outer layer, and where the braid angle changes as the flexible tube bends in the flexible configuration; and (2) when the rigidizing device has reached a desired location in the body lumen, activating vacuum or pressure between the flexible tube and the outer layer to transition the rigidizing device into a rigid configuration that is stiffer than the flexible configuration.

This and other embodiments can include one or more of the following features. The method can further include releasing vacuum or pressure after activating the vacuum or pressure to transition the rigidizing device back to the flexible configuration. The braid angle can be between 10 and 35 degrees. The braid angle can be between 15 and 25 degrees. The method can further include passing a scope through the rigidizing device while the rigidizing device is in the rigid configuration. The method can further include steering a steerable distal end of the rigidizing device through the body lumen. The body lumen can be in the gastrointestinal tract. The body lumen can be in the heart. The body lumen can be in the kidneys. The body lumen can be in the lungs. The body lumen can be in the brain.

In general, in one embodiment, a rigidizing device includes an elongate flexible tube, a braid layer positioned over the elongate flexible tube, an outer layer over the flexible tube and the braid layer, and an inlet between the elongate flexible tube and the outer layer and configured to attach to a source of vacuum or pressure. The rigidizing device is configured to have a rigid configuration when vacuum or pressure is applied through the inlet and a flexible configuration when vacuum or pressure is not applied through the inlet. A ratio of stiffness of the rigidizing device in the rigid configuration to stiffness of the rigidizing device in the flexible configuration is greater than 5.

This and other embodiments can include one or more of the following features. The ratio can be greater than 6. The ratio can be greater than 10. The braid layer can have a plurality of strands braided together at a braid angle of 5-40 degrees relative to a longitudinal axis of the elongate flexible tube when the elongate flexible tube is straight. The braid angle can be between 10 and 35 degrees. The rigidizing device can further include a slip layer adjacent to the braid layer and having a lower coefficient of friction than the braid layer. The elongate flexible tube can include a reinforcement element extending therein. The reinforcement element can include a coil or plurality of hoop elements. The braid layer can include a plurality of strands braided together at 4-60 picks per inch. The braid layer can include a plurality of strands braided together, and the strands can include polyethylene terephthalate or stainless steel. The braid layer can provide a coverage of 30-70% relative to the elongate flexible tube. The braid layer can include 96 strands or more strands braided together. The inlet can be configured to attach to a source of pressure. The rigidizing device can further include a bladder layer therein, and the bladder layer can be configured to be pushed against the braid layer when pressure is supplied through the inlet. The outer layer can further include a plurality of reinforcement elements therein. The inlet can be configured to attach to a source of vacuum. The outer layer can be a thin flexible sheath. The rigidizing device can further include a radial gap between the braid layer and the outer layer. The gap can have a thickness of 0.00002"-0.04". The rigidizing device can further include a steerable distal end. The rigidizing device can further include a sealed channel between the elongate flexible tube and the outer layer. The sealed channel can include a working channel, a cable guide, or an inflation lumen.

In general, in one embodiment, a method of advancing a rigidizing device through a body lumen includes: (1) inserting a rigidizing device into the body lumen while the rigidizing device is in a flexible configuration, where the rigidizing device includes an elongate flexible tube, a braid layer, and an outer layer; and (2) when the rigidizing device has reached a desired location in the body lumen, activating vacuum or pressure between the flexible tube and the outer layer to transition the rigidizing device into a rigid configuration that is stiffer than the flexible configuration. A ratio of stiffness in the rigid configuration to stiffness in the flexible configuration is greater than 5.

This and other embodiments can include one or more of the following features. The method can further include releasing vacuum or pressure after activating the vacuum or pressure to transition the rigidizing device back to the flexible configuration. The ratio can be greater than 6. The ratio can be greater than 10. The method can further include passing a scope through the rigidizing device while the rigidizing device is in the rigid configuration. The method can further include steering a steerable distal end of the rigidizing device through the body lumen. The body lumen can be in the gastrointestinal tract. The body lumen can be in the heart. The body lumen can be in the kidneys. The body lumen can be in the lungs. The body lumen can be in the brain.

In general, in one embodiment, a rigidizing device includes an elongate flexible tube, a braid layer positioned radially outwards the elongate flexible tube, a slip layer adjacent to the braid layer, an outer layer, and a vacuum or pressure inlet between the elongate flexible tube and the outer layer. The outer layer is over the flexible tube, the braid layer, and the slip layer. The inlet is configured to attach to a source of vacuum or pressure. The rigidizing device is configured to have a rigid configuration when vacuum or pressure is applied through the inlet and a flexible configuration when vacuum or pressure is not applied through the inlet. The slip layer is configured to reduce friction between the braid layer and the elongate flexible tube or the outer layer when the rigidizing device is in the flexible configuration.

This and other embodiments can include one or more of the following features. The slip layer can have a lower coefficient of friction than the braid layer. The slip layer can include a powder. The rigidizing device in the rigid configuration can be at least two times stiffer than the rigidizing device in the flexible configuration. The rigidizing device in the rigid configuration can be at least 5 times stiffer than the rigidizing device in the flexible configuration. The braid layer can have a plurality of strands braided together at a braid angle of 5-40 degrees relative to a longitudinal axis of the elongate flexible tube when the elongate flexible tube is straight. The braid angle can be between 10 and 35 degrees. The elongate flexible tube can include a reinforcement element extending therein. The reinforcement element can include a coil or plurality of hoop elements. The braid layer can include a plurality of strands braided together at 4-60 picks per inch. The braid layer can include a plurality of strands braided together, and the strands can include polyethylene terephthalate or stainless steel. The braid layer can provide a coverage of 30-70% relative to the elongate flexible tube. The braid layer can include 96 strands or more strands braided together. The inlet can be configured to attach to a source of pressure. The rigidizing device can further include a bladder layer therein. The bladder layer can be configured to be pushed against the braid layer when pressure is supplied through the inlet. The outer layer can further include a plurality of reinforcement elements therein. The inlet can be configured to attach to a source of vacuum. The outer layer can be a thin flexible sheath. The rigidizing device can further include a radial gap between the braid layer and the outer layer. The gap can have a thickness of 0.00002"-0.04". The rigidizing device can further include a steerable distal end. The rigidizing device can further include a sealed channel between the elongate flexible tube and the outer layer. The sealed channel can include a working channel, a cable guide, or an inflation lumen.

In general, in one embodiment, a method of advancing a rigidizing device through a body lumen includes: (1) inserting a rigidizing device into the body lumen while the rigidizing device is in a flexible configuration, where the rigidizing device includes an elongate flexible tube, a braid layer, a slip layer adjacent to the braid layer, and an outer layer, and where the slip layer reduces friction between the braid layer and the elongate flexible tube or the outer layer while the rigidizing device is in the flexible configuration; and (2) when the rigidizing device has reached a desired location in the body lumen, activating vacuum or pressure between the flexible tube and the sheath to transition the rigidizing device into a rigid configuration that is stiffer than the flexible configuration.

This and other embodiments can include one or more of the following features. The method can further include releasing vacuum or pressure after activating the vacuum or pressure to transition the rigidizing device back to the flexible configuration. The slip layer can have a lower coefficient of friction than the braid layer. The slip layer can include a powder. The method can further include passing a scope through the rigidizing device while the rigidizing device is in the rigid configuration. The method can further include steering a steerable distal end of the rigidizing device through the body lumen. The body lumen can be in the gastrointestinal tract. The body lumen can be in the heart. The body lumen can be in the kidneys. The body lumen can be in the lungs. The body lumen can be in the brain.

In general, in one embodiment, a rigidizing device includes an inner elongate flexible tube including a reinforcement element and a matrix, a braid layer positioned radially outwards the elongate flexible tube, an outer layer over the braid layer, and a vacuum or pressure inlet between the elongate flexible tube and the outer layer and configured to attach to a source of vacuum or pressure. The reinforcement element has a width to thickness aspect ratio of over 5:1. The rigidizing device is configured to have a rigid configuration when vacuum or pressure is applied through the vacuum inlet and a flexible configuration when vacuum or pressure is not applied through the vacuum inlet.

This and other embodiments can include one or more of the following features. The reinforcement element can be a coil. The reinforcement element can include a plurality of closed rings. The closed rings can include a plurality of pockets and notches. The reinforcement element can include an undulating wire. The reinforcement element can be a fiber or a metal wire. The aspect ratio can be over 10:1 The aspect ratio can be over 11:1. There can be a plurality of reinforcement elements in the elongate flexible tube. A spacing between each of the reinforcement elements can be 0.0006" inches or less. The elongate flexible tube can further include a matrix within which the reinforcement element is embedded. The matrix can include TPU or TPE.

In general, in one embodiment, a method of advancing a rigidizing device through a body lumen includes: (1) inserting a rigidizing device into the body lumen while the rigidizing device is in a flexible configuration, where the rigidizing device includes an elongate flexible tube having a reinforcement element and a matrix, a braid layer, and an outer layer, and where the reinforcement element has a width to thickness aspect ratio of over 10:1; and (2) when the rigidizing device has reached a desired location in the body lumen, activating vacuum or pressure between the flexible tube and the outer layer to transition the rigidizing device into a rigid configuration that is stiffer than the flexible configuration.

This and other embodiments can include or more of the following features. The elongate flexible tube can resist compression when vacuum or pressure is applied.

In general, in one embodiment, a rigidizing device includes an elongate flexible tube, a braid layer positioned over the elongate flexible tube, an outer layer over the flexible tube and the braid layer, and an inlet between the elongate flexible tube and the outer layer and configured to attach to a source of vacuum or pressure. The braid layer has a plurality of strands braided together. The rigidizing device is configured to have a rigid configuration when vacuum or pressure is applied through the inlet and a flexible configuration when vacuum or pressure is not applied through the inlet. Ends of the strands are embedded in or surrounded by an annular ring that allows relative movement of the ends when the rigidizing device is in the flexible configuration.

This and other embodiments can include one or more of the following features. The annular ring can include a coating of material. The annular ring can include silicone or urethane. The annular ring can be approximately 0.005-0.250 inches thick.

In general, in one embodiment, a method of advancing a rigidizing device through a body lumen includes: (1) inserting a rigidizing device into the body lumen while the rigidizing device is in a flexible configuration, where the rigidizing device includes an elongate flexible tube, a braid layer having a plurality of strands braided together, and an outer layer; and (2) when the rigidizing device has reached a desired location in the body lumen, activating vacuum or pressure between the flexible tube and the sheath to transition the rigidizing device into a rigid configuration that is stiffer than the flexible configuration. Ends of the strands are embedded in or surrounded by an annular ring such that the ends move relative to one another while the rigidizing device is in the flexible configuration. The ends are substantially fixed relative to one another while the rigidizing device is in the rigid configuration.

In general, in one embodiment, a rigidizing device includes an elongate flexible tube, a braid layer positioned over the elongate flexible tube, an outer layer sealed over the flexible tube and the braid layer, and an inlet between the elongate flexible tube and the outer layer and configured to attach to a source of vacuum. The braid layer has a plurality of strands braided together and a plurality of hoop fibers woven into the braid. The rigidizing device is configured to have a rigid configuration when vacuum is applied through the inlet and a flexible configuration when vacuum is not applied through the inlet.

In general, in one embodiment, a method of advancing a rigidizing device through a body lumen includes: (1) inserting a rigidizing device into the body lumen while the rigidizing device is in a flexible configuration, where the rigidizing device includes an elongate flexible tube, a braid layer and an outer layer; and (2) when the rigidizing device has reached a desired location in the body lumen, activating vacuum between the flexible tube and the outer layer to transition the rigidizing device into a rigid configuration that is stiffer than the flexible configuration. The braid layer has a plurality of strands braided together and a plurality of hoop fibers woven into the braid.

In general, in one embodiment, a rigidizing device includes an elongate flexible tube, a bladder layer positioned over the elongate flexible tube, a braid layer positioned over the bladder layer, an outer layer positioned over the flexible tube and the braid layer, a pressure inlet between the bladder layer and the elongate flexible tube, and a vent outlet between the bladder layer and the outer layer. The pressure inlet configured to attach to a source of pressure. The braid layer includes a plurality of strands braided together. The rigidizing device is configured to achieve a rigid configuration when pressure is supplied through the pressure inlet and a flexible configuration when pressure is not supplied through the pressure inlet. Fluid or gas surrounding the strands moves out of the vent outlet as the rigidizing device transitions from the flexible configuration to the rigid configuration.

This and other embodiments can include one or more of the following features. The rigidizing device can further include a handle attached to the elongate flexible tube. The handle can include a vent port in communication with the vent outlet.

In general, in one embodiment, a method of advancing a rigidizing device through a body lumen includes: (1) inserting a rigidizing device into the body lumen while the rigidizing device is in a flexible configuration, where the rigidizing device includes an elongate flexible tube, a bladder layer, a braid layer having a plurality of strands braided together, and an outer layer; and (2) when the rigidizing device has reached a desired location in the body lumen, providing pressure through an inlet between the elongate flexible tube and the bladder layer and venting gas or fluid surrounding the strands out of a vent outlet to transition the rigidizing device into a rigid configuration that is stiffer than the flexible configuration.

In general, in one embodiment, a rigidizing device includes an elongate flexible tube, a braid layer positioned over the elongate flexible tube, an outer layer over the flexible tube and the braid layer, a channel extending between the outer layer and the elongate flexible tube, and an inlet. The inlet is between the elongate flexible tube and the outer layer and configured to attach to a source of vacuum or pressure. The channel includes a working channel, a steering cable channel, or an inflation lumen. The rigidizing device is configured to have a rigid configuration when vacuum or pressure is applied through the inlet and a flexible configuration when vacuum or pressure is not applied through the inlet.

In general, in one embodiment, a method of advancing a medical tool through a body lumen includes: (1) inserting a rigidizing device into the body lumen while the rigidizing device is in a flexible configuration, where the rigidizing device includes an elongate flexible tube, a braid layer, and an outer layer; (2) when the rigidizing device has reached a desired location in the body lumen, activating vacuum or pressure between the flexible tube and the outer layer to transition the rigidizing device into a rigid configuration that is stiffer than the flexible configuration; and (3) passing a medical tool through a sealed working channel that is positioned between the elongate flexible tube and the outer layer.

In general, in one embodiment, a method of advancing a medical tool through a body lumen includes: (1) inserting a rigidizing device into the body lumen while the rigidizing device is in a flexible configuration, where the rigidizing device comprises an elongate flexible tube, a braid layer, and an outer layer; (2) when the rigidizing device has reached a desired location in the body lumen, activating vacuum or pressure between the flexible tube and the outer layer to transition the rigidizing device into a rigid configuration that is stiffer than the flexible configuration; and (3) activating at least one cable that is positioned between the elongate flexible tube and the outer layer to orient a distal end of the rigidizing device.

In general, in one embodiment, a method of advancing a medical tool through a body lumen includes: (1) inserting a rigidizing device into the body lumen while the rigidizing device is in a flexible configuration, where the rigidizing device includes an elongate flexible tube, a braid layer, and an outer layer; (2) when the rigidizing device has reached a desired location in the body lumen, activating vacuum or pressure between the flexible tube and the outer layer to transition the rigidizing device into a rigid configuration that is stiffer than the flexible configuration; and (3) inflating a balloon on the rigidizing device by passing an inflation medium through a sealed inflation lumen that is positioned between the elongate flexible tube and the outer layer.

In general, in one embodiment, a rigidizing device includes an elongate flexible tube having a central lumen, a braid layer positioned over the elongate flexible tube, an outer layer over the flexible tube and the braid layer, a plurality of sealed working channels extending within the central lumen, and an inlet between the elongate flexible tube and the outer layer and configured to attach to a source of vacuum or pressure. The rigidizing device is configured to have a rigid configuration when vacuum or pressure is applied through the inlet and a flexible configuration when vacuum or pressure is not applied through the inlet.

In general, in one embodiment, a method of advancing a plurality of medical tools through a body lumen includes: (1) inserting a rigidizing device into the body lumen while the rigidizing device is in a flexible configuration, where the rigidizing device includes an elongate flexible tube, a braid layer, and an outer layer; (2) and when the rigidizing device has reached a desired location in the body lumen, activating vacuum or pressure between the flexible tube and the outer layer to transition the rigidizing device into a rigid configuration that is stiffer than the flexible configuration; (3) passing a first medical tool through a first sealed working channel of the rigidizing device, and (4) passing a second medical tool through a second sealed working channel of the rigidizing device.

In general, in one embodiment, an overtube includes an elongate tube and a distal tip attached to the elongate tube. The distal tip has an annular distal face with one or more vacuum holes extending therethrough. The one or more vacuum holes are configured to draw tissue towards the annular distal face upon application of vacuum therethrough.

This and other embodiments can include one or more of the following features. The elongate tube can be a rigidizing device, and the rigidizing device can be configured to have a rigid configuration when vacuum or pressure is applied to a wall thereof and a flexible configuration when vacuum or pressure is not applied to the wall. The elongate tube can include a braid layer and an outer layer thereover. The annular distal face can be angled relative to a longitudinal axis of the elongate tube.

In general, in one embodiment, a rigidizing device includes an elongate flexible tube, a braid layer positioned over the elongate flexible tube, an outer layer over the flexible tube and the braid layer, and a distal tip attached to the elongate flexible tube. The braid layer has a plurality of strands braided together at a first braid angle relative to a longitudinal axis of the elongate flexible tube when the elongate flexible tube is straight. The distal tip includes a second braid layer having a plurality of strands braided together at a second braid angle that is different from the first braid angle. An inlet between the elongate flexible tube and the outer layer is configured to attach to a source of vacuum or pressure. The rigidizing device is configured to have a rigid configuration when vacuum or pressure is applied through the inlet and a flexible configuration when vacuum or pressure is not applied through the inlet.

This and other embodiments can include one or more of the following features. The second braid angle can be greater than the first braid angle. The first and second braid layers can be bonded to one another.

In general, in one embodiment, a rigidizing device includes an elongate flexible tube including a plurality of reinforcement elements therein. The elongate flexible tube includes a proximal section and a distal section. A braid layer is positioned over the proximal section and not the distal section. The braid layer has a plurality of strands braided together at a first braid angle relative to a longitudinal axis of the elongate flexible tube when the elongate flexible tube is straight. An outer layer is positioned over the braid layer. A plurality of steerable linkages extend over the distal section and not the proximal section. An inlet is between the elongate flexible tube and the outer layer and is configured to attach to a source of vacuum or pressure. The rigidizing device is configured to have a rigid configuration when vacuum or pressure is applied through the inlet and a flexible configuration when vacuum or pressure is not applied through the inlet.

This and other embodiment can include one or more of the following features. The rigidizing device can further include a plurality of cables attached to the steerable linkages. The cables can extend between the elongate flexible tube and the outer layer.

In general, in one embodiment, a rigidizing device includes a rigidizing assembly and plurality of linkages. The rigidizing assemble includes an elongate flexible tube, a braid layer positioned over the elongate flexible tube, an outer layer over the flexible tube and the braid layer, and an inlet. The inlet is between the elongate flexible tube and the outer layer and is configured to attach to a source of vacuum or pressure. The plurality of steering linkages are mounted over a distal portion of the rigidizing assembly. The rigidizing assembly is configured to have a rigid configuration when vacuum or pressure is applied through the inlet and a flexible configuration when vacuum or pressure is not applied through the inlet.

This and other embodiments can include one or more of the following features. The rigidizing device can further include a plurality of cables attached to the steerable linkages. The cables can extend between the elongate flexible tube and the outer layer.

In general, in one embodiment, a rigidizing device includes an elongate flexible tube, a plurality of steerable linkages and an outlet. The elongate flexible tube includes a proximal section and a distal section. The elongate flexible tube includes a plurality of reinforcement elements therein, a braid layer positioned over the proximal section the distal section, an outer layer including a plurality of reinforcement elements. The plurality of steerable linkages extends over the distal section and not the proximal section. The inlet is between the elongate flexible tube and the outer layer and configured to attach to a source of vacuum or pressure. The braid layer has a plurality of strands braided together at a first braid angle relative to a longitudinal axis of the elongate flexible tube when the elongate flexible tube is straight. The outer layer is positioned over the proximal section and not the distal section. The rigidizing device is configured to have a rigid configuration when vacuum or pressure is applied through the inlet and a flexible configuration when vacuum or pressure is not applied through the inlet.

This and other embodiments can include one or more of the following features. The rigidizing device can further include a plurality of cables attached to the steerable linkages. The cables can extend between the elongate flexible tube and the outer layer.

In general, in one embodiment, a rigidizing device includes a rigidizing assembly and a plurality of linkages. The rigidizing assembly includes an elongate flexible tube, a braid layer positioned over the elongate flexible tube, an outer layer over the flexible tube and the braid layer, and an inlet between the elongate flexible tube and the outer layer and configured to attach to a source of vacuum or pressure. A spine extends through a distal section of the rigidizing assembly. The spine is configured to provide bending of the rigidizing assembly in a set direction. The plurality of steering linkages are distal to the rigidizing assembly. The rigidizing assembly is configured to have a rigid configuration when vacuum or pressure is applied through the inlet and a flexible configuration when vacuum or pressure is not applied through the inlet.

This and other embodiments can include one or more of the following features. The rigidizing device can further include a pullwire configured to bend the device at the spine when activated. The rigidizing device can further include a plurality of cables attached to the steerable linkages. The cables can extend between the elongate flexible tube and the outer layer.

In general, in one embodiment, a rigidizing device includes a rigidizing assembly and a distal tip. The rigidizing assembly includes an elongate flexible tube, a braid layer positioned over the elongate flexible tube, an outer layer over the flexible tube and the braid layer, and an inlet between the elongate flexible tube and the outer layer and configured to attach to a source of vacuum or pressure. The distal tip is attached to the elongate flexible tube. The distal tip includes a plurality of linkages connected together at pivot points. The rigidizing assembly and the distal tip are configured to assume a rigid configuration when vacuum or pressure is applied through the inlet and a flexible configuration when vacuum or pressure is not applied through the inlet.

In general, in one embodiment, a handle for use with a rigidizing device includes a handle body configured to attach to a rigidizing device, a vacuum feed line attached to the handle body and configured to connect to a source of vacuum, a vacuum port in communication with a wall of the rigidizing device, and an activation element on the handle body. The activation element is configured to move between a first position and a second position. The activation element in the first position connects the vacuum feed line with the vacuum port to provide vacuum to the wall of the rigidizing device, and the activation element in the second position disconnects the vacuum feed line from the vacuum port to vent the wall of the rigidizing device.

This and other embodiments can include one or more of the following features. The activation element can include a magnetic element thereon. The magnetic element can be configured to hold the activation element in the first position or the second position. The vacuum feed line can be coiled within the handle.

In general, in one embodiment, a method of advancing a rigidizing device through a body lumen includes: (1) holding a handle of the rigidizing device; (2) inserting an elongate body of the rigidizing device into the body lumen while the rigidizing device is in a flexible configuration; (3) when the rigidizing device has reached a desired location in the body lumen, moving an activation element in a first direction to connect a vacuum feed line of the handle with a vacuum port to a wall of the elongate body such that vacuum flows into the wall of the elongate body to transition the elongate body to a rigid configuration; and (4) moving the activation element in a second direction to disconnect the vacuum feed line from the vacuum port such that the elongate body vents to transition the elongate body to the flexible configuration.

In general, in one embodiment, a handle for use with a rigidizing device includes a handle body configured to attach to a rigidizing device, a fluid chamber within the handle body, an outlet in fluid communication with the fluid chamber and with a wall of the rigidizing device, and an activation element configured to move between a first position and a second position. The activation element is configured to transfer fluid from the fluid chamber to the wall of the rigidizing device when moving from the first position to the second position and to transfer fluid back into the fluid chamber when moving from the second position to the first position.

This and other embodiments can include one or more of the following features. The handle can further include an overflow chamber within the handle body and a pressure relief valve between the fluid chamber and the overflow chamber. The pressure relief valve can be configured to open to allow fluid to flow into the overflow chamber when pressure in the fluid chamber reaches a predetermined maximum pressure. The handle can further include a piston and rolling diaphragm within the handle body. The piston can be configured to push on the rolling diaphragm as the activation element is moved between the first position and the second position.

In general, in one embodiment, a method of advancing a rigidizing device through a body lumen includes: (1) holding a handle of the rigidizing device, (2) inserting an elongate body of the rigidizing device into the body lumen while the rigidizing device is in a flexible configuration; (3) when the rigidizing device has reached a desired location in the body lumen, moving an activation element in a first direction to move fluid from a fluid chamber of the handle into a wall of the rigidizing element to transition the rigidizing device to a rigid configuration; and (4) moving the activation in a second direction to move fluid from the wall of the rigidizing element back into the handle to transition the rigidizing device to the flexible configuration.

In general, in one embodiment, a nested system includes a first rigidizing device and a second rigidizing device positioned radially within the first rigidizing device. The second rigidizing device is axially slideable relative to the first rigidizing device. The first and second rigidizing devices are configured to be alternately rigidized by vacuum or pressure.

This and other embodiments can include one or more of the following features. The pressure can be greater than 1 atm. The first rigidizing device can be configured to be rigidized by vacuum and the second rigidizing device can be configured to be rigidized by pressure of greater than 1 atm. Each of the first and second rigidizing devices can include a plurality of layers. The vacuum or pressure can be configured to be supplied between the plurality of layers. At least one of the plurality of layers can be a braid layer.

In general, in one embodiment, a method of advancing through a body lumen includes: (1) inserting a first rigidizing device into the body lumen while the first rigidizing device is in a flexible configuration; (2) supplying vacuum or pressure to the first rigidizing device to transition the first rigidizing device into a rigid configuration that is stiffer than the flexible configuration; (3) inserting a second rigidizing device in a flexible configuration through the first rigidizing device while the first rigidizing device is in the rigid configuration such that the second rigidizing device takes on a shape of the first rigidizing device in the rigid configuration; and (4) supplying vacuum or pressure to the second rigidizing device to transition the second rigidizing device from the flexible configuration to a rigid configuration.

This and other embodiments can include one or more of the following features. Each rigidizing device can include an elongate flexible tube and a braid layer. Supplying vacuum or pressure can compress the braid layer to transition the rigidizing device to the rigid configuration.

In general, in one embodiment, a method of advancing through a body lumen includes: (1) moving a first rigidizing device in a flexible configuration until the first rigidizing device reaches a desired location; (2) after the first rigidizing device has reached the desired location, transitioning the first rigidizing device into a rigid configuration by supplying vacuum or pressure to the first rigidizing device; (3) after the first rigidizing device is rigidized, moving a second rigidizing device in a flexible configuration over the first rigidizing device in the rigidized configuration; (4) transitioning the second rigidizing element into a rigid configuration by supplying vacuum or pressure to the second rigidizing device; (5) transitioning the first rigidizing device into a flexible configuration by removing the vacuum or pressure; and (6) moving the first rigidizing device in the flexible configuration through the second elongate rigidizing device until the first rigidizing device reaches a desired location.

This and other embodiments can include one or more of the following features. The method can further include periodically moving both the first and second rigidizing devices into a flexible configuration to allow a curvature of the first and second rigidizing devices to increase to match surrounding anatomy.

In general, in one embodiment, a rigidizing rod includes an inner bladder layer, a braid layer positioned over the inner bladder layer, an outer sheath sealed over the inner bladder layer and the braid layer, and an inlet between the outer sheath and the inner bladder layer configured to attach to a source of vacuum. The rigidizing rod is configured to have a rigid configuration when vacuum is applied through the inlet and a flexible configuration when vacuum or pressure is not supplied through the inlet. The rigidizing rod does not have a through-lumen extending therethrough.

In general, in one embodiment, a method of advancing a rigidizing device through a body lumen includes: (1) advancing the rigidizing device through the body lumen; (2) inserting a rod having an elongate flexible tube, a braid layer, and a bladder into a lumen of the rigidizing device while the rod is in a flexible configuration; (3) when the rod has reached a desired location in the lumen of the rigidizing device, supplying pressure of greater than 1 atm to a central sealed lumen of the rod to force the braid layer against the elongate flexible tube to transition the rigidizing device into a rigid configuration that is stiffer than the flexible configuration; and (4) further advancing the rigidizing device over the rod while the rod is in the rigid configuration.

In general, in one embodiment, a method of performing cholangioscopy includes: (1) inserting an overtube into colon while the overtube is in a flexible configuration, where the overtube includes an elongate flexible tube, a braid layer having a plurality of strands braided together, and an outer layer; (2) steering a distal end of the overtube towards a papilla; (3) activating vacuum or pressure between the flexible tube and the outer layer to transition the overtube into a rigid configuration that is stiffer than the flexible configuration; (4) while the overtube is in the rigid configuration, advancing a guidewire through the overtube and into a bile duct or pancreatic duct; and (5) advancing a scope over the guidewire to the bile duct or pancreatic duct.

In general, in one embodiment, a method of accessing the cardiac anatomy includes: (1) inserting a sheath into the cardiac anatomy while the sheath is in the flexible configuration, where the sheath includes an elongate flexible tube, a braid layer having a plurality of strands braided together, and an outer layer; (2) steering a distal end of the sheath towards a desired final location; (3) activating vacuum or pressure between the flexible tube and the outer layer to transition the overtube into a rigid configuration that is stiffer than the flexible configuration; and (4) passing a cardiac device through the rigid sheath.

This and other embodiments can include one or more of the following features. The desired final location can be the aortic valve. The cardiac device can be a transcatheter aortic valve replacement. The desired final location can be the mitral valve. The cardiac device can be a mitral valve replacement or a mitral valve repair element.

Any of the devices described here can include one or more of the following. The rigidizing device can further include a slip layer adjacent to the braid layer. The slip layer can have a lower coefficient of friction than the braid layer. The rigidizing device in the rigid configuration can be at least two times stiffer than the rigidizing device in the flexible configuration. The rigidizing device in the rigid configuration can be at least 5 times stiffer than the rigidizing device in the flexible configuration. The braid layer can have a plurality of strands braided together at a braid angle of 5-40 degrees relative to a longitudinal axis of the elongate flexible tube when the elongate flexible tube is straight. The braid angle can be between 10 and 35 degrees. The elongate flexible tube can include a reinforcement element extending therein. The reinforcement element can include a coil or plurality of hoop elements. The braid layer can include a plurality of strands braided together at 4-60 picks per inch. The braid layer can include a plurality of strands braided together. The strands can include polyethylene terephthalate or stainless steel. The braid layer can provide a coverage of 30-70% relative to the elongate flexible tube. The braid layer can include 96 strands or more strands braided together. The inlet can be configured to attach to a source of pressure. The rigidizing device can further include a bladder layer therein. The bladder layer can be configured to be pushed against the braid layer when pressure is supplied through the inlet. The outer layer can further include a plurality of reinforcement elements therein. The inlet can be configured to attach to a source of vacuum. The outer layer can be a thin flexible sheath. The rigidizing device can further include a radial gap between the braid layer and the outer layer. The gap can have a thickness of 0.00002"-0.04". The rigidizing device can further include a steerable distal end. The rigidizing device can further include a sealed channel between the elongate flexible tube and the outer layer. The sealed channel can include a working channel, a cable guide, or an inflation lumen.

Any of the methods described here can include one or more of the following. The method can further include releasing vacuum or pressure after activating the vacuum or pressure to transition the rigidizing device back to the flexible configuration. The method can be performed in the gastrointestinal tract. The method can be performed in the heart. The method can be performed in the kidneys. The method can be performed in the lungs. The method can be performed in the brain.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 12A-12B show exemplary rigidized shapes of a rigidizing device.

FIGS. 41A-41B show a rigidizing device with a distal end section having linkages over a rigidizing section.

FIG. 42A shows a rigidizing device with a distal end section having linkages within a rigidizing section.

FIG. 42B shows a rigidizing device with a steering cable attached to a wall near the distal end thereof.

FIGS. 43A-43C show a rigidizing device having an actively deflected distal end section.

FIGS. 52A-52C show an embodiment of an activation element with a coupling for a handle of a rigidizing device.

FIGS. 55A-55C show an embodiment of an activation element for a handle of a rigidizing device.

FIGS. 68A-68B show an exemplary rigidizing device with a scope therein.

DETAILED DESCRIPTION

In general, described herein are rigidizing devices (e.g., overtubes) that are configured to aid in transporting a scope (e.g., endoscope) or other medical instrument through a curved or looped portion of the body (e.g., a vessel). The rigidizing devices can be long, thin, and hollow and can transition quickly from a flexible configuration (i.e., one that is relaxed, limp, or floppy) to a rigid configuration (i.e., one that is stiff and/or holds the shape it is in when it is rigidized). A plurality of layers (e.g., coiled or reinforced layers, slip layers, braided layers, bladder layers and/or sealing sheaths) can together form the wall of the rigidizing devices. The rigidizing devices can transition from the flexible configuration to the rigid configuration, for example, by applying a vacuum or pressure to the wall of the rigidizing device or within the wall of the rigidizing device. With the vacuum or pressure removed, the layers can easily shear or move relative to each other. With the vacuum or pressure applied, the layers can transition to a condition in which they exhibit substantially enhanced ability to resist shear, movement, bending, and buckling, thereby providing system rigidization.

The rigidizing devices described herein can provide rigidization for a variety of medical applications, including catheters, sheaths, scopes (e.g., endoscopes), wires, or laparoscopic instruments. The rigidizing devices can function as a separate add-on device or can be integrated into the body of catheters, sheaths, scopes, wires, or laparoscopic instruments. The devices described herein can also provide rigidization for non-medical structures.

Figure 1:
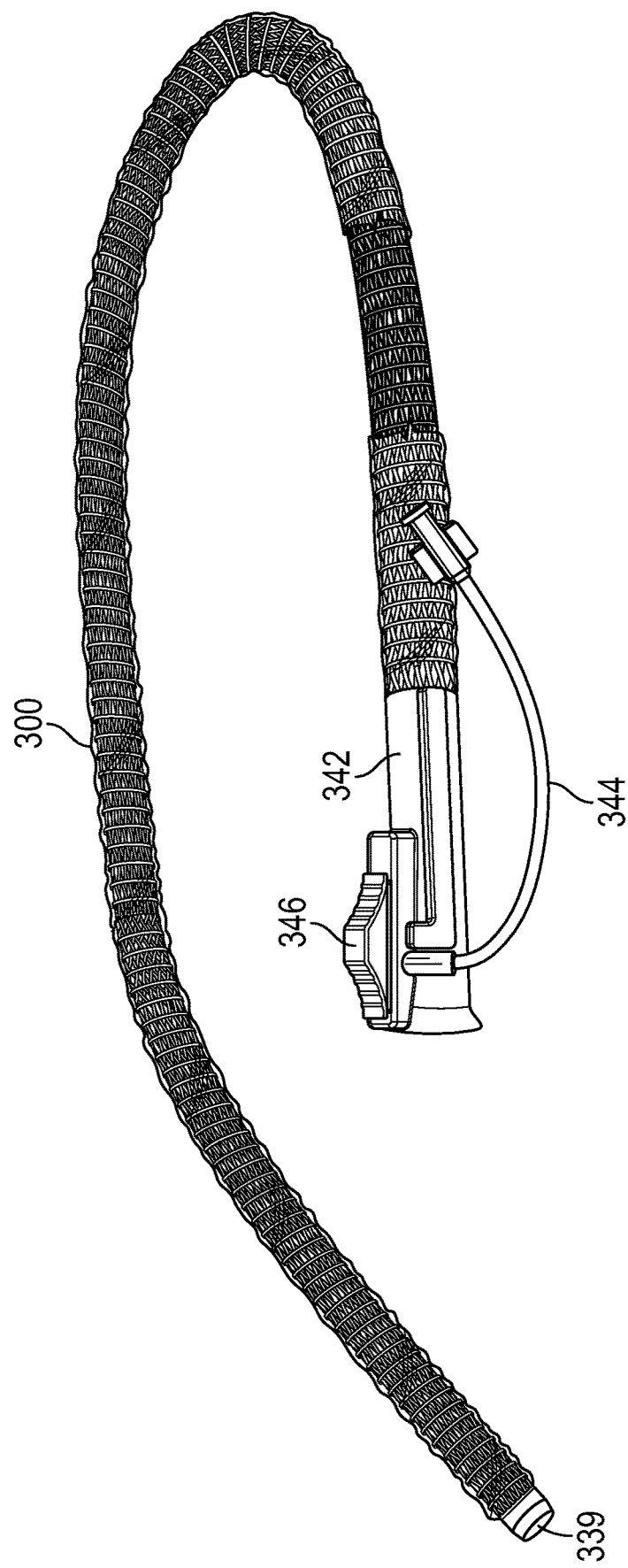
FIG. 1 shows a rigidizing device.

An exemplary rigidizing device system is shown in FIG. 1. The system includes a rigidizing device 300 having a wall with a plurality of layers including a braid layer, an outer layer (part of which is cut away to show the braid thereunder), and an inner layer. The system further includes a handle 342 having a vacuum or pressure inlet 344 to supply vacuum or pressure to the rigidizing device 300. An actuation element 346 can be used to turn the vacuum or pressure on and off to thereby transition the rigidizing device 300 between flexible and rigid configurations. The distal tip 339 of the rigidizing device 300 can be smooth, flexible, and atraumatic to facilitate distal movement of the rigidizing device 300 through the body. Further, the tip 339 can taper from the distal end to the proximal end to further facilitate distal movement of the rigidizing device 300 through the body.

Figure 2A:
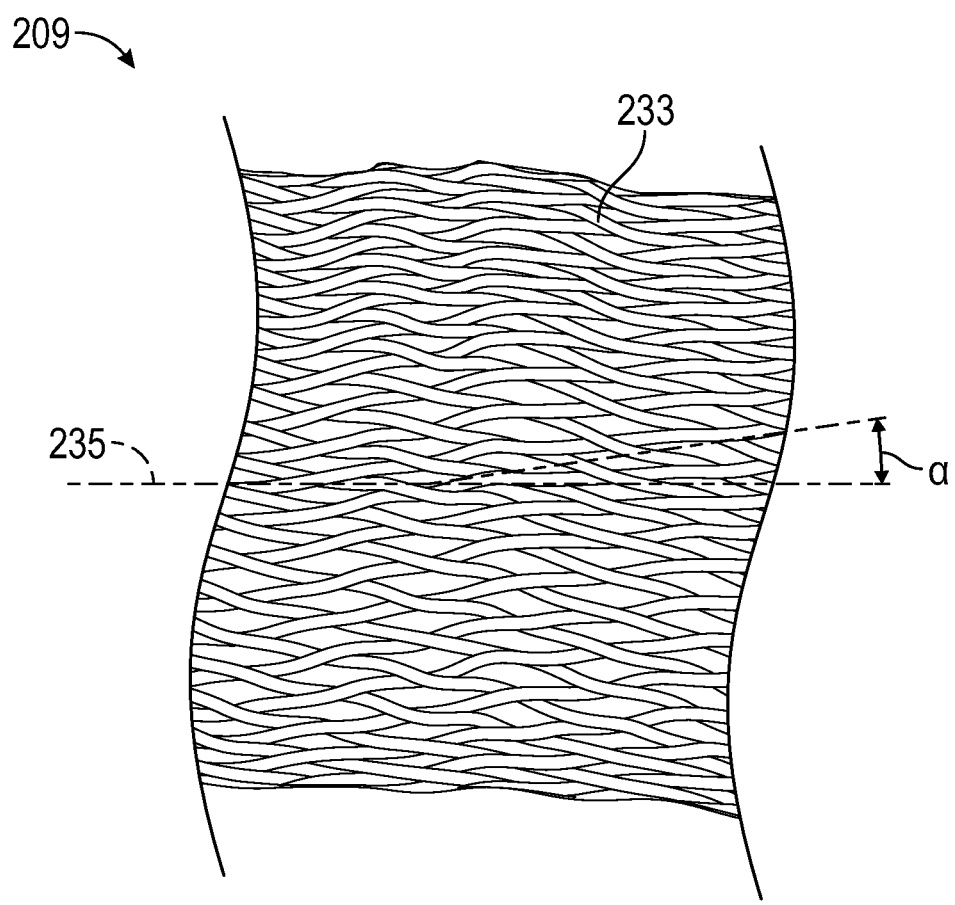
FIGS. 2A-2B show portions of a braid layer of a rigidizing device.
Figure 2B:
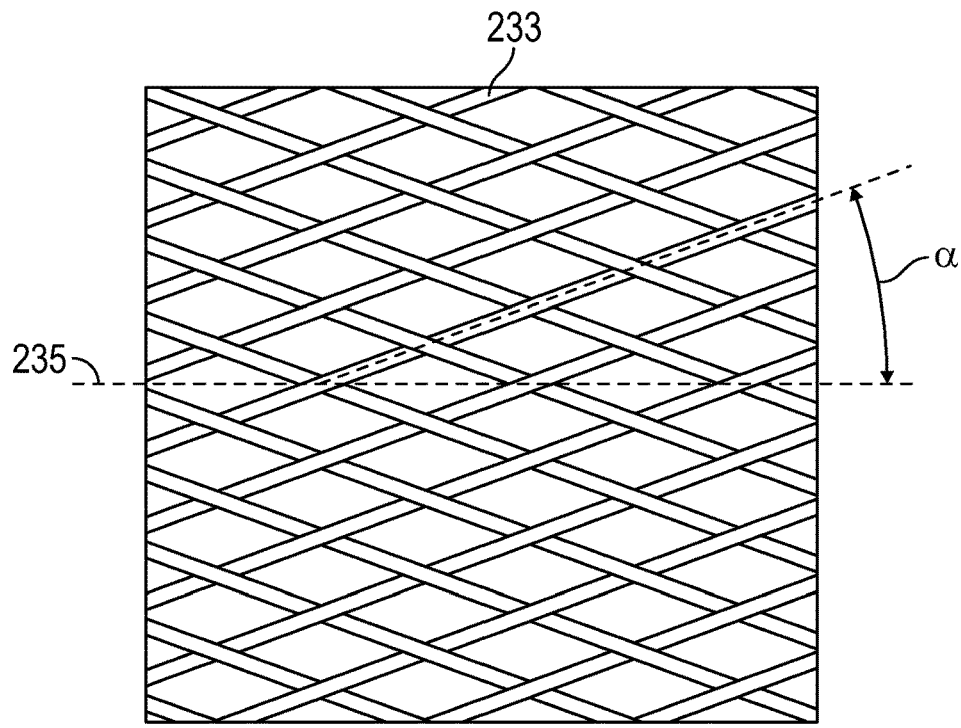

A portion of an exemplary braid layer 209 for a rigidizing device similar to device 300 is shown in FIGS. 2A-2B. The braid layer 209 can included braided strands 233. The braid layer 209 can, for example, be a tubular braid.

Figure 3:
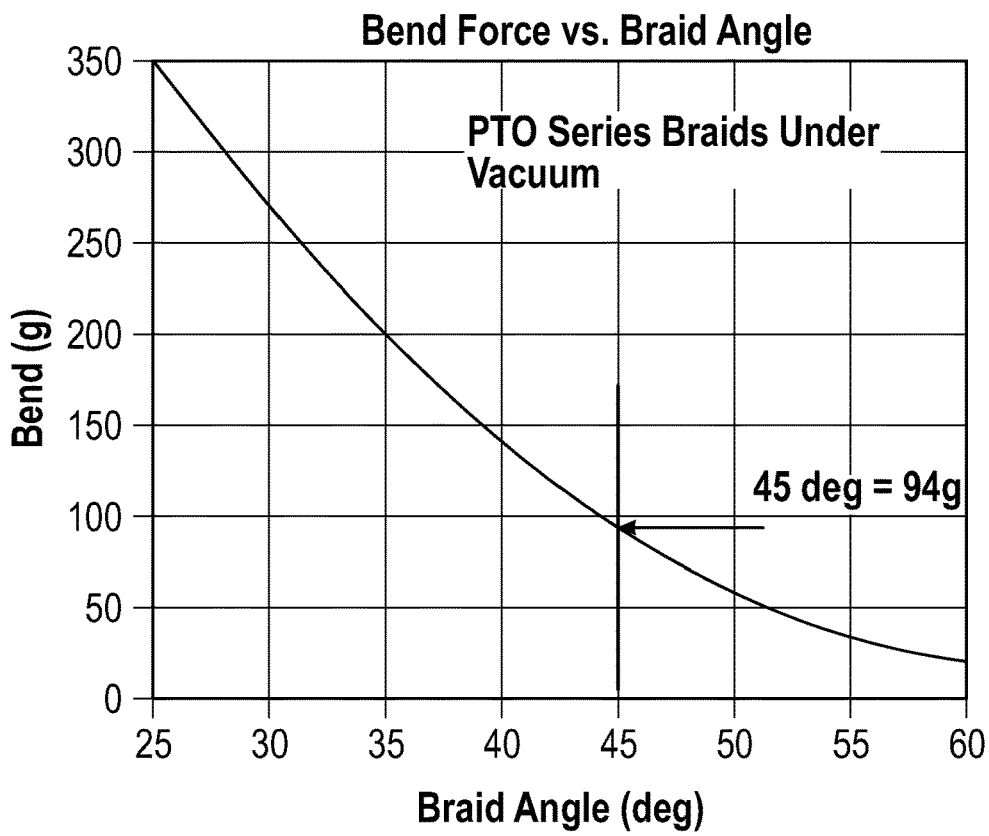
FIG. 3 is a graph of bend force vs braid angle when a rigidizing device is placed under vacuum.

The braid angle α of the strands 233 relative to the longitudinal axis 235 of the rigidizing device when the rigidizing device (e.g., device 300) is in a straight (unbent) configuration can be less than 45 degrees, such as less than or equal to 40 degrees, less than or equal to 35 degrees, or less than or equal to 25 degrees. Referring to FIG. 3, the bending strength of the rigidizing device decreases as the braid angle α (when the rigidizing device is straight or unbent) increases. That is, the bending strength under vacuum of the rigidizing device with a braid angle of 45 degrees (a typical minimum angle for a torque or torsion braid. Still larger angles are typically used for catheter shaft reinforcement) under vacuum is 27% of the bending strength under vacuum of a rigidizing device with a braid angle of 25 degrees. Accordingly, having a lower braid angle (e.g., less than 45 degrees, such as 40 degrees or less or 35 degrees or less) advantageously ensures that the rigidizing device (e.g., device 300) remains stiff in bending (resistant to a change in configuration) under vacuum (and similarly under pressure). Additionally, the braid angle α when the rigidizing device is in a straight (unbent) configuration can be greater than 5 degrees, such as greater than 8 degrees, such as greater than 10 degrees, such as 15 degrees or greater. Having a braid angle α within this range ensures that the braid remains flexible enough to bend when in the flexible configuration (i.e., when not rigidized under vacuum or pressure). Thus, the braid angle α of the strands 233 relative to the longitudinal axis 235 of the rigidizing device when the rigidizing device is in a straight configuration can be 5 to 40 degrees, such as 10 to 35 degrees, such as 15 to 25 degrees, such as approximately 5, 10, 15, 20, 25, 30, 35, or 40 degrees. The braid angle α of the strands 233 relative to the longitudinal axis 235 of the rigidizing device when the rigidizing device is in a straight (unbent) configuration of 5-40 degrees ensures that the rigidizing device is flexible enough to bend in the flexible configuration (e.g., when not under vacuum/pressure) yet stiff when in the rigid configuration (e.g., when placed under vacuum or pressure). Additionally, it should be understood that the strands 233 are configured to slide over one another, and therefore that the braid angle α will change the rigidizing device flexes and bends. Having an angle α that is between 5 and 40 degrees also advantageously ensures that the strands 233 can move freely relative to one another without causing the fibers to collide with one another and prevent further angular change.

Further, the braid for braid layer 209 can be between 4-60 picks per inch, such as 8, 10, 12, 14, 16, 18, 20, or 25 picks/inch. In one embodiment, the tube formed by the layer 209 has a diameter of 0.578", and the braid is 12-14 picks per inch.

In some embodiments, the braid layer 209 (or any braid layer described herein) can be configured such that the rigidizing devices described herein have a high stiffness ratio (i.e., the ratio of the stiffness in the rigid configuration, such as when vacuum or pressure is applied, to stiffness in the flexible configuration, such as when vacuum or pressure is not applied). For example, the stiffness ratio can be greater than 5, such as greater than 6, greater than 9, greater than 9, or greater than 10. Referring to Table 1 below, six vacuum rigidizing devices (samples A-F) were built and tested over a length of 4" and a deflection of ½" for cantilevered bending stiffnesses at atmospheric pressure (flexible configuration) and under vacuum (rigid configuration). As shown, lowering the braid angles raises the stiffness of the rigidized devices. Samples E and F show, in particular, the stiffness difference between a braid at a typical torque angle (sample E, 47.7 degrees and rigid stiffness of 0.529 lbf) and a braid with a lower angle (sample F, 27.2 degrees, and a rigid stiffness of 1.455 lbf). As is also shown in Table 1, rigidizing devices with lower angles (e.g., angles under 45 degrees or 35 degrees, such as samples A-D and F) can have a much higher stiffness ratio (e.g., ratio of greater than 5, greater than 6, greater than 9, or greater than 10) than rigidizing devices with higher angles (e.g., angles of 45 degrees or above, such as sample F), which can have a stiffness ratio of under 5. It can also be observed from Table 1 that both samples A and B have a stiffness ratio above 5. Sample B, at a 14.9 degree braid angle, has a lower stiffness ratio but a higher absolute stiffness than sample because the strands of sample B are oriented close to the longitudinal axis (and therefore sample B has a higher stiffness in the flexible configuration).

TABLE 1

Vacuum Rigidizing Devices

| Sample | Inside diameter (Inches) | Braid angle (degrees) | Strand | Picks per Inch | Flexible stiffness (lbf) | Rigid stiffness (lbf) | Stiffness ratio | Change in Stiffness (lbf) |
|---|---|---|---|---|---|---|---|---|
| A | 0.37 | 20.4 | 0.010" PET | 14.3 | 0.046 | 0.441 | 9.6 | 0.395 |
| B | 0.37 | 14.9 | 0.010" PET | 12.8 | 0.097 | 0.653 | 6.7 | 0.556 |
| C | 0.576 | 32.8 | 0.010" PET | 16.2 | 0.099 | 0.661 | 6.7 | 0.562 |
| D | 0.576 | 20 | 0.010" PET | 11.5 | 0.115 | 1.102 | 9.6 | 0.987 |
| E | 0.77 | 47.7 | 0.010" PET | 19.8 | 0.115 | 0.529 | 4.6 | 0.414 |
| F | 0.77 | 27.2 | 0.010" PET | 12.2 | 0.137 | 1.455 | 10.6 | 1.318 |

Referring to Table 2 below, three pressure rigidizing devices (samples G-I) were built and tested over a length of 4" and a deflection of ½" for cantilevered bending stiffnesses at atmospheric pressure atmospheric pressure (flexible configuration) and under 4atm pressure (rigid configuration). The samples all included a coverage of 35-45% and a braid with 96 strands and one filament per strand. As shown, lowering the braid angles raises the stiffness of the rigidizing devices. As is also shown in Table 2, rigidizing devices with lower angles can have a higher stiffness ratio than rigidizing devices with higher angles. In some embodiments, the pressure rigidizing devices described herein have a stiffness ratio of greater than 10, such as greater than 15, such as greater than 20.

TABLE 2

Pressure Rigidizing Devices

| Sample | Inside diameter (inches) | Braid angle (degrees) | Strand | Picks per inch | Flexible stiffness (lbf) | Rigid stiffness (lbf) | Stiffness ratio | Change in Stiffness (lbf) |
|---|---|---|---|---|---|---|---|---|
| G | 0.35 | 30 | 0.005" stainless steel | 24.1 | 0.044 | 0.448 | 10.2 | 0.404 |
| H | 0.35 | 22.7 | 0.005" stainless steel | 17.5 | 0.037 | 0.611 | 16.5 | 0.574 |
| 1 | 0.35 | 15.6 | 0.005" stainless steel | 11.7 | 0.051 | 1.091 | 21.4 | 1.04 |

Further, in some embodiments, the braid of braid layer 209 can have a coverage of 30%-70%, such as 40%-60%, e.g., 30%, 40%, 50%, 60%, or 70%, where the coverage area is the percentage of an underlying surface that is covered or obstructed by the braid.

In some embodiments, the braid layer 209 can be formed by running each individual strand around an inner tube or the rigidizing device and/or a separate mandrel in a helix such that the strands 233 are interlaced with one another. In one embodiment, the braid layer 209 can be heat formed over a 0.50"-0.60", e.g., 0.56" mandrel. Further, in some embodiments, the braid layer during manufacturing can be mounted over a tube or mandrel to a diameter that is smaller than the core diameter (i.e., smaller than the diameter at which the braid was originally manufactured). Compressing the braid radially in this way can decrease the braid angle in the range that provides a high rigidization multiple (while also decreasing the PPI, increasing the total length of the tubular braid layer, and increasing the braid coverage percentage).

The strands 233 can be rectangular/flat (e.g., with a long edge of 0.001"-0.060", such as 0.005", 0.007", 0.010", or 0.012", and a short edge of 0.0003"-0.030", such as 0.001", 0.002", or 0.003"), round (e.g., with a diameter of 0.001"-0.020", such as 0.005", 0.01", or 0.012"), or oval. In some embodiments, some of the strands 233 can be flat and some of the strands 233 can be round.

In some embodiments, the strands 233 can be made of metal filaments (e.g., stainless steel, aluminum, nitinol, tungsten, or titanium), plastic (nylon, polyethylene terephthalate, PEEK, polyetherimide), or high strength fiber (e.g., aramids, ultra-high molecular weight UHMW polyethylene, or liquid crystal polymers such as Vectran). In some embodiments, the strands 233 can be made of a multi-layer composite, such as a metal core with a thin elastomeric coating. In one specific example, the strands 233 can include round nylon having a diameter of 0.010" (or metal filaments having a diameter of 0.003") intertwined with flat aluminized PET with cross-sectional dimensions of 0.002" by 0.002". In some embodiments, the material for the strands 233 of the braid can be a material with a known high coefficient of friction. For example, the strands 233 can be a monolithic structure or have a coating such that the strands include aluminum on aluminum, copper on copper, silver on silver, or gold on gold. As another example, the strands 233 can be coated with an elastomeric material (e.g., lower durometer elastomers can be coated on top of a higher modulus substrate). As another example, the strands 233 can be made of styrene co-polymer, polycarbonate, or acrylic.

There can be between 12-800 strands 233, such as 24, 48, 96, 120, 144 or more strands 233 extending within braid layer 209. In some embodiments, there are 96 strands or more, 120 strands or more, 200 strands or more, or 240 strands or more. A higher number of strands may advantageously help rigidize the braid due to the increased interaction between strands.

Figure 4A:
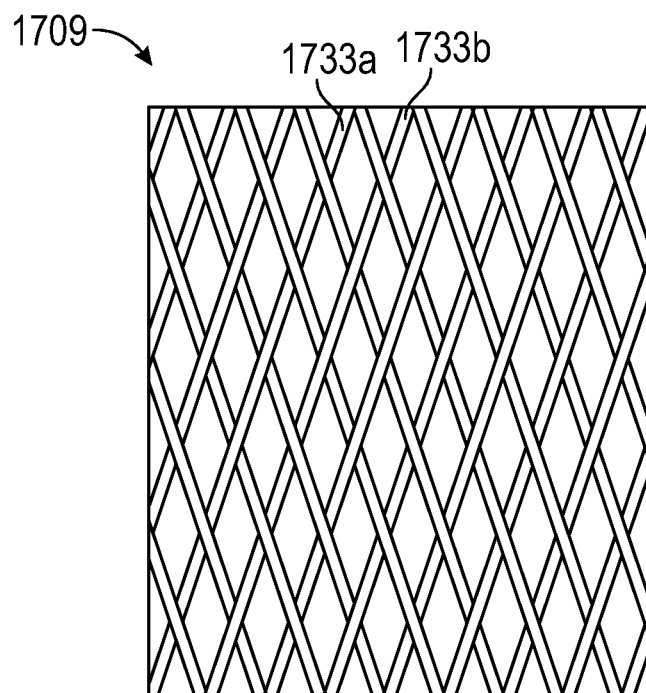
FIGS. 4A-4D show exemplary braid formations.
Figure 4B:
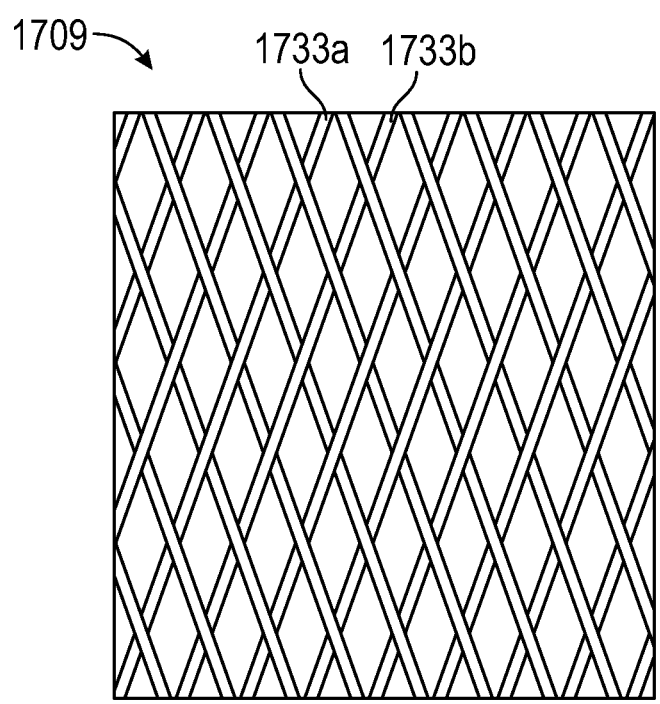
Figure 4C:
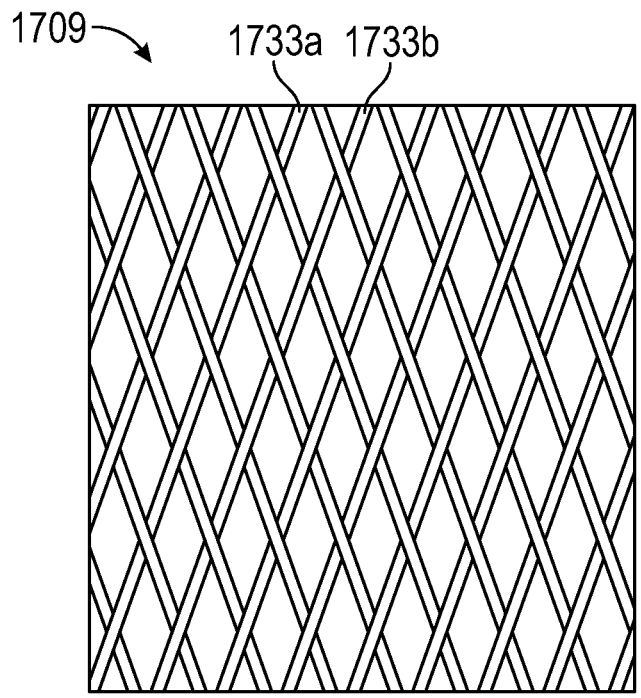
Figure 4D:
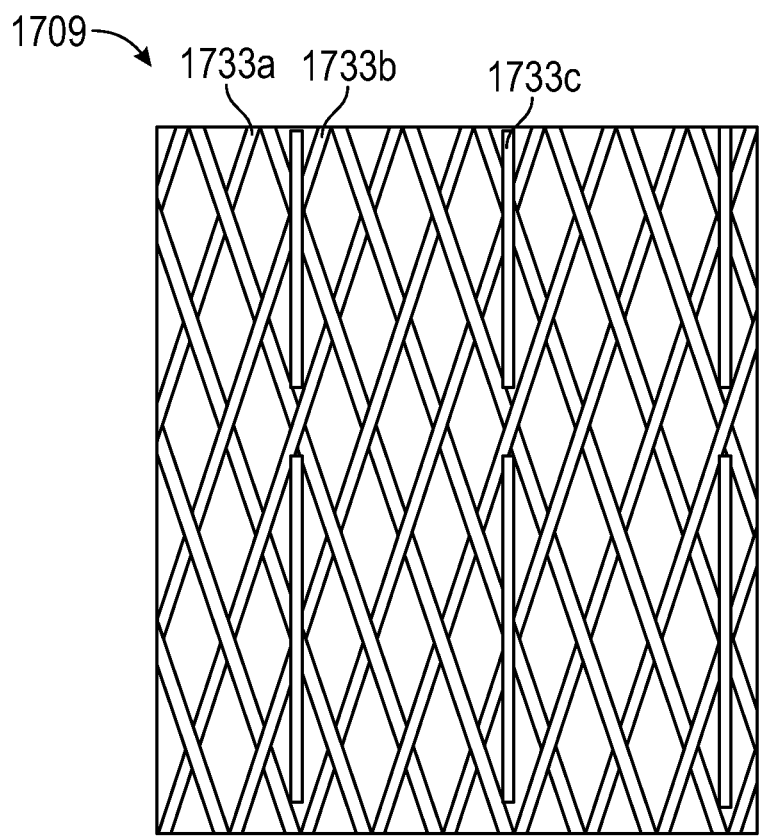

Referring to FIGS. 4A-4D, the braid of any of the rigidizing devices described herein can be in a variety of different braid patterns. For example, referring to FIG. 4A, the braid of layer 1709 can be a diamond full load pattern in which two neighboring strands 1733*a,b* extend over two strands and then under two strands. Referring to FIG. 4B, the braid of layer 1709 can be a full load pattern, in which each strand 1733*a* extends over two strands and under two strands in a manner that is opposite to the neighboring strand 1733*b*. Referring to FIG. 4C, the braid of layer 1709 can be a diamond half load pattern in which each strand 1733*a* extends over one strand and under one strand opposite to the neighboring strand 1733*b*. Referring to FIG. 4D, the braid of layer 1709 can include one or more longitudinal strands 1733*c* running through the crossed strands 1733*a*, 1733*b*.

Figure 5A:
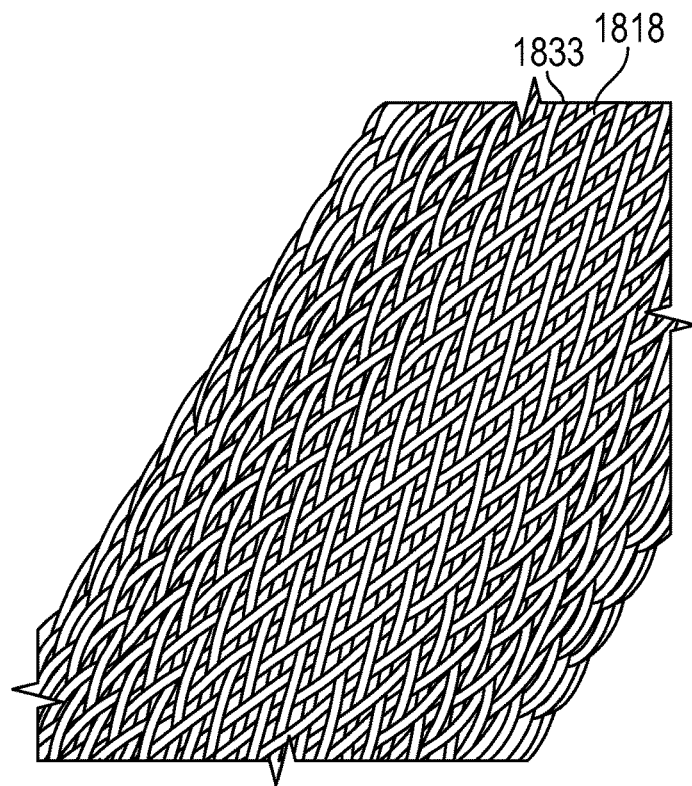
FIGS. 5A-5B show exemplary braid formations.
Figure 5B:
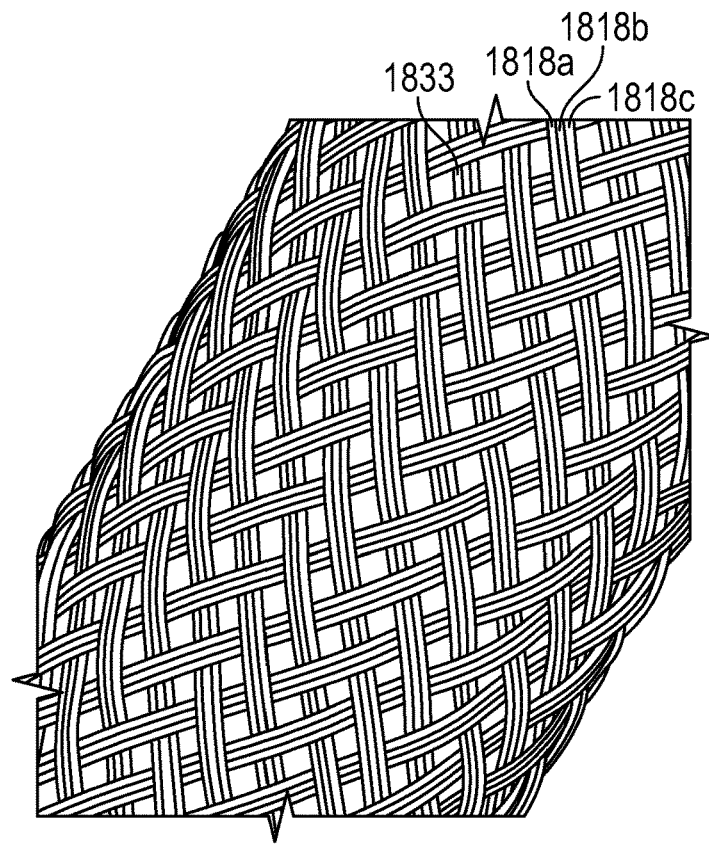

Referring to FIGS. 5A-5B, each strand 1833 can include a single filament 1818 (FIG. 5A) or multiple filaments 1818*a-c* (three filaments 1818*a-c* are shown in each strand 1833 in FIG. 5B). The filaments 1818 can be chosen (i.e., diameter, spacing, and modulus can be specifically tailored) to reduce crimp (the waviness or bending of the filaments). Reduced crimp can help the system provide enhanced compression buckling resistance, which can translate to enhanced system stiffness.

Exemplary specific braid layer embodiments J-N are shown in Table 3.

as described herein can be bonded to another layer of the device 5600 to prevent the strands 5633 of the braid from coming unbraided. Further, the ends of the strands 5633 can be bonded in such a way so as to allow relative movement of the strands 5633 during flexing of the rigidizing device 5600 when it is in the flexible configuration (i.e., so as to prevent rigidity or buckling of the device 5600, which in turn can lead to drag at the tip 5629, that might otherwise occur if the strands 5633 were constrained).

Figure 6A:
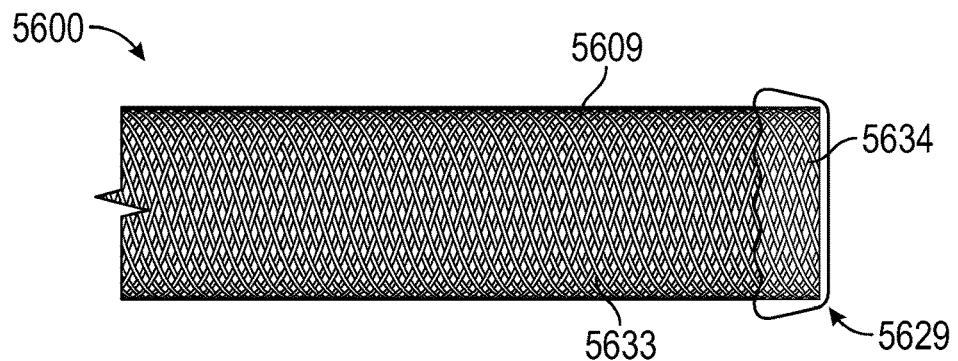
FIGS. 6A-6D various designs for the termination of braid layers of a rigidizing device.

For example, as shown in FIG. 6A, the tip 5629 of the braid layer 5609 can include a coating 5634 thereover of low durometer material, such as silicone or urethane, that is stretchable and/or flexible. As a result, the ends of the strands 5633 can be encapsulated by the coating 5634 (and therefore prevented from unbraiding) while still moving with coating 5634 as it stretches and/or flexes. The coating 5634 can be thin, such as between 0.005-0.250 thick (e.g., approximately ⅟₃₂" thick).

Figure 6B:
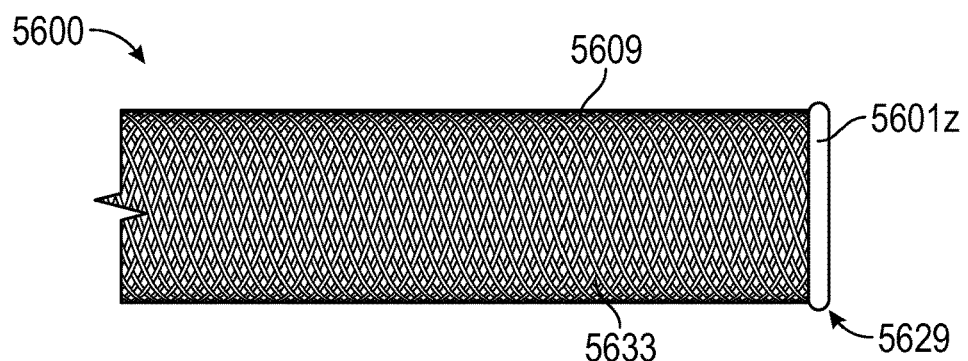

As another example, as shown in FIG. 6B, the tip 5629 of the braid layer 5609 can include an annular ring 5601*z* therearound. In some embodiments, the ring 5601*z* can be formed by melting the tips of the strands 5633. In other embodiments, the ring 5601*z* can be a separate element that is bonded to the strands 5633 (e.g., bonded to less than 20%, less than 10%, or less than 5% of the strands 5633). In some embodiments, there can be two bonding positions approxi-

TABLE 3

Exemplary braids

| Sample | Inside diameter (inches) | Braid angle (degrees) | Strand | Picks per inch | Number of strands | Number of filaments per strand | Pattern of crossing | Braid coverage | Rigidizing medium |
|---|---|---|---|---|---|---|---|---|---|
| J | 0.576 | 20 | PET, round, 0.010" | 12 | 120 | 1 | Full load | 56.7% | Vacuum |
| K | 0.21 | 15.1 | Stainless steel, round, 0.005" | 18.7 | 96 | 1 | Full load | 59% | Pressure |
| L | 0.35 | 25.7 | Stainless steel, round, 0.005" | 20.45 | 96 | 1 | Full load | 42% | Pressure |
| M | 0.21 | 15.1 | Stainless steel, round, 0.004" | 18.7 | 96 | 1 | Full load | 50% | Pressure |
| N | 0.33 | 14 | Stainless steel, round, 0.005" | 11.7 | 96 | 1 | Full load | 42% | Pressure |

In use, vacuum or pressure can be supplied between the walls of the rigidizing devices described herein, causing the braided layer and neighboring layer(s) to constrict and/or separate to transition between flexible and rigid configurations. The rigidizing devices described herein can thus advantageously transition from very flexible to very stiff upon activation by the user. When a vacuum or pressure is applied, the braids or strands can radially constrict or expand to become mechanically fixed or locked in place relative to one another. As a result, the rigidizing device can go from a flexible configuration to a rigid configuration when vacuum or pressure is applied (thereby fixing the rigidizing device in the shape that the rigidizing device was in just prior to application of the vacuum or pressure).

Referring to FIGS. 6A-6D, in some embodiments, one or both ends of the braid layer 5609 of a rigidizing device 5600 mately 180 degrees apart from one another. The ring 5601*z* can advantageously ensure that the strands 5633 do not unwind and yet can substantially move relative to one another underneath the ring 5601*z*. The ring 5601*z* can be made, for example, of rubber, Kapton, PTFE, silicone, urethane, latex, or ePTFE.

Figure 6C:
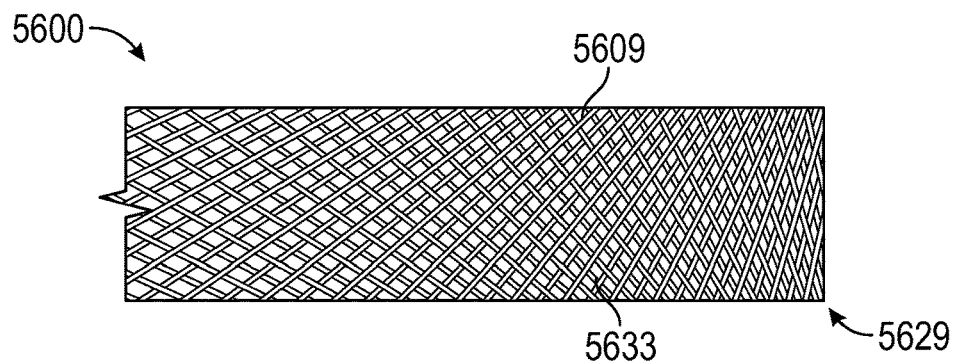

As another example, as shown in FIG. 6C, the tip 5629 of the braid layer 5609 can have a varying pick count along the tip 5629 with a greater pick count at the tip and a lower pick count towards the center. As a result, the strands 5633 can have a greater angle relative to the longitudinal axis at the tip 5629 than in the rest of the layer 5609. For example, while the strands 5633 in the central portion of the device 5600 can have an angle of 45° or less relative to the longitudinal axis of the device 5600 (for example, 40 degrees or less, 35 degrees or less, 25 degrees or less, or 20 degrees or less), the strands 5633 at the tip 5629 can have an angle of greater than 45°, such as between 45° and 60°, relative to the longitudinal axis (for example, 35 degrees, 45 degrees, or 55 degrees). The change in braid angle can be a continuous change at the tip 5629 and/or can be created by joining two separate braids together. The strands 5633 of greater angle can be glued down to the innermost layer at the tip 5629. By having a braid with a greater angle at the tip 5629, the tip 5629 can remain flexible as it curves or bends even when the strands 5633 are fixed to the inner layer 5615. In some embodiments, the increasing braid angle at the tip 5629 can be created by changing the speed of pulling the core inside the tubular braid during manufacturing.

Figure 6D:
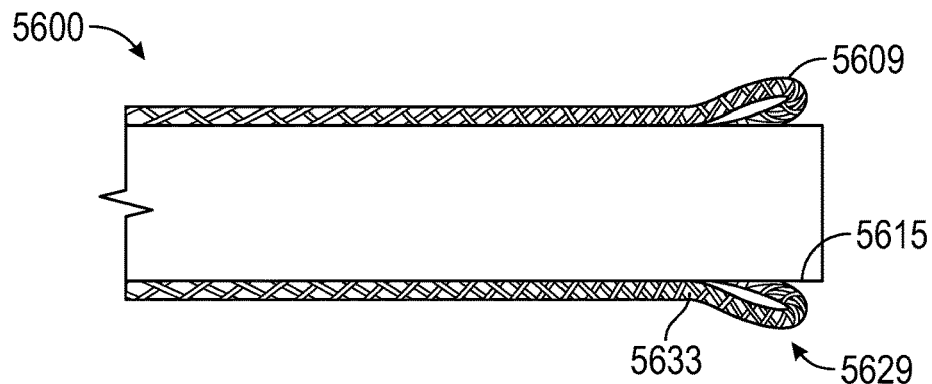

As another example, as shown in FIG. 6D, the tip 5629 of the braid layer 5609 can be everted and bonded to the innermost layer 5615 (and/or other layer that is radially inwards of the braid layer 5609). The tip 5629 can be more flexible relative to a non-everted tip 5629 because it includes an extra (everted) length within which to allowed the strands 5633 to move.

In some embodiments, the proximal and distal ends of the braid layer 5609 can have different treatments (e.g., the distal end may have a first treatment as described in FIGS. 6A-6D while the proximal end may have a second treatment as described in FIGS. 6A-6D).

In some embodiments, the rigidizing devices described herein (e.g., rigidizing device 300) can include one or more slip layers bordering the braid layer (e.g., braid layer 209). The slip layer can be configured to reduce friction between the braid and the bordering layers to allow the bordering layers (and in particular the braid layer) to more easily shear or move relative to each other, particularly when no vacuum or pressure is applied to the rigidizing device, to maximize flexibility in the flexible configuration. The slip layer can advantageously enhance the baseline flexibility of the rigidizing device to allow the layers to move relative to one another. In one embodiment, the slip layer can include a powder, such as talcum or cornstarch. In particular, a powder slip layer can advantageously reduce friction without adding significant thickness to the device, thereby enhancing flexibility of the rigidizing device in the flexible configuration. The slip layer can be made of a low coefficient of friction material, such as a thin film fluoropolymer (FEP, Chemfilm, PTFE, with thicknesses from 2-50 microns). In one embodiment, the slip layer can be a coating. In one embodiment, the slip layer can be a slip additive added to an elastomer. In one embodiment, the slip layer can be a sheath of thin plastic film that is inherently lubricious, such as low-density polyethylene (LDPE). In one embodiment, the slip layer can be made of a thin spiral-wrapped film, such at 0.0005" FEP or 0.00025" Chemfilm (St. Gobain). In one embodiment, the slip layer can be made of a grease, oil or other liquid.

Figure 7:
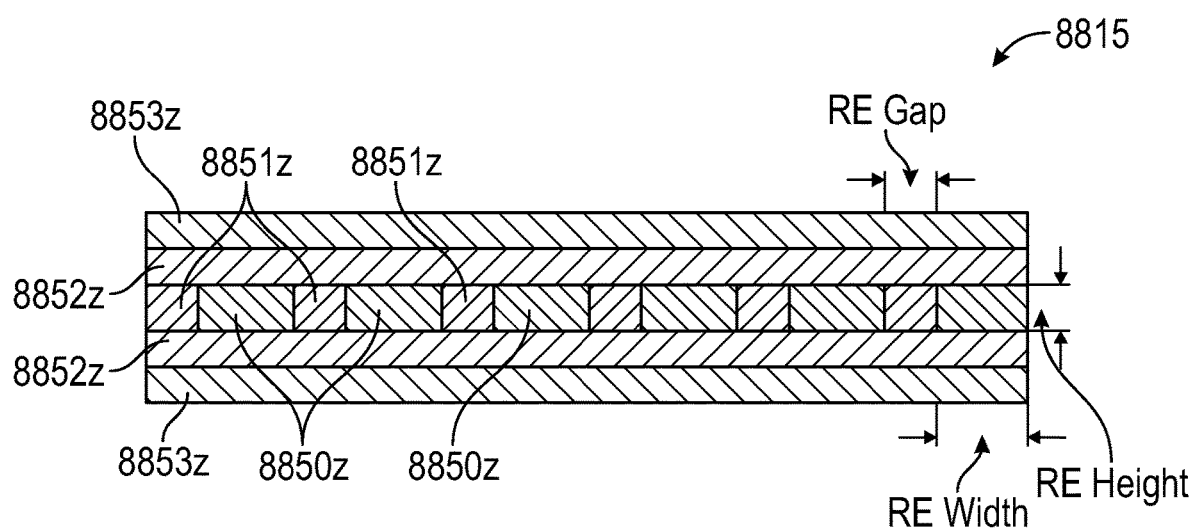
FIG. 7 shows an inner layer of a rigidizing device.

The rigidizing devices described herein can include an innermost layer configured to provide an inner surface against which the additional layers (e.g., braid layer) can be consolidated, for example, when a vacuum or pressure is applied within the walls of the rigidizing device. The layer can further provide a seal for the wall (i.e., can be leakproof) and can be strong enough to provide resistance to diametrical collapse even during bending of the rigidizing device and/or compression of the rigidizing device during rigidization. Referring to FIG. 7, in some embodiments, the innermost layer 8815 can include a reinforcement element 8850z or coil within a matrix 8851z. The reinforcement element 8850z can be a continuous spiral coil or closed rings with gaps in between them (which may exhibit more resistance to collapse than a spiral coil). Additionally, the inner layer 8815 can include an inner film 8852z and an outer film 8853z on one or both sides thereof. In some embodiments, each of the elements 8853z, 8852z, 8850z/8851z can have a thickness of 0.0002"-0.015".

The reinforcement element 8850z can be, for example, a metal wire, such as a metal wire made of stainless steel, nitinol, or Tungsten. The reinforcement element 8850z can be, for example, a high strength fiber (e.g., Kevlar, Dyneema, Vectran, Technora, or carbon fiber). The reinforcement element 8850z can be, for example, a stent, a structure cut from a tube, or a braid. In some embodiments, the reinforcement element 8850z can be a round wire (e.g., 0.0005"-0.030" in diameter, such as 0.001", 0.003", 0.005", 0.007" or 0.009" in diameter). In some embodiments, the reinforcement element 8850z can be a rectangular wire (e.g., having a width of 0.001" to 0.100" inch, for instance, 0.010", 0.020", 0.030", 0.040", 0.050", 0.060", 0.070", 0.080", 0.090", or 0.100" and/or The rectangular wire can have a thickness from 0.0003" to 0.020", for instance, 0.001", 0.003", 0.005", 0.007" or 0.010"). In other embodiments, the reinforcement element 8850z can have an oval cross-section and/or can include a plurality of individual strands and/or can have a rectangular cross section in which the four sharp corners are rounded. In some embodiments, the reinforcement element 8850z can be cut from a single tube using, for instance, a laser to create the gaps. In some embodiments, no reinforcement element is used.

In some embodiments, the reinforcement element 8850z can be an element with a high aspect ratio (e.g., have a high RE width relative to RE height, such as an aspect ratio of over 5:1, such as over 10:1, such as over 11:1, such as approximately 12:1). Note that in FIG. 7, RE width is the width of reinforcement element 8850z, RE height is height or thickness of reinforcement element 8850z, and RE Gap is distance between reinforcement elements 8850z. The high ratio of width to height of the reinforcement element 8850z can advantageously help prevent external pressure caused parallelogramming-type collapse of the reinforcement elements 8850z within the innermost layer 8815. Parallelogramming-type collapse occurs when the spirals of the coil move from being approximately normal to the axis of the center of the coil towards being parallel to the axis of the center of the coil (the spirals essentially "tip over"). Further, it may be advantageous in preventing parallelogramming if the RE gap between the reinforcement elements 8850z is no more than 3 times the RE height, such as no more than 2 times the RE height, such as no more than 1.5 times the RE height. Additionally, a ratio of the inner diameter of a hollow tube with an innermost layer 8815 to the width of the reinforcement layer 8850z in the innermost layer 8815 of less than 5, such as less than 4.5, such as approximately 4.3, can likewise help prevent parallelogramming-type collapse.

The matrix 8851z may be a very low durometer, for example a TPU or TPE, with a durometer equal to or less than 60A, 50A, 40A, 30A, 20A or 10A. In some embodiments, the matrix 8851z can be TPU, TPE, PET, PEEK, Mylar, urethane, or silicone. Inner and outer films 8852z, 8853z can similarly include TPU, TPE, PET, PEEK, Mylar, urethane, or silicone. In some embodiments, the inner and outer films 8852z, 8853z can be applied by spraying, dipping, wrapping as a sheet or tube, pulling through a bath of solvent, melted, and/or consolidated. In some embodiments, the layer 8815 does not include inner and/or outer films 8852z, 8853z and/or additional films can be included. The inner and/or outer films 8852z, 8853z can create a smooth inner and outer surface.

In a specific example of an innermost layer 8815 for a pressure system, the layer is made at 0.260" inside diameter as a hollow tube with an RE width of 0.050", an RE height of 0.008", and an RE Gap of 0.010". Film 8853z is omitted on both sides. Film 8852z (on both sides of the matrix 8851z and reinforcement elements 8850z) are all made of urethane (600 psi to 100% strain). The thickness of both the matrix 8851z and each film 8852z is about 0.006", giving a total wall thickness of 0.018". This structure can resist collapse at over 10 atm of external pressure.

In a second specific example of an innermost layer 8815 for a pressure system, film 8853z is omitted on both sides. The RE width is 0.050", the RE height is 0.008", and the RE Gap is 0.010". The film 8852z is a higher durometer elastomer, for example an elastomer that has a stress of 2000 psi@ 100% strain and has a thickness of about 0.001" thick. The matrix 8851z can be an 50A urethane. The matrix 8851z can be deposited as thermoplastic elastomer cord stock, for example at 0.008" rectangular cross section or 0.010" round cross section. This cord stock can also be deposited with increased axial modulus (but not transverse modulus) by co-extruding the stock with a wire (for example, 0.001" diameter) or fiber at its core.

In a third specific example of an innermost layer 8815 for a pressure system, the reinforcement element 8850z can be a wire with a high aspect ratio. For example, the layer 8815 can have an RE height of 0.005", an RE width of 0.060" and an RE gap of 0.006" in a square stainless steel wire. The inner diameter of the tube formed with the innermost layer 8815 is 0.26". Elements 8852z and 8851z can be 80A urethane and can be approximately 0.002" thick. Further, layer 8851z can be a 50A urethane (e.g., deposited from a heated tank with melted urethane therein and an orifice for precise dispensing via pressure). The structure of this exemplary innermost layer 8815 can resist collapse at over 10 atm of external pressure, such as over 12atm of pressure, such as over 13atm of pressure.

In a specific example of an innermost layer 8815 for a vacuum system, the outer film 8853z on one side (e.g., the outer or top side) is omitted, the film 8852z above (outside of) the reinforcement/matrix includes a 0.005" 50A urethane, the matrix 8851z is made of 0.005" thick 50A urethane, the reinforcement element 8850z is a stainless steel wire, the film 8852z below (inside of) the reinforcement/matrix includes 0.0025" thick 50A urethane, and the bottom outer film 8853z is a 0.004" thick 80A urethane. The RE width is 0.020", the RE height is 0.005", and the RE Gap is 0.010". The bottom outer film 8853z is hydrophilically coated. The inner diameter of the tube formed by layer 8815 is 0.551".

Although shown in FIG. 7 as symmetrical, it should be understood that the innermost layer 8815 need not have a symmetrical arrangement of films 8852z, 8853z. For example, neither layer may be on the bottom (inside of the matrix/reinforcement) while both layers are present on top. Additionally, it should be understood that the material for both innermost films 8852z need not be the same, nor need the material for the both of the outermost films 8853z be the same.

Figure 8D:
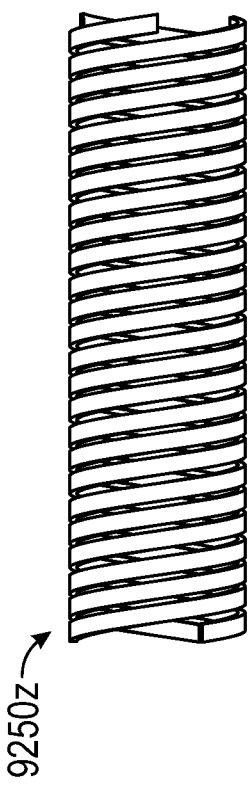
FIGS. 8A-8F show different coil designs for a layer of a rigidizing device.
Figure 8E:
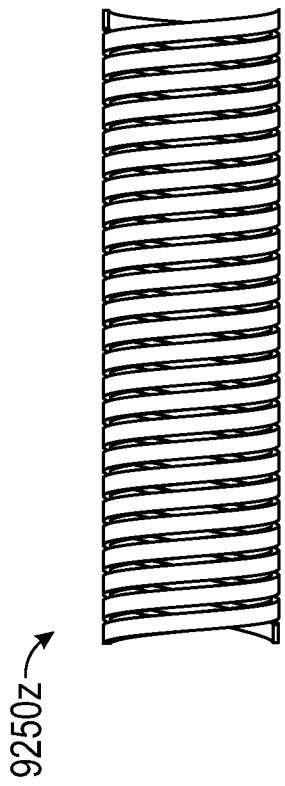
Figure 8F:
Figure 8A:
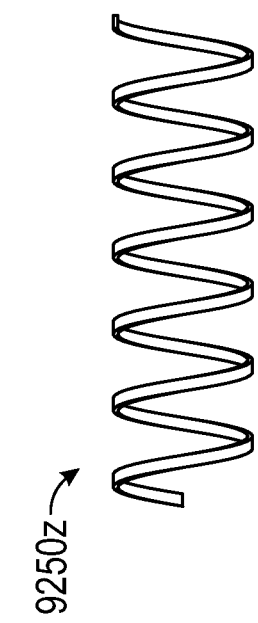
Figure 8B:
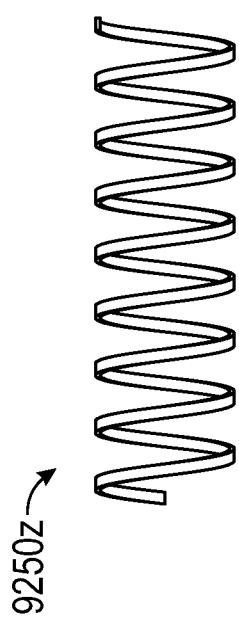
Figure 8C:
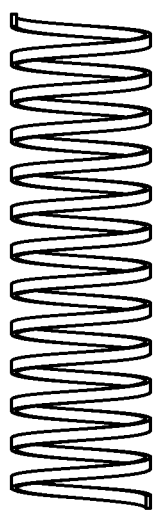

The reinforcement elements of the innermost layer can be in a variety of configurations. As shown in FIGS. 8D-8F, the reinforcement element 9205z can be a multi-start coil winding (e.g., 2 starts as shown in FIG. 8F, three starts as shown in FIG. 8E, or four starts as shown in FIG. 8D). When multi-start coil windings are used the gap between reinforcement elements along the longitudinal axis can be the same as with a single coil, but number of starts can be 2, 3, 4, 5, 6, 7, 8, 9 or even more. While a single start creates a wire angle that is nearly vertical (for example, 2 degrees off of vertical), a multi-start approach creates a wire angle that biases the coils to tilt in one direction, much further away from vertical (for example, 4, 6, 10, 15, or even 20 degrees). This larger angle may serve to make the innermost layer less likely to tilt or structurally collapse under pressure, as the coils with the larger pitch tend to brace against one another for stability. FIGS. 8A-8C show individual starts (coils) from the multistart reinforcement elements 9205Z. FIG. 8C shows one coil from FIG. 8F, FIG. 8B shows one coil from FIG. 8E and FIG. 8A shows one coil from FIG. 8D.

Figures 9A, 9B:
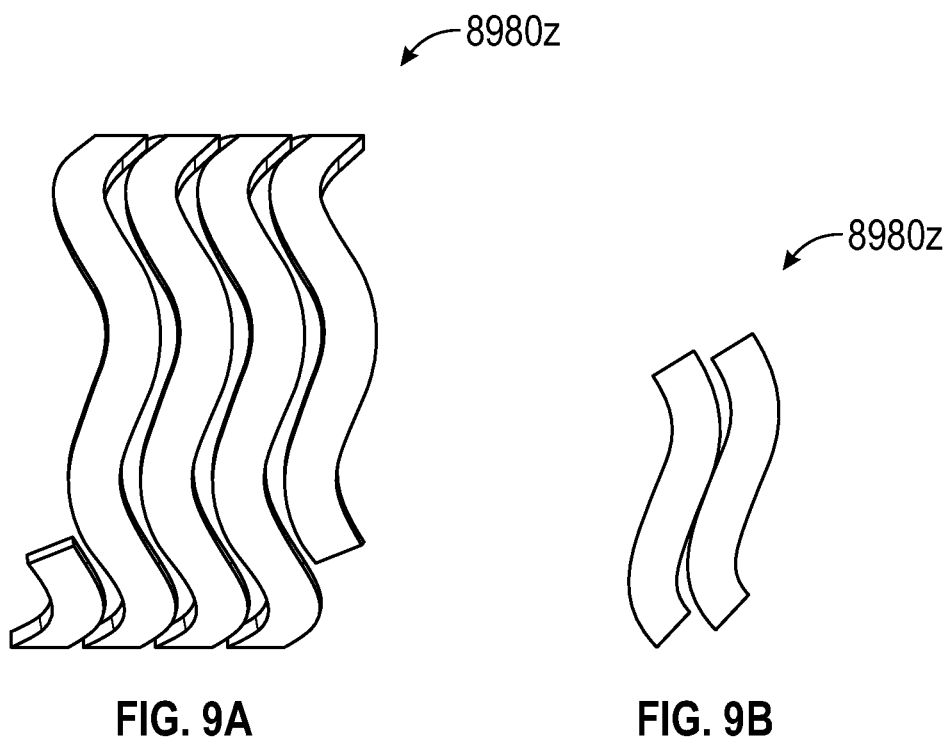
FIGS. 9A-9B show undulating reinforcement elements for a layer of a rigidizing device.

In some embodiments, referring to FIGS. 9A-9B, the reinforcement elements 8950z can be a series of wavy or undulated wires (or an undulated wire that is coiled as described herein). As shown in FIG. 9B, when the device is loaded, the undulated reinforcement elements 8950z moves toward colliding with itself, compressing the matrix 8851Z in between the wires and resisting a parallelogram-type collapse. In one specific embodiment, an innermost layer with such an undulating wire can have an RE height of 0.005", an RE width of 0.060" and an RE gap of just 0.006". The undulating wave can vary+/−0.03" from a centerline (that is, have a wave amplitude of 0.060"). The wave can repeat every 0.3" (that is, have a wavelength of 0.3").

Figure 10A:
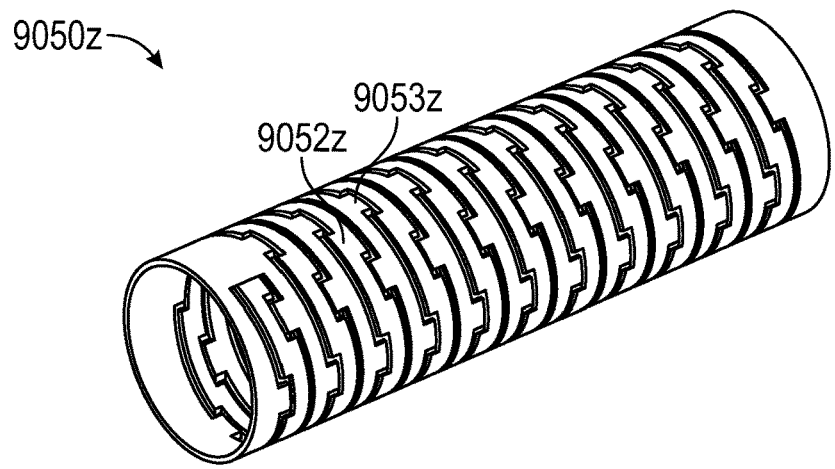
FIGS. 10A-10E show notch and pocket reinforcement elements for a layer of a rigidizing device.
Figure 10B:
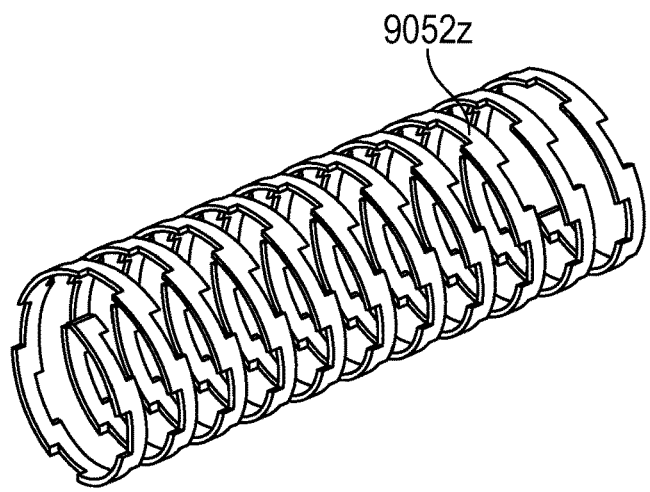
Figure 10C:
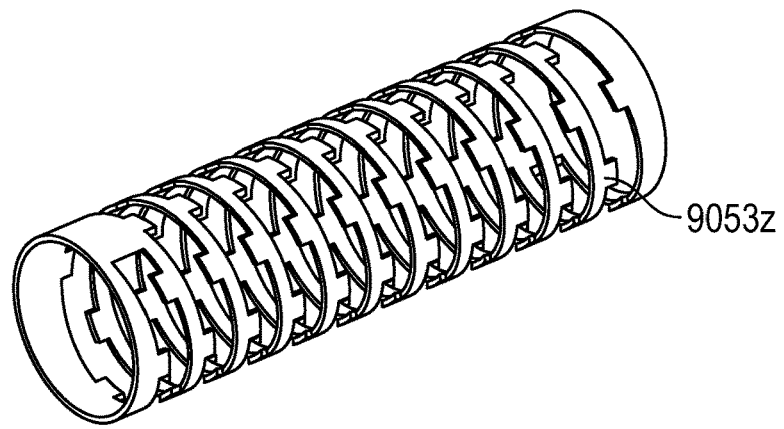
Figure 10D:
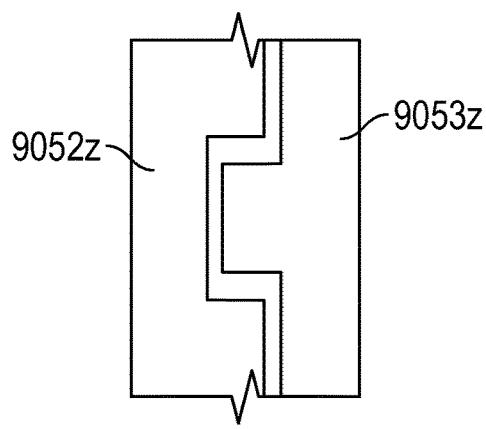
Figure 10E:
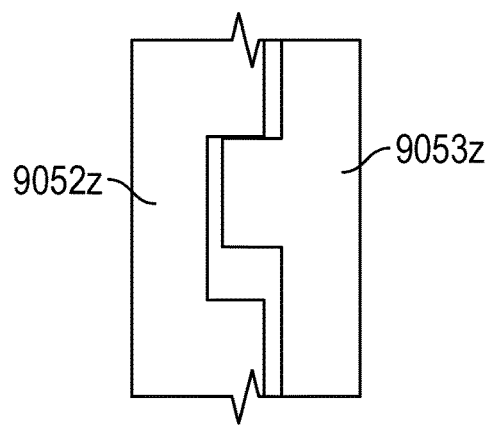

In some embodiments, referring to FIGS. 10A-10C, the reinforcement elements 9050z can include alternating pocket wires 9052z and notched wires 9053z. When unloaded, the pockets and notches of each respective element can be separate (as shown in FIG. 10D). However, when loaded, the notch of wire 9053z moves toward colliding with the pocket of wire 9052z (as shown in FIG. 10E) compressing the matrix 8851z in between the wires and resisting a parallelogram-type collapse.

Figure 11A:
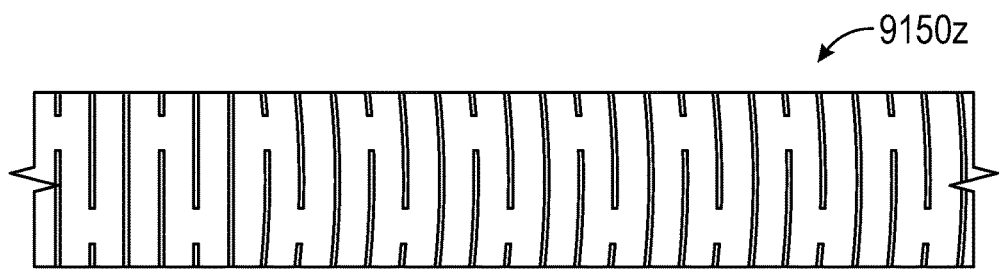
FIGS. 11A-11B show a cut tubing reinforcement element for a layer of a rigidizing device.
Figure 11B:
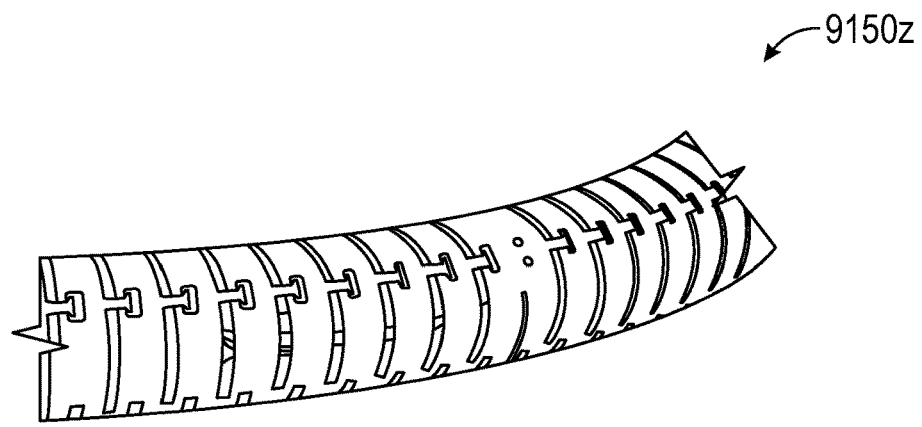

In some embodiments, referring to FIGS. 11A-11B, the reinforcing elements 9150z can be a flexure design, e.g., cut from a laser tube.

In some instances, the reinforcement element can be separate from the inner layer. For instance, the reinforcement element can be positioned diametrically inside or outside the inner layer. The innermost layer can have a hardness, for example, of 30A to 80A. Further, the innermost layer can have a wall thickness of between 0.0005" and 0.060". In some embodiments, the innermost layer can include lubrication or a coating (e.g., hydrophilic coating) on the inner surface thereof to improve sliding of an endoscope or other instrument therethrough. The coating can be hydrophilic (e.g., a Hydromer® coating or a Surmodics® coating) or hydrophobic (e.g., a fluoropolymer). The coating can be applied, for example, by dipping, painting, or spraying the coating thereon. The innermost layer can be a laminated layer with a low frictional coefficient.

Exemplary rigidizing devices in the rigidized configuration are shown in FIGS. 12A and 12B. As the rigidizing device is rigidized, it does so in the shape it was in before vacuum or pressure was applied, i.e., it does not straighten, bend, or otherwise substantially modify its shape (e.g., it may stiffen in a looped configuration as shown in FIG. 12A or in a serpentine shape as shown in FIG. 12B). This can be because the air stiffening effect on the inner or outer layers (e.g., made of coil-wound tube) can be a small percentage (e.g., 5%) of the maximum load capability of the rigidizing device in bending, thereby allowing the rigidizing device to resist straightening. Upon release of the vacuum or pressure, braids or strands can unlock relative to one another and again move so as to allow bending of the rigidizing device. Again, as the rigidizing device is made more flexible through the release of vacuum or pressure, it does so in the shape it was in before the vacuum or pressure was released, i.e., it does not straighten, bend, or otherwise substantially modify its shape. Thus, the rigidizing devices described herein can transition from a flexible, less-stiff configuration to a rigid configuration of higher stiffness by restricting the motion between the strands of braid (e.g., by applying vacuum or pressure).

The rigidizing devices described herein can toggle between the rigid and flexible configurations quickly, and in some embodiments with an indefinite number of transition cycles. As interventional medical devices are made longer and inserted deeper into the human body, and as they are expected to do more exacting therapeutic procedures, there is an increased need for precision and control. Selectively rigidizing devices (e.g., overtubes) as described herein can advantageously provide both the benefits of flexibility (when needed) and the benefits of stiffness (when needed). Further, the rigidizing devices described herein can be used, for example, with classic endoscopes, colonoscopes, robotic systems, and/or navigation systems, such as those described in International Patent Application No. PCT/US2016/050290, filed Sep. 2, 2016, titled "DEVICE FOR ENDOSCOPIC ADVANCEMENT THROUGH THE SMALL INTESTINE," the entirety of which is incorporated by referenced herein.

The rigidizing devices described herein can be provided in multiple configurations, including different lengths and diameters. In some embodiments, the rigidizing devices can include working channels (for instance, for allowing the passage of typical endoscopic tools within the body of the rigidizing device), balloons, nested elements, and/or side-loading features.

Referring to FIGS. 13A-13D, in one embodiment, a tubular rigidizing device 100 can include a wall having a plurality of layers positioned around the lumen 120 (e.g., for placement of an instrument or endoscope therethrough). A vacuum can be supplied between the layers to rigidize the rigidizing device 100.

The innermost layer 115 can be configured to provide an inner surface against which the remaining layers can be consolidated, for example, when a vacuum is applied within the walls of the rigidizing device 100. The structure can be configured to minimize bend force/maximize flexibility in the non-vacuum condition. In some embodiments, the innermost layer 115 can include a reinforcement element 150z or coil within a matrix, as described above.

The layer 113 over (i.e., radially outwards of) the innermost layer 115 can be a slip layer.

The layer 111 can be a radial gap (i.e., a space). The gap layer 111 can provide space for the braided layer(s) thereover to move within (when no vacuum is applied) as well as space within which the braided or woven layers can move radially inward (upon application of vacuum).

The layer 109 can be a first braid layer including braided strands 133 similar to as described elsewhere herein. The braid layer can be, for example, 0.001" to 0.040" thick. For example, a braid layer can be 0.001", 0.003", 0.005", 0.010", 0.015", 0.020", 0.025" or 0.030" thick.

Figure 13A:
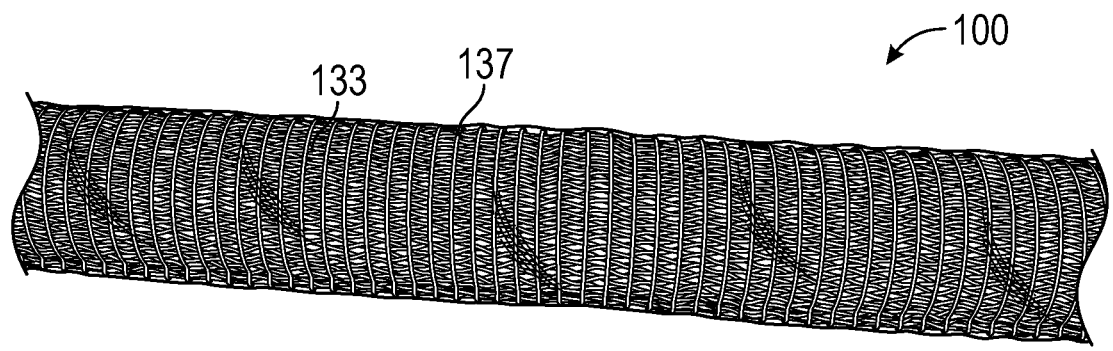
FIGS. 13A-13D show an exemplary vacuum rigidizing device.
Figure 13B:
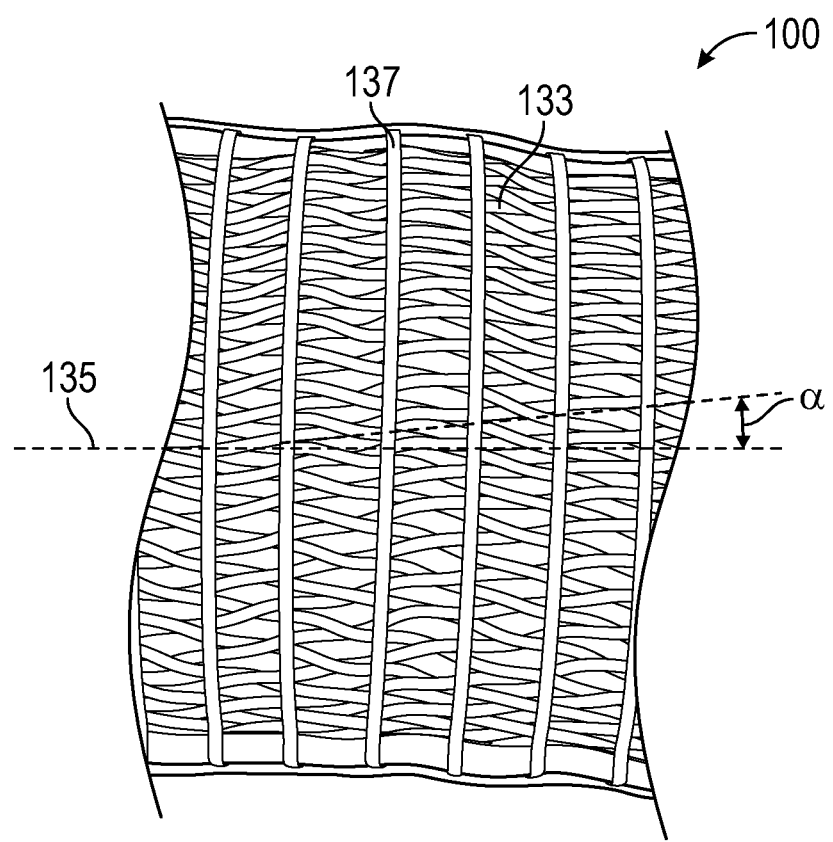

In some embodiments, as shown in FIG. 13B, the braid can have tensile or hoop fibers 137. Hoop fibers 137 can be spiraled and/or woven into a braid layer. Further, the hoop fibers 137 can be positioned at 2-50, e.g., 20-40 hoops per inch. The hoop fibers 137 can advantageously deliver high compression stiffness (to resist buckling or bowing out) in the radial direction, but can remain compliant in the direction of the longitudinal axis 135 of the rigidizing device 100. That is, if compression is applied to the rigidizing device 100, the braid layer 109 will try to expand in diameter as it compresses. The hoop fibers 137 can resist this diametrical expansion and thus resist compression. Accordingly, the hoop fiber 137 can provide a system that is flexible in bending but still resists both tension and compression.

The layer 107 can be another radial gap layer similar to layer 111.

Figure 13C:
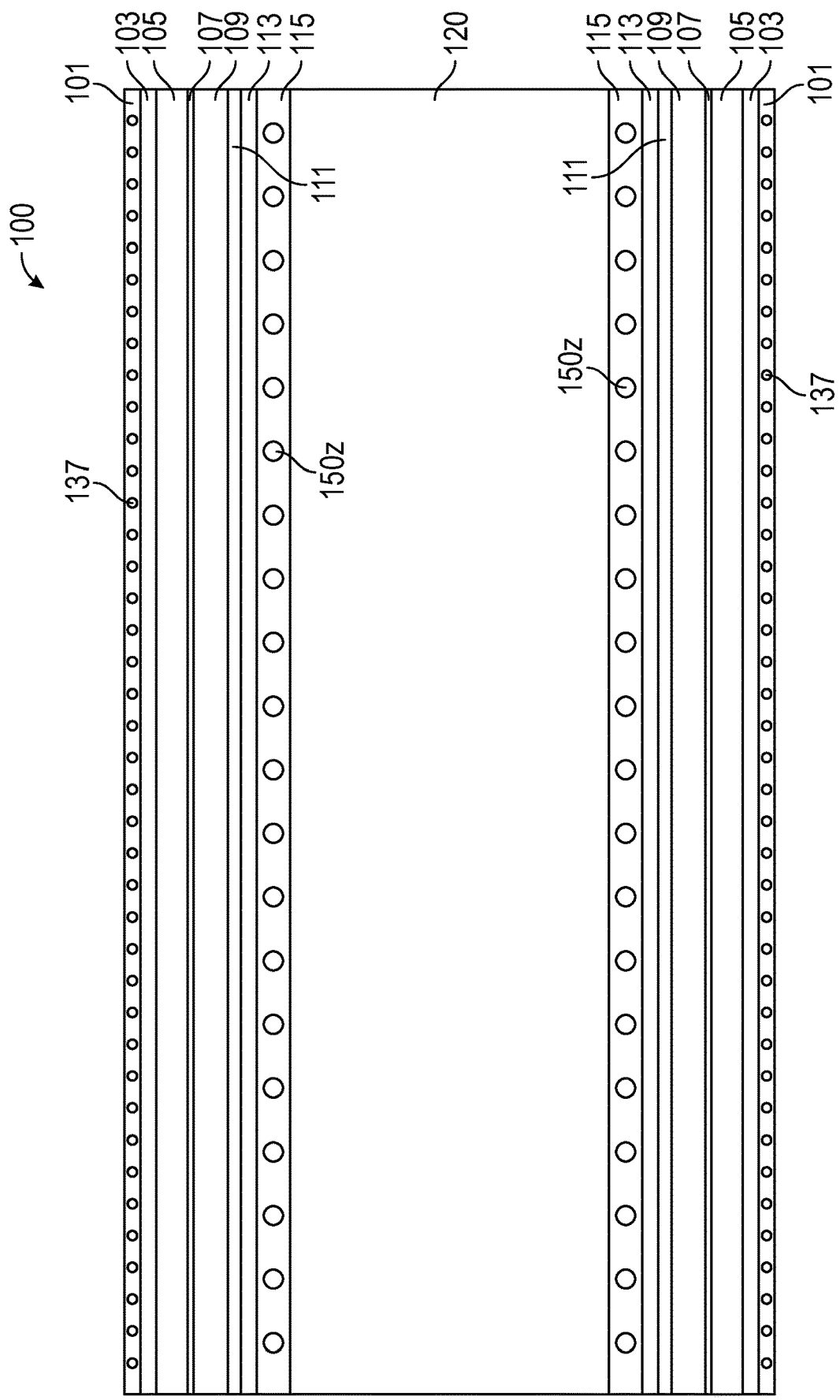
Figure 13D:
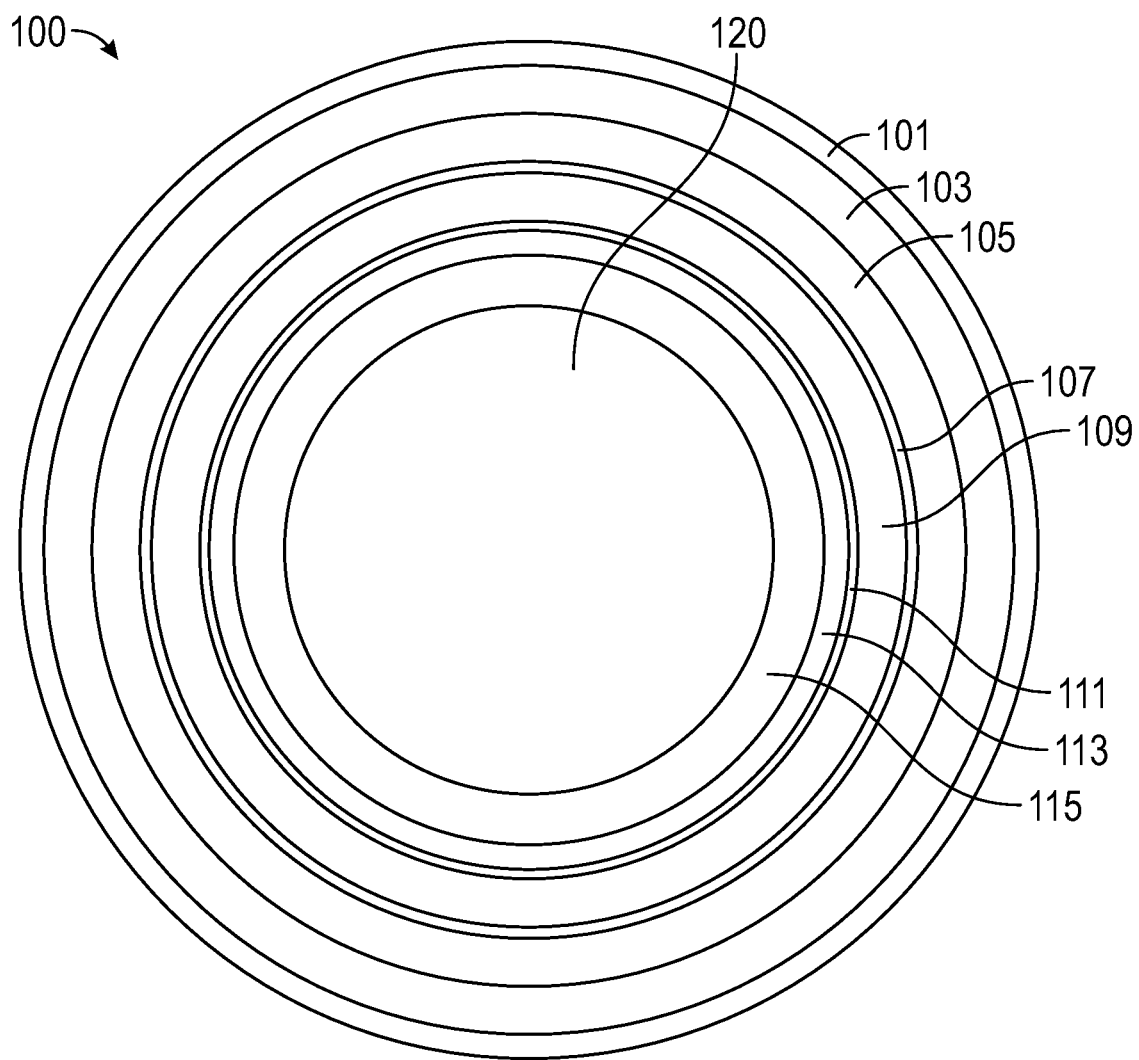

In some embodiments, the rigidizing devices described herein can have more than one braid layer. For example, the rigidizing devices can include two, three, or four braid layers. Referring to FIG. 13C, the layer 105 can be a second braid layer 105. The second braid layer 105 can have any of the characteristics described with respect to the first braid layer 109. In some embodiments, the braid of second braid layer 105 can be identical to the braid of first braid layer 109. In other embodiments, the braid of second braid layer 105 can be different than the braid of the first braid layer 109. For example, the braid of the second braid layer 105 can include fewer strands and have a larger braid angle α than the braid of the first braid layer 109. Having fewer strands can help increase the flexibility of the rigidizing device 100 (relative to having a second strand with equivalent or greater number of strands), and a larger braid angle α can help constrict the diameter of the of the first braid layer 109 (for instance, if the first braid layer is compressed) while increasing/maintaining the flexibility of the rigidizing device 100. As another example, the braid of the second braid layer 105 can include more strands and have a larger braid angle α than the braid of the first braid layer 109. Having more strands can result in a relatively tough and smooth layer while having a larger braid angle α can help constrict the diameter of the first braid layer 109.

The layer 103 can be another radial gap layer similar to layer 111. The gap layer 103 can have a thickness of 0.0002-0.04", such as approximately 0.03". A thickness within this range can ensure that the strands 133 of the braid layer(s) can easily slip and/or bulge relative to one another to ensure flexibility during bending of the rigidizing device 100.

The outermost layer 101 can be configured to move radially inward when a vacuum is applied to pull down against the braid layers 105, 109 and conform onto the surface(s) thereof. The outermost layer 101 can be soft and atraumatic and can be sealed at both ends to create a vacuum-tight chamber with layer 115. The outermost layer 101 can be elastomeric, e.g., made of urethane. The hardness of the outermost layer 101 can be, for example, 30A to 80A. Further, the outermost layer 101 can be have a thickness of 0.0001-0.01", such as approximately 0.001", 0.002, 0.003" or 0.004". Alternatively, the outermost layer can be plastic, including, for example, LDPE, nylon, or PEEK.

In some embodiments, the outermost layer 101 can, for example, have tensile or hoop fibers 137 extending therethrough. The hoop fibers 137 can be made, for example, of aramids (e.g., Technora, nylon, Kevlar), Vectran, Dyneema, carbon fiber, fiber glass or plastic. Further, the hoop fibers 137 can be positioned at 2-50, e.g., 20-40 hoops per inch. In some embodiments, the hoop fibers 137 can be laminated within an elastomeric sheath. The hoop fibers can advantageously deliver higher stiffness in one direction compared to another (e.g., can be very stiff in the hoop direction, but very compliant in the direction of the longitudinal axis of the rigidizing device). Additionally, the hoop fibers can advantageously provide low hoop stiffness until the fibers are placed under a tensile load, at which point the hoop fibers can suddenly exhibit high hoop stiffness.

In some embodiments, the outermost layer 101 can include a lubrication, coating and/or powder (e.g., talcum powder) on the outer surface thereof to improve sliding of the rigidizing device through the anatomy. The coating can be hydrophilic (e.g., a Hydromer® coating or a Surmodics® coating) or hydrophobic (e.g., a fluoropolymer). The coating can be applied, for example, by dipping, painting, or spraying the coating thereon.

The innermost layer 115 can similarly include a lubrication, coating (e.g., hydrophilic or hydrophobic coating), and/or powder (e.g., talcum powder) on the inner surface thereof configured to allow the bordering layers to more easily shear relative to each other, particularly when no vacuum is applied to the rigidizing device 100, to maximize flexibility.

In some embodiments, the outermost layer 101 can be loose over the radially inward layers. For instance, the inside diameter of layer 101 (assuming it constitutes a tube) may have a diametrical gap of 0"-0.200" with the next layer radially inwards (e.g., with a braid layer). This may give the vacuum rigidized system more flexibility when not under vacuum while still preserving a high rigidization multiple. In other embodiments, the outermost layer 101 may be stretched some over the next layer radially inwards (e.g., the braid layer). For instance, the zero-strain diameter of a tube constituting layer 101 may be from 0-0.200" smaller in diameter than the next layer radially inwards and then stretched thereover. When not under vacuum, this system may have less flexibility than one wherein the outer layer 101 is looser. However, it may also have a smoother outer appearance and be less likely to tear during use.

In some embodiments, the outermost layer 101 can be loose over the radially inward layers. A small positive pressure may be applied underneath the layer 101 in order to gently expand layer 101 and allow the rigidizing device to bend more freely in the flexible configuration. In this embodiment, the outermost layer 101 can be elastomeric and can maintain a compressive force over the braid, thereby imparting stiffness. Once positive pressure is supplied (enough to nominally expand the sheath off of the braid, for example, 2 psi), the outermost layer 101 is no longer is a contributor to stiffness, which can enhance baseline flexibility. Once rigidization is desired, positive pressure can be replaced by negative pressure (vacuum) to deliver stiffness.

A vacuum can be carried within rigidizing device 100 from minimal to full atmospheric vacuum (e.g., approximately 14.7 psi). In some embodiments, there can be a bleed valve, regulator, or pump control such that vacuum is bled down to any intermediate level to provide a variable stiffness capability. The vacuum pressure can advantageously be used to rigidize the rigidizing device structure by compressing the layer(s) of braided sleeve against neighboring layers. Braid is naturally flexible in bending (i.e. when bent normal to its longitudinal axis), and the lattice structure formed by the interlaced strands distort as the sleeve is bent in order for the braid to conform to the bent shape while resting on the inner layers. This results in lattice geometries where the corner angles of each lattice element change as the braided sleeve bends. When compressed between conformal materials, such as the layers described herein, the lattice elements become locked at their current angles and have enhanced capability to resist deformation upon application of vacuum, thereby rigidizing the entire structure in bending when vacuum is applied. Further, in some embodiments, the hoop fibers through or over the braid can carry tensile loads that help to prevent local buckling of the braid at high applied bending load.

The stiffness of the rigidizing device 100 can increase from 2-fold to over 30- fold, for instance 10-fold, 15-fold, or 20-fold, when transitioned from the flexible configuration to the rigid configuration. In one specific example, the stiffness of a rigidizing device similar to rigidizing device 100 was tested. The wall thickness of the test rigidizing device was 1.0 mm, the outer diameter was 17 mm, and a force was applied at the end of a 9.5 cm long cantilevered portion of the rigidizing device until the rigidizing device deflected 10 degrees. The forced required to do so when in flexible mode was only 30 grams while the forced required to do so in rigid (vacuum) mode was 350 grams.

In some embodiments of a vacuum rigidizing device 100, there can be only one braid layer. In other embodiments of a vacuum rigidizing device 100, there can be two, three, or more braid layers. In some embodiments, one or more of the radial gap layers or slip layers of rigidizing device 100 can be removed. In some embodiments, some or all of the slip layers of the rigidizing device 100 can be removed.

The braid layers described herein can act as a variable stiffness layer. The variable stiffness layer can include one or more variable stiffness elements or structures that, when activated (e.g., when vacuum is applied), the bending stiffness and/or shear resistance is increased, resulting in higher rigidity. Other variable stiffness elements can be used in addition to or in place of the braid layer. In some embodiments, engagers can be used as a variable stiffness element, as described in International Patent Application No. PCT/US2018/042946, filed Jul. 19, 2018, titled "DYNAMICALLY RIGIDIZING OVERTUBE," the entirety of which is incorporated by reference herein. Alternatively or additionally, the variable stiffness element can include particles or granules, jamming layers, scales, rigidizing axial members, rigidizers, longitudinal members or substantially longitudinal members.

Figure 14A:
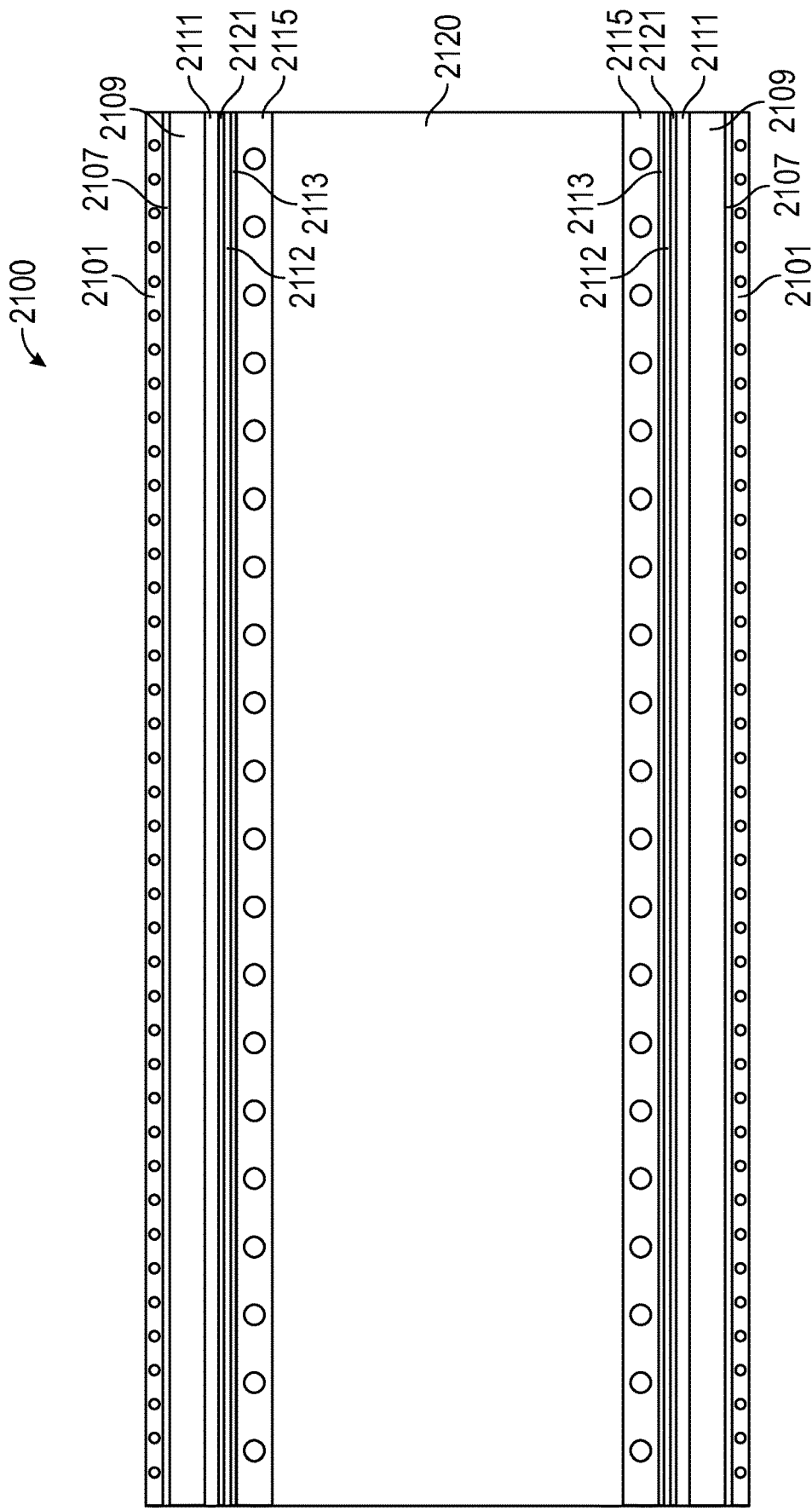
FIGS. 14A-14B show an exemplary pressure rigidizing device.
Figure 14B:
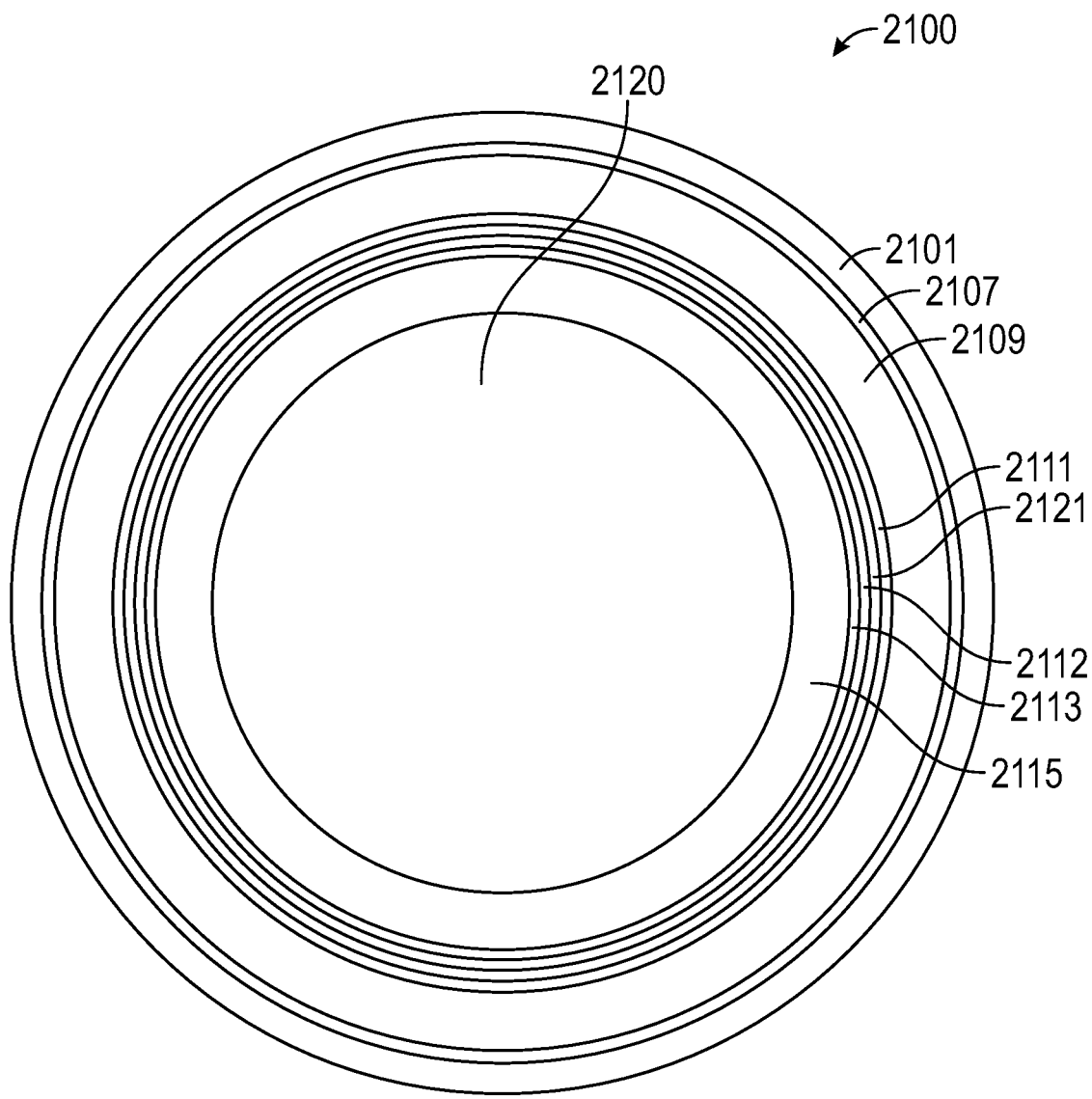

In some embodiments, the rigidizing devices described herein can rigidize through the application of pressure rather than vacuum. For example, referring to FIGS. 14A-14B, the rigidizing device 2100 can be similar to rigidizing device 100 except that it can be configured to hold pressure (e.g., of greater than 1 atm) therein for rigidization rather than vacuum. The rigidizing device 2100 can thus include a plurality of layers positioned around the lumen 2120 (e.g., for placement of an instrument or endoscope therethrough). The rigidizing device 2100 can include an innermost layer 2115 (similar to innermost layer 115), a slip layer 2113 (similar to slip layer 113), a pressure gap 2112, a bladder layer 2121, a gap layer 2111 (similar to gap layer 111), a braid layer 2109 (similar to braid layer 109) or other variable stiffness layer as described herein, a gap layer 2107 (similar to layer 107), and an outermost containment layer 2101.

The pressure gap 2112 can be a sealed chamber that provides a gap for the application of pressure to layers of rigidizing device 2100. The pressure can be supplied to the pressure gap 2112 using a fluid or gas inflation/pressure media. The inflation/pressure media can be water or saline or, for example, a lubricating fluid such as soil or glycerin. The lubricating fluid can, for example, help the layers of the rigidizing device 2100 flow over one another in the flexible configuration. The inflation/pressure media can be supplied to the gap 2112 during rigidization of the rigidizing device 2100 and can be partially or fully evacuated therefrom to transform the rigidizing device 2100 back to the flexible configuration. In some embodiments, the pressure gap 2112 of the rigidizing device 2100 can be connected to a pre-filled pressure source, such as a pre-filled syringe or a pre-filled insufflator, thereby reducing the physician's required set-up time.

The bladder layer 2121 can be made, for example, of a low durometer elastomer (e.g., of shore 20A to 70A) or a thin plastic sheet. The bladder layer 2121 can be formed out of a thin sheet of plastic or rubber that has been sealed lengthwise to form a tube. The lengthwise seal can be, for instance, a butt or lap joint. For instance, a lap joint can be formed in a lengthwise fashion in a sheet of rubber by melting the rubber at the lap joint or by using an adhesive. In some embodiments, the bladder layer 2121 can be 0.0002-0.020" thick, such as approximately 0.005" thick. The bladder layer 2121 can be soft, high-friction, stretchy, and/or able to wrinkle easily. In some embodiments, the bladder layer 2121 is a polyolefin or a PET. The bladder 2121 can be formed, for example, by using methods used to form heat shrink tubing, such as extrusion of a base material and then wall thinning with heat, pressure and/or radiation. When pressure is supplied through the pressure gap 2112, the bladder layer 2121 can expand through the gap layer 2111 to push the braid layer 2109 against the outermost containment layer 2101 such that the relative motion of the braid strands is reduced.

The outermost containment layer 2101 can be a tube, such as an extruded tube. Alternatively, the outermost containment layer 2101 can be a tube in which a reinforcing member (for example, metal wire, including round or rectangular cross-sections) is encapsulated within an elastomeric matrix, similar to as described with respect to the innermost layer for other embodiments described herein. In some embodiments, the outermost containment layer 2101 can include a helical spring (e.g., made of circular or flat wire), and/or a tubular braid (such as one made from round or flat metal wire) and a thin elastomeric sheet that is not bonded to the other elements in the layer. The outermost containment layer 2101 can be a tubular structure with a continuous and smooth surface. This can facilitate an outer member that slides against it in close proximity and with locally high contact loads (e.g., a nested configuration as described further herein). Further, the outer layer 2101 can be configured to support compressive loads, such as pinching. Additionally, the outer layer 2101 (e.g., with a reinforcement element therein) can be configured to prevent the rigidizing device 2100 from changing diameter even when pressure is applied.

Because both the outer layer 2101 and the inner layer 2115 include reinforcement elements therein, the braid layer 2109 can be reasonably constrained from both shrinking diameter (under tensile loads) and growing in diameter (under compression loads).

Figure 15:
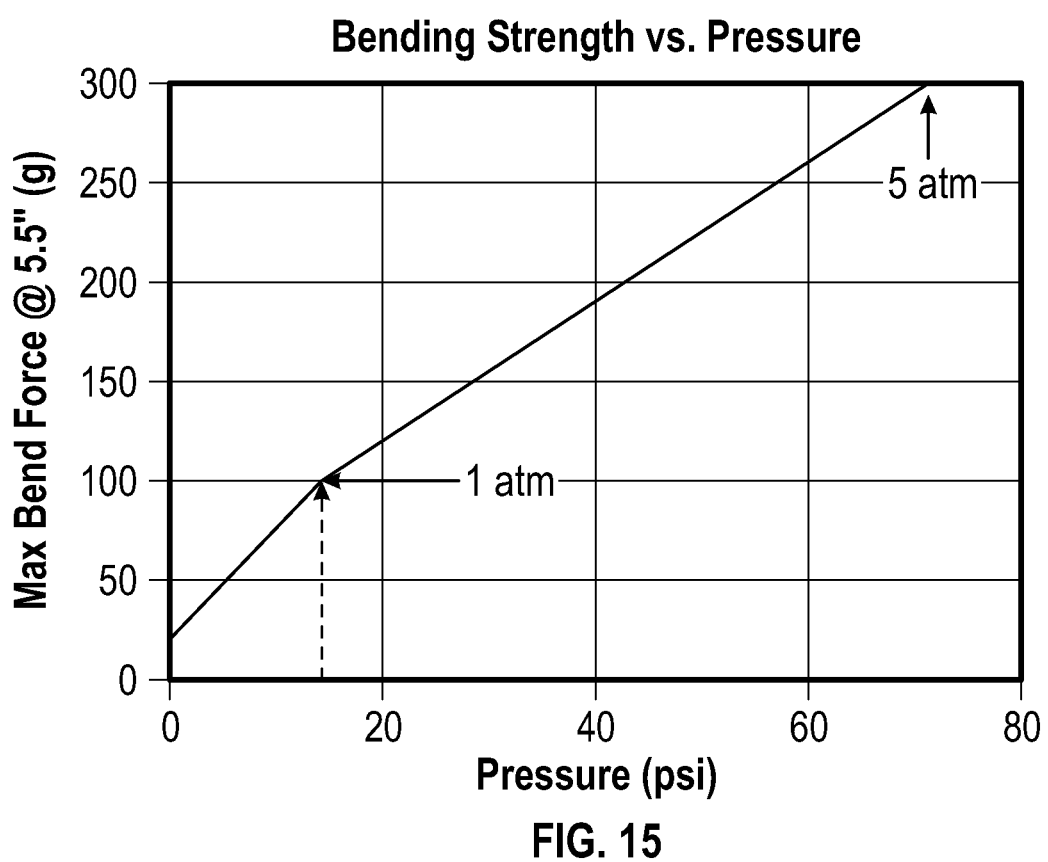
FIG. 15 is a graph of bending strength vs pressure for a rigidizing device.

By using pressure rather than vacuum to transition from the flexible state to the rigid state, the rigidity of the rigidizing device 2100 can be increased. For example, in some embodiments, the pressure supplied to the pressure gap 2112 can be between 1 and 40 atmospheres, such as between 2 and 40 atmospheres, such as between 4 and 20 atmospheres, such as between 5 and 10 atmospheres. In some embodiments, the pressure supplied is approximate 2 atm, approximately 4 atmospheres, approximately 5 atmospheres, approximately 10 atmospheres, approximately 20 atmospheres. In some embodiments, the rigidizing device 2100 can exhibit change in relative bending stiffness (as measured in a simple cantilevered configuration) from the flexible configuration to the rigid configuration of 2-100 times, such as 10-80 times, such as 20-50 times. For example, the rigidizing device 2100 can have a change in relative bending stiffness from the flexible configuration to the rigid configuration of approximately 10, 15, 20, or 25, 30, 40, 50, or over 100 times. FIG. 15 shows a graph of bending strength vs pressure for a rigidizing device as described herein. As shown, the bending strength of the rigidizing device increases as the pressure supplied to the wall increases.

Figure 16G:
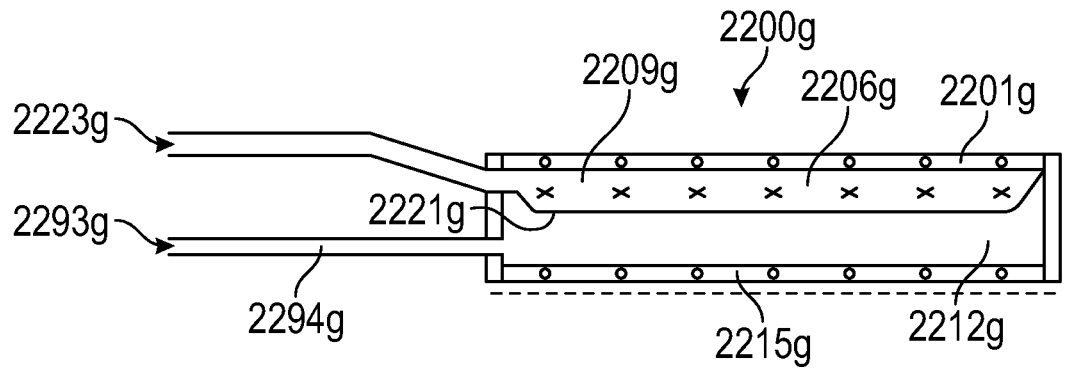
FIG. 16A-16O show various examples of pressure rigidizing devices.
Figure 16H:
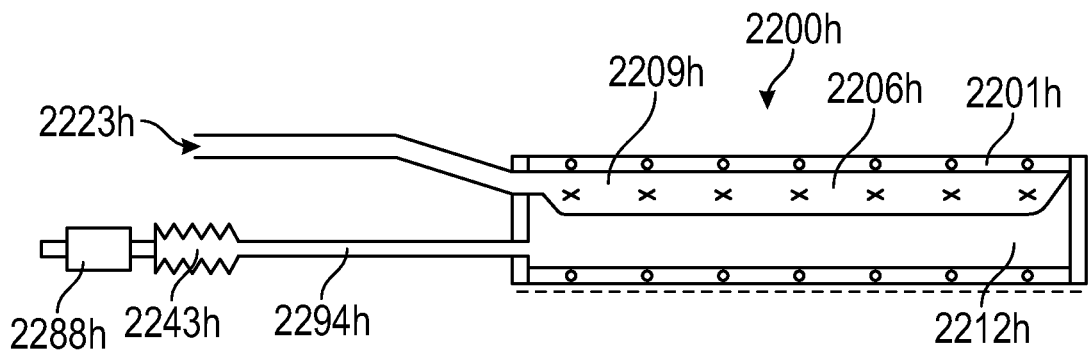
Figure 16I:
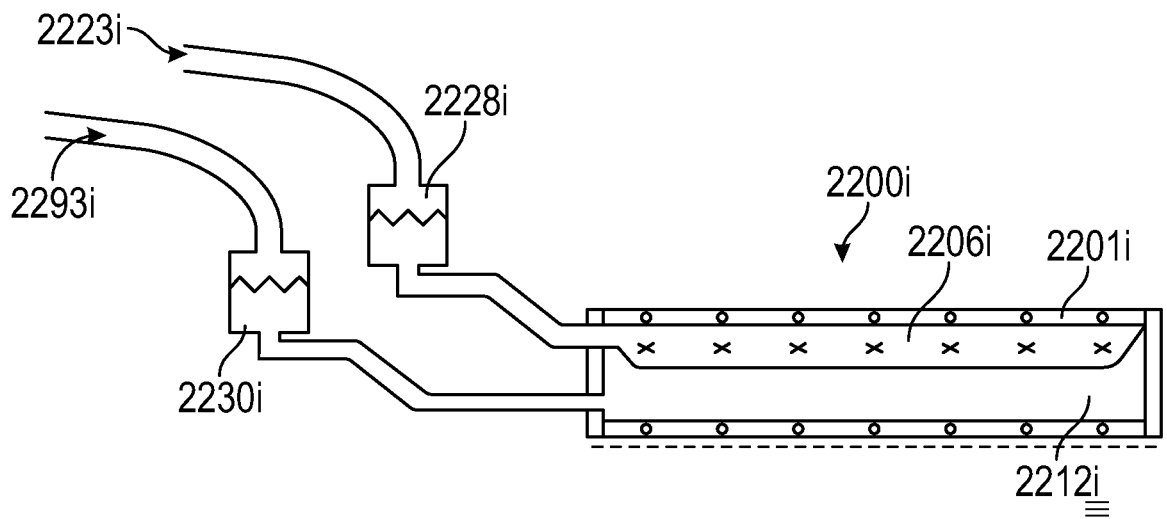
Figure 16J:
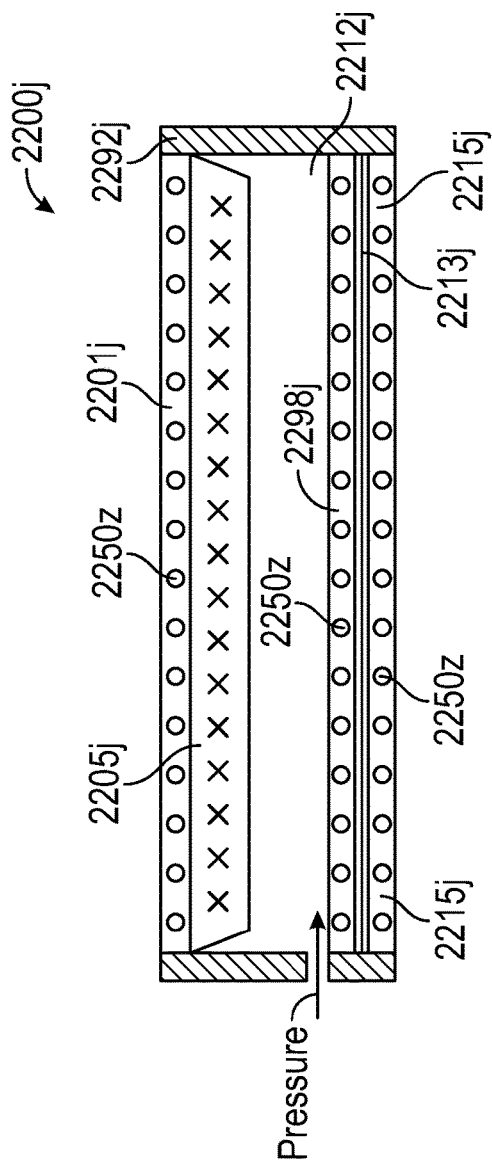
Figure 16K:
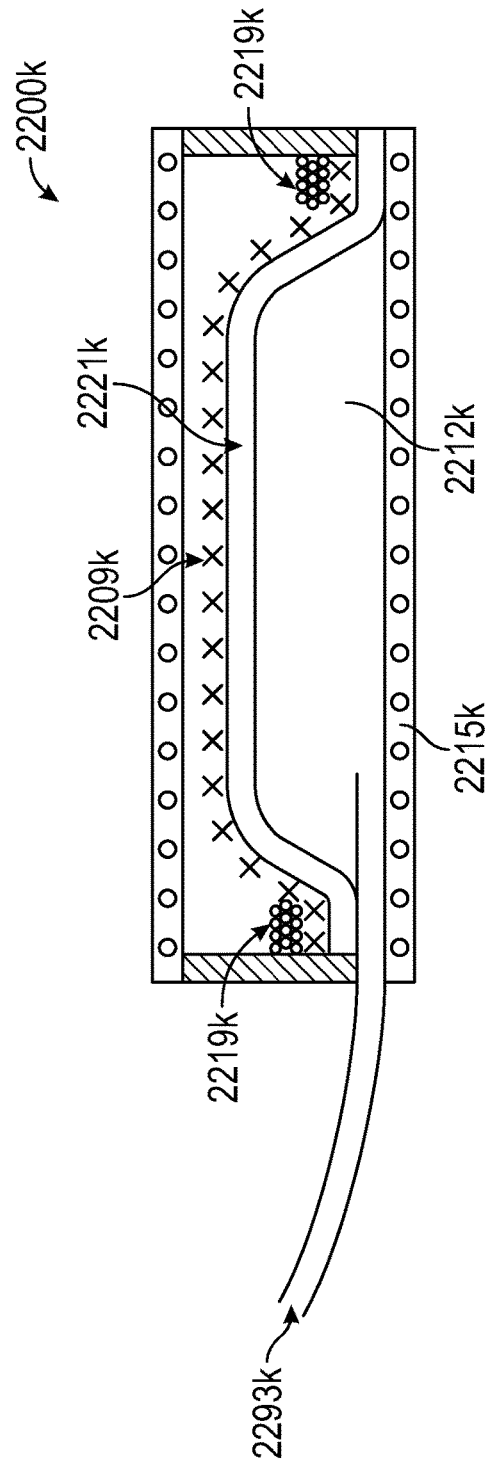
Figure 16L:
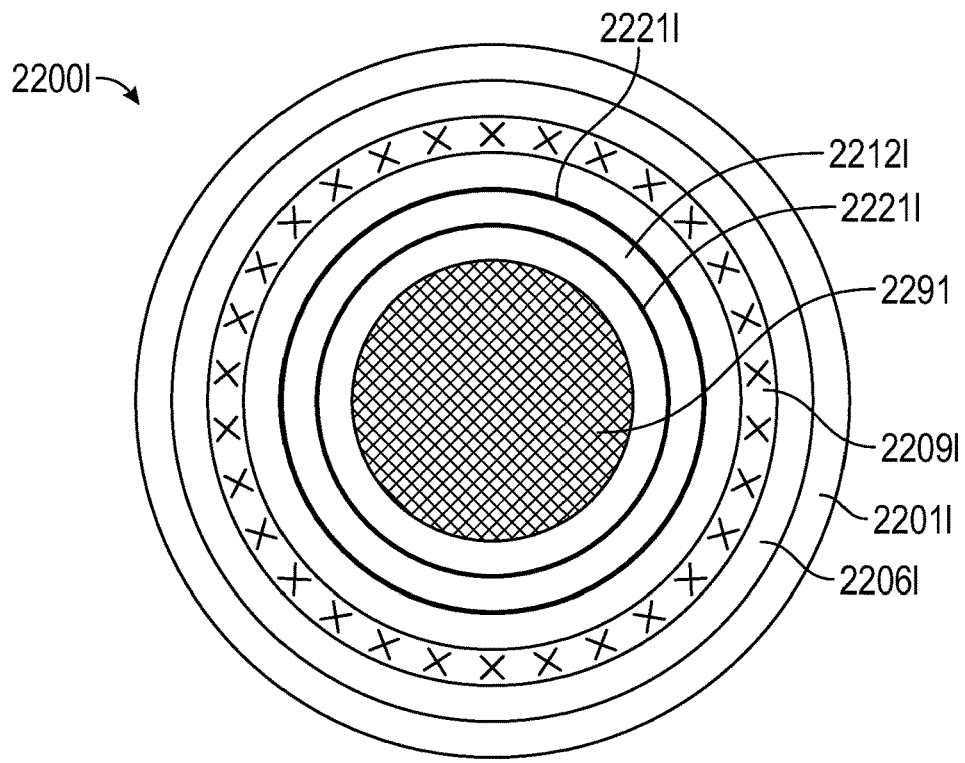
Figure 16M:
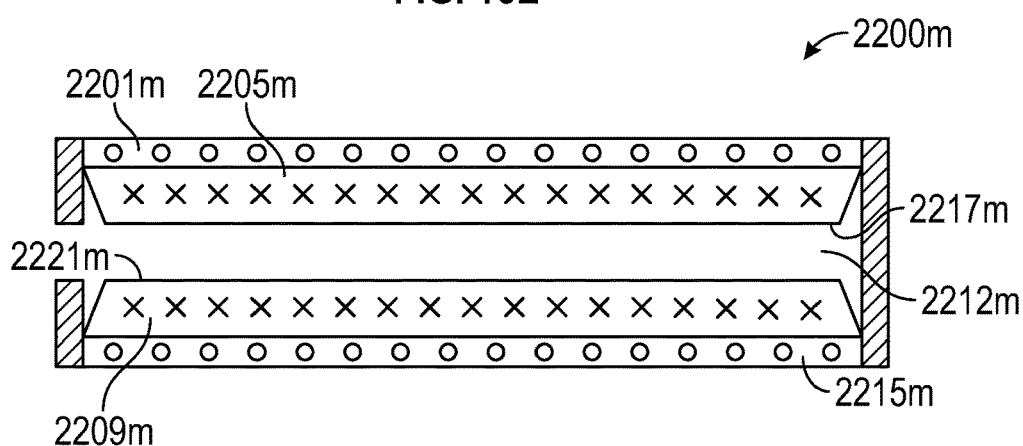
Figure 16N:
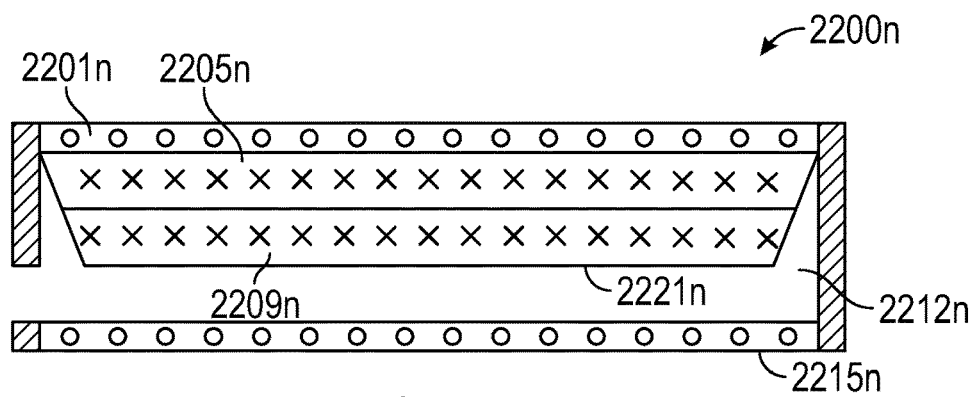
Figure 16O:
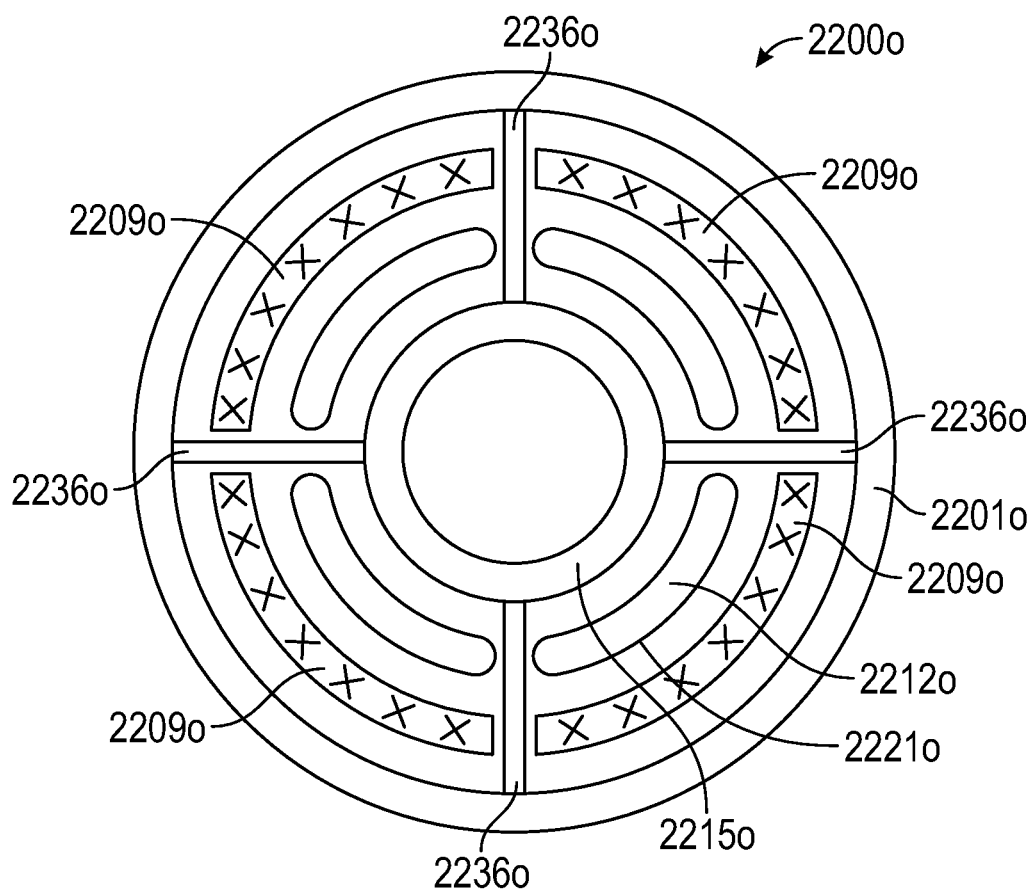

Simplified versions of a wall of various pressurized rigidizing devices similar to rigidizing device 2100 are shown in FIGS. 16A-16O. For example, rigidizing device 2200a of FIG. 16A includes the innermost layer 2215a, pressure gap 2212a, bladder layer 2221a that is sealed to the outermost layer 2201a, braid layer 2209a, and outer containment layer 2201a (similar as described with respect to rigidizing device 2100). The rigidizing device 2200a further includes end caps 2292a at the proximal and distal ends thereof to seal the pressure therein. When pressure is supplied to the pressure gap 2212a via inlet 2293a, the bladder layer 2221a is pressed against the braid layer 2209a, which in turn is pressed against the outermost layer 2201a, preventing the strands of the braid from moving relative to one another.

Referring to FIG. 16J, rigidizing device 2200j is similar to rigidizing device 2200a except that slip layer 2213j and stiffening layer 2298j are added. Layer 2213j can be a slip layer as described herein, for example comprising a coating film or powder. Layer 2298j can be a stiffening layer that, similar to layers 2201j and 2215j, can include a reinforcement element 2250z as described elsewhere herein. The additional stiffening layer 2298j can work in concert with the inner layer 2215j. For example, the two layers 2215j and 2298j can easily slip past one another (via slip layer 2213j) in the flexible configuration and stick to one another to form a stiff composite structure in the rigid configuration (i.e., when pressure is applied). Layer 2298j can be a high durometer elastomeric rubber, for example a TPU or TPE with a durometer greater than or equal to 60A, 70A, 80A or 90A. When the tube is in a flexible state, layers 2215j and 2298j may easily shear or move with respect to each other (e.g., due to slip layer 2213j) such that the flexibility of the system is lower than it would be if the layers were bonded together. When the tube is in a rigid state (for example, when pressure is applied), layers 2215j, 2298j and 2213j may lock to each other and act like a single bonded layer in order to resist collapse of the wall of the rigidizing device 2200j. Similar to other embodiments, the braid layer 2205j can push against the outer layer 2201j when pressure is supplied to gap 2212j to rigidize the device 2200j.

Referring to FIG. 16B, rigidizing device 2200b is similar to rigidizing device 2200a except that the pressure gap 2212b is surrounded by an everted bladder layer 2221b (or a double-layered bladder), i.e., such that the bladder layer 2221b includes one side that borders the braid layer 2205b and one side that borders the innermost layer 2215b. As pressure is supplied to the pressure gap 2212b (inside of the two sides of the bladder layer 2221b), the bladder layer 2221b can expand both against the innermost layer 2215b and against the braid 2209b (which in turn can be pushed against the outermost layer 2201b).

Referring to FIG. 16C, rigidizing device 2200c is similar to rigidizing device 2200a except that the bladder layer 2221c is sealed to the innermost layer 2215c rather than the outermost layer 2201c. When pressure is supplied to the pressure gap 2212c via inlet 2293c, the bladder layer 2221c is pressed against the braid layer 2209c, which in turn is pressed against the outermost layer 2201c.

Referring to FIG. 16D, rigidizing device 2200d is similar to rigidizing device 2200b except that the innermost layer 2215d is a spring element rather than a coil-wound tube. Because the pressure is in the everted bladder layer 2221d, the inner layer 2215d need not be sealed itself.

Referring to FIG. 16E, rigidizing device 2200e is similar to rigidizing device 2200a except that the innermost layer 2215a is replaced with an inner payload 2294e that is sealed at both the proximal and distal ends and can include a plurality of lumens therein (e.g., a working channel 2291e, a pressure channel 2292e, and a rinse channel 2293e).

Referring to FIG. 16F, rigidizing device 2200f is similar to rigidizing device 2200a except that the braid layer 2209f is inside of the pressure gap 2212f and the bladder layer 2221f such that pressure supplied to the pressure gap 2212f causes the bladder layer 2221f to push inwards against the braid layer 2209f, which in turn pushes against innermost layer 2215f.

In some embodiments, a pressure rigidizing device can include two braid layers (e.g., of the same or different braid characteristics). For example, an exemplary rigidizing device 2200m with two braid layers 2209m and 2205m is shown in FIG. 16M. The two braid layers 2209m and 2205m sandwich two bladders 2221m and 2217m (and/or a single annular bladder) therebetween. When pressure is supplied to the pressure gap 2212m between the two bladders, the outer braid layer 2205m will be pushed radially outwards against the outer layer 2201m while the inner braid layer 2209m will be pushed radially inwards against the inner braid layer 2215m to rigidize the device 2200m.

Another exemplary rigidizing device 2200n with two braid layers 2209n, 2205n is shown in FIG. 16N. The two braid layers 2209n, 2205n are positioned adjacent to one another between the bladder layer 2221n (not labeled in figure) and the outer tube 2201n. When pressure is supplied to the pressure gap 2212n, the bladder 2221n forces the two braid layers 2209n, 2205n together and against the outer tube 2201n. The braid layers 2209n, 2205n may interdigitate with one another when pressurized, thereby strengthening the rigidity of the device 2200n.

Referring to FIG. 16K, rigidizing device 2200k is similar to rigidizing device 2200a except that an annular ring 2219k, e.g., including fibers and adhesive, is positioned around each of the ends of the braid layer 2209k and bladder layer 2221k to attach the bladder layer 2221k to the innermost layer 2215k (and thereby hold pressure within the pressure gap 2212k when pressure is supplied through the inlet 2293k). The annular ring 2219k can, for example, include a high strength fiber, such as Kevlar or Dyneema. Further, the adhesive can be, for example, a cyanoacrylate. In some embodiments, adhesive can also be placed at the ends between the innermost layer 2215k and the bladder layer 2221k and also encompassing the inlet tube.

FIG. 16G shows a rigidizing device 2200g with gap inlet 2293g and vent inlet 2223g. Inlet 2293g connects to pressure gap 2212g (via pressure line 2294g). Inlet 2223g connects to gap 2206g around the braid layer 2209g (between bladder 2221g and outermost layer 2201g). The device 2200g can be rigidized in one or more different configurations. In a first rigidizing configuration, pressure can be applied to inlet 2293g while the vent inlet 2223g can be open or vented to atmospheric pressure. The pressure supplied to the pressure gap 2212g through the inlet 2293g can thus push the braid 2209g against the outermost layer 2201g, which in turn can force any air in the gap 2206g out through the vent inlet 2223g. Allowing the air to escape through the vent inlet 2223g can enable a tighter mechanical fit between the braid layer 2209g and the outer layer 2201g, thereby strengthening the rigidization of the device 2200g. In a second rigidizing configuration, pressure can be applied to inlet 2293g and a vacuum can be applied to vent inlet 2223g. This may cause the rigidizing device 2200g to become even stiffer than in the first configuration, as the vacuum can assist in moving the braid layer 2209g towards the outer layer 2201g. The device 2200g can likewise be made flexible in one or more different configurations. In a first flexible configuration, both inlet 2293g and vent inlet 2223g can be opened to atmospheric pressure. This will loosen the braid layer 2209g relative to the outer layer 2201g and cause the rigidizing device 2200g to be flexible as the braid layer 2209g moves freely relative to the outer layer 2201g. In a second flexible configuration, a low pressure (e.g., 5-10% above atmospheric pressure) can be provided to both inlet 2293g and vent inlet 2223g. This may cause the outermost layer 2201g and the innermost layer 2215g to separate slightly, which can provide additionally area for the braid layer 2209g to move freely. As a result, this may cause the rigidizing device 2200g to become even more flexible than in the first rigidizing configuration. Additionally, providing a low pressure above atmospheric pressure in the flexible configuration can allow the rigidizing device 2200g to be introduced into the body with a very small diameter (e.g., such that the pressure gap 2212g is essentially zero) and then the low pressure can be provided to both inlet 2293g and vent inlet 2223g to slightly expand the pressure gap 2212g to provide more room for the braid layer 2209g to move freely.

FIG. 16H shows a rigidizing device 2200h with bellows 2243h connected to pressure line 2294h. Pressure gap 2212h, pressure line 2294h, and bellows 2243h can all be configured to be filled with a sealed pressure transmitting medium, such as distilled water or saline solution or an oil. The pressure transmitting medium may be a radiopaque fluid that advantageously will show the rigidized device more clearly during a procedure using fluoroscopy. The pressure transmitting medium can be added to the rigidizing device immediately before use and/or when the device is being manufactured. In use, activating the actuator 2288h can compress bellows 2243h, thus reducing the volume of pressure medium in the bellows 2243h, which flows through the pressure line 2294h to the pressure gap 2212h, causing a rise in pressure in the pressure gap 2212h and movement of the braid layer 2209h against the outer layer 2201h. The vent inlet 2223h can be open to the atmosphere to allow gas to escape from the space 2206h around the braid layer 2209h. Further, reversing the action of the actuator 2288h can cause the pressure in the pressure gap 2212h to fall as the pressure medium moves back to the bellows 2243h. Actuator 2288h can be, for example, a solenoid, a voice coil, a lead screw, a valve, or a rotary cam. In some embodiments, the pressure line 2294h can be pinched or flattened to raise the pressure in pressure gap 2212h rather than using bellows 2243h.

FIG. 16I shows a rigidizing device 2200i including sumps 2230i and 2228i respectively. Sumps 2230i and 2228i may comprise a fluid medium, such as water and a gaseous medium such as air. Pressure or vacuum or combinations thereof may be applied to inlets 2293i, 2223i. Using the sump configuration shown may mean that there is no air or gas in the rigidizing device regardless of the pressurization state of each gap 2206i or 2212i (increased pressure, vacuum or atmospheric pressure). In the event that the gaps leaks during a procedure, this may mean that only the fluid medium enters into the patient. This may offer patient protection from gaseous (e.g. air) embolization.

In some embodiments, the rigidizing devices described herein can include a plurality of individual bladders running longitudinally down the length of the device. For example, referring to FIG. 16O, device 2200o includes four different circumferential bladders 22210 surrounding pressure gaps 2212o. In this embodiment, the braid layer is likewise divided into four longitudinal flat braids 2209o, each of which is positioned radially outwards from a bladder 2221o. In other embodiments, the braid layer can include tubular braids wrapped around the bladders 22210 (similar to as described with respect to FIG. 67 below). Further, the outer and inner layers 2201o, 2215o are connected by dividers 2236o. In some embodiments, the dividers 2236o can be formed by elements of the outer or inner layers 2201o, 2215o (e.g., be continuous elements of one or both layers 2201o, 2215o). In some embodiments, the dividers 2236o can be configured to help maintain the thickness of the wall. When pressure is supplied to the pressure gaps 2212o, the bladders 22210 expand to push the flat braids 2209o against the outer layer 2201o.

In some embodiments, referring to FIG. 16L, the pressure rigidizing devices described herein do not include an innermost layer (e.g., do not include an innermost layer with a reinforcement element therein). Rather, the rigidizing device 22001 can include an outer layer 22011, gap layer 22061, braid layer 22091, and an everted or tubular bladder 22211 (with a pressure gap 22121 therein). The tubular bladder 22211 can be configured to be positioned around the inner device (such as a scope 2291). As the pressure gap 22121 is filled with pressurizing medium, the bladder 22211 can expand against the scope 2291 and the braid layer 22091. It should be understood that any of the features described herein with respect to vacuum rigidizing devices can be substituted or replaced with any of the features described with respect to pressure rigidizing devices.

Figure 17A:
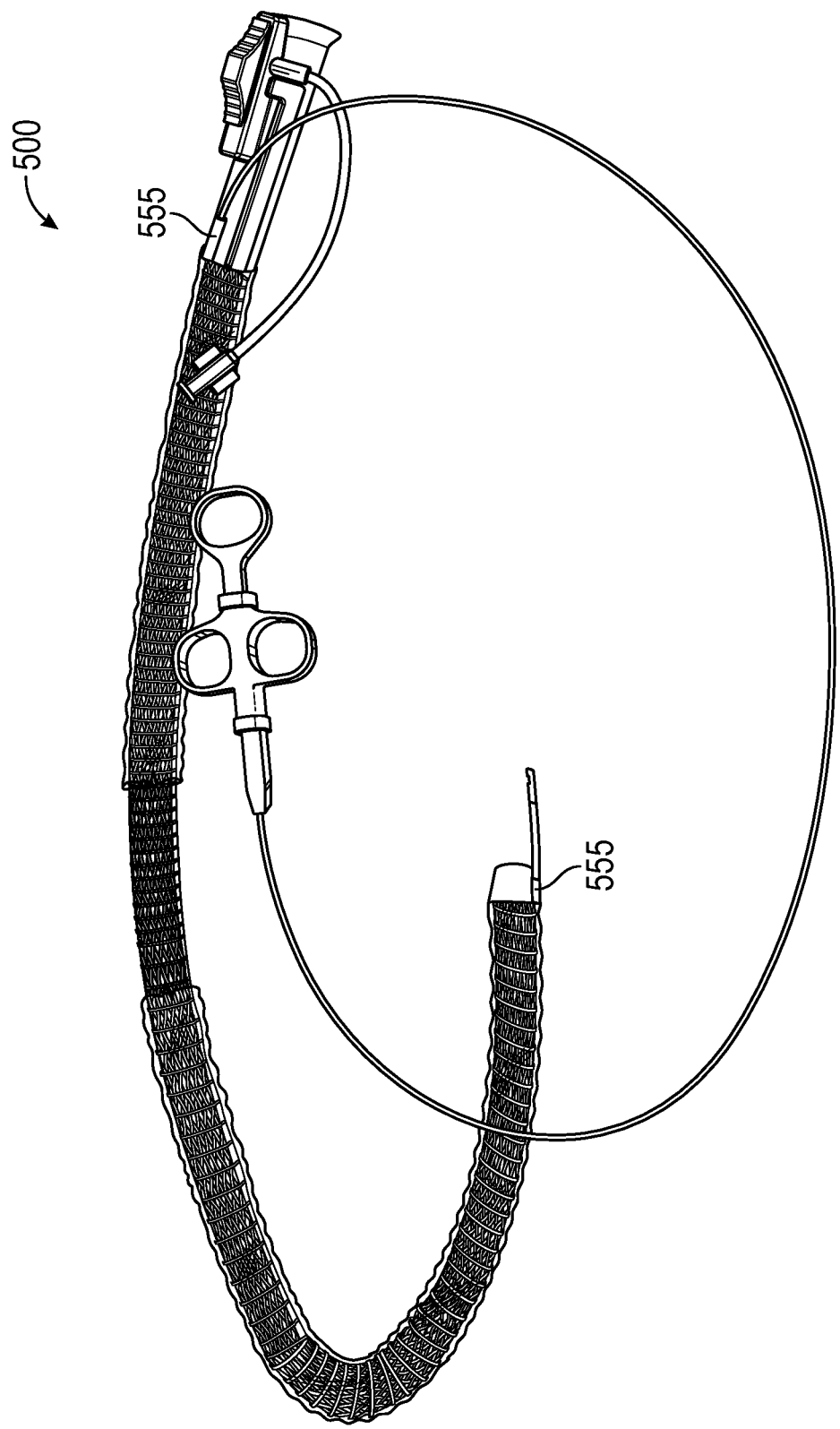
FIGS. 17A-17D show a rigidizing device with an incorporated working channel.
Figure 17B:
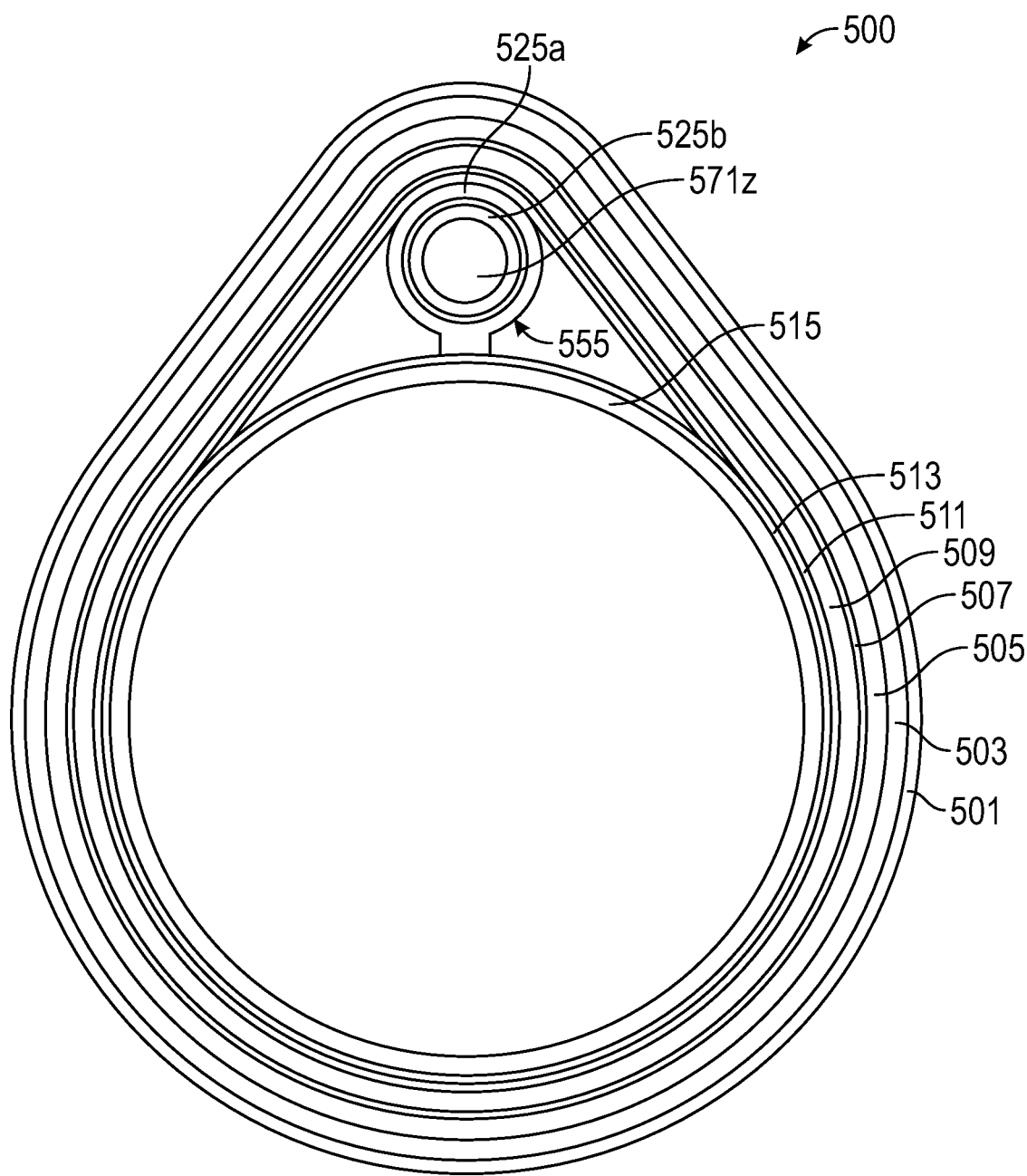
Figure 17C:
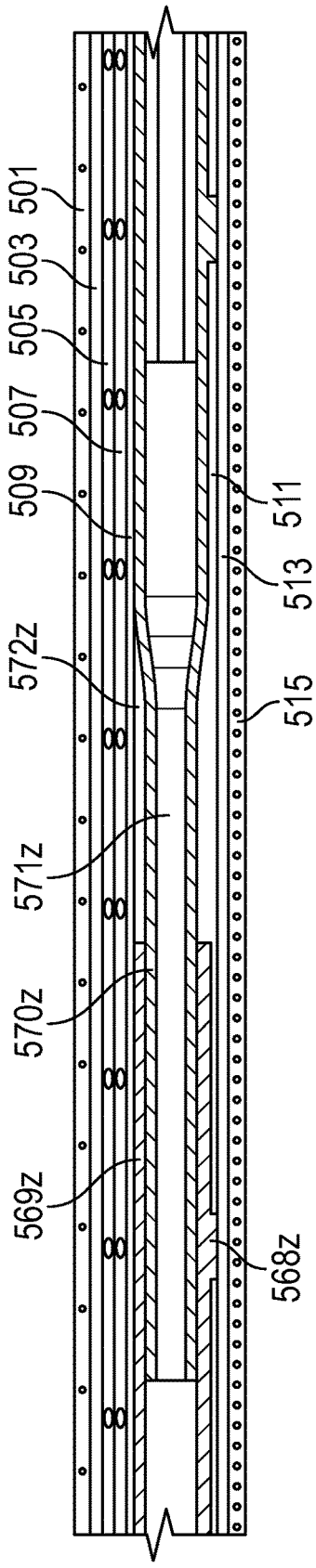
Figure 17D:
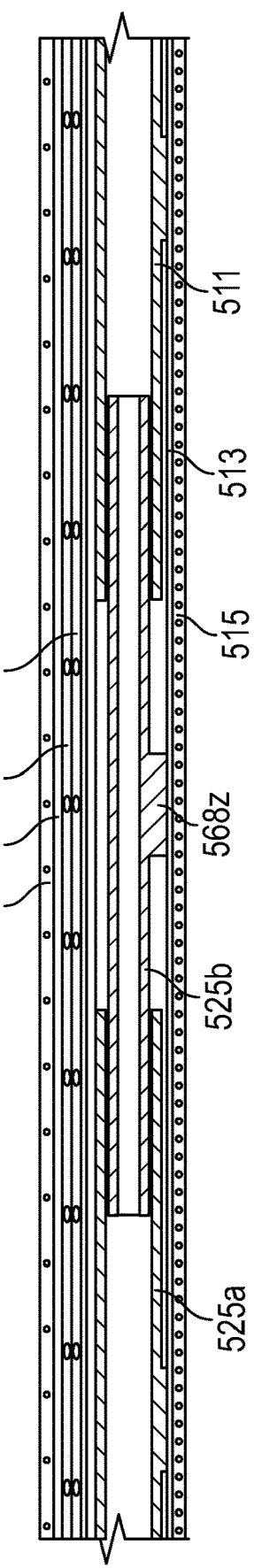

In some embodiments, the rigidizing devices described herein can incorporate a tool or working channel therein. The working channel can be designed so as to not significantly add to the rigidizing device's bending stiffness. Referring to FIGS. 17A-17C, in one embodiment, a rigidizing device 500 can include a working channel 555 extending therethrough. The working channel 555 can include a central lumen 571z (e.g., for passage of a working element therethrough) formed by alternating telescoping tubular sections that are locally necked or tapered from a larger diameter end 569z to a smaller diameter end 570z. Each of the sections can be connected to the underlying layer of the wall (e.g., the slip layer 513 over the innermost layer 515) at a discrete location or anchor point 568z and can be otherwise free to move. As the rigidizing device 500 bends, the smaller diameter end 570z can move within the larger diameter end 559z of a neighboring section so as to allow for bending of the working channel 555. The working channel 555 can be positioned within the wall of the rigidizing device 500, such as in the radial gap 511 between the slip layer 513 and the first braid layer 509 (and can therefore also be positioned underneath the radial gap layer 507, the second braid layer 505, the radial gap layer 503, and the outermost layer 501). The working channel 555 can thus be positioned within the sealed vacuum (or pressure chamber) of the rigidizing device 500. In some embodiments, the working channel 555 can itself be positioned within a sealed bag or layer 572z so as to ensure that there is no vacuum or pressure leak path. In other embodiments, the sections can include sliding seals therebetween to ensure that there is no vacuum or pressure leak path. In some embodiments, as shown in FIG. 17D, rather than having tapered sections, there can be alternative large diameter sections 525a and small diameter sections 525b. The smaller diameter sections 525b can move within the large diameter sections 525a during bending over the rigidizing device 500. The working channel can be placed within the sealed volume formed by layers 501 and 515 or it can be placed outside of this sealed volume, such as on top of layer 501.

Figure 18A:
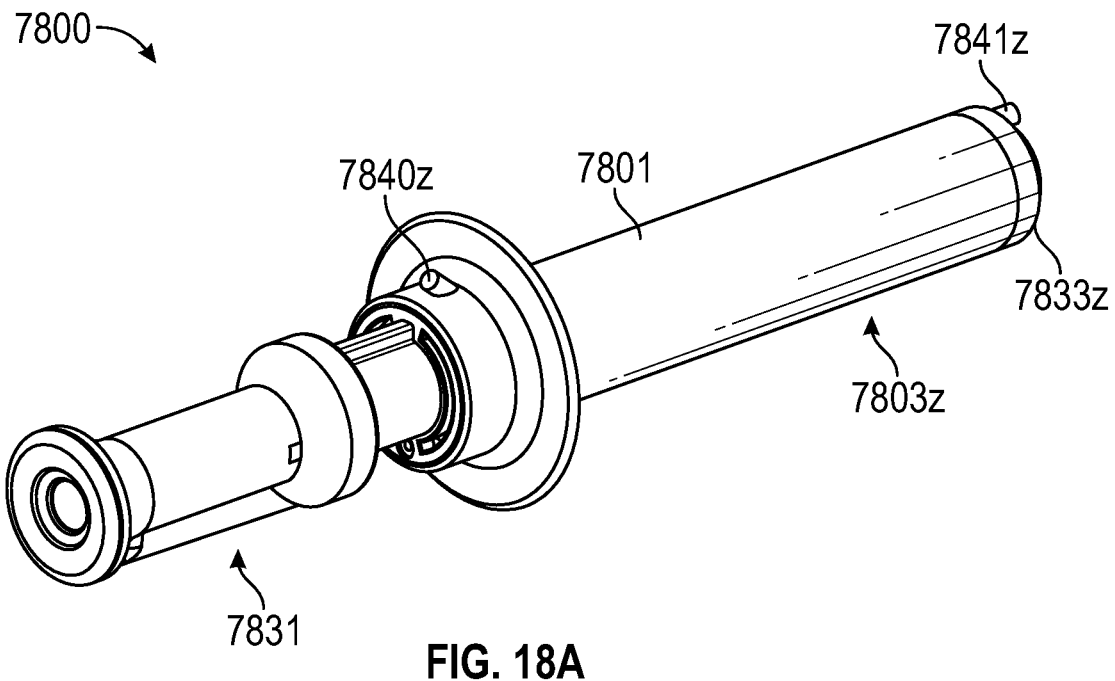
FIGS. 18A-18B show a rigidizing device with a spiraled working channel.
Figure 18B:
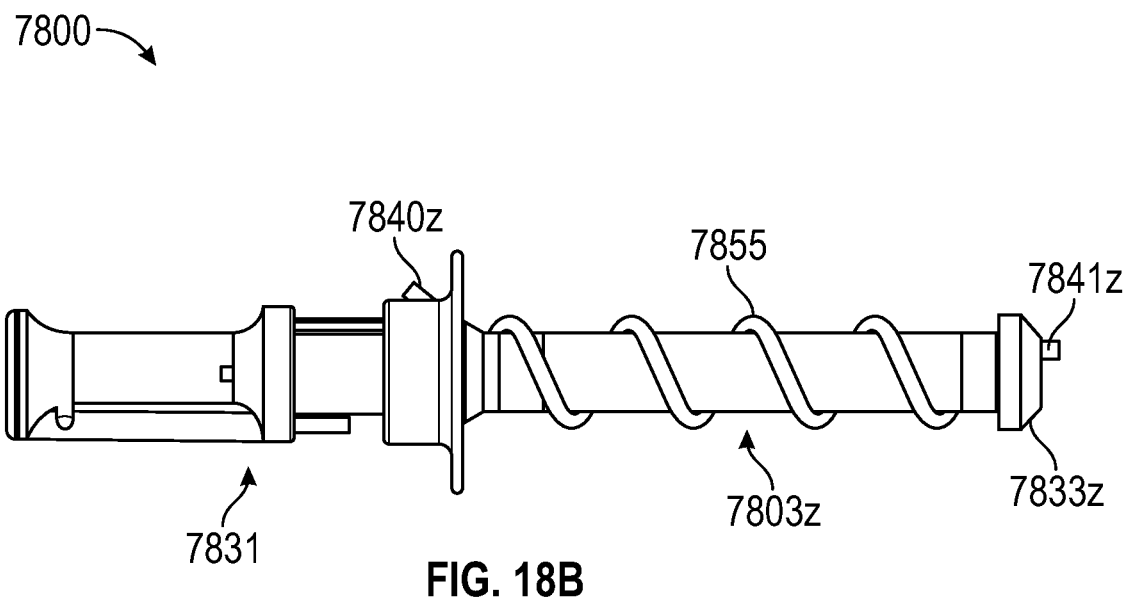

Referring to FIGS. 18A-18B, in some embodiments, a rigidizing device 7800 can include a working channel 7855 spiraled around a portion of the elongate body 7803z of the rigidizing device 7800. For example, the working channel 7855 can be spiraled at a 40-50 degree angle, such as approximately a 45 degree angle, relative to the longitudinal axis of the device 7800. A spiraled working channel 7855 can advantageously deform into a curved path as the rigidizing device 7800 bends without resisting bending and/or without forcing path length adjustments along its length. The working channel 7855 can include a proximal port 7840z integrated into the handle 7831 and a distal port 7841z (through which a working tool may exit) molded onto end of the tip 7833z of the rigidizing device 7800. The spiraled working channel 7855 can be positioned over the outermost layer 7801, under the outer layer 7801 (as shown in FIGS. 18A-18B where the outer layer 7801 has been removed for clarity), or further within the layers of the wall (.e., under the braid layer).

Figure 19A:
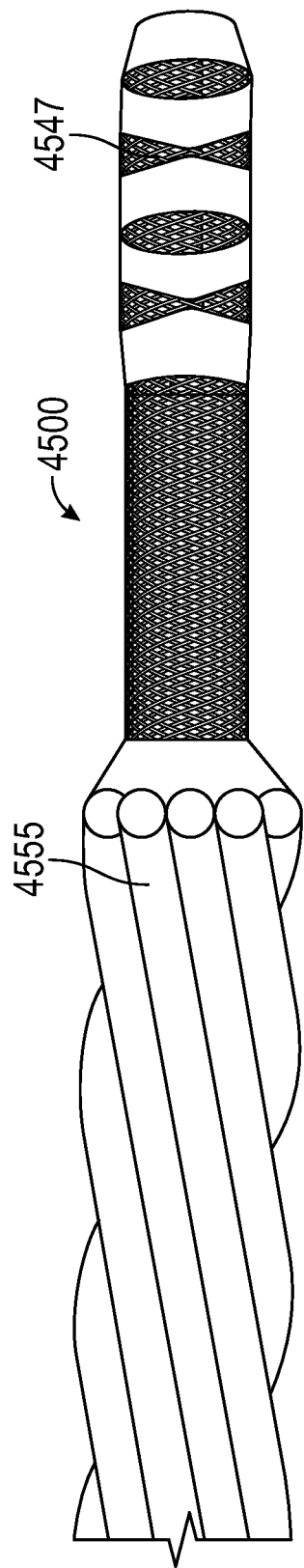
FIGS. 19A-19B show a rigidizing device with a plurality of spiraled working channels.
Figure 19B:
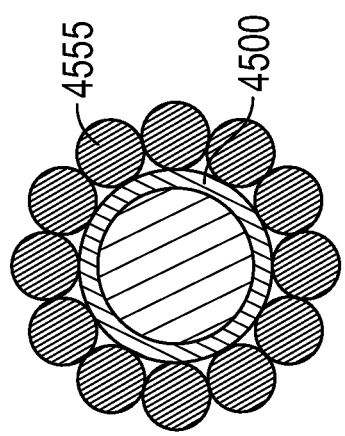

Referring to FIGS. 19A-19B, in some embodiments, a rigidizing device 4500 can include a plurality of working channels 4555 spiraled around the outside thereof. As shown in FIGS. 19A-19B, the working channels 4555 can, for example, form a spiral shield around the rigidizing device 4500. In some embodiments, the working channels 4555 can be configured together to form a second rigidizing element that can be rigidized separately from the inner rigidizing device 4500. The second rigidizing element can advantageously be highly flexible due to the relative movement of the individual spiraling working channels 4555. In some embodiments, the working channels 4555 can include a thin flexible ring and/or thin flexible sheath to contain the working channels 4555 in a circular cross section. In some embodiments, the device 4500 can further include a steerable distal tip 4547, e.g., to help with placement of the tools that extend through the working channels 4555.

Figure 20A:
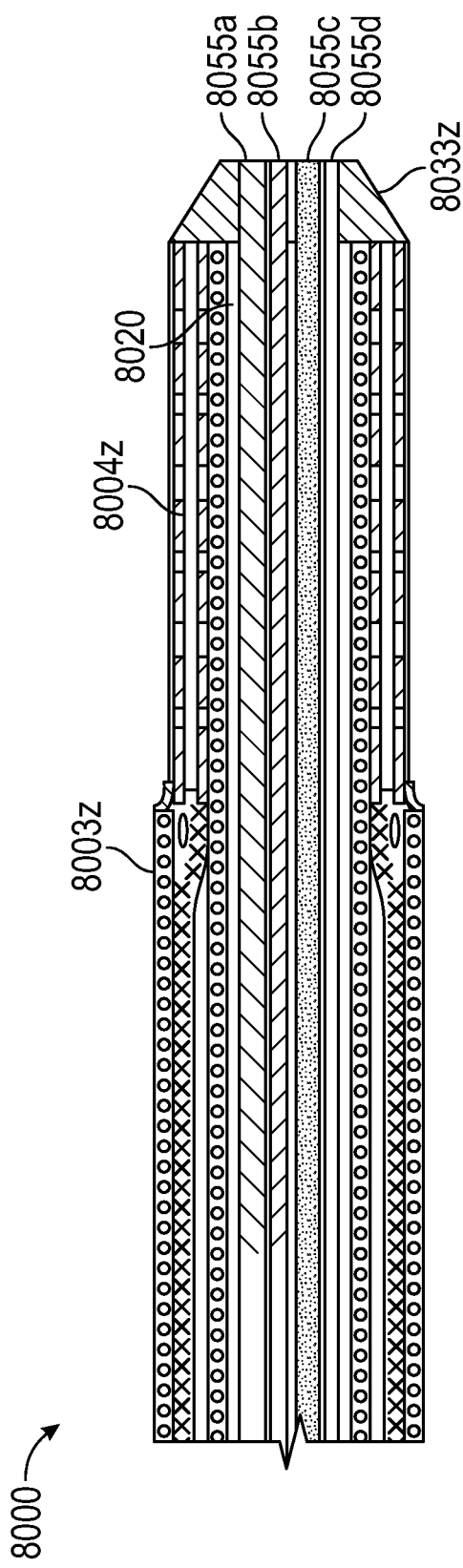
FIGS. 20A-20B show a rigidizing device with a plurality of working channels extending down the central lumen.
Figure 20B:
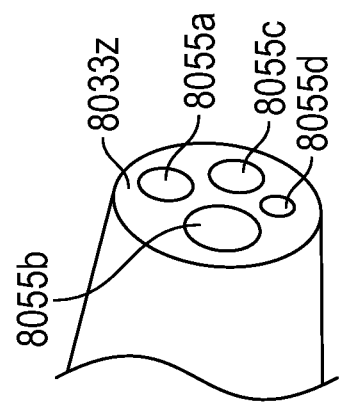

Referring to FIGS. 20A-20B, in some embodiments, a rigidizing device 8000 can include a rigidizing elongate body 8003z with a plurality of working channels 8055a-d (such as 1-10, 3-5, or 4-5 working channels) extending down the central lumen 8020 thereof to the tip 8033z. The working channels 8055a-d can be used for a plurality of different tools throughout a procedure. For example, one of the working channels 8055a-d can be used for a catheter with a camera and lighting, another could be used for traction, another could be used for cutting, another could be used for suction, etc. The elements extended down the working channels 8055a-d can be interchanged throughout the procedure. In some embodiments, the rigidizing elongate body 8003z can be disposable while the tools can be cleanable and/or sterilizable. In some embodiments, the rigidizing device 8000 can further include passive or active linkages 8004z.

Figure 21:
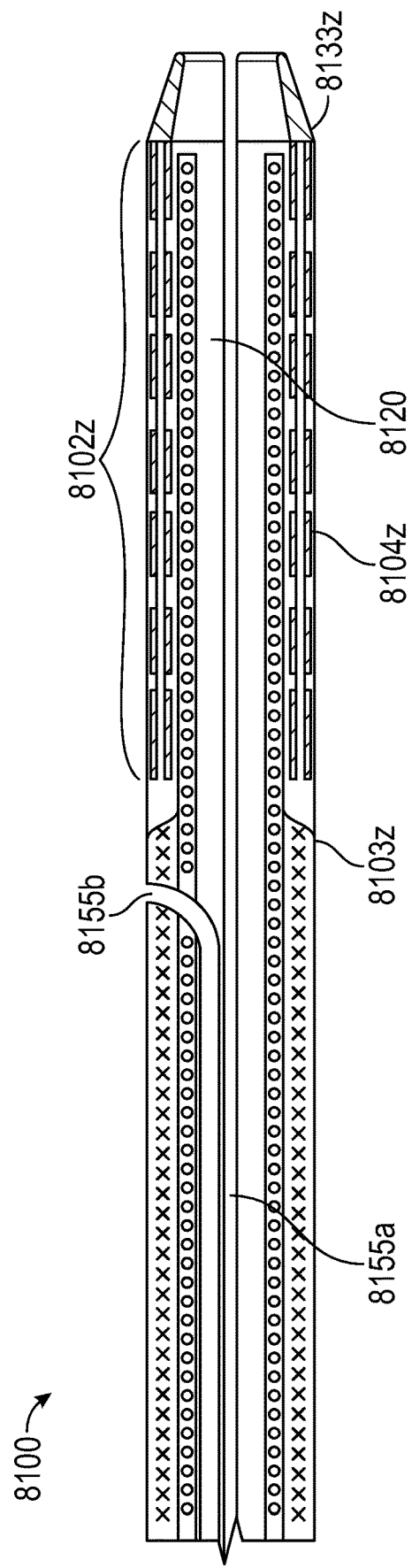
FIG. 21 shows a rigidizing device with a working channel extending out the side thereof.

Referring to FIG. 21, in some embodiments, a rigidizing device 8100 can include a first working channel 8155a and a second working channel 8155b. The first working channel 8155b can extend down the central lumen 8120 (or within the walls of the elongate body 8103z) to the distal end 8133z. The second working channel can similarly extend down the central lumen 8120 or within the walls of the elongate body 8103z, but can exit the side of the elongate body 8103z proximal to the distal section 8102z (e.g., prior to the linkages 8104z). Having tool channel 8155b exit proximal to the distal section can advantageously limit interference with steering or bending of the linkages 8104z.

Figure 22:
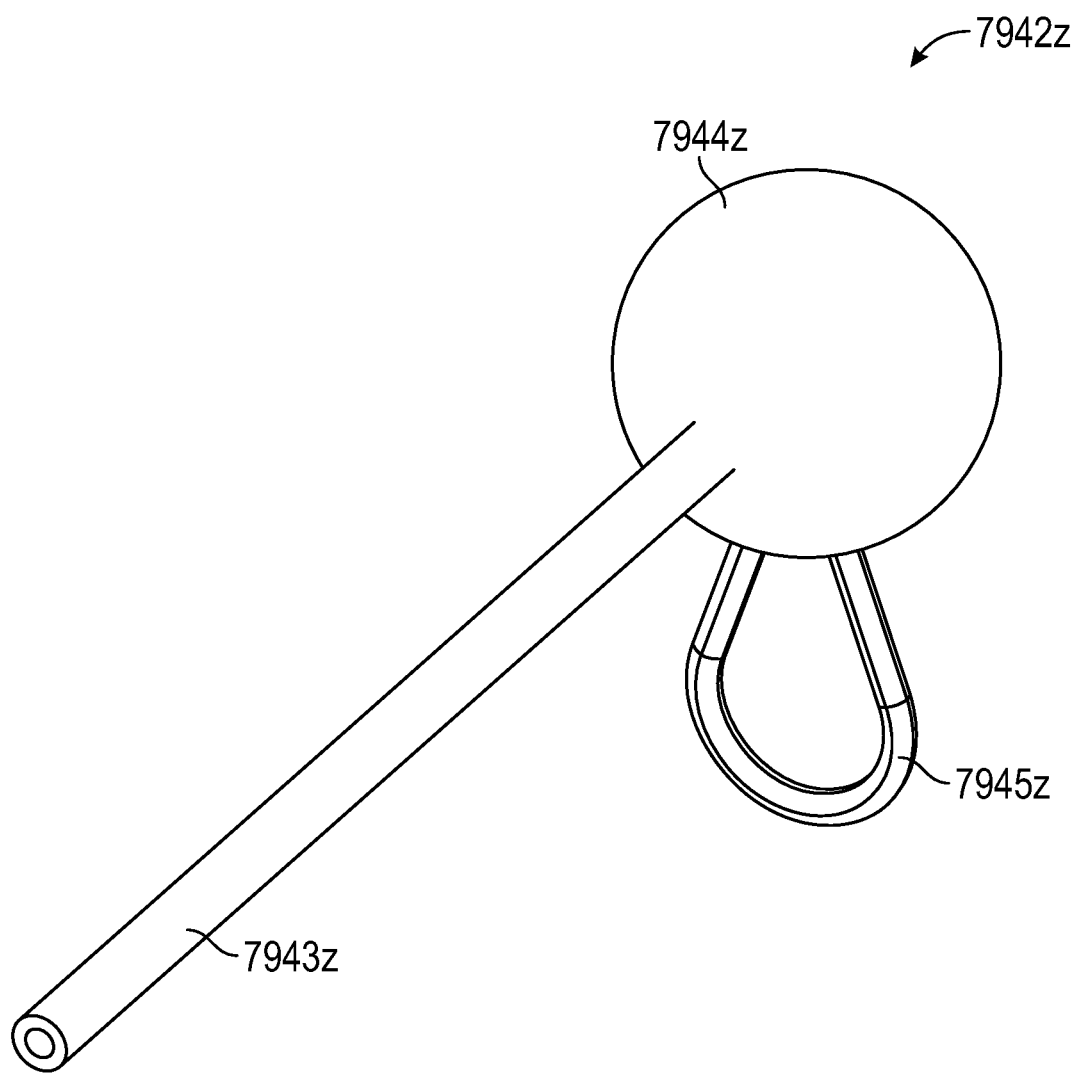
FIG. 22 shows a tool that can be used with a working channel of a device, such as a rigidizing device.

Referring to FIG. 22, in some embodiments, a tool 7942z can be specifically designed for use with a working channel of a rigidizing device as described herein. The tool 7942z can include a flexible shaft 7943z and an expandable atraumatic tip 7944z. The atraumatic tip 7944z can be an expandable balloon or a nitinol cage with foam therearound. In some embodiments, the expandable tip 7944z can be configured to be collapsed (e.g., sheathed) for delivery through the working channel and to self-expand after sheath withdrawal and placement through the working channel. The atraumatic tip 7944z can be sized, for example, so as to not fill the lumen of the gastrointestinal tract and therefore so as to not contact the walls of the gastrointestinal tract. The tool 7942z can further have a flexible loop 7945z that is attached to the tip 7944z or to the shaft 7943z. In some embodiments, the loop 7945z can be attached to an endoscopic clip (often used to close a variety of defects in the GI tract) to provide traction during an ESD procedure. By sliding the shaft 7943z longitudinally, the user can provide traction to the clip. The expandable atraumatic tip 7944z can advantageously allow the tool 7942z to be advanced freely ahead of the rigidizing device without being concerned that it will cause trauma or get caught in the GI tract. By hooking the flexible loop 7945z onto the clip, the tool 7942z can get good traction with a simple back and forth motion of the flexible shaft 7943z.

Figure 23:
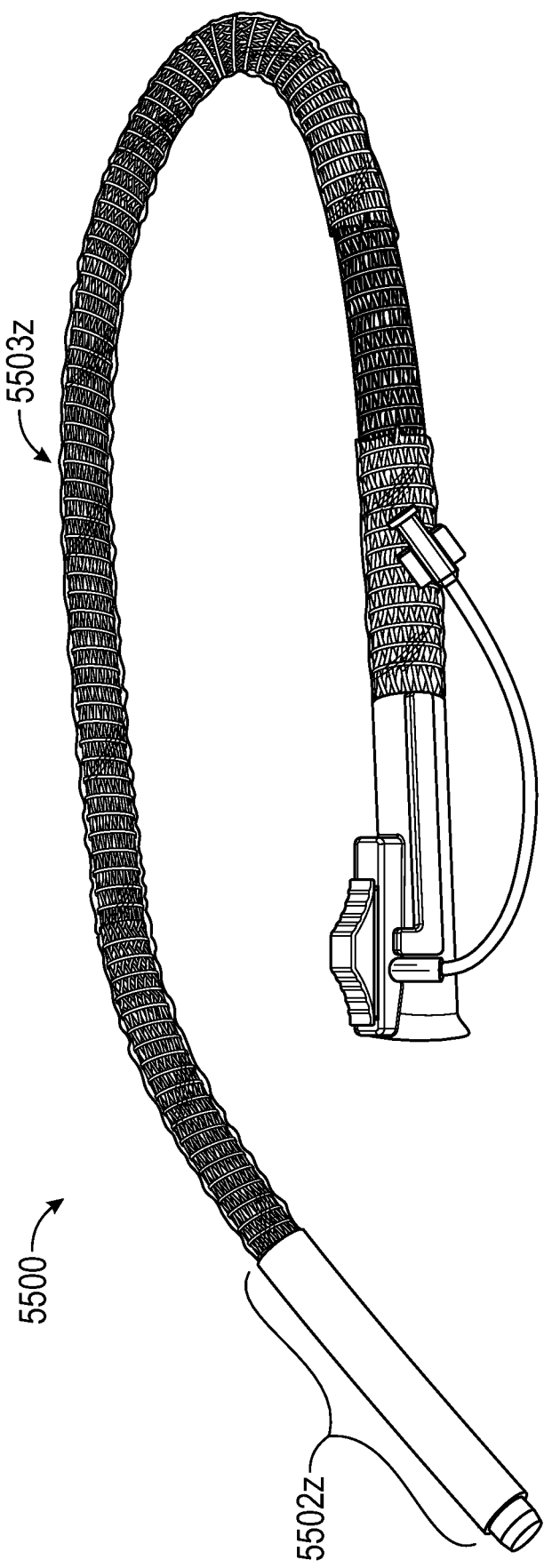
FIG. 23 shows a rigidizing device with a distal end section.

Any of the rigidizing devices described herein can have a distal end section or sections with a different design that the main elongate body of the rigidizing device. As shown in FIG. 23, for example, rigidizing device 5500 can have a main elongate body 5503z and a distal end section 5502z. Only the distal end section 5502z, only the main elongate body 5503z, or both the distal end section 5502z and the main elongate body 5503z can be rigidizing as described herein (e.g., by vacuum and/or pressure). In some embodiments, one section 5502z, 5503z is activated by pressure and the other section 5502z, 5503z is activated by vacuum. In other embodiments, both sections 5502z, 5503z are activated by pressure or vacuum, respectively.

Figure 24:
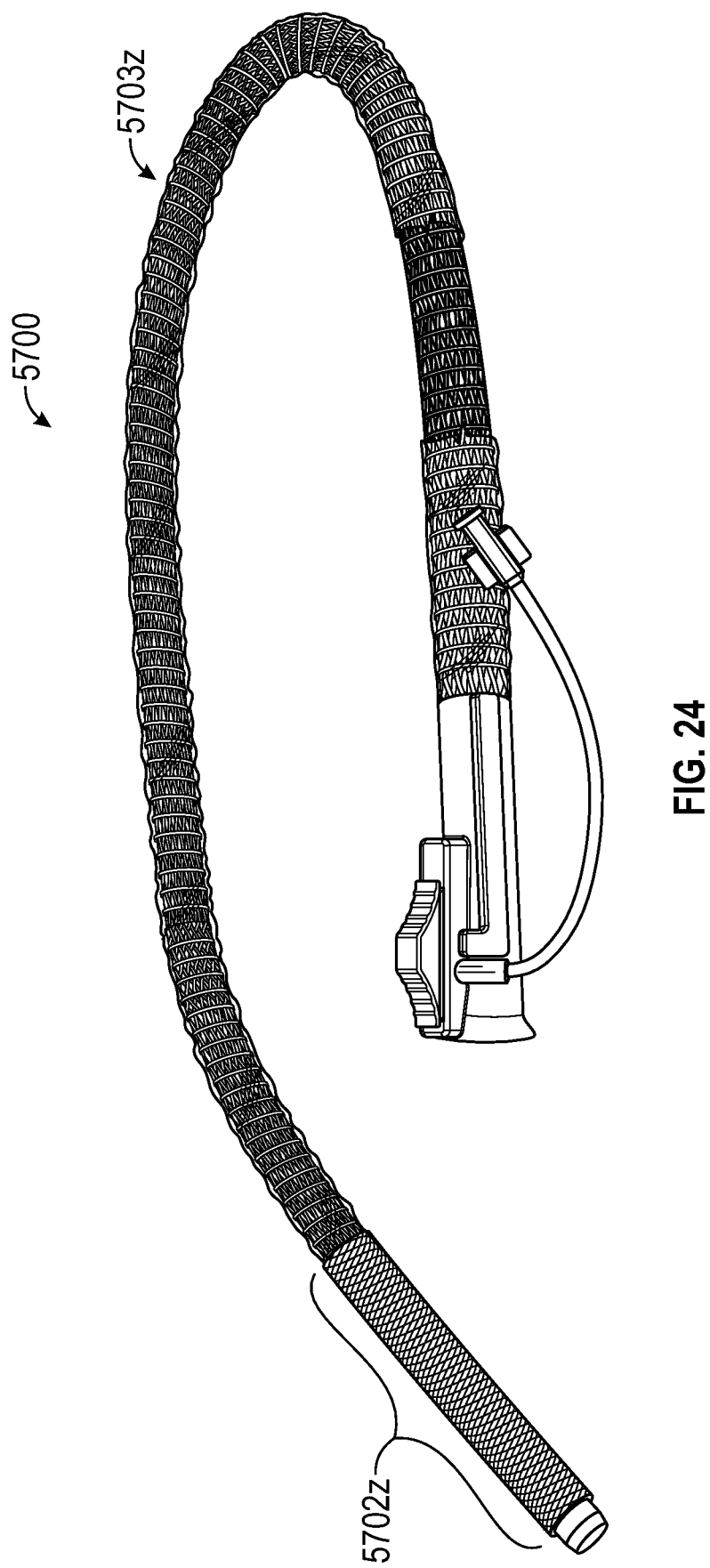
FIG. 24 shows a rigidizing device with a distal end section having a separate braid pattern from the proximal section of the device.

Referring to FIG. 24, in some embodiments, the distal section 5702z can include a rigidizing braid that differs from the braid of the main elongate section 5703z. For example, in one embodiment, the braid angle relative to the longitudinal axis in the distal end section 5702z can be greater than the braid angle of the main elongate body 5703z. For instance, the braid angle in distal section may be 40 degrees while the braid angle in the main elongate body may be 20 degrees. The braids may overlap somewhat and be joined with a flexible adhesive. These designs may give the distal end section 5702z more bending flexibility in a non-rigidized state than the main elongate section 5703z. Having a more flexible distal tip can, for example, advantageously prevent buckling and drag at the tip (caused by fixing the braid ends) and/or can advantageously provide flexibility during navigation through a body lumen to prevent trauma to the anatomy. In another embodiment, the braid angle relative to the longitudinal axis in the distal end section 5702z can be less than the braid angle of the main elongate body 5703z. This may give distal end section 5702z more stiffness in the rigidized state relative to the main elongate body 5703z. Having more stiffness in the distal end section 5702z can, for example, advantageously provide a stable platform for movement or delivery of a medical device through the central lumen and out the distal end of the rigidizing device 5700.

Figure 25:
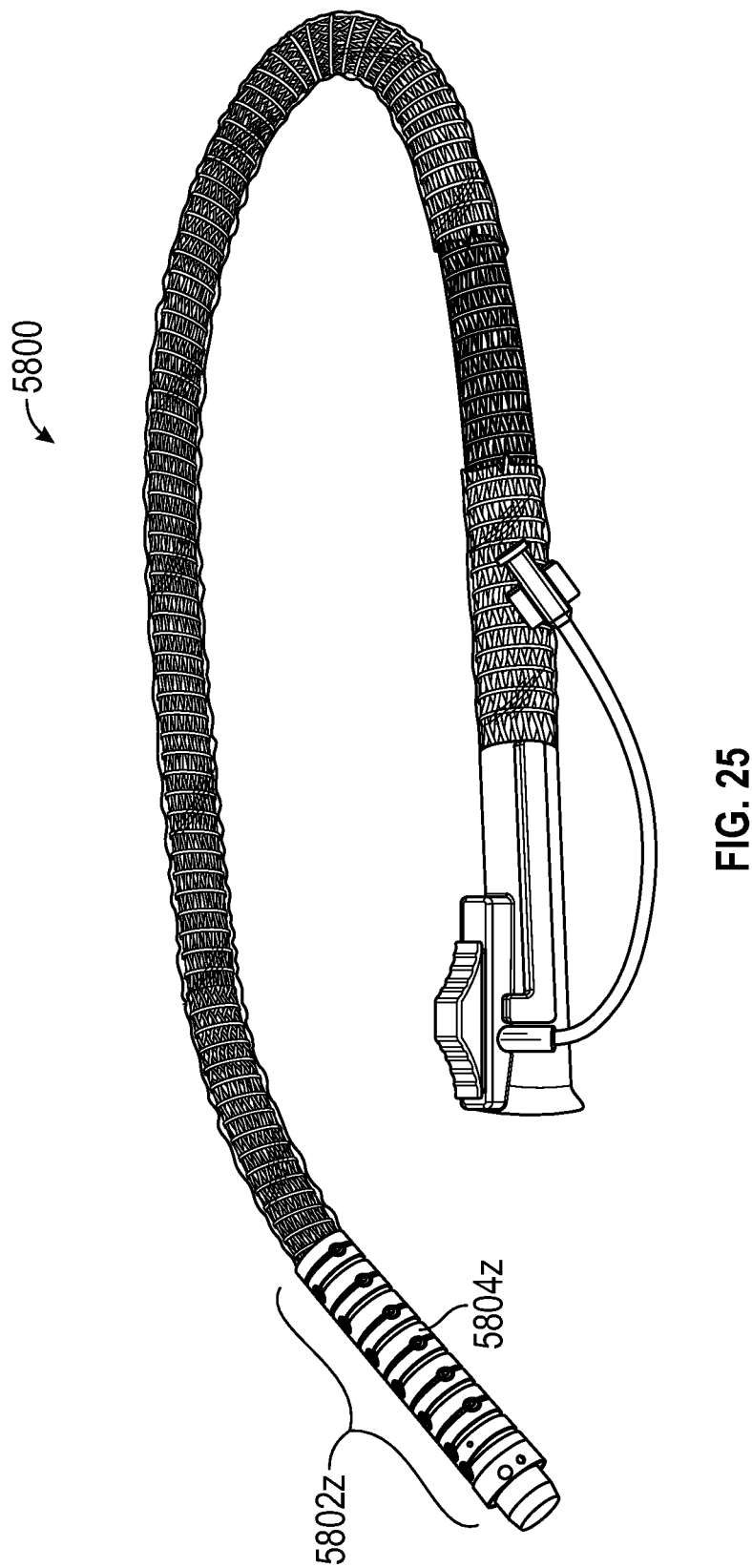
FIG. 25 shows a rigidizing device with a distal end section having a plurality of passive linkages.

Referring to FIG. 25, in some embodiments, the distal end section 5802z can include a plurality of linkages 5804z that are passively activated. The linkages 5804z can be connected together at one or more pivot points and can advantageously provide deterministic bending (i.e., bending in a specific and predetermined direction). Additionally, the linkages 5804z can advantageously provide torsional rigidity to the distal end section 5802z while providing high flexibility for bending. The linkages 5804z can be activated passively, e.g., via flexing as the device 5800 is moved through the anatomy. The distal end section 5802z may, for example, include 1-100 linkages 5804z, such as 1, 2, 4, 6, 8, 10, 16, 20, 30, or 40 links 5504z. In some embodiments, the linkages 5804z can be formed by passively cut flexures, such as laser cut tubes or stents.

Figure 26:
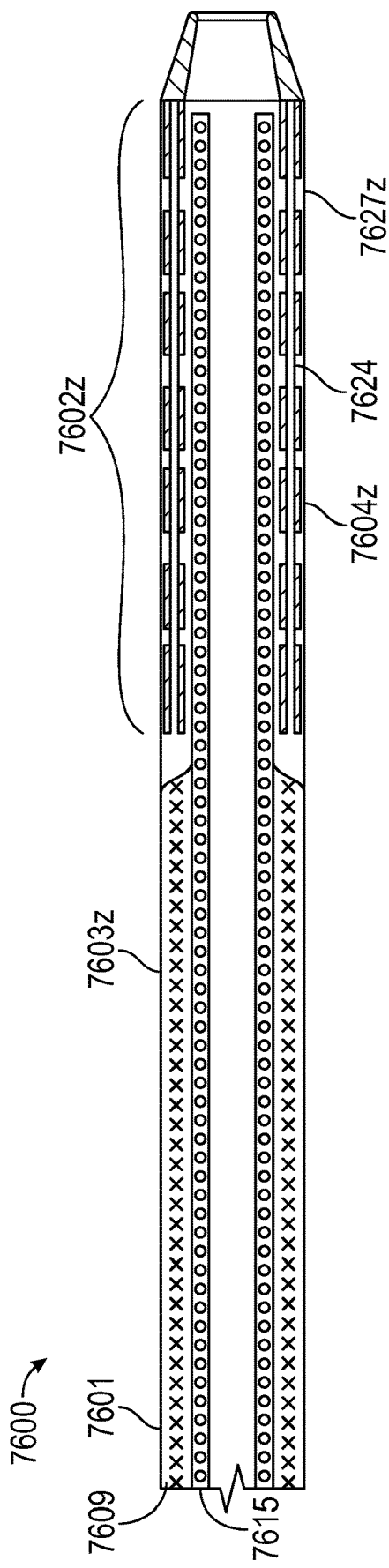
FIG. 26 shows a rigidizing device with a distal end section having a plurality of actively controlled linkages.
Figure 27A:
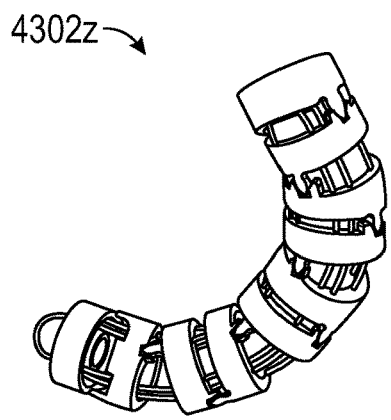
FIGS. 27A-27E shows a plurality of actively controlled linkages.
Figure 27B:
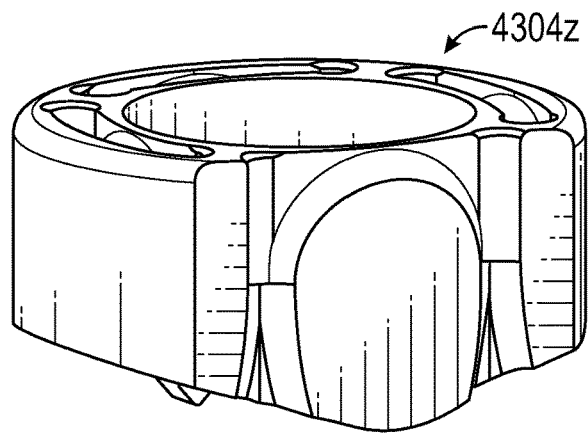
Figure 27C:
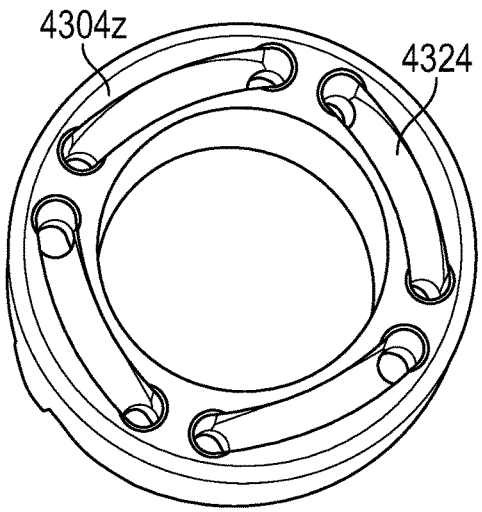
Figure 27D:
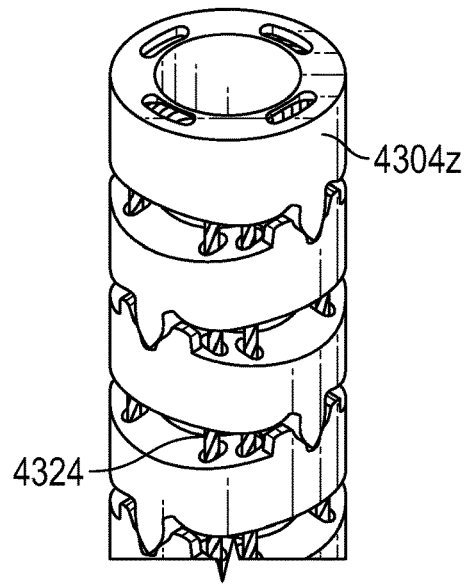
Figure 27E:
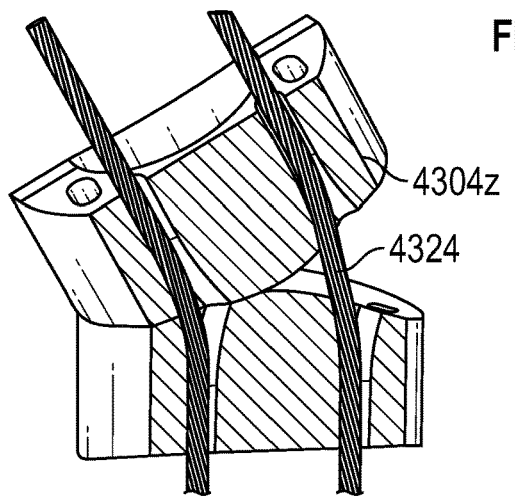

Referring to FIG. 26, in other embodiments, the distal end section 7602z can include a plurality of linkages 7604z that are actively controlled, such as via cables 7624, for steering of the rigidizing device 7600. The device 7600 is similar to device 5800 except that it includes cables 7624 configured to control movement of the device. While the passage of the cables 7624 through the rigidizing elongate body 7603z (i.e., with outer wall 7601, braid layer 7609, and inner layer 7615) is not shown in FIG. 26, the cables 7624 can extend therethrough in any manner as described elsewhere herein. In some embodiments, one or more layers of the rigidizing elongate body 7603z can continue into the distal end section 7602z. For example, and as shown in FIG. 26, the inner layer 7615 can continue into the distal end section 7602z, e.g., can be located radially inwards of the linkages 7604z. Similarly, any of the additional layers from the rigidizing proximal section (e.g., the braid layer 7609 or the outer layer 7601 may be continued into the distal end section 7602z and/or be positioned radially inwards of the linkages 7604z). In other embodiments, none of the layers of the rigidizing elongate body 7603z continue into the distal end section 7602z. The linkages 7604z (and any linkages described herein) can include a covering 7627z thereover. The covering 7627z can advantageously make the distal end section 7602z atraumatic and/or smooth. The covering 7627z can be a film, such as expanded PTFE. Expanded PTFE can advantageously provide a smooth, low friction surface with low resistance to bending but high resistance to buckling.

FIGS. 27A-E show another exemplary distal end section 4302z that includes a plurality of linkages 4304z that are actively controlled, such as via cables 4324, for steering of the rigidizing device. In some embodiments, the pivots for the linkages 4304z can be involutes, similar to gear teeth, as shown in FIGS. 27A-E, to reduce the local contact drag. The cables 4324 can be positioned within cable guides (e.g., jackets or coil pipes) that extend the length of the rigidizing device. In some embodiments, the cables 4324 (and cable guides) can extend within the wall of the rigidizing device. The cable guides can advantageously ensure that tensile load is carried through the cable guide, rather than through the wall of the rigidizing device, so that the structure of the wall is not adversely deflected as the load is applied to the linkages 4304z. In some embodiments, the cable guides and cables 4324 can have excess length to account for bending of the rigidizing device. This excess length can, for example, be woven or curled within the wall of the rigidizing device. Further, the cables 4324 can run through apertures and/or grooves in the linkages 4304z (see, e.g., FIG. 27C) while remaining otherwise free to float within the wall (and thereby to account for bending of the rigidizing device. As the cables 4324 are activated, the linkages 4304z pivot relative to one another, thereby providing steering for the distal end section of a rigidizing device. Articulation of the linkages 4304z and cables 4324 for steering can be achieved by actuators (e.g., local motors, current-activated (heat) nitinol wires, proximal actuators (typically stainless steel, tungsten, or composites), hydraulics, and/or EAP (electroactive polymers)). Such steering mechanisms can advantageously provide increased clinical utility. Further, such steering allows the device that is positioned through the central lumen (for example, an endoscope or a guidewire) be steered towards and more easily reach the desired anatomical location.

Figure 28:
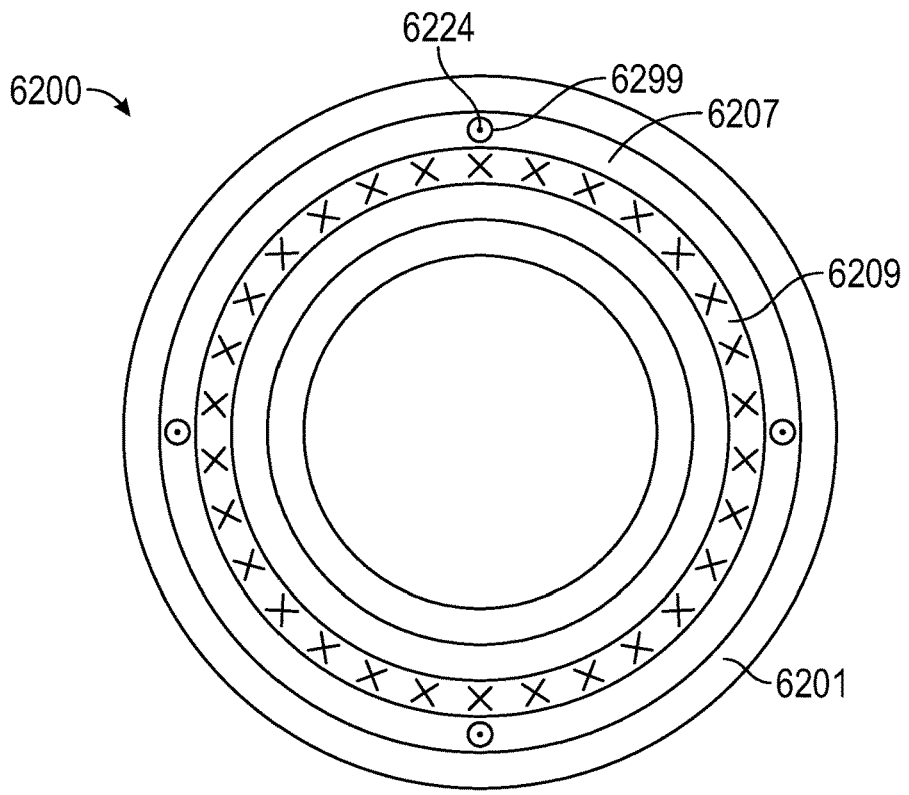
FIG. 28 shows one embodiment of a rigidizing device including cables extending within the layered wall.

When cables are used for steering the distal end section, the cables (which can be in cable guides or not) can be routed through the wall of the rigidizing devices described herein in a number of different ways. FIGS. 28-39B show exemplary configurations of rigidizing devices with cable guides (some wall layers have been omitted in FIGS. 28-39B for clarity). For example, FIG. 28 shows a rigidizing device 6200 having cables 6224 extending in cable guides 6299 within the outer radial gap layer 6207 (and thus between the braid layer 6209 and the outer layer 6201). In some embodiments, each of the cables 6224 and cable guides 6299 can be positioned approximately equidistant around the circumference (i.e., approximately 90 degrees away from neighboring cables when four cables are used). In other embodiments, one or more of the cables 6224 and cable guides 6299 can be grouped closely together (e.g., within the same quadrant) rather than spaced apart. Further, in some embodiments, the cables 6224 and/or guides 6299 can be asymmetrically positioned around the circumference of the rigidizing device 6200.

Figure 29:
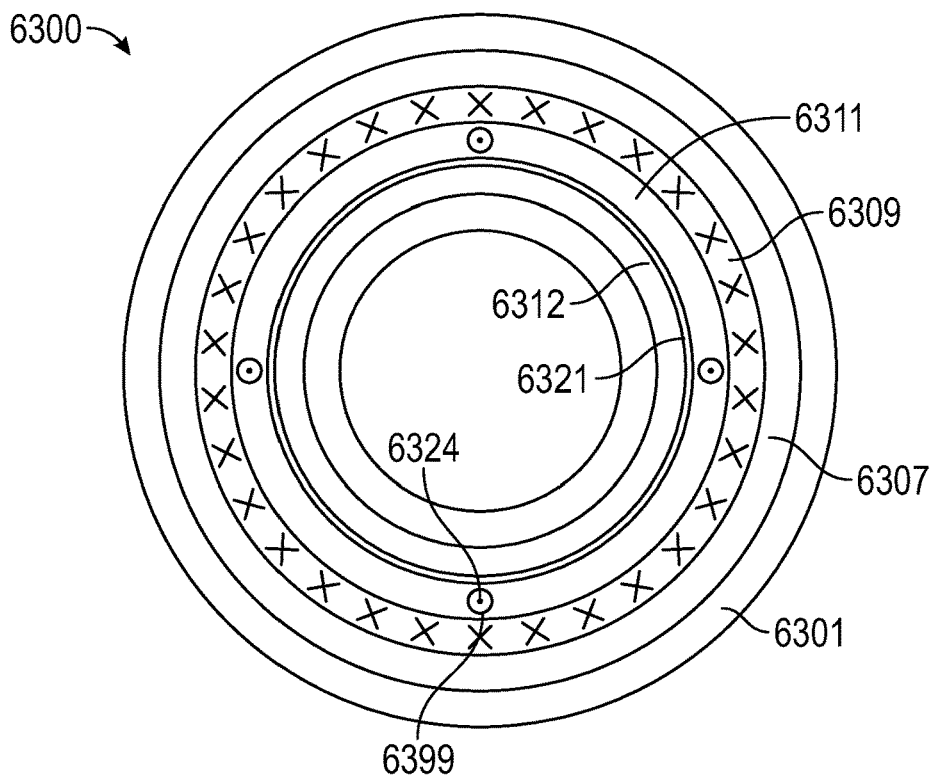
FIG. 29 shows one embodiment of a rigidizing device including cables extending within the layered wall.

FIG. 29 shows a rigidizing device 6300 in which the cables 6324 and cable guides 6399 are positioned within the inner radial gap layer 6311 (and thus between the braid layer 6309 and the inner layers of the rigidizing device, such as the bladder 6321). When, for example, pressure is supplied to pressure gap 6312, the bladder 6321 can push against the braid layer 6309, and the braid layer and correspondingly push against the outer layer 6301 without the braid layer 6309 squeezing or otherwise impacting the cables 6324. Again, the cables 6324 and cable guides can be positioned equidistant or asymmetrically about the circumference of the rigidizing device 6300.

Figure 30:
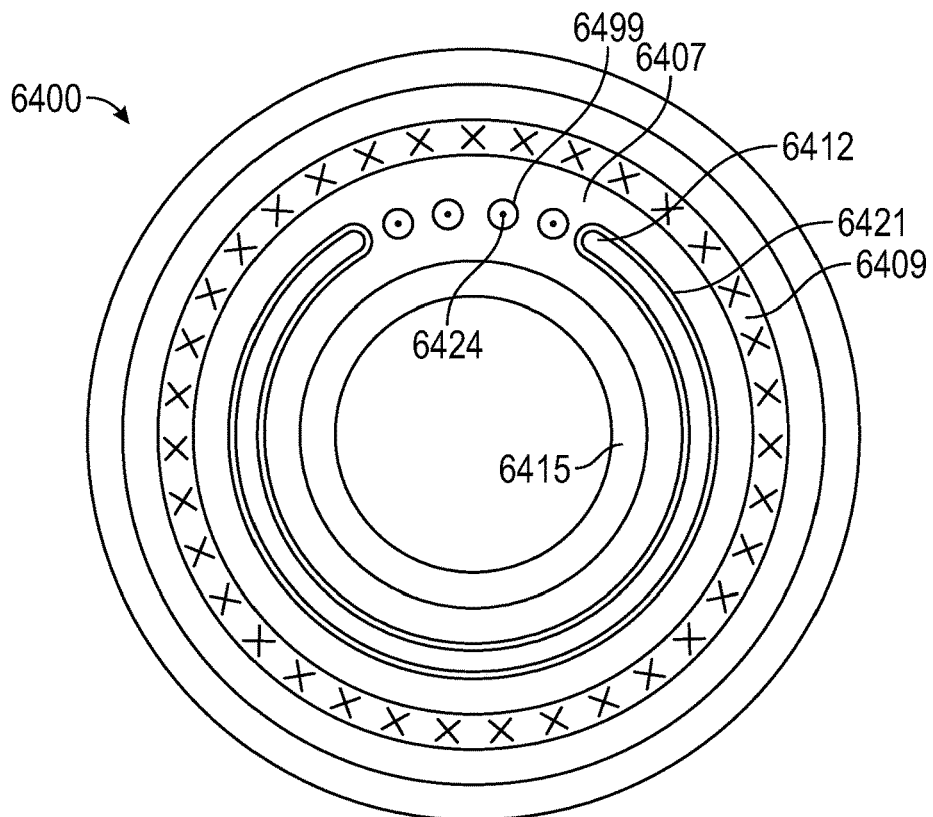
FIG. 30 shows one embodiment of a rigidizing device including cables extending within the layered wall.

Referring to FIG. 30, in some embodiments, the rigidizing device 6400 can have cables 6424 and cable guides 6499 at least partially separated from the pressurized or vacuum zone. For example, as shown in FIG. 30, a tubular bladder layer 6421 can surround the pressure gap 6412. Some or all of the cables 6424 and cable guides 6499 can be positioned in the gap 6407 between the inner layer 6415 and the braid layer 6409 and circumferentially adjacent to the tubular bladder layer 6421. Advantageously, in this configuration, the cables 6424 and cable guides 6499 can both be minimally impacted by pressurization of the bladder layer 6421 and provide substantially no additive stack height or thickness to the wall.

Figure 31:
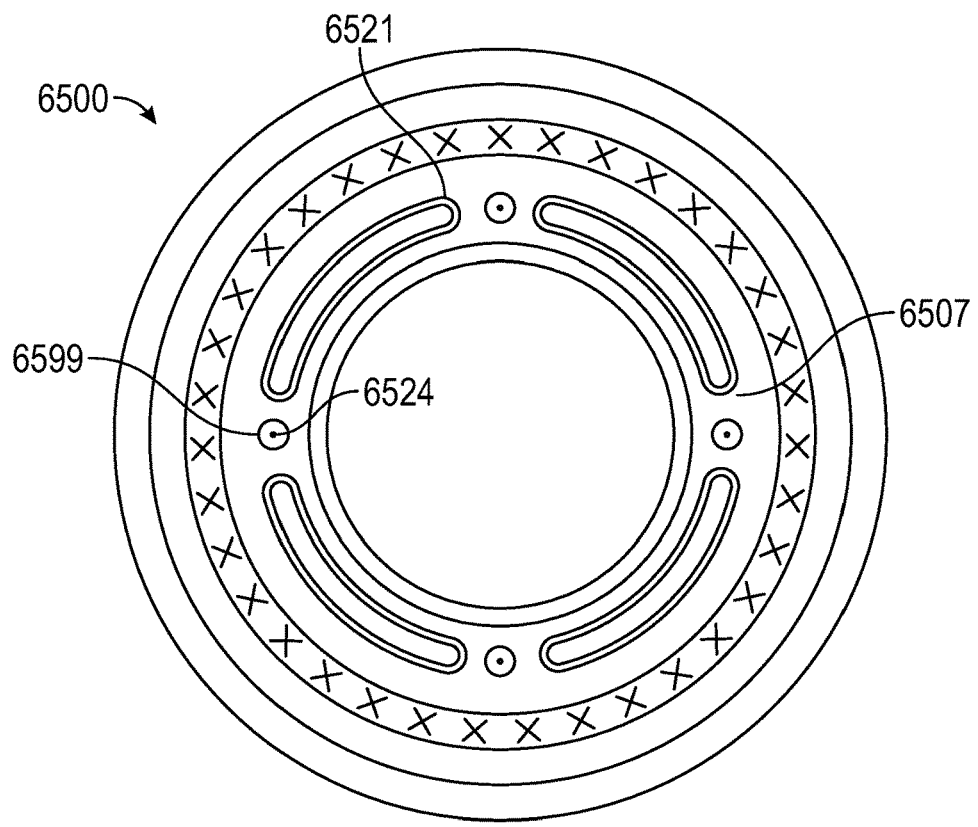
FIG. 31 shows one embodiment of a rigidizing device including cables extending within the layered wall.

Referring to FIG. 31, in some embodiments, the rigidizing device 6500 can include a plurality of tubular bladders 6521 spaced circumferentially apart such that each cable 6524 and cable guide 6599 can fit in the gap 6507 between adjacent tubular bladders 6521.

Figure 32:
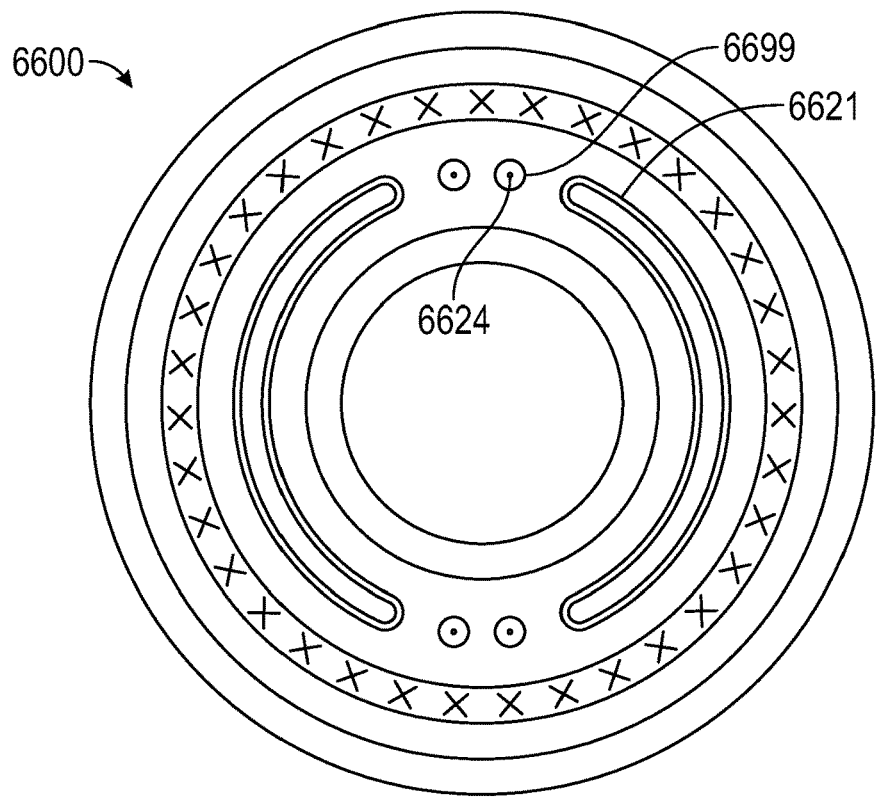
FIG. 32 shows one embodiment of a rigidizing device including cables extending within the layered wall.

Referring to FIG. 32, rigidizing device 6600 is similar to device 6500 except that cables 6624 and guides 6699 are grouped in pairs to reduce the number of tubular bladders 6621 necessary (e.g., there can be two tubular bladders 6621 and a two pair of cables 6624 and guides 6699 positioned therebetween).

Figure 33:
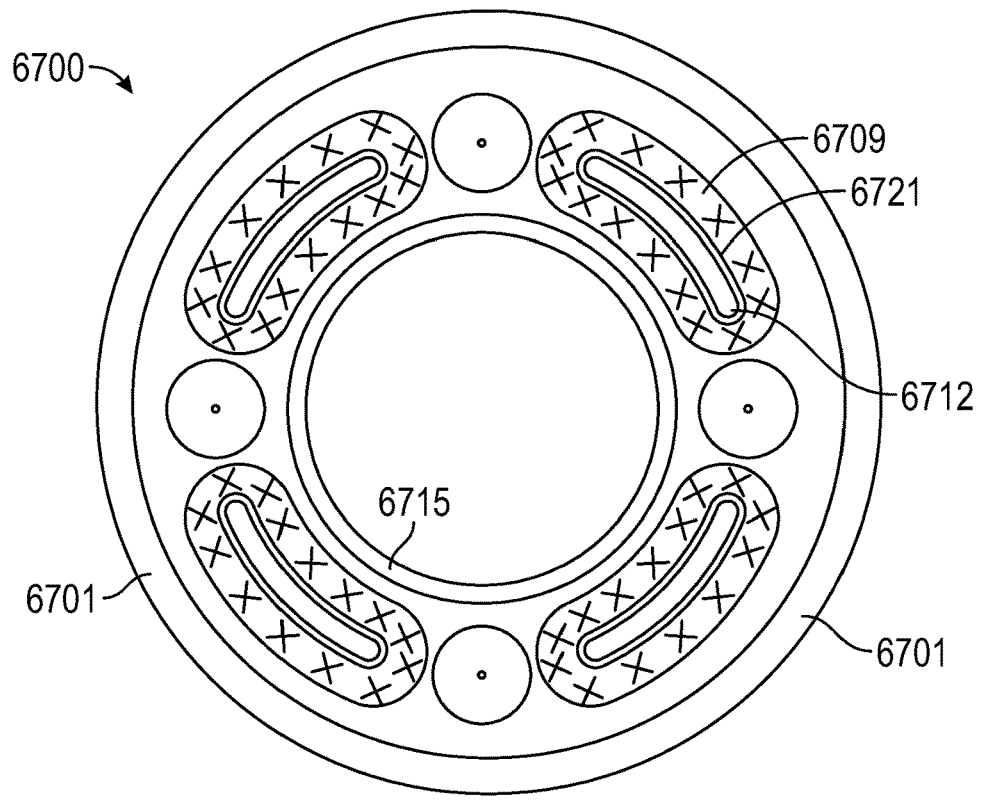
FIG. 33 shows one embodiment of a rigidizing device including cables extending within the layered wall.

Referring to FIG. 33, rigidizing device 6700 is similar to device 6500 except that each tubular bladder 6721 includes a tubular braid layer 6709 therearound (i.e., rather than having a single braid layer 6509 as with device 6500). As pressurizing medium is provided to pressure gaps 6712, the bladder 6721 can expand to press each individual tubular braid 6709, which can expand to press against the inner and outer layers 6715, 6701. Alternately, not all of the bladders can be pressurized at the same time (for instance, just 1 or 2) such that the device is only stiffened partway around the circumference. This may create stiffness along only a portion of the device, while still enabling flexibility amongst the other portion, which may create preferential motion should the device be imparted with a deflection load.

Figure 34:
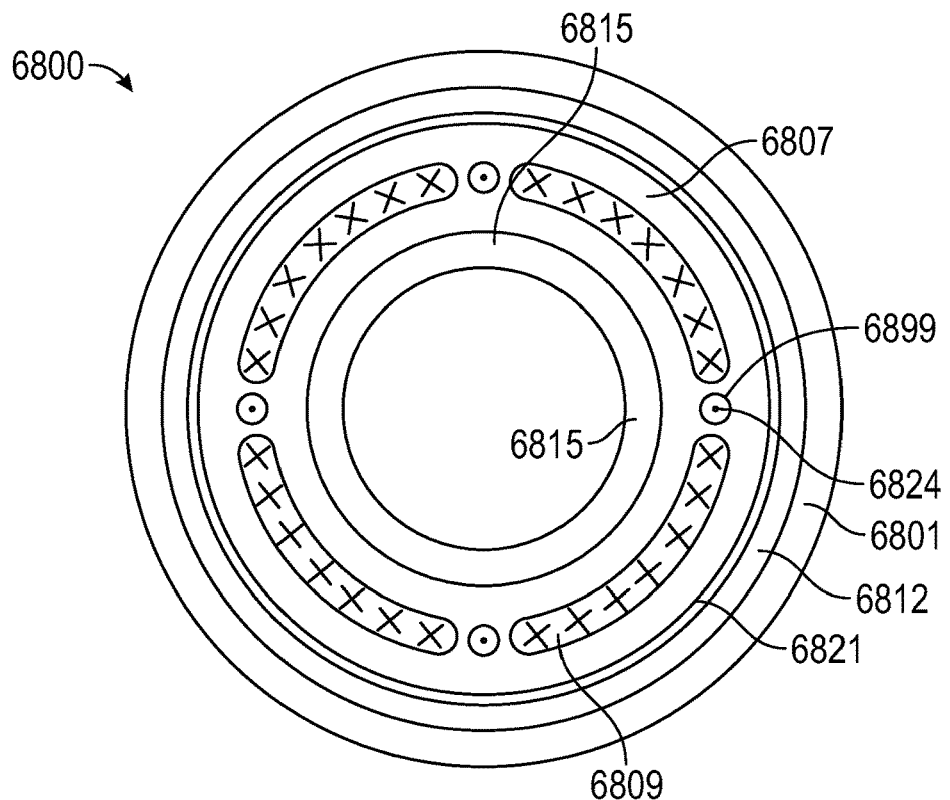
FIG. 34 shows one embodiment of a rigidizing device including cables extending within the layered wall.

Referring to FIG. 34, in some embodiments, a rigidizing device 6800 can include strips of braid layer 6809 (i.e., flat braid rather than tubular braid). Each strip of braid layer 6809 and each cable 6824 and cable guide 6899 can be positioned in the radial gap 6807. Further, the strips of braid layer 6809 can alternate with the cables 6824/6899 so as to minimize the thickness of the wall of the rigidizing device 6800. The bladder 6821 can be positioned radially outwards of the strips of braid layer 6809 and cables 6824/guides 6899. When pressure medium is supplied to the pressure gap 6812, the bladder 6821 can push the strips of braid layer 6809 radially inwards against the innermost layer 6815 to rigidize the device 6800. In other embodiments, the bladder 6821 can be radially inwards of the strips of braid layer 6809 (and cables 6824/guides 6899) and be configured to push the strips of braid layer 6809 against the outer layer 6801.

Figure 35:
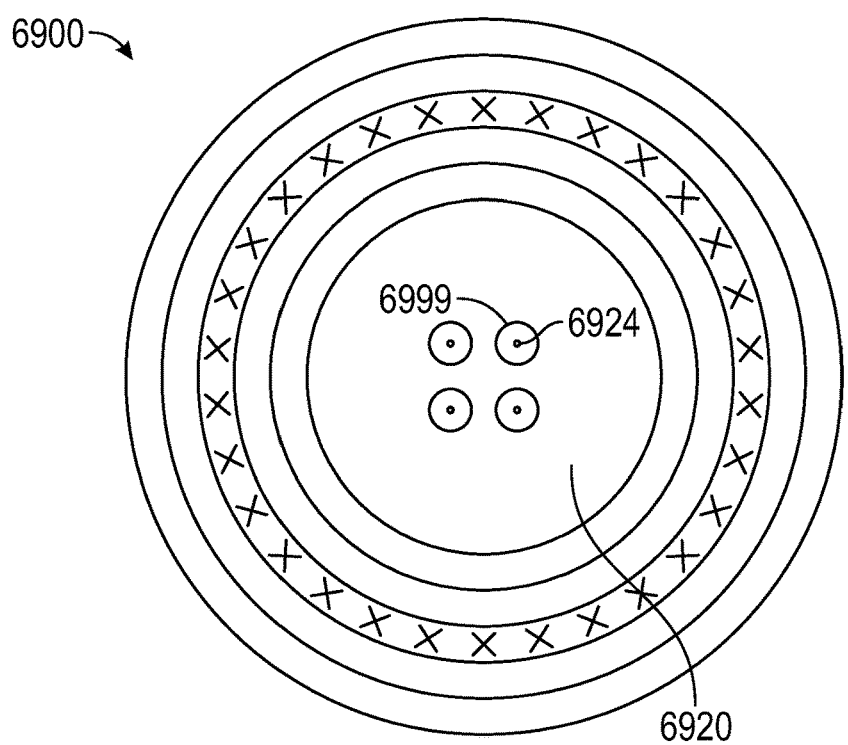
FIG. 35 shows a rigidizing device including cables extending down the central lumen.

In some embodiments, referring to FIG. 35, the cables 6924 and cable guides 6999 can be positioned so as to extend down the central lumen 6920 of the rigidizing device 6900.

Figure 36:
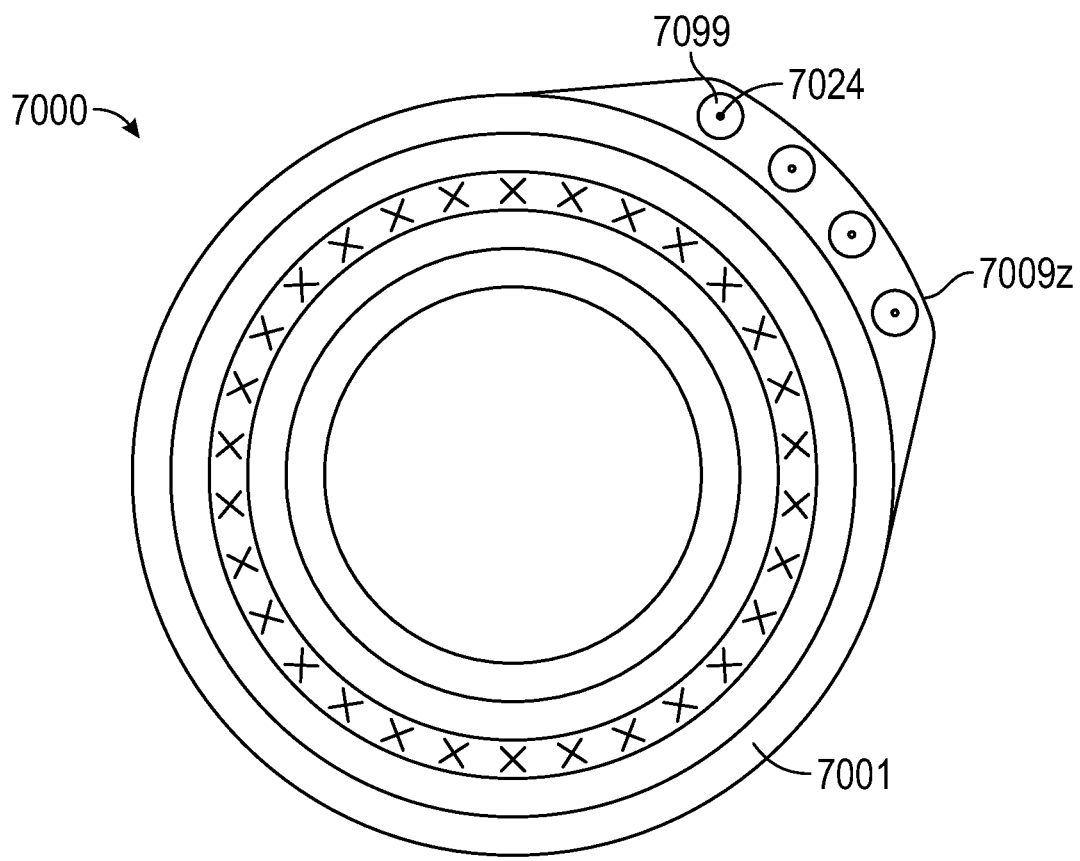
FIG. 36 shows an embodiment of rigidizing device including a cable spiraled therearound.

In some embodiments, referring to FIG. 36, the cables 7024 and cable guides 7099 can be positioned radially outwards of the outer layer 7001. The cables 7024 and guides 7099 can, for example, be positioned in a sheath 7009z that can extend only over the cables 7024 or that can fully encompass the outer layer 7001. The guides 7099 can be only minimally constrained within the sheath 7009z so as to freely bend during movement of the device 7000 (e.g., so as to curl or extend to full length depending on whether the guides 7099 are positioned on the inside or outside of the cure of the rigidizing device 7000 as it bends).

Figure 37:
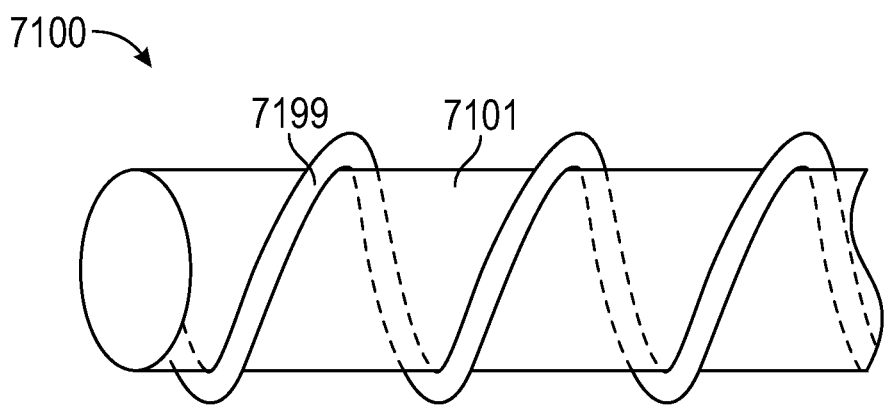
FIG. 37 shows an embodiment of a rigidizing device with a cable spiraled therearound.

Referring to FIG. 37, in some embodiments, a cable guide 7199 (with one or more cables therein) can be spiraled around the outside of the outer layer 7101 of the rigidizing device 7100. Additional cable guides can likewise be spiraled therearound. In some embodiments, the cable guide 7199 can be spiraled around other layers of the rigidizing device 7100, such as around the inner layer.

Figure 38A:
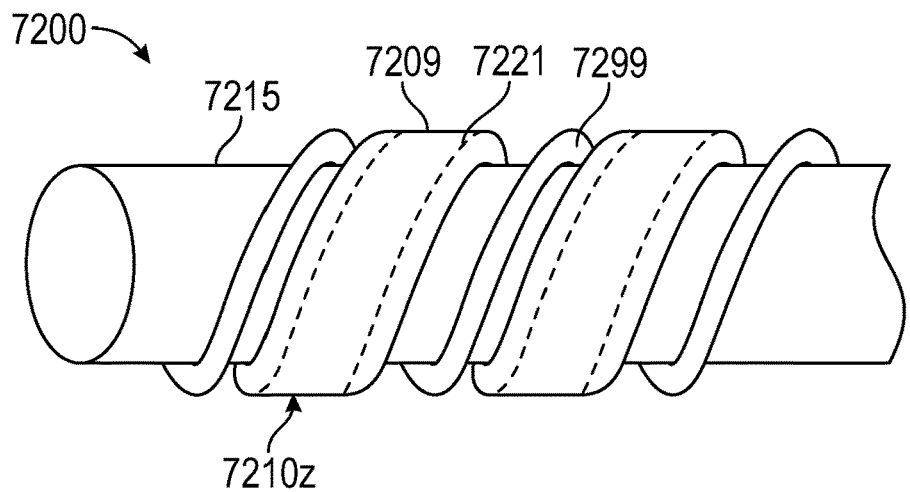
FIGS. 38A-38B show an embodiment of a rigidizing device with a cable spiraled therearound.
Figure 38B:
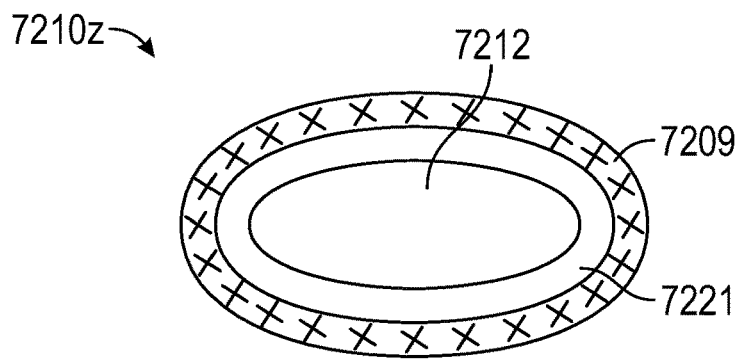

Referring to FIGS. 38A-38B, in some embodiments, a cable guide 7299 (with one or more cables therein) and a tubular element 7210z can be alternately spiraled around the inner layer 7215 (i.e., such that the cable guide 7299 and the tubular element 7210z form approximately a single layer down the length of the rigidizing device 7200. The tubular element 7210z can include an outer tubular braid 7209 with an inner tubular bladder 7221. As pressurizing medium is provided to pressure gap 7212, the bladder 7221 can expand to press outwards on the tubular braid 7209, which can push outwards on the outer layer (not shown for clarity).

Figure 39A:
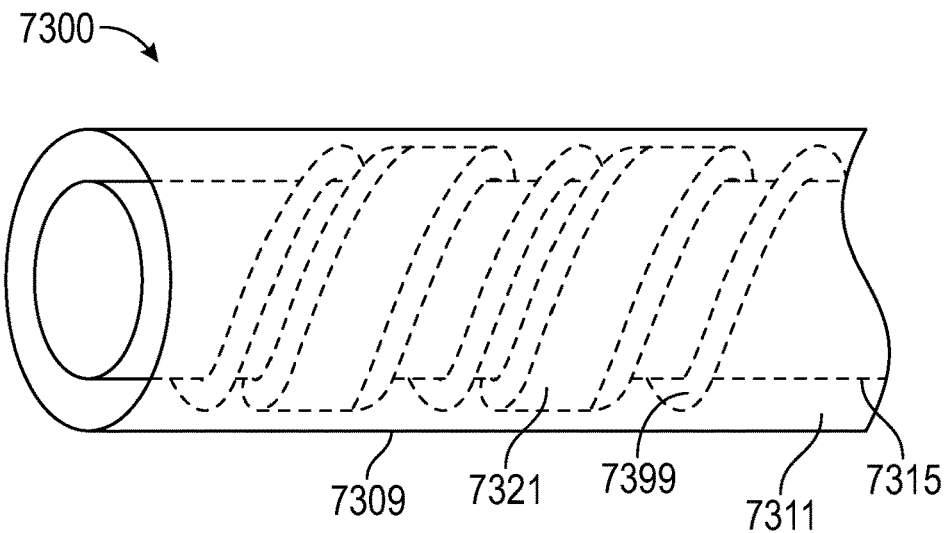
FIGS. 39A-39B show a rigidizing device with a cable spiraled therein.
Figure 39B:
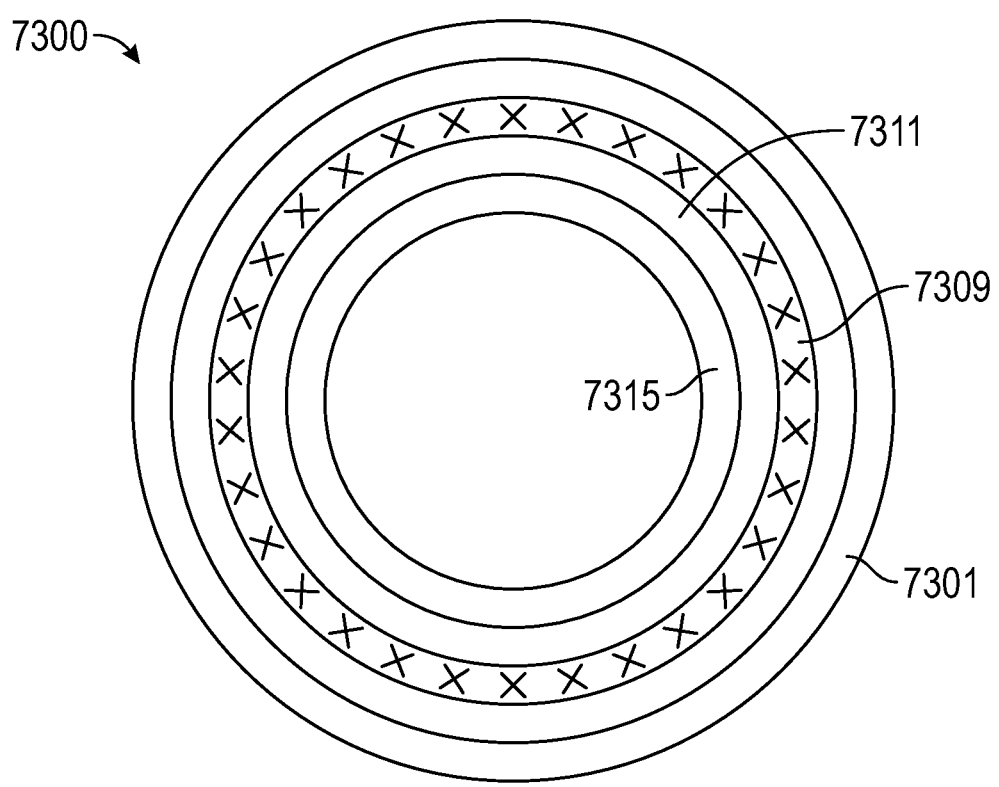
Figure 40A:
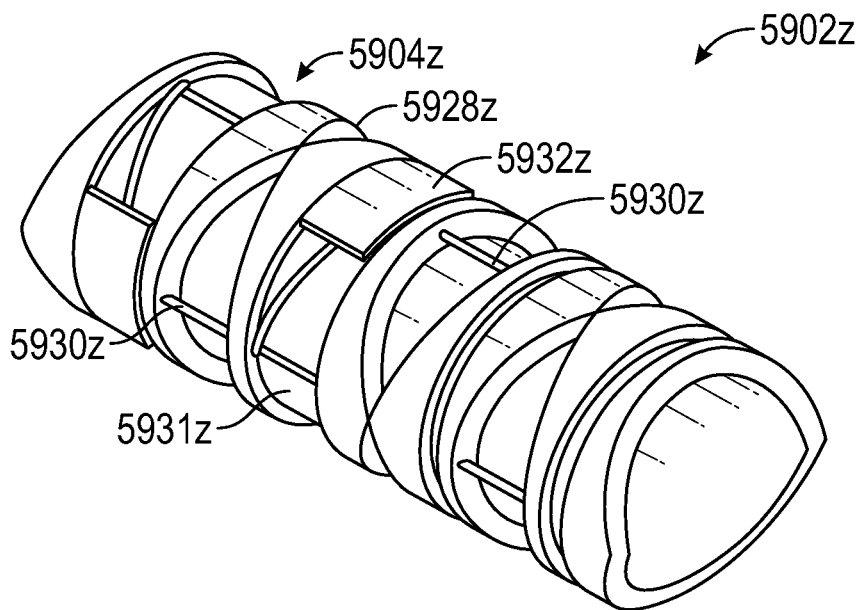
FIGS. 40A-40D show exemplary linkages for a distal end section.
Figure 40B:
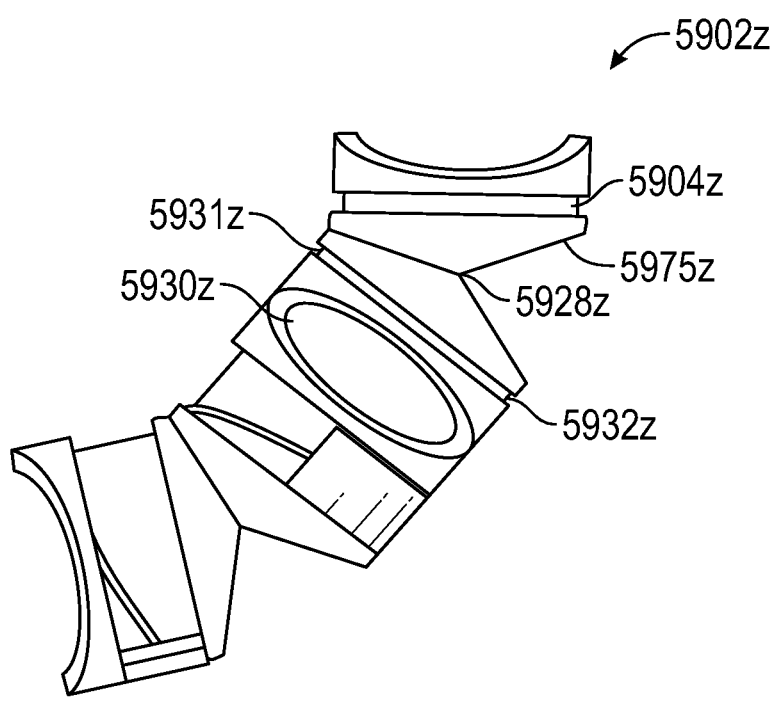
Figure 40C:
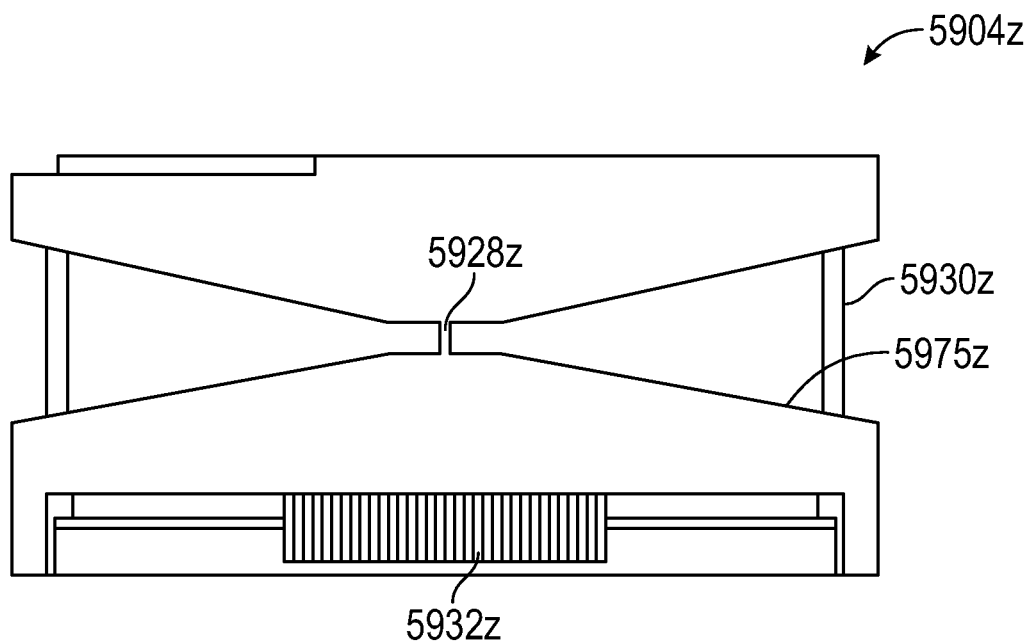
Figure 40D:
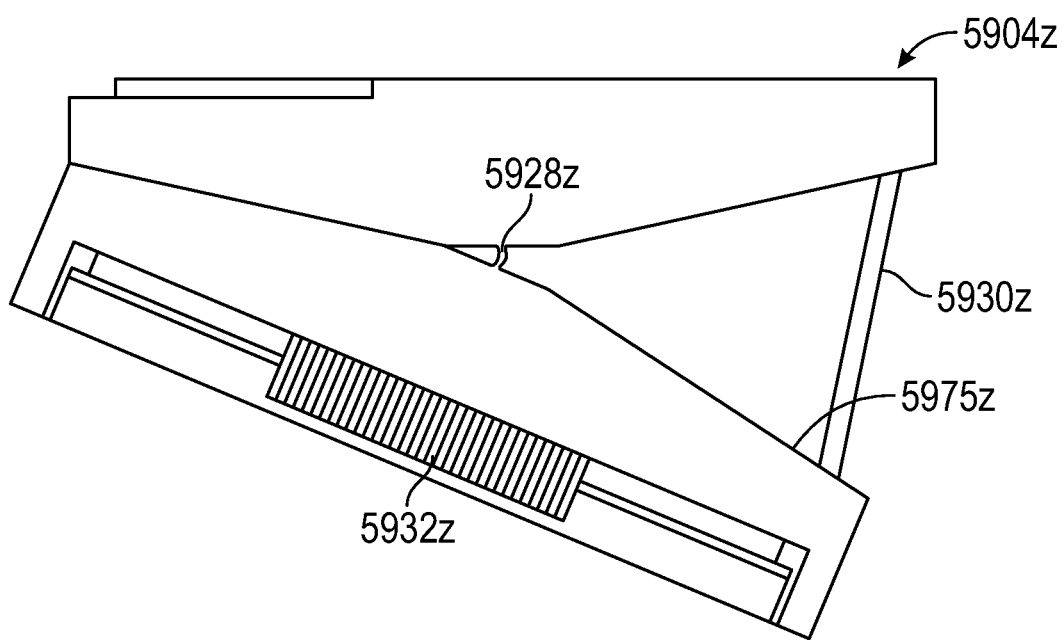

Referring to FIGS. 39A-39B, a rigidizing device 7300 can be similar to device 7200 except that only the cable guide 7399 and a tubular bladder 7321 can be spiraled around the inner layer 7315 within gap 7311 (note that cable guide 7399 and tubular bladder 7321 are not shown in FIG. 39B for clarity). A braid layer 7309 can then be wrapped radially around the gap 7311. When a pressure medium is supplied to the tubular bladder 7321, the bladder 7321 can expand to push the braid layer 7309 against the outer layer 7301 (not shown in FIG. 39A for clarity).

It should be understood that the cable configurations described with respect to FIGS. 28-39B can be used with any number of cables (such as 1, 2, 3, 4, 5, 6, 8, 12, or 16 cables). Further, the cables can be used to steer any tip or a rigidizing device and/or to steer any distal end section (e.g., sections with linkages or different braid angles). Further, the cable guides described herein can be round with round cables, flat, rectangular with flat ribbon tensile elements, or a combination thereof. Further, in some embodiments, other steering elements can be used in addition to or in place of the cables (e.g., pneumatics, hydraulics, shape memory alloys, EAP (electro-active polymers), or motors). Intentionally separating the elements required for steering and the elements required for rigidization can enable the structure to exhibit a continuously high rigidization performance as a function of length, even if the forces available for steering are demonstrably lower than the forces required for nested system rigidization.

Additionally, it should be understood that the cable configurations and placement described with respect to FIGS. 28-39B can similarly be used for the placement of working channels or other lumens (for example, inflation lumens for balloons) within the rigidizing devices.

Referring to FIGS. 40A-40D, in some embodiments, the distal end section 5902z may include a series of linkages 5904z (either active or passive) that are specifically designed to rigidize via the application of pressure or vacuum. For example, the linkages 5904z can be connected to each other through a pivot point 5928z (which can, for example, be wire pivot points). Each pivot point 5928z can allow bending with one degree of freedom between linkages. Further, the linkages 5904z can be arranged in alternating fashion with every other linkage connected with the pivot points 5928z positioned 90 degrees away from the previous linkage. Each linkage 5904z can have cut-outs 5975z at the proximal and distal ends thereof extending from the pivot-points 5928z to as to allow bending of the linkages 5904z relative to one another. Further, each linkage 5904z can be connected to a neighboring linkage 5904z by a respective tensile member 5930z. The tensile member 5930z can be fixed relative to one linkage and at least partially movable within a track 5931z of the neighboring linkage (e.g., within track 5931z of linkage 5904z). Movement of the linkages 5904z allows the tensile member 5930z to lengthen when on the outside of the curve and shorten when on the inside of the curve during bending of the rigidizing device. Further, the proximal end section 5902z can include two sliding clamps 5932z attached to tensile member 5930z along opposite axis (i.e., 90 degrees away from one another). The two tensile members 5930z extend from each of the sliding clamps 5932z to the distal-most end of the distal section 5902z. As the distal end section 5902z is bent, one cable element of each sliding clamp 5932z gets shorter and one cable element of each sliding clamp 5932z gets longer, resulting in circumferential movement of the sliding clamps 5932z. When vacuum or pressure is applied, the outer sleeve can compress the sliding clamps 5932z to the track 5931z surface. The sliding clamps 5932Z and the track 5931z surface may be smooth, rough or have teeth. This compression force may case the sliding clamps 5932Z to lock in place with respect to the links 5904z, thereby fixing the position of tensile members 5930z and making the distal end section stiffer in its current shape. Additional rigidizing linkages and/or engages are described in International Patent Application No. PCT/US2018/042946, filed Jul. 19, 2018, titled "DYNAMICALLY RIGIDIZING OVERTUBE," now PCT Publication No. WO 2019/018682, the entirety of which is incorporated by reference herein.

Referring to FIGS. 41A-41B, in some embodiments, the distal end section 6002z can include linkages 6004z (either active or passive) that are placed over a section 6007z that rigidizes via vacuum or pressure as otherwise described herein (i.e., over a rigidizing wall with inner layer 6015, pressure gap 6012, bladder 6021, braid layer 6009, and outer layer 6001). Placing the linkages 6004z over the rigidizing section can provide the advantages of a linked system (e.g., flexibility in bending and torsional stiffness) together with a steering or deterministic bending tip that can be rigidized when the remaining structure is rigidized. Alternatively, linkages can be positioned radially inwards of a rigidizing section. As shown in FIG. 41B, cables 6024 in cable guides 6099 can extend through linkages 6004z to provide optional active steering of the linkages 6004z.

Referring to FIG. 42A, in some embodiments, the distal end section 6102z can include a series of linkages 6104z (either active or passive) sealed within a thin layer of material 6108z (e.g., made of an elastomer, PVC, or PEEK). The linkages 6104z and thin layer of material 6108z can, for example, be positioned over (i.e., radially outwards from) the braid layer 6109 and can be continuous with the coil wound tube 6101 of the main elongate body 6103z. In this embodiment, when pressure or vacuum is supplied to the gap 6112, the braid layer 6109 can be compressed by the bladder 6121 against the coil wound tube 6101 in the main elongate body 6103z and against the linkage sheath 6108z in the distal end section 6102z to rigidize. The linkage sheath 6108z is supported by the linkages 6104z such that it can resist the pressure of the braid expanding. This design advantageously provides both rigidization and linkages while maintaining a low wall thickness and/or diameter. The distal end section 6102z can, for example, include cables 6124 extending within cable guides to activate the linkages 6104z.

In some embodiments, the rigidizing structure can be steered from within the wall of the rigidizing structure and optionally without any links. FIG. 42B shows a cross section of a pressure rigidizing structure 2500 where a cable guide 2599 is placed in the pressure gap 2512 and can be attached to the inner layer 2515. The cable 2524 extends from the cable guide 2599 into the distal end section 2502z and is anchored to the inner layer 2515 at anchor point 2568. Pulling on the cable 2524 will cause the distal end section 2502z (distal to the end of the cable guide 2599) to deflect. In some embodiments, the cable guide 2599 can be omitted, and the rigidizing device 2500 will bend along its entire length when the cable 2524 is pulled. In some embodiments, the device 2500 can be built with a distal end section 2502z that has a lower bending stiffness than the proximal elongate body 2503z (as described herein, for instance by varying the braid angle or using a more flexible reinforcement element in either the inner or outer layer) so that the distal end section 2502z bends more than the body 2503z. The cable guide 2599 and cables 2524 can be located between the bladder 2521 and the braid 2509 or between the braid 2509 and outer layer 2501. The cable guide 2599 and/or the cables 2524 can be attached to the outer wall 2501. Alternately, in a vacuum rigidized structure, the cable guide 2599 and cables 2524 can be located between the inner layer and the braid or between the braid and the outer layer. In some embodiments, the bladder 2521 and the braid of the braid layer 2509 can be omitted in the section where the cable 2524 is not inside the cable guide 2599, leaving only inner and outer layers 2515, 2501, or just an outer layer or just an inner layer.

Figure 43C:
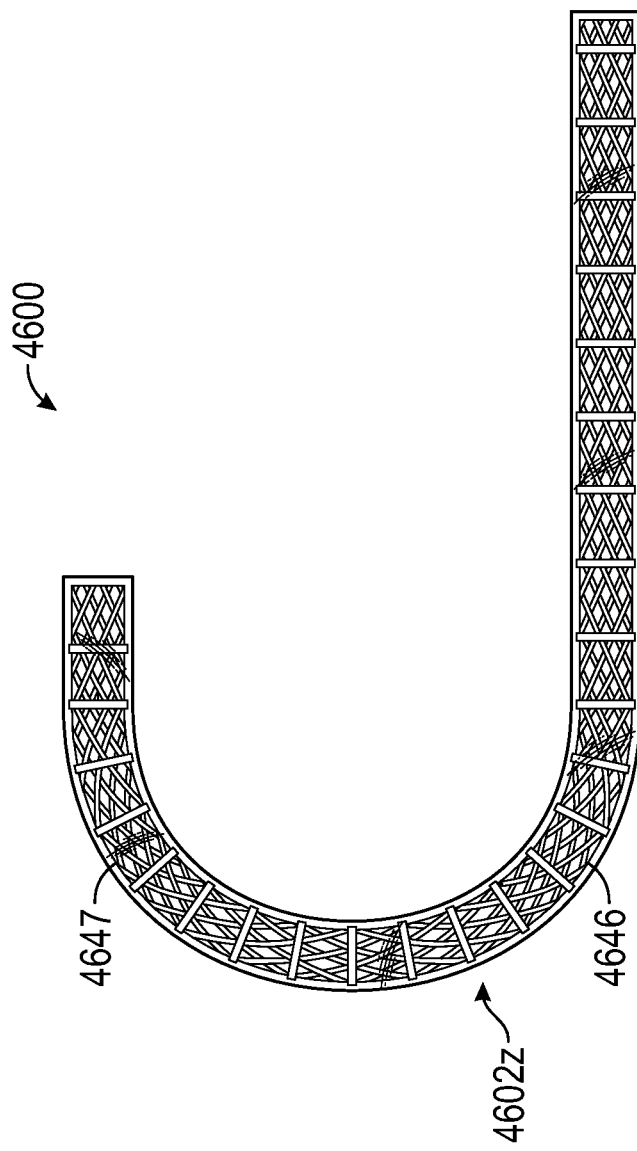

Referring to FIGS. 43A-43C, in some embodiments, the distal end section 4602z can include active deflection segment 4646. The deflection segment 4646 can include a ribbon or spine extending therethrough that provides bending only in one or more predetermined directions upon activation. The active deflection segment 4646 can be deflected, for example, using one or more cables, bladders, pullwires, and/or introduction of a guide wire, to a predetermined shape. The active deflection segment 4646 can thus provide bending of the rigidizing device 4600 at a fixed location and in a fixed direction. In some embodiments, markers (e.g., radiopaque markers) can be positioned within or proximate to the active deflection segment 4646 to indicate where the bend will occur and/or in which direction the active deflection segment 4646 will bend. Bending of the rigidizing device 4600 using the active deflection segment 4646 can be advantageous, for example, where bending is required without assistance from the anatomy (i.e., when the anatomical path for the rigidizing device 4600 is not predefined or constrained by the anatomy). For example, such bending might be useful to create a bend across the open or relatively unconstrained space between the inferior vena cava (IVC) and the atrial septum during transseptal procedures in the mitral valve. The active bending segment 4646 can be configured to be rigidized (i.e., via pressure or vacuum) as described herein to fix or lock the active deflection segment 4646 in the bent configuration. Further, the rigidizing device 4600 can include a steerable distal section 4647 (e.g., with linkages) in addition to the active deflection segment 4646. The steerable distal section 4647 can be used to point or orient the distal end of the rigidizing device 4646 in the desired direction (e.g., via cables and/or along four axes), as described elsewhere herein.

Figure 44A:
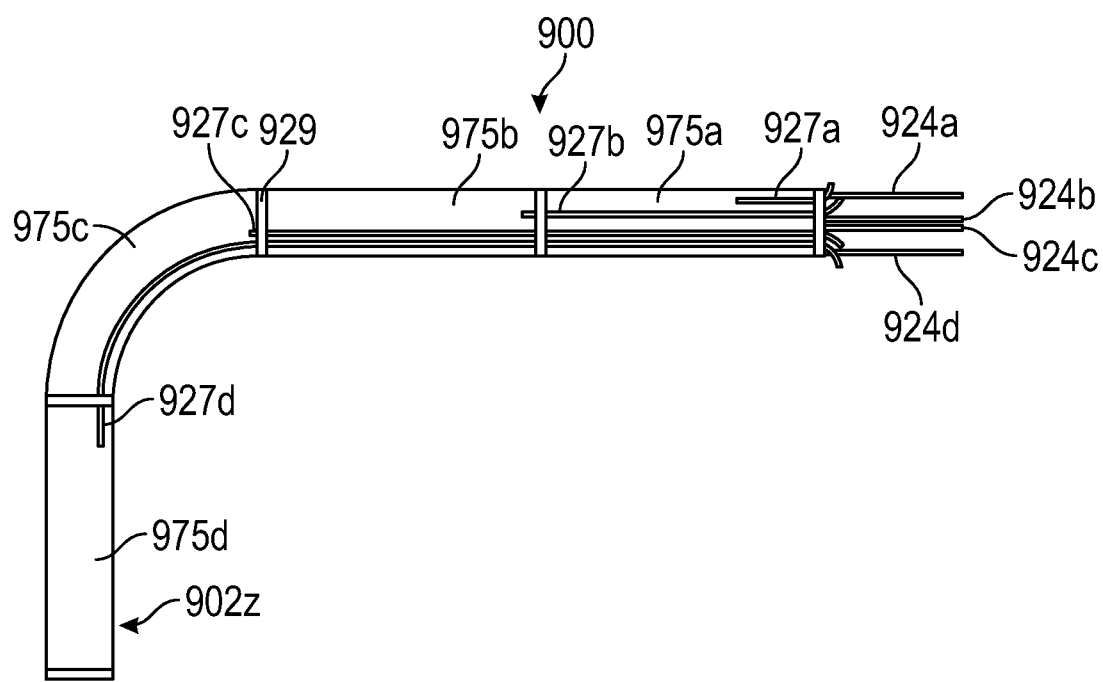
FIGS. 44A-44C show a rigidizing device with separate rigidizing chambers along the length thereof.
Figure 44C:
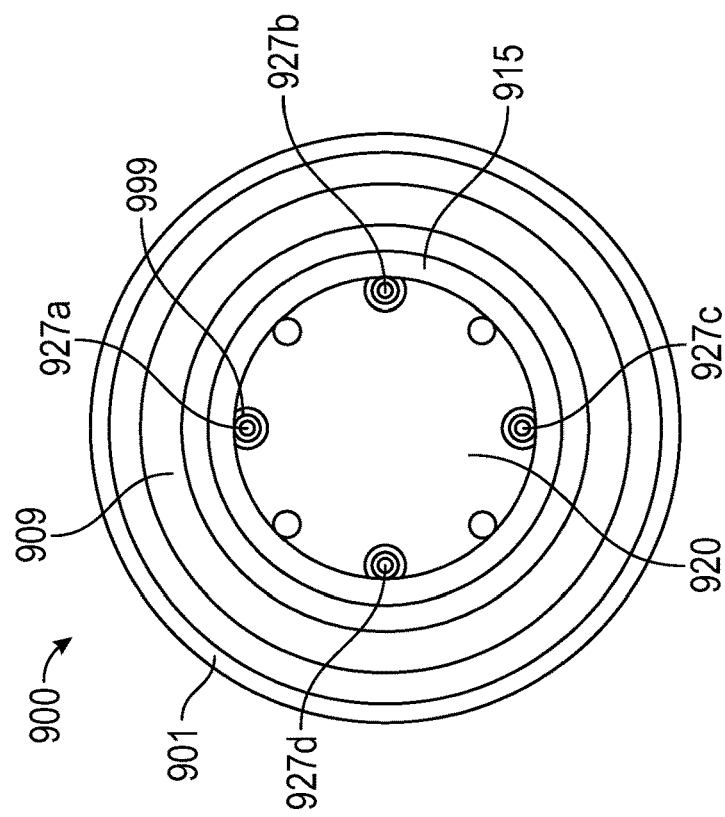
Figure 44B:
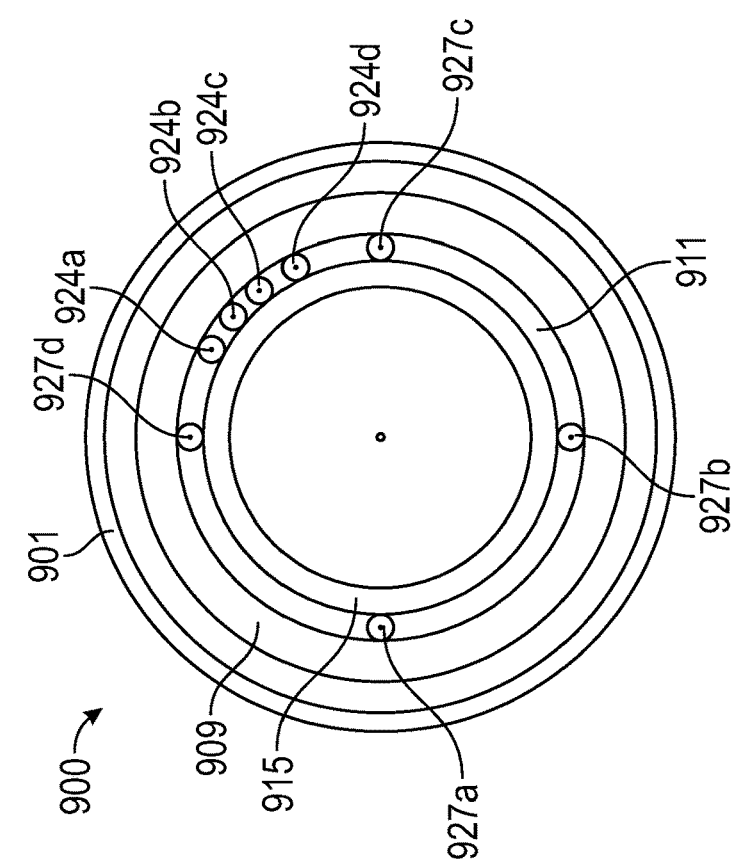

Any of the rigidizing devices described herein can include one or more separately rigidizing sections. For example, referring to FIGS. 44A-44C, in some embodiments, a rigidizing device 900 can have separate vacuum/pressure chambers 975a-d (e.g., four vacuum or pressure chambers) along the length thereof. Each chambers 975a,b,c,d can have its own vacuum/pressure line 927a-d extending thereto for individual rigidization of the chambers 975a,b,c,d. Pressure seals 929 can extend between each chamber and/or at the distal end. The rigidizing device 900 with separately rigidizing chambers 975a,b,c,d can, in some embodiments, include a steerable distal section 902z (e.g., with linkages as otherwise described herein). The cables 924a-d to control the steerable distal section 902z can be managed using cable guides 999 (e.g., there can be at least one, such as 1-4 cable guides 999 in each vacuum chamber 975). In some embodiments, shown in FIG. 44B, the cables 924a-d, cable guides 999a-d, and/or vacuum/pressure lines 927a-d can extend within a radial gap 911 between the innermost layer 915 and the braid layer 909 (and thus also beneath the outermost layer 901). In other embodiments, shown in FIG. 44C, the cables 924a-d, cable guides 999a-d, and/or vacuum/pressure lines 927a-d can extend within the central lumen 920 of the rigidizing device 900. In use of the rigidizing device 900, any of the chambers 975a-d that are in the flexible state can be steered or deflected in the direction of cable tension while the chambers 975a-d that are rigidized will remain in their position and not be deflected. Advantageously, this design allows alternating which chambers 975a-d are under vacuum/pressure and/or direction of steering to form a variety of complex shapes and provide navigation through the anatomy with minimal looping.

Figure 45A:
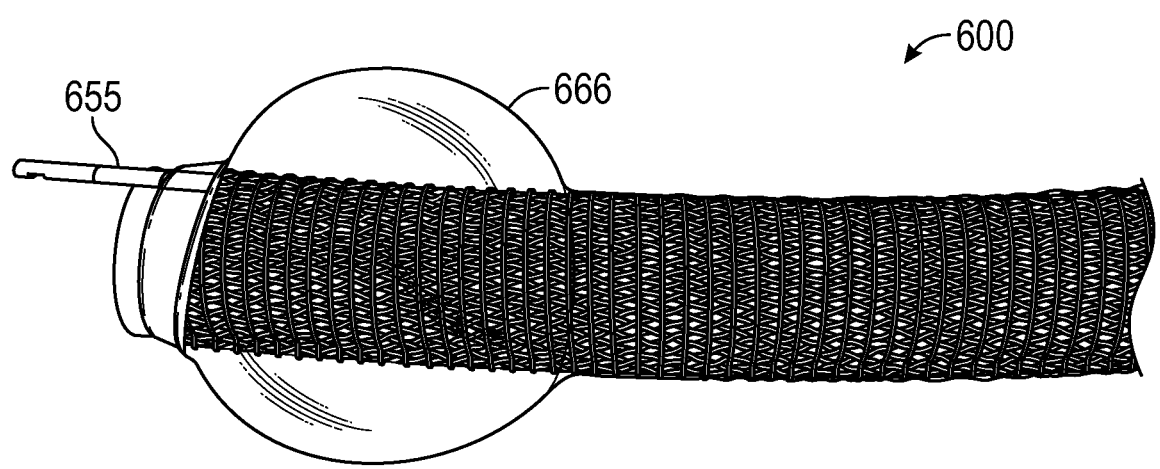
FIGS. 45A-45D show a rigidizing device with a balloon and inflation lumen.
Figure 45B:
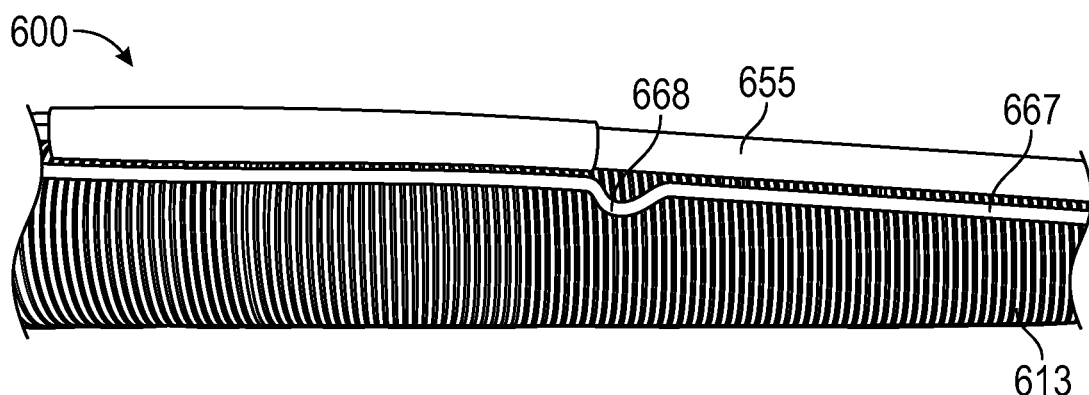
Figure 45C:
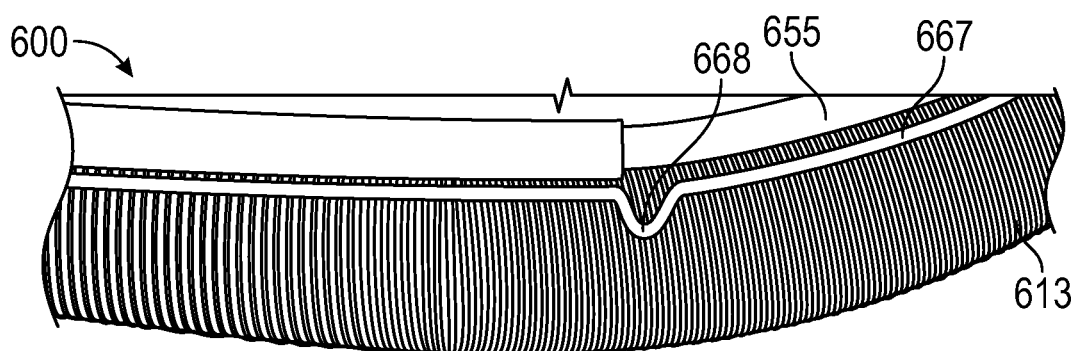
Figure 45D:
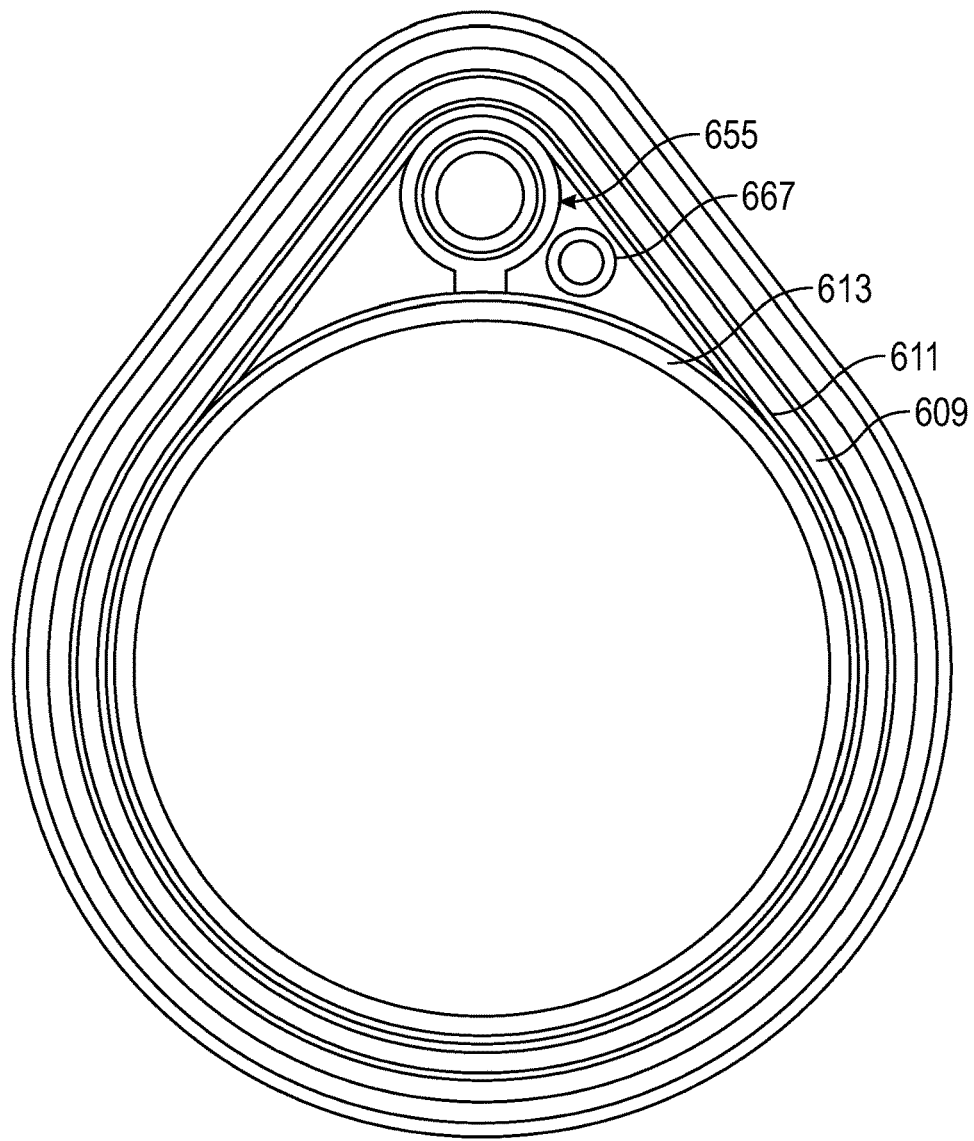

In some embodiments, the distal end section of the rigidizing devices described herein can include an element for local tissue stabilization, such as suction, a balloon or a cage element. For example, referring to FIGS. 45A-45D, in one embodiment, a rigidizing device 600 can include a balloon 666 and a balloon inflation lumen or tube 667 extending thereto. As shown in FIGS. 45B-45D (the outer layers have been removed in 6B-6C for clarity), the balloon inflation tube 667 can extend alongside the working channel 655 (and thus within the radial gap 611 between the slip layer 613 and the first braid layer 609). As shown in FIGS. 45B-45C, the inflation tube 667 can be configured to include a service loop 668 that can change lengths (i.e., straighten as in FIG. 45B or obtain a greater bend as in 45C) to accommodate bending of the rigidizing device 600. In some embodiments, the balloon inflation tube can be spiraled about its axis to accommodate bending. In some embodiments, a vacuum rigidizing device can include a balloon inflation tube between the innermost layer and the braid, between the braid and the outer layer, radially inwards of the inner layer, or radially outwards of the outer layer. In some embodiments, a pressure rigidizing device can include an inflation lumen in the pressure gap, between the bladder and braid, between the braid and outer layer, radially inwards if the inner layer, or radially outwards of the outer layer. For example, the inflation lumen can be positioned similar to as described herein with respect to working channels and/or cables.

Figure 46A:
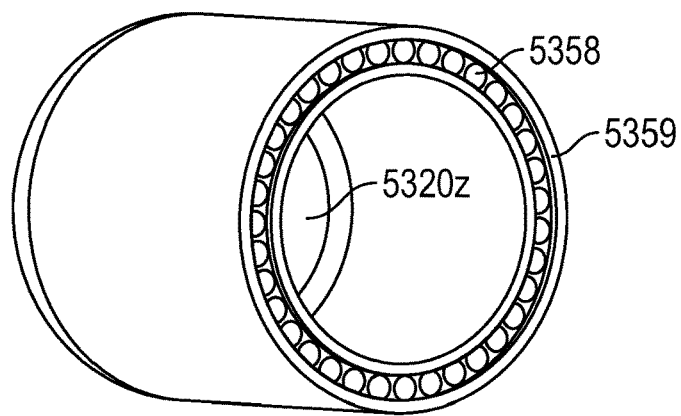
FIGS. 46A-46B show an embodiment of a suction tip for a device such as a rigidizing device.
Figure 46B:
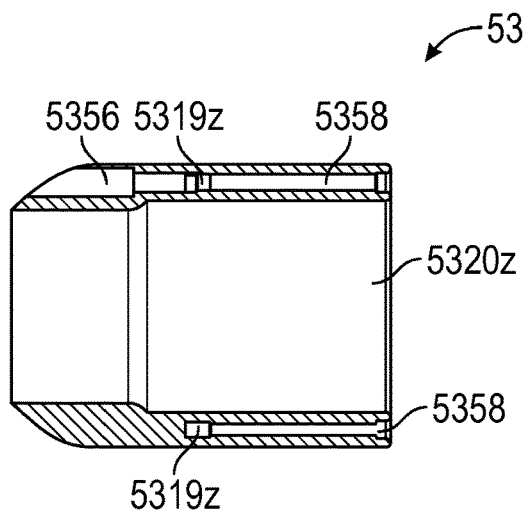

As another example, FIGS. 46A-46B show an exemplary vacuum tip 5354 for use with a rigidizing device. The vacuum tip 5354 can include a circumferential array of vacuum holes 5358 on the distal-most face 5359. Further, the array of vacuum holes 5358 can be connected to a vacuum line 5356 that runs along the rigidizing device (e.g., within or alongside the layered walls of the rigidizing device). The vacuum line 5356 can be connected to a source of vacuum such that, when activated, vacuum is provided through the vacuum line 5356 to each of the holes 5358 of the array (e.g., through an annular inlet 5319z). As a result, suction can be provided on the distal-most face 5359 of the tip 5354 (and thus the distal-most face of the rigidizing device). Such suction can be useful, for example, to suction tissue thereto (e.g., for stabilization during interventional procedures such as for cannulation of the papilla, e.g., for access to the pancreatic duct or bile duct). The suction can also be useful, for example, for Endoscopic Submucosa Dissection (ESD), or Endoscopic Full Thickness Resection (EFTR).

In some embodiments, the vacuum tip 5354 can be positioned just distal to a steering section of the rigidizing device, which can advantageously be used to orient the vacuum tip 5354 in the desired direction. Further, in some embodiments, a tool (e.g., guidewire or scope) can pass through the central lumen 5320z of the tip 5354 and between the array of vacuum holes 5358 to allow for procedures to be performed while suction is activated.

Figure 47A:
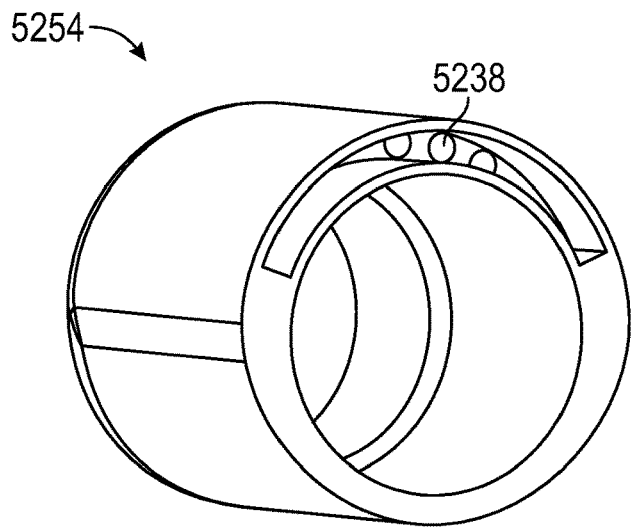
FIGS. 47A-47B show an embodiment of a suction tip for a device such as a rigidizing device.
Figure 47B:
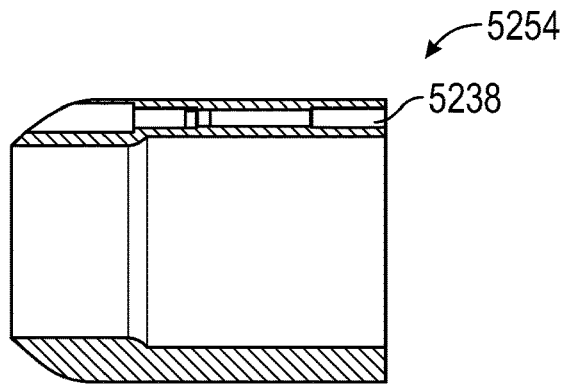

Referring to FIGS. 47A-47B, in some embodiments, the vacuum tip 5254 can include a semi-annular array of holes 5238 at the distal-most face 5259 rather than a circumferential array of holes.

Figure 48A:
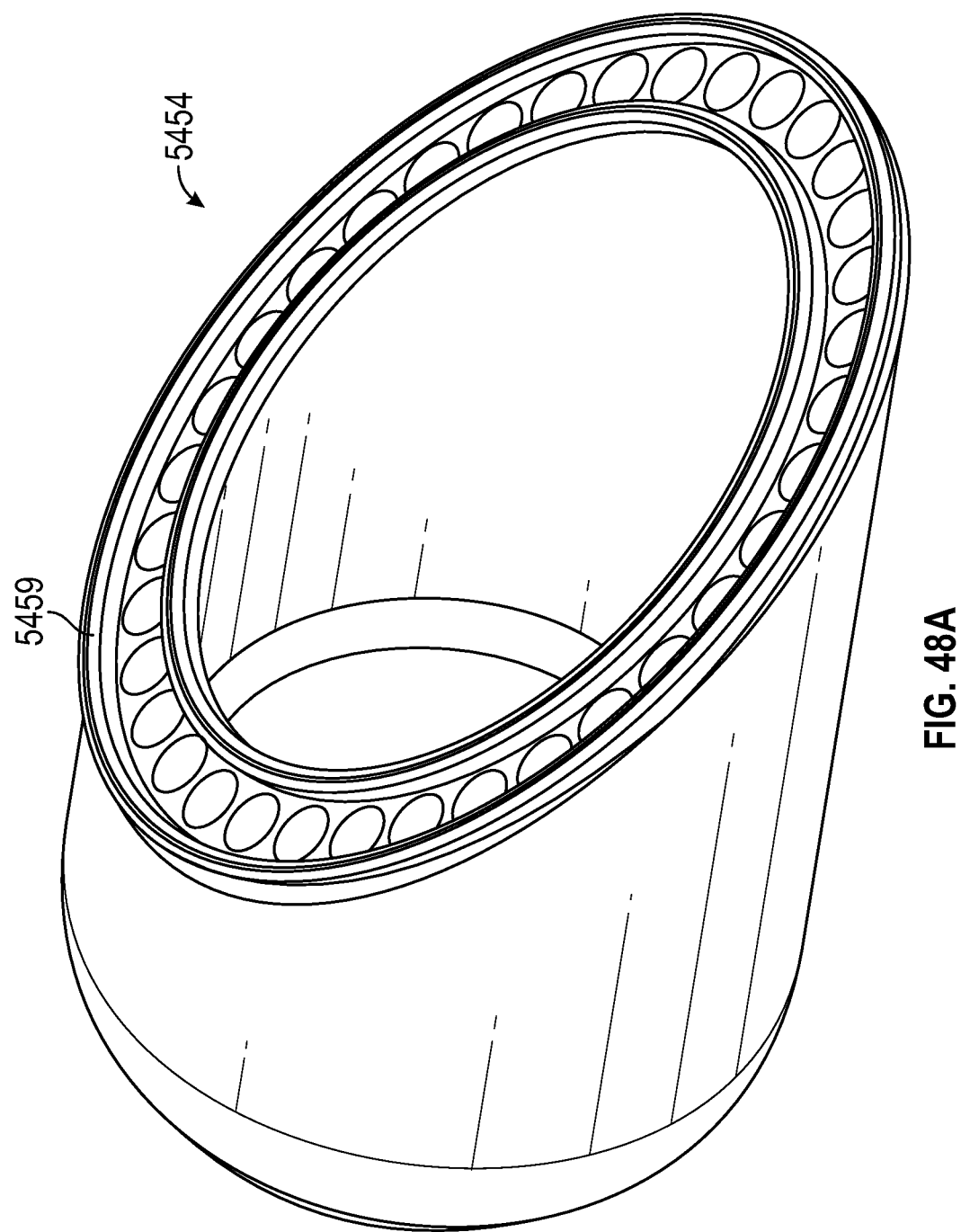
FIGS. 48A-48B show an embodiment of a suction tip for a device such as a rigidizing device.
Figure 48B:
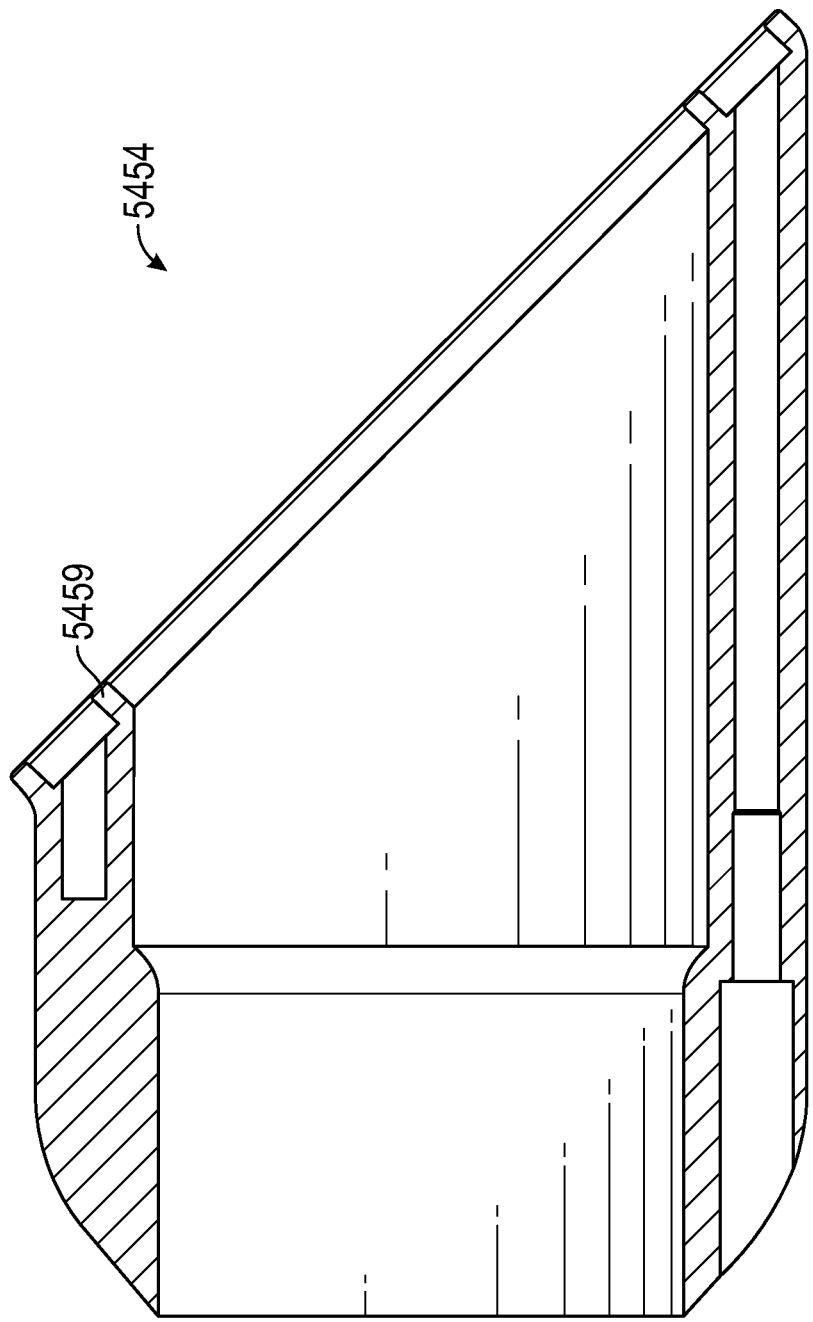

Referring to FIGS. 48A-48B, in some embodiments, the vacuum tip 5454 can have an angled distal face 5459 (e.g., angled at 30-80 degrees relative to the longitudinal axis of the tip 5454, such as 30, 45, 60, 70, or 80 degrees). The angled distal face can advantageously help approach angled anatomy to more easily adhere to the local surface.

The vacuum tips described herein can advantageously provide suction without causing "red-out" of the endoscopic lens, as the suction can occur locally (e.g., at the holes 5358) and not at the lens of the scope. Accordingly, the scope can provide visualization of the tissue even when suction is applied.

In some embodiments, the vacuum tips described herein can include a metallized portion and/or have co-joined wires such that the vacuum tips can conduct current. Such current can be used, for example, to cut or coagulate the suctioned tissue.

In some embodiments, the vacuum tips described herein can be used with a standard endoscope or endoscopic type device that does not include rigidization.

Any of the rigidizing devices described herein can be used with a handle configured to allow manual manipulation and/or activation of the device.

Figure 49A:
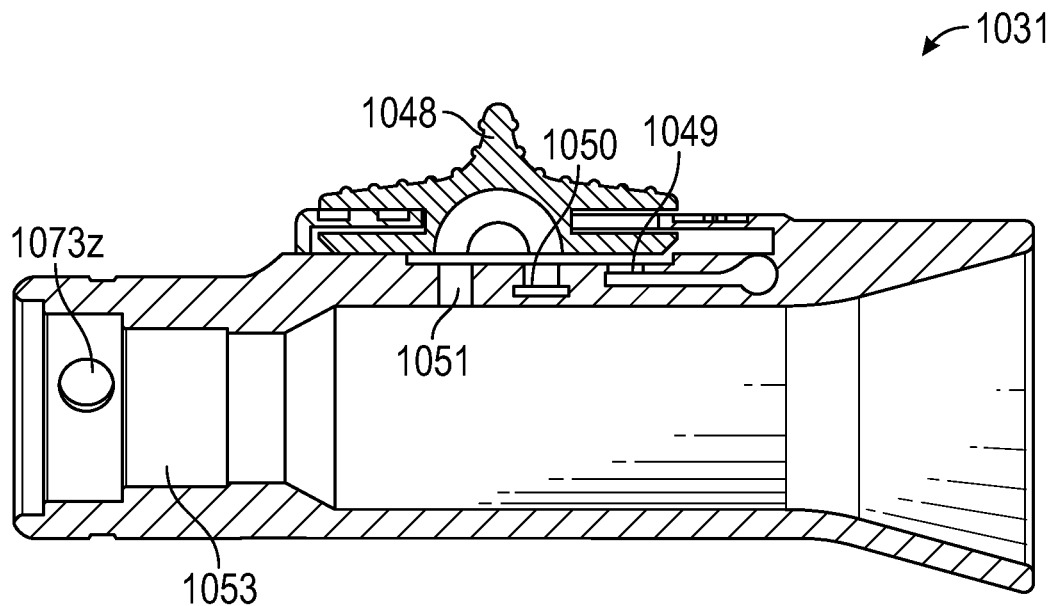
FIGS. 49A-49D show an embodiment of a handle for use with a rigidizing device.
Figure 49B:
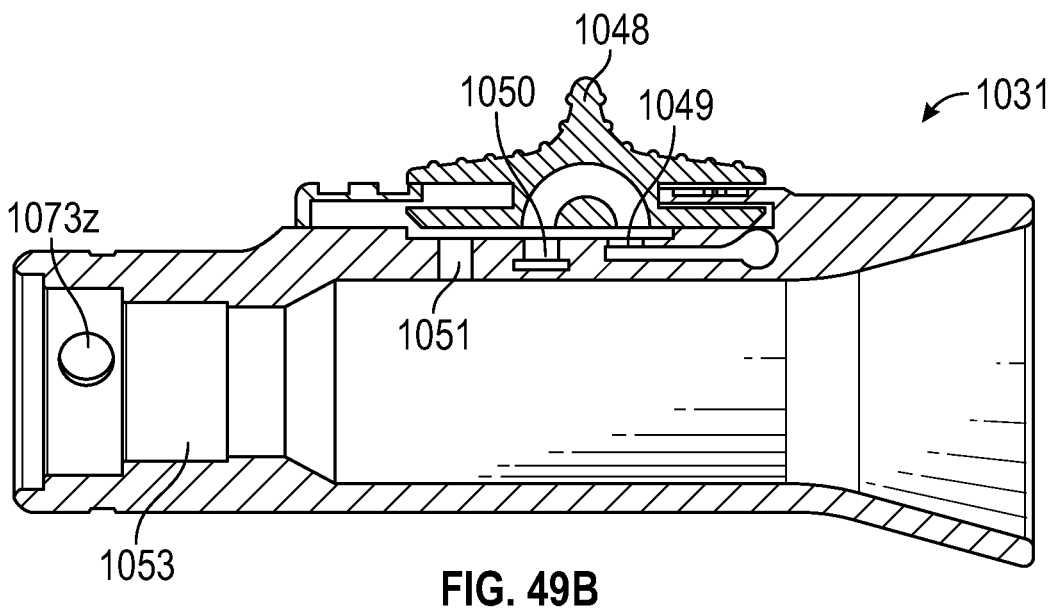
Figure 49C:
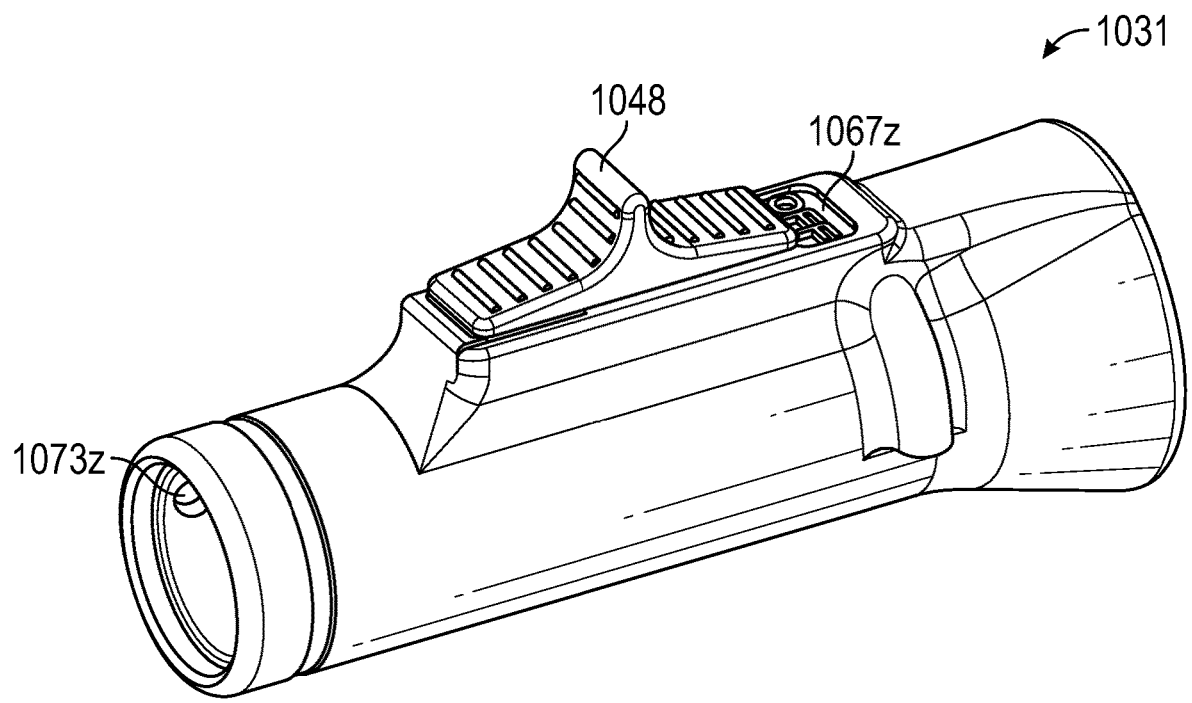
Figure 49D:
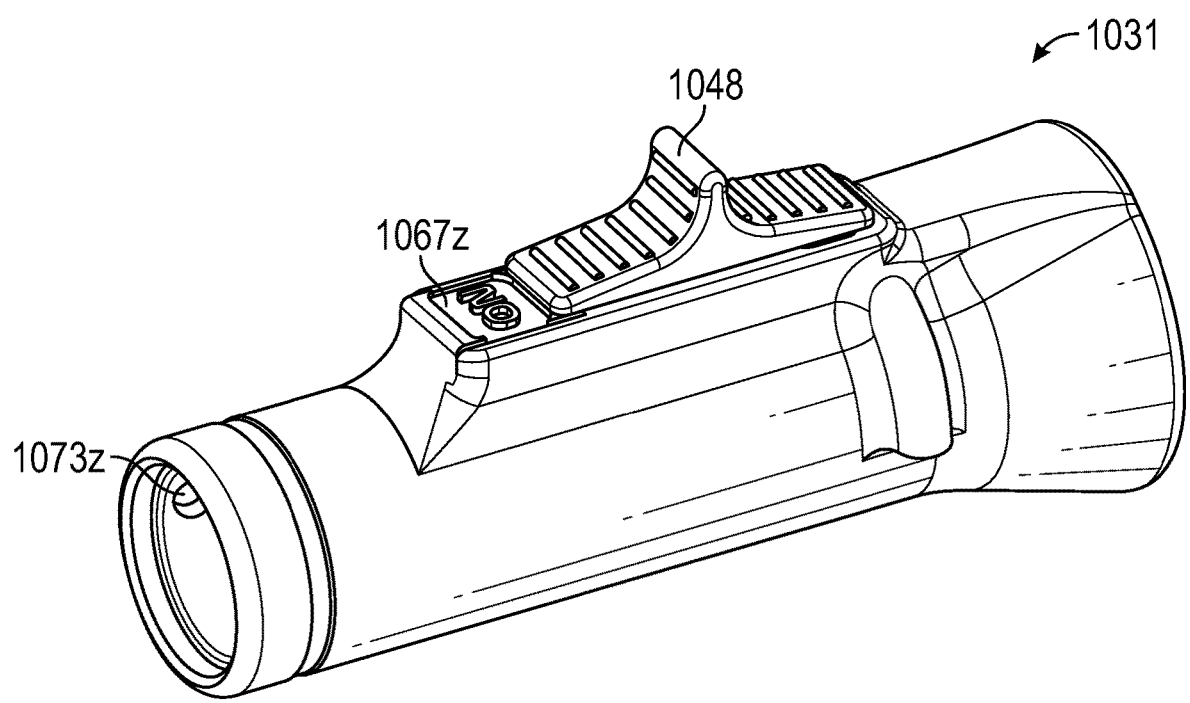

An exemplary handle 1031 is shown in FIGS. 49A-49D. The handle 1031 includes an activation element 1048 in the form of a button configured to activate the vacuum or pressure (the button is shown off in FIGS. 49A and 49C and on in FIGS. 49B and 49D). Further, a flow path within the handle 1031 can include a vacuum or pressure inlet port 1049 configured to be attached to the vacuum or pressure source, a rigidizing device port 1050 that connects to the rigidizing device via output 1073$z$, and a vent port 1051 that connects to atmosphere. As shown in FIG. 49A, when the activation element 1048 is in a distal "off" position (i.e., such that vacuum or pressure for rigidization to the rigidizing device is off), the vent port 1051 and rigidizing device port 1050 are in communication with one another, thereby venting any rigidizing pressure or vacuum to the air and allowing the rigidizing device to be in a flexible configuration. As shown in FIG. 49B, when the activation element 1048 is in a proximal "on" position (i.e., such that vacuum or pressure to the rigidizing device is on), the rigidizing device port 1050 and the vacuum or pressure inlet port 1049 are in communication with one another, thereby supplying pressure or vacuum to the rigidizing device to allow the device to rigidize. In some embodiments, the handle 1031 can be configured to be bonded to the rigidizing device (e.g., to an inner coil wound tube over the rigidizing device) at bonding region 1053. As shown in FIGS. 49C-D, the handle includes a status indicator element 1067$z$ to indicate whether the rigidizing device is in the flexible or rigid configuration. In this embodiment, the status indicator 1067$z$ is such that the word "on" shows when the button is placed in the "on" position, and the word "off" shows when the button is placed in the "off" position. In other embodiments, the status indicator can be a symbol, color, light, or moving indicator.

Figure 50A:
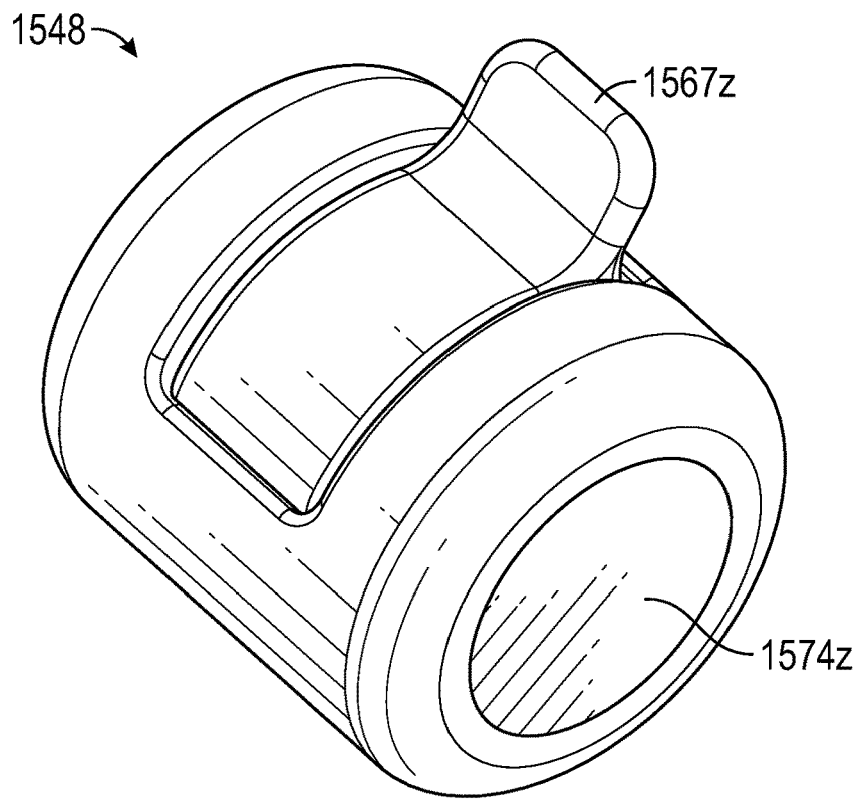
FIGS. 50A-50B show an embodiment of an activation element for a handle of a rigidizing device.
Figure 50B:
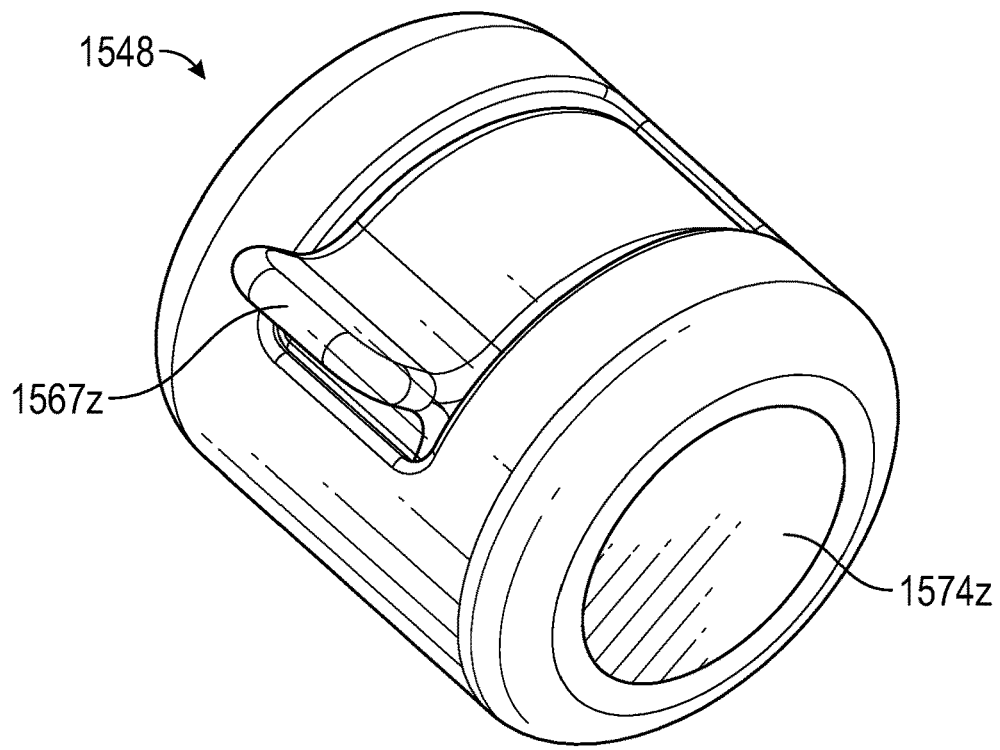
Figure 51A:
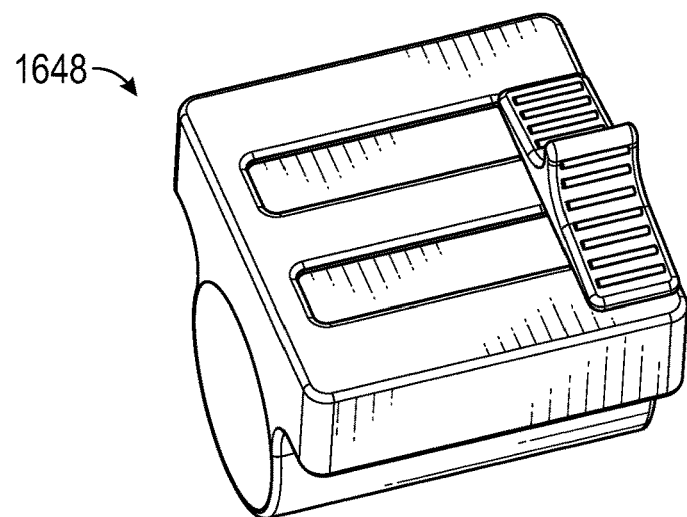
FIGS. 51A-51C show an embodiment of an activation element for a handle of a rigidizing device.
Figure 51B:
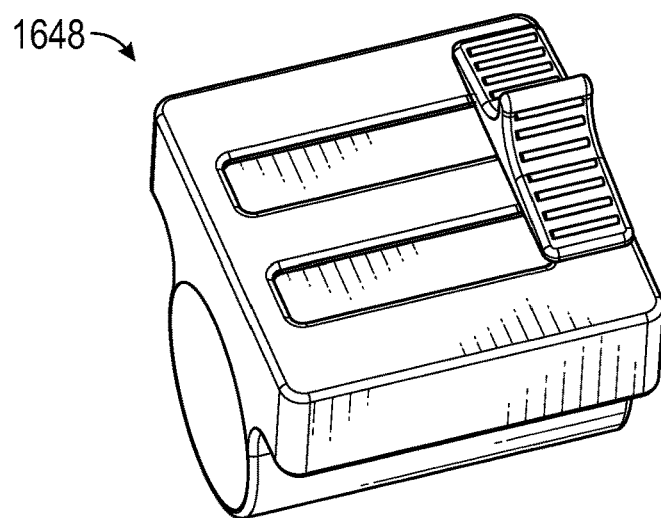
Figure 51C:
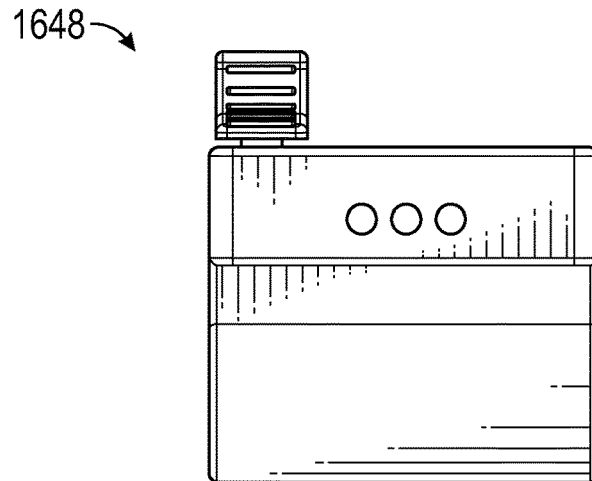
Figure 53B:
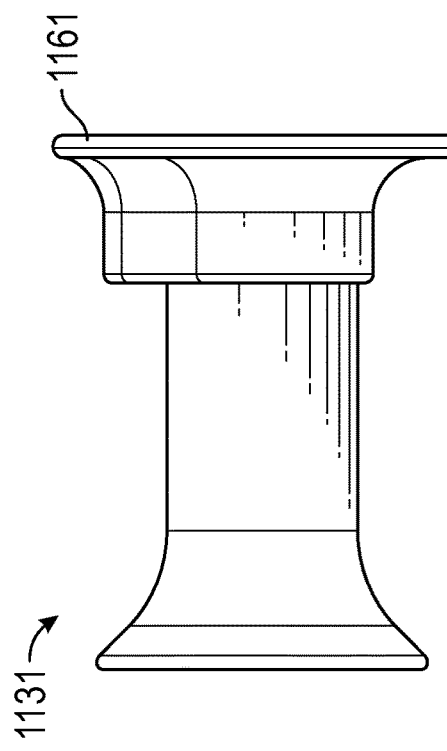
FIGS. 53A-53D show an embodiment of a handle for use with a rigidizing device.
Figure 53D:
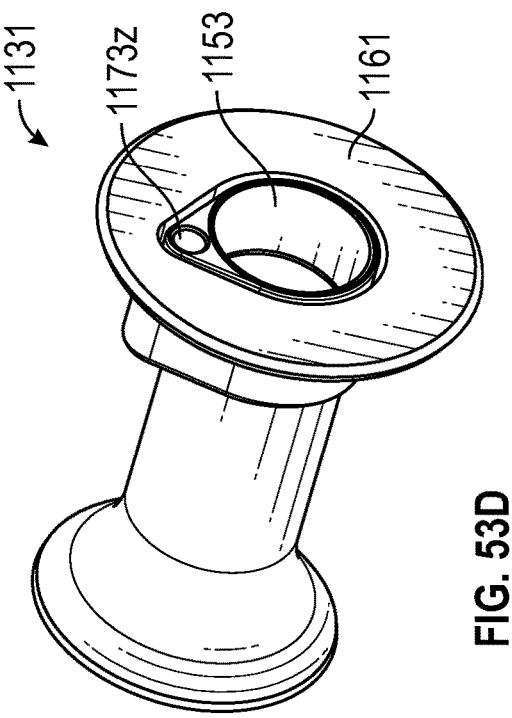
Figure 53A:
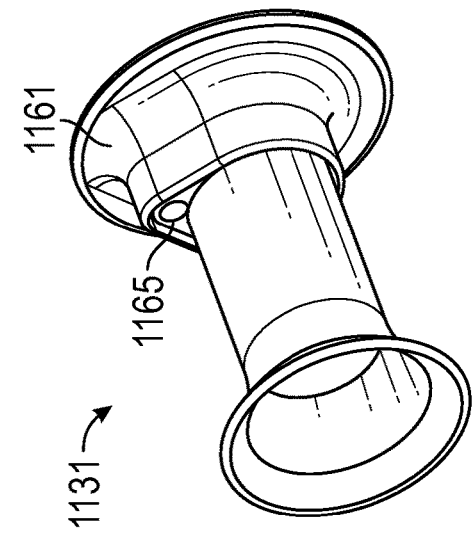
Figure 53C:
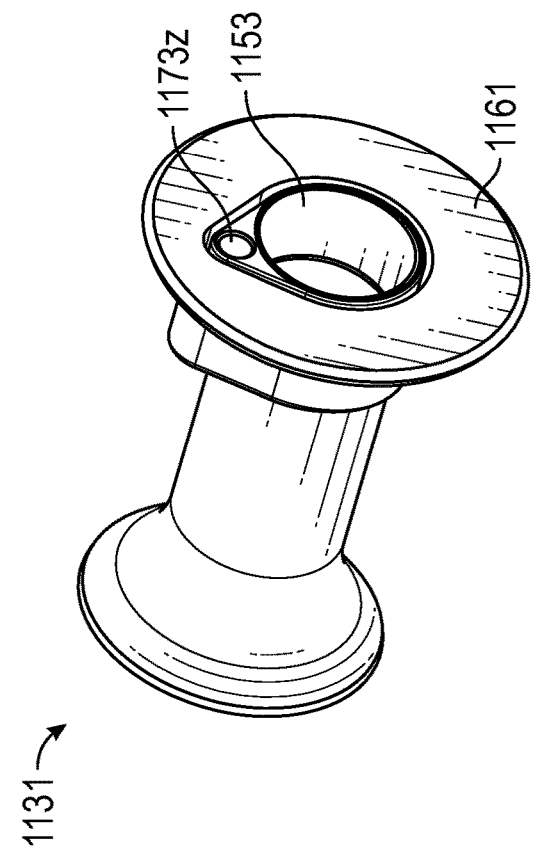

The activation element for a rigidizing device handle as described herein can be a button, switch, toggle, slider, screwed connection, squeeze handle, or stop-cock. Further, the activation element can be planar, a sector, or omnidirectional. The indicator element can include words, lights, or an element that spins with flow of vacuum or pressure. For example, referring to FIGS. 50A-50B, in some embodiments, the activation element 1548 can be a slider element. The activation element 1548 can include a connection element 1574$z$ (e.g., a hollow tube or snap-fit element) configured to slide over a handle. The indicator element 1567$z$ can be built into the slider (e.g., indicate "rigid" when the slider is in one position and "flexible" when the slider is in another position). A similar slider actuation element 1648 (this one orthogonal) can be seen in FIGS. 51A-51C.

In some embodiments, rather than including the activation element and indicator element on the handle, one or both can be on separate elements. For example, the activation element can be positioned along the vacuum or pressure line between the handle and the vacuum or pressure pump, can be actuated by a foot pedal, can be on the scope umbilical, on the scope shaft, or can be clipped on the patient's bed. In some embodiments, the actuation element can be separate from the handle, but can clip onto the handle during part of the procedure. For example, FIGS. 52A-52C show an activation element 1448 that includes an attachment mechanism 1452 (e.g., a c-shaped clip) for detachable coupling to a handle 1431. Having the indicator element and/or activation element separate from the handle can advantageously allow the actuator and indicator to be seen more clearly (i.e., not be obstructed by the person's anatomy) and/or can allow the actuator and indicator to be controlled/used more easily by an additional person (e.g., a procedural assistant).

FIGS. 53A-D show a handle 1131 that is designed to allow manipulation of a rigidizing device, but that does not include an activation element or an indicator element. The handle 1131 includes a large stopper or flange 1161 at the distal end thereof that can act as an insertion blocker for the handle 1131 (i.e., to stop the handle 1131 from moving into the anatomy) and to act as a face against which the operator can push during use. The rigidizing device can connect at bond region 1153. Further, the handle 1131 can include an input 1165 from the remote activation element connected to an output 1173$z$ to the rigidizing device.

Figure 54A:
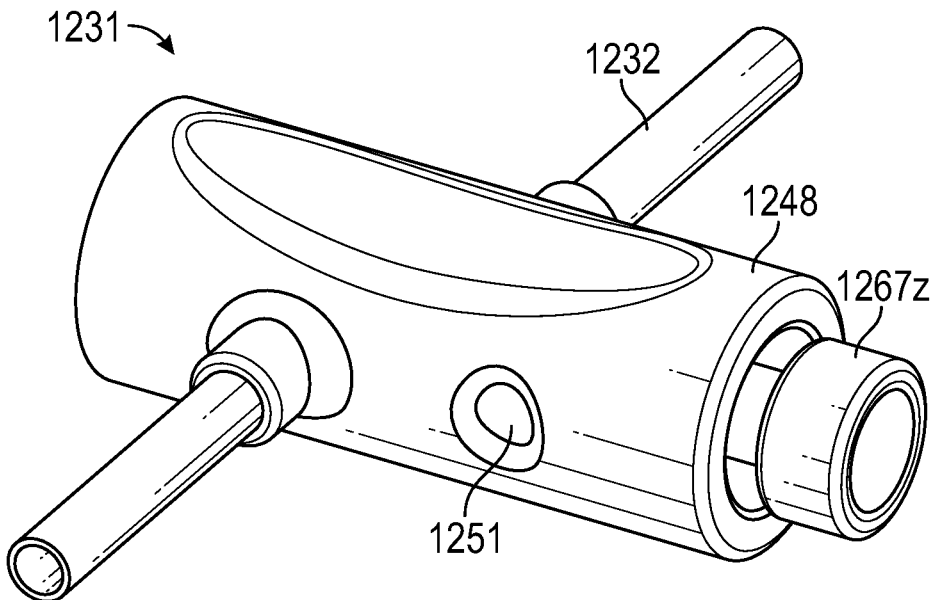
FIGS. 54A-54B show an embodiment of a handle for use with a rigidizing device.
Figure 54B:
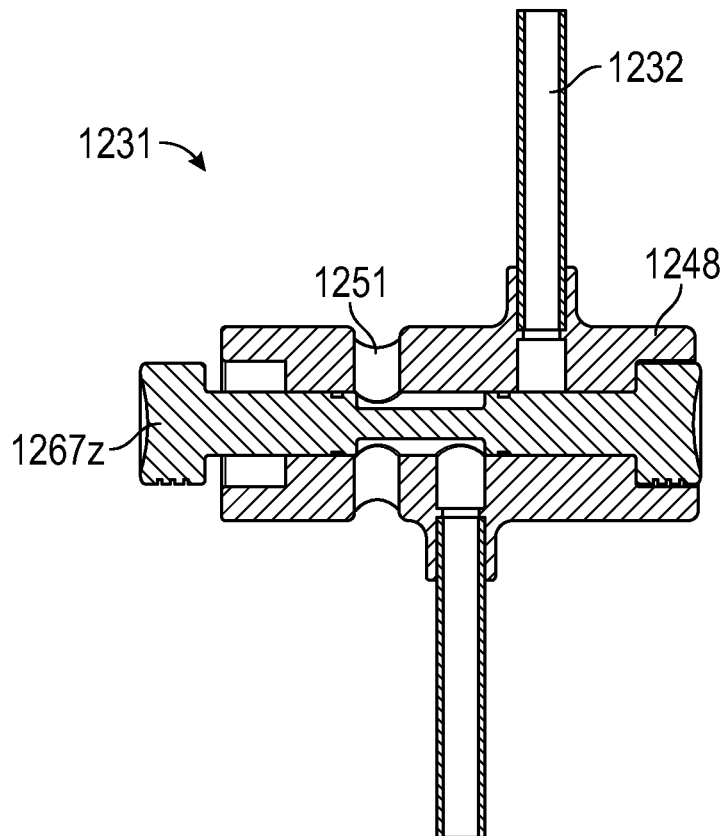

In some embodiments, a handle for use with a vacuum rigidizing device can include a vent port to vent the rigidizing device when vacuum is not supplied (i.e., when the rigidizing device is in the flexible configuration). For example, FIGS. 54A-54B show a handle 1231 having spool valve activation element 1248 that is shuttled in one direction to activate the vacuum in the rigidizing device and can be shuttled in the opposite direction to deactivate the vacuum or pressure. When deactivating vacuum or pressure to the rigidizing device, the activation element 1248 can provide venting via vent port 1251. The activation element 1248 can be positioned on the vacuum or pressure line 1232 leading to the handle, such as 4"-8", e.g., 6" away from the handle. As shown in FIG. 54A, the spool valve with end button indicator element 1267$z$ can indicate that the rigidizing device is in the flexible configuration (as shown) or the rigid configuration (when pushed in the opposite direction).

Referring to FIGS. 55A-55C, the activation element 1348 can be a rotary valve (e.g., connected to the handle or elsewhere as described herein), and a sliding indicator 1367$z$ on the rotary valve activation element 1348 can show that the vacuum or pressure is on (as shown in FIGS. 55A and 55C) or off and vented (as shown in FIG. 55B).

Figure 56A:
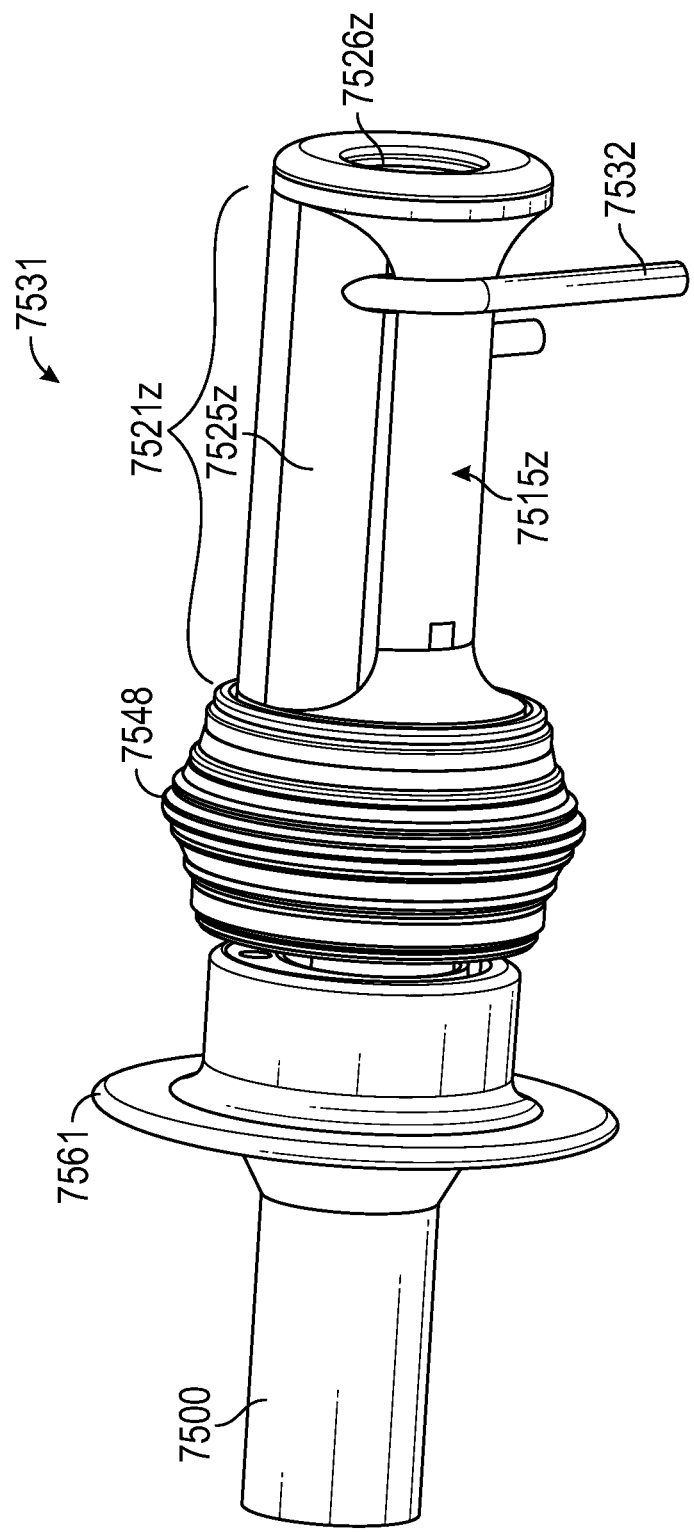
FIGS. 56A-56G show an embodiment of a handle for use with a vacuum rigidizing device.
Figure 56B:
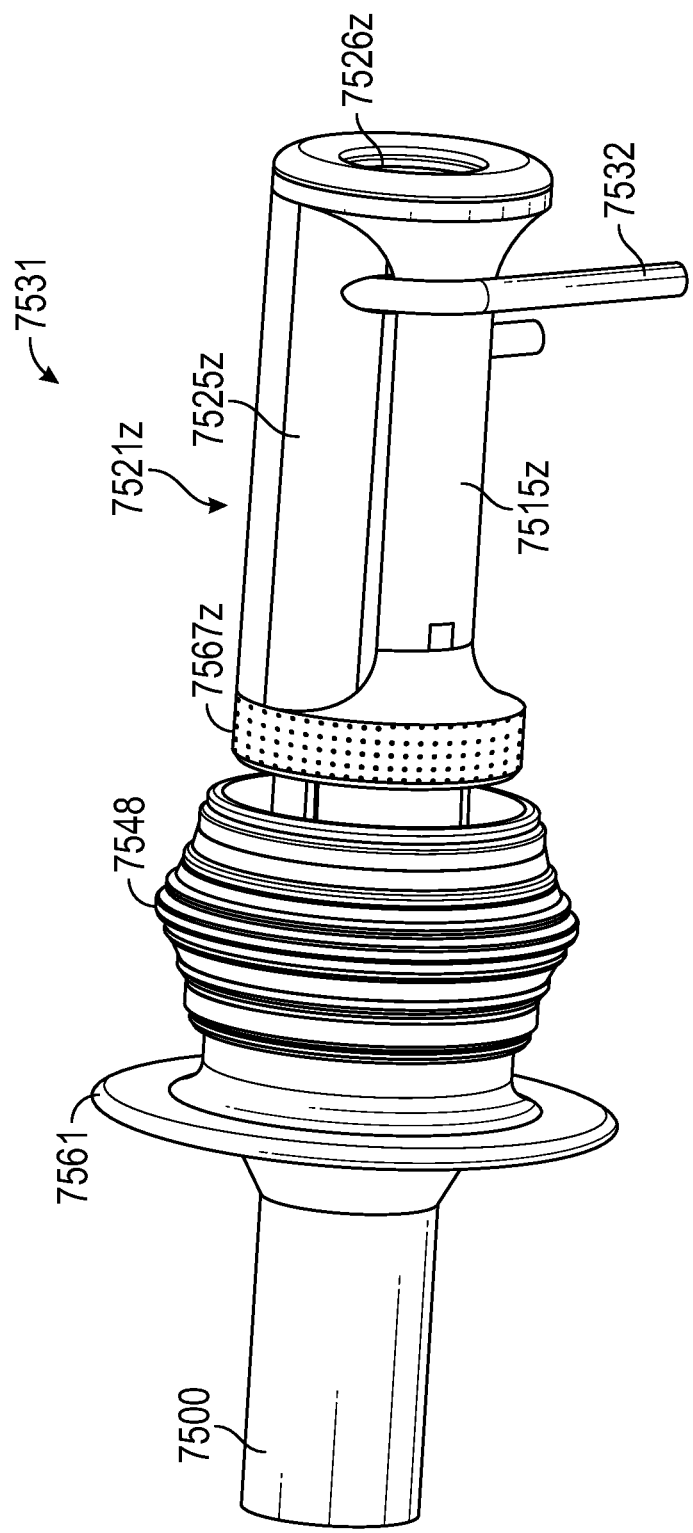
Figure 56C:
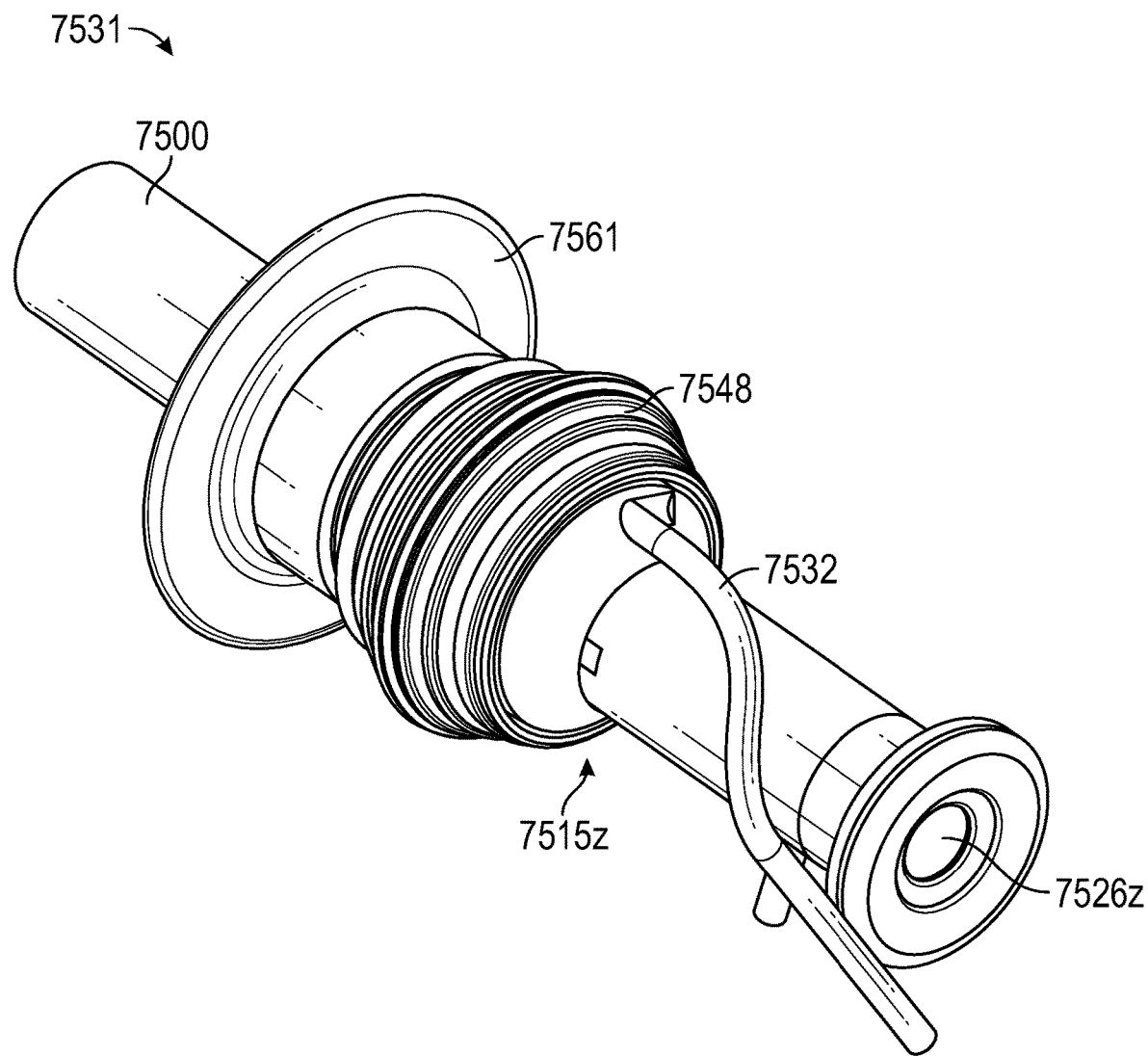
Figure 56D:
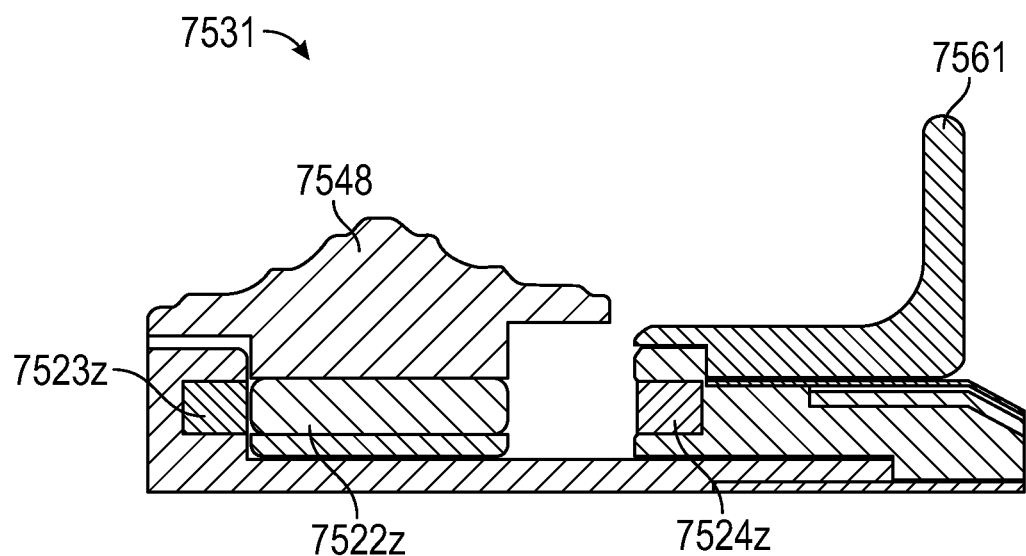
Figure 56E:
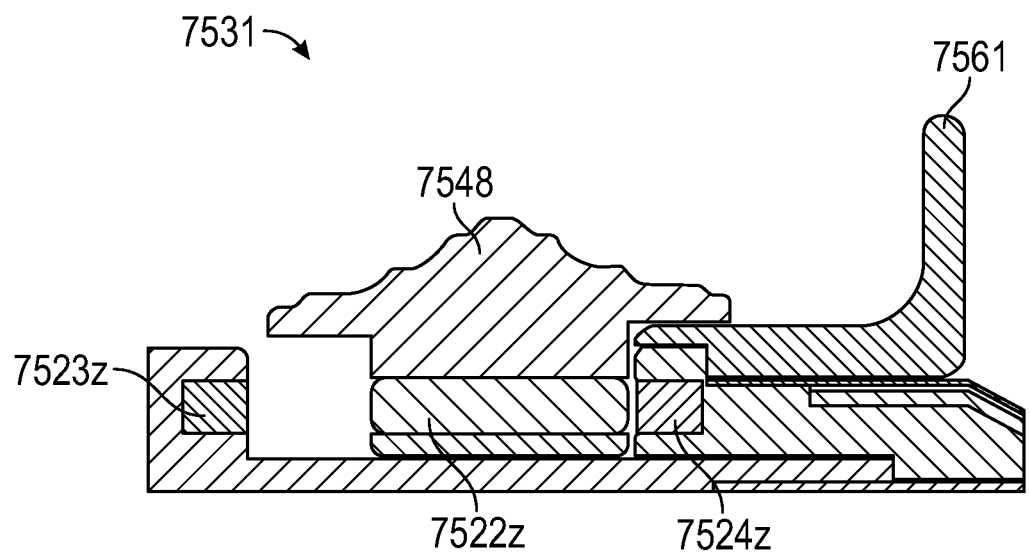
Figure 56F:
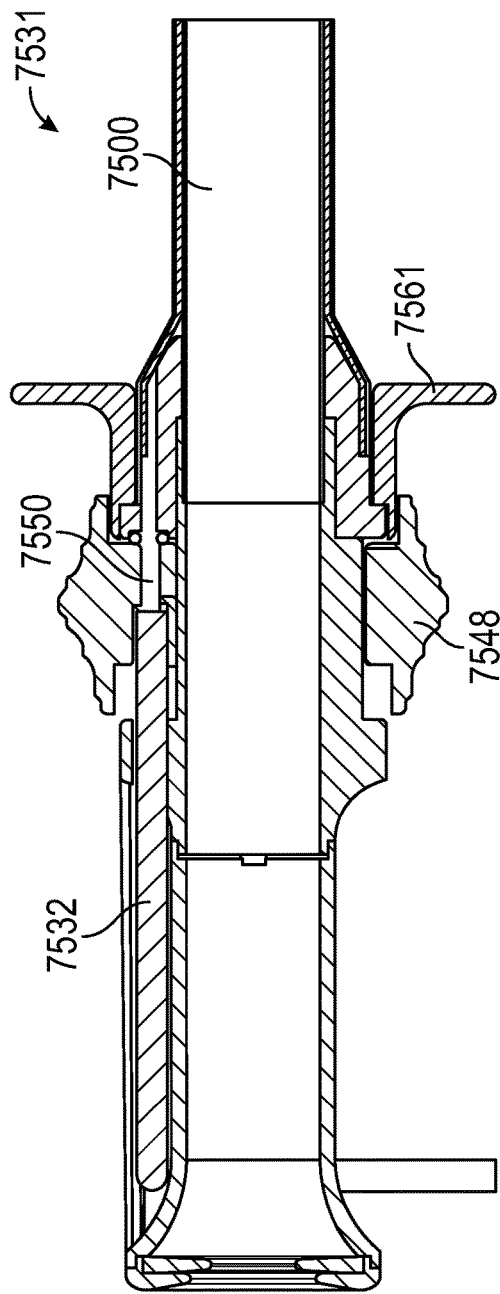
Figure 56G:
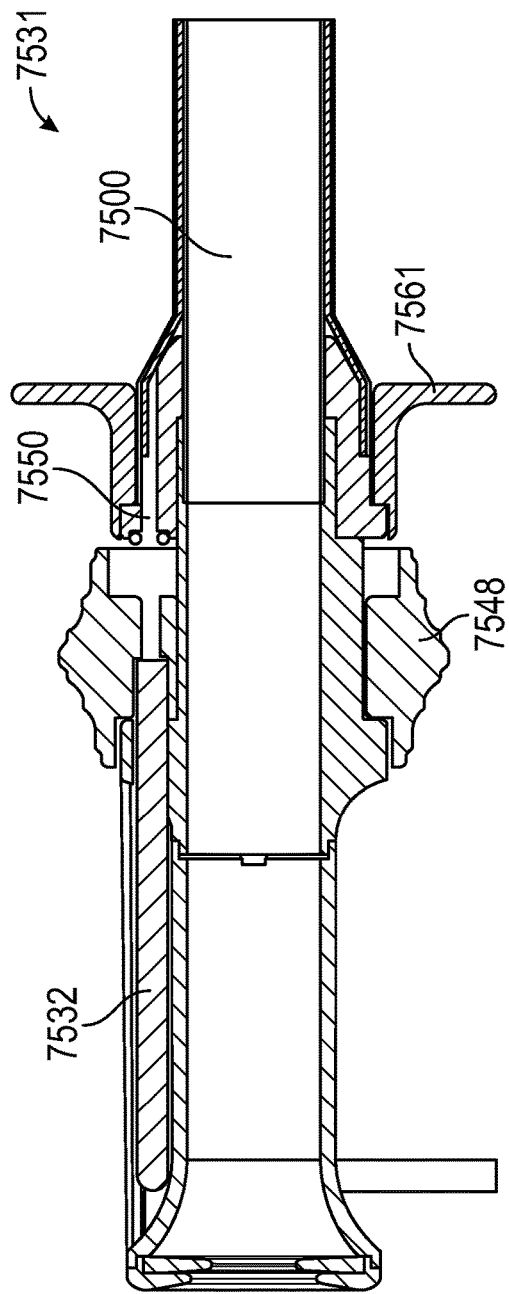

In some embodiments, a handle for use with a vacuum rigidizing device can include a mechanism configured to automatically lock the handle in the vacuum or vented configuration. For example, handle 7531 for use with a vacuum rigidizing device 7500 is shown in FIGS. 56A-56G. The handle 7531 includes a handle body 7515$z$ configured to attach to the rigidizing device 7500. The handle 7531 further includes an activation element 7548 in the form of a switch ring for supplying vacuum to the rigidizing device 7500. The switch ring activation element 7548 can include a magnet 7522$z$ that is configured to mate with either a proximal magnet 7523z (as shown in FIG. 56D) or a distal magnet 7524z (as shown in FIG. 56E). When the switch ring magnet 7522z is mated with the proximal magnet 7523z, the vacuum feed line 7532 in the handle 7531 is disconnected from the vacuum port 7550 to the rigidizing device, and both the rigidizing device and the vacuum are vented or open to the atmosphere (as shown in FIG. 56F). When the switch ring magnet 7522z is mated with the distal magnet 7523z, the vacuum feed line 7532 in the handle 7531 is connected to the vacuum port 7550 to the rigidizing device so as to supply vacuum thereto (as shown in FIG. 56G). Advantageously, the magnets 7522z, 7523z, 7524z can lock the switch ring 7548 in the vacuum or vent configurations, thereby preventing harm to the patient that could result if in the unintended configuration (e.g., attempted movement of the device 7500 through the anatomy when in a rigid configuration when it could damage the anatomy). In some embodiments, the magnet 7522z can be a ferrous material while the magnets 7523z, 7524z can be magnets or vice versa. As shown in FIGS. 56A-56B, the handle 7531 can further include a user grip 7521z for the user's hand with a grip cover 7525z configured to cover the vacuum feed tube line 7532 in the handle 7531. Further, the vacuum feed tube line 7532 can connect directly to the switch ring activation element 7548. The vacuum feed line 7532 may have a spiral or winding shape under the grip cover 7525z, which can allow the switch ring activation element 7548 to move proximally and distally without restricted motion caused by the vacuum feed line 7532. The spiraling of the vacuum feed line 7532 may be from 30 to about 1440 degrees. For instance, 90 degrees (as shown in FIG. 56C where the grip cover is removed for clarity) 180, 360 and 720 degrees. The grip cover 7525z may be designed such that it covers the whole vacuum feed line 7532 even when the spiral goes all the way around the handle 7531. The handle 7531 can further include a stopper flange 7561 to prevent the handle 7531 from moving into the anatomy (for instance, the stopper flange may prevent the device from passing through the anus or through an oral bite guard), a proximal handle port 7526z for insertion of a scope or other working tool therethrough, and/or an indicator element 7567z. The indicator element 7567z is a band that is visible only when the switch ring activation element 7548 is in the distal position. The indicator element 7567z may have a different color and/or value than the rest of the handle, preferably a color that contrasts sharply and is visible in reduced lighting configurations. For instance, the handle 7531 may be white and the indicator element 7567z may be a medium to dark blue. The indicator element 7567z band may also have a different texture than the rest of the handle 7531. For instance, it may have raised bumps or a cross-hatching. This may allow a physician to easily feel the state of the handle 7531.

Figure 57B:
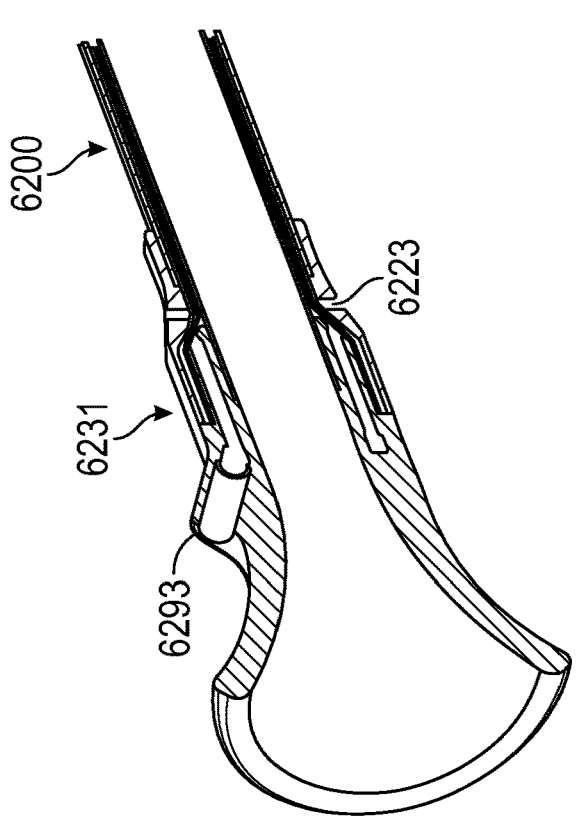
FIGS. 57A-57C show an embodiment of a handle for use with a pressure rigidizing device.
Figure 57A:
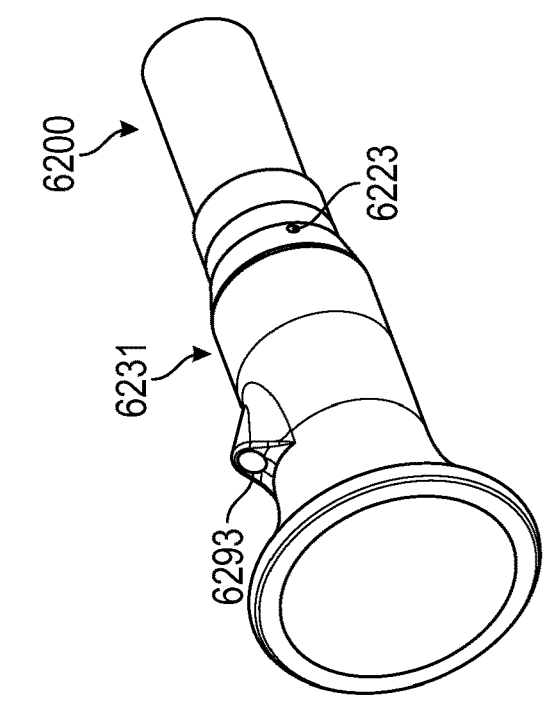
Figure 57C:
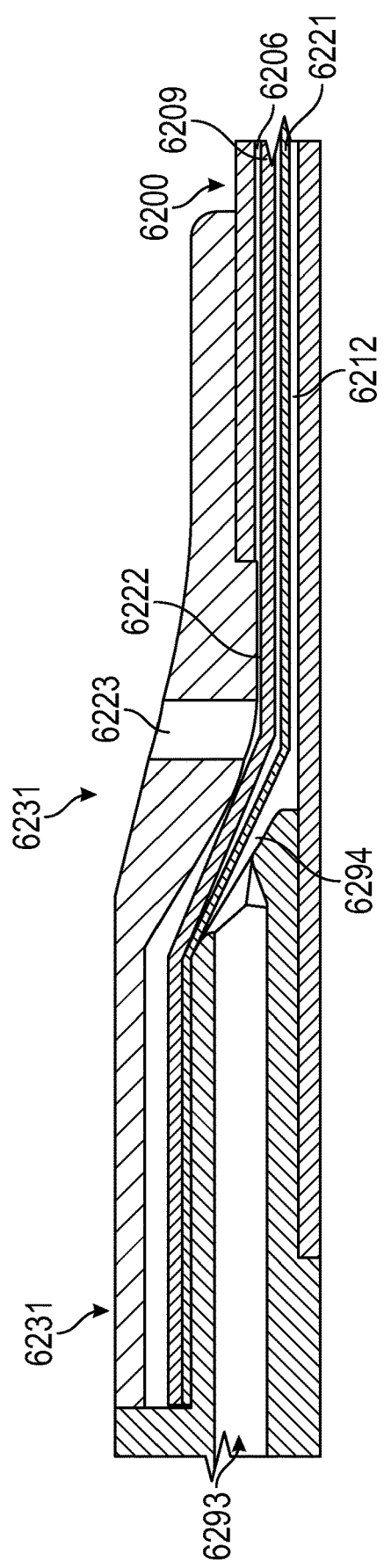
Figure 58A:
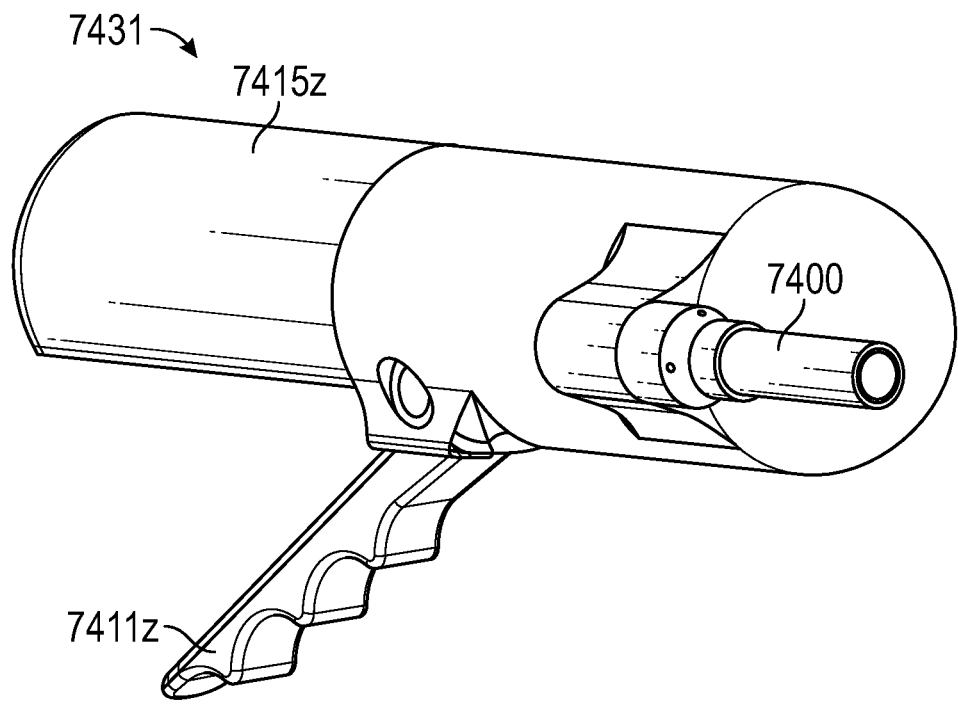
FIGS. 58A-58E show a pre-filled handle for use with a pressure rigidizing device.
Figure 58B:
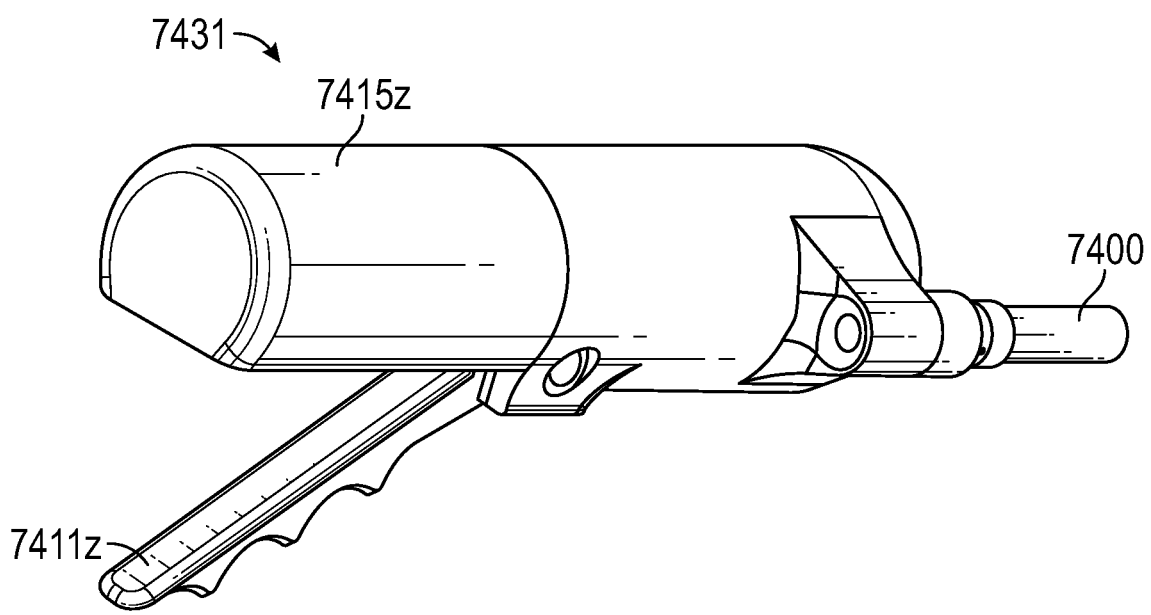
Figure 58C:
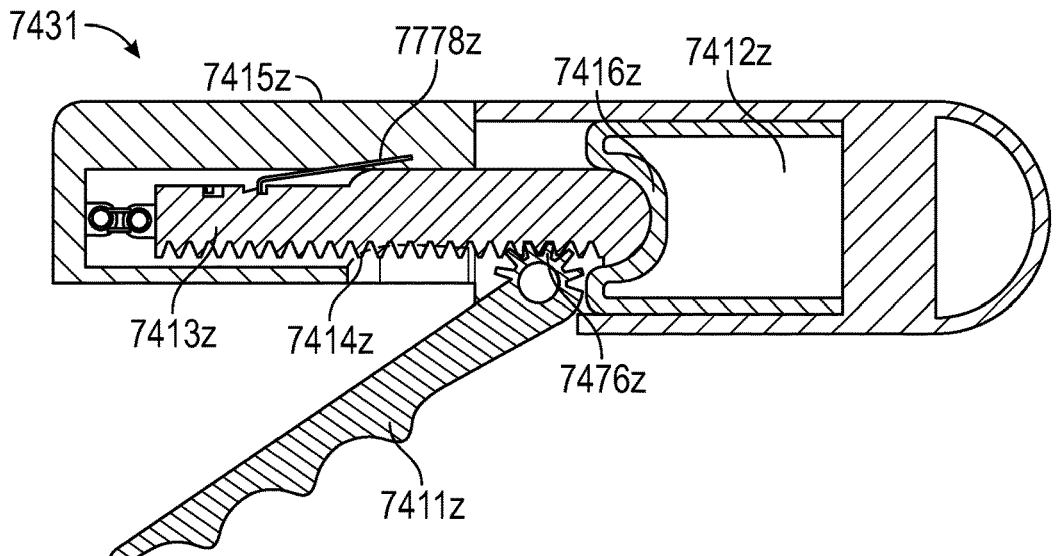
Figure 58D:
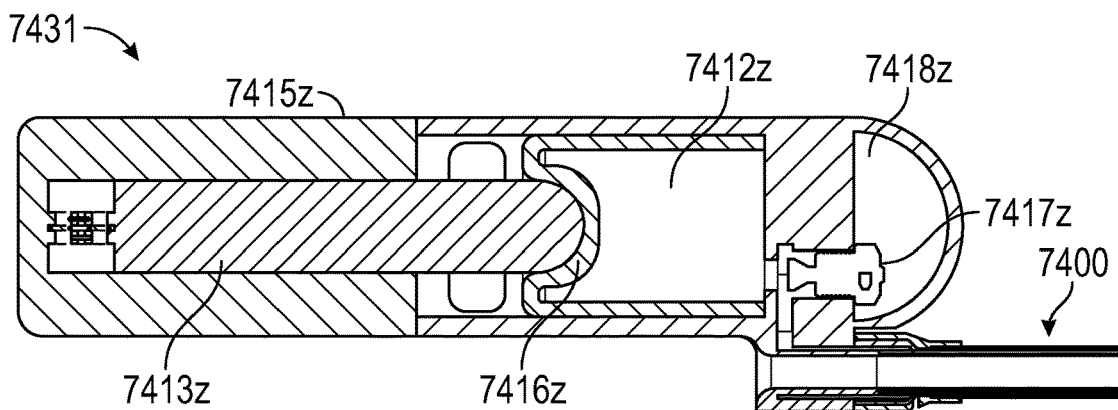
Figure 58E:
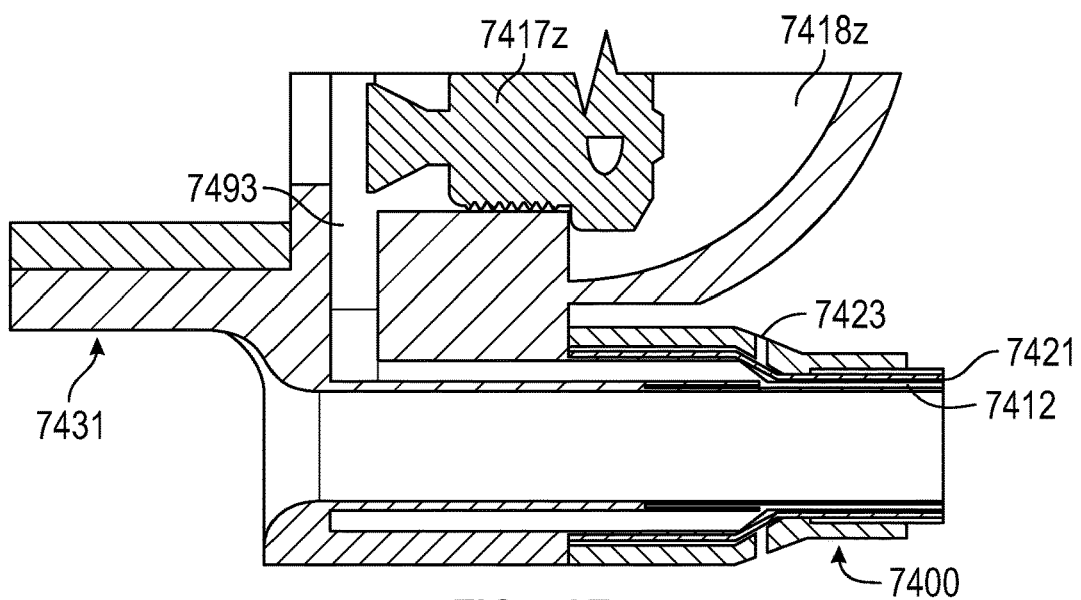

In some embodiments, a handle for use with a pressure rigidizing device can include a pressure gap inlet and a vent gap inlet. An exemplary handle 6231 attached to a pressure rigidizing device 6200 is shown in FIGS. 57A-57C. The handle includes a gap inlet 6293 and a vent gap inlet 6223. Pressure gap inlet 6293 connects to pressure gap 6212 (via pressure line 6294). Vent gap inlet 6223 (which can extend all the way through the handle to exit on both sides thereof) connects to gap 6206 around the braid layer 6209 (between the bladder 6221 and the outermost layer 6201). The vent inlet 6223 can be open to atmosphere while the gap inlet 6293 can be connected to a pressure source (e.g., and activated with an activation element). The handle 6231 can, for example, be used to operate the device 2200g described with respect to FIG. 16G. In some embodiments, a fitting can be added to the gap inlet 6293 so that the handle 6231 can be used to operate the device 2200i as described with respect to FIG. 16I.

In some embodiments, a handle for use with a pressure rigidizing device can include a pre-filled pressure medium therein. For example, an exemplary handle 7431 attached to a pressure rigidizing device 7400 is shown in FIGS. 58A-58E. The handle 7431 includes a handle body 7415z and a grip/lever 7411z that can be activated to provide pressure medium to the rigidizing device 7400, such as pressure medium pre-filled or stored in the fluid chamber 7412z of the handle 7431. The chamber 7412z can, for example, be bordered by a rolling diaphragm 7416z. The grip/lever 7411z can include teeth 7476z that mate with a rack 7414z of a piston 7413z. As the grip/lever 7411z is moved towards the handle body 7415z, the piston 7413z can move distally towards the rolling diaphragm 7416z of the fluid chamber 7412z. As the rolling diaphragm 7416z is pushed distally, it forces the pressure medium from the chamber 7412z through the gap inlet 7493 to the pressure gap 7412 outside of the bladder 7421 for stiffening (and air or other fluids can likewise escape from around the braid layer via vent 7423). In some embodiments, the handle 7431 can include a locking mechanism (e.g., via a click on/click off mechanism, such as that found in a ball point pen) with spring and feeler 7778z configured to lock the grip/lever 7411z against the body 7415z so as to lock the rigidizing device 7400 in the rigid configuration. Similarly, when the grip/lever 7411z is pushed against the body again, the grip/lever 7411 can be released, and the fluid can move back into the fluid chamber 7412z via inlet 7493.

In some embodiments, the handle 7431 can further include a pressure relief valve 7417z between the chamber 7412z and an overflow chamber 7418z. When the pressure in the fluid chamber 7412z reaches a predetermined maximum pressure (e.g., 5atm), the pressure relief valve 7417z can open to allow fluid to be channeled into the overflow chamber 7418z. The fluid chamber 7412z can be overfilled during manufacturing such that the valve 7417 always opens upon the first activation of the grip/lever 7411z, which can ensure calibration of the handle 7431 to the desired pressure. One exemplary method of filling the fluid chamber 7412z can include:

(1) attaching the handle 7431 to a filling fitting that attaches to a tube leading to the pressure system; (2) drawing a vacuum on the handle to remove air through that filling fitting; (3) while maintaining vacuum, introducing water, DI, Saline, an oil or another incompressible fluid into the system through the filling fitting; and (4) crimping and sealing the tube (via a mechanical crimp, via melting the tube, etc.) distal to the pressure fitting and then removing the pressure fitting, leaving the crimped/sealed tube in the handle.

Any of the handles described herein can have a pressure indicating feature built in. For instance, the handles may have a pressure gauge. The handles may include a feature, such as a piston, that is displaced to give a visual indication that the device is pressurized. The handles may have a feature that flips or turns such that it displays a different color; for instance, it may display a green dot at atmospheric pressure and red dot when rigidized. In some embodiments, the visual indication can be seen on fluoroscopy.

Any of the pressure rigidizing handles described may have an emergency venting feature if, for some reason, the handle passageways became clogged. The emergency venting feature can, for example, allow for incising of the device, thereby breaking its pressure cavity. The emergency venting feature can, for example, be a valve distal to the handle (for example, a swabable valve), such that should the valve be actuated, the device would vent pressure and therefore de-rigidize.

Figure 59:
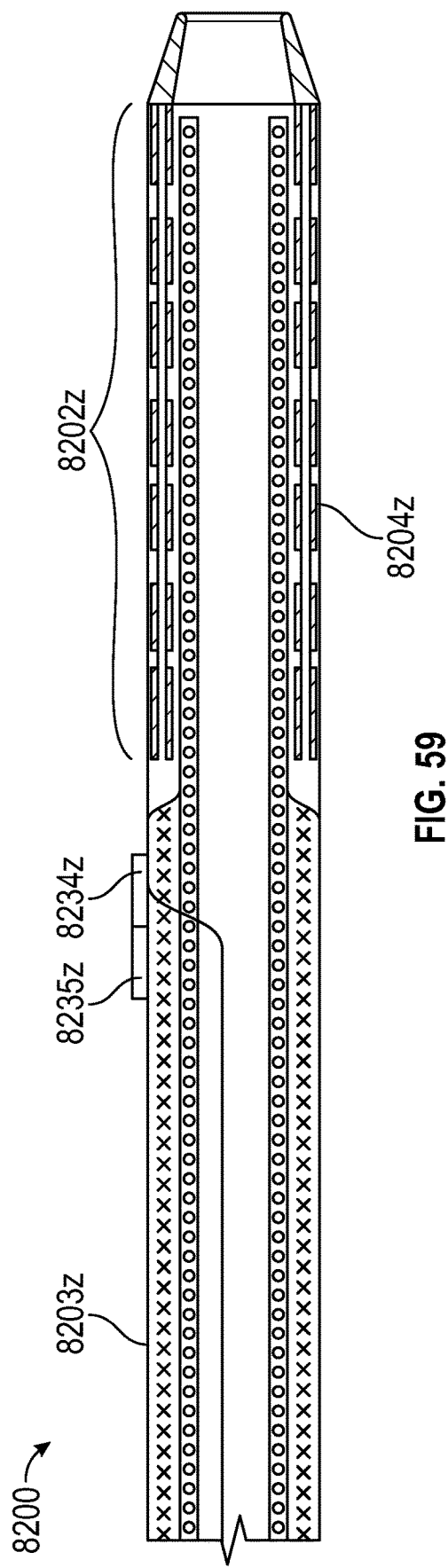
FIG. 59 shows a rigidizing device with imaging elements mounted on a side thereof.

Any of the rigidizing devices described herein can include built-in cameras, lighting, etc. to provide for on-board imaging. In some embodiments (and as shown below in FIG. 63), the cameras and lighting can be positioned at the distal tip of the device. In other embodiments, and as shown in FIG. 59, a rigidizing device 8200 can include a camera 8234z and lighting 8235z mounted on the elongate body 8203z proximal to the distal end 8202z of the device (e.g., proximal to steering linkages 8204z).

Figure 60:
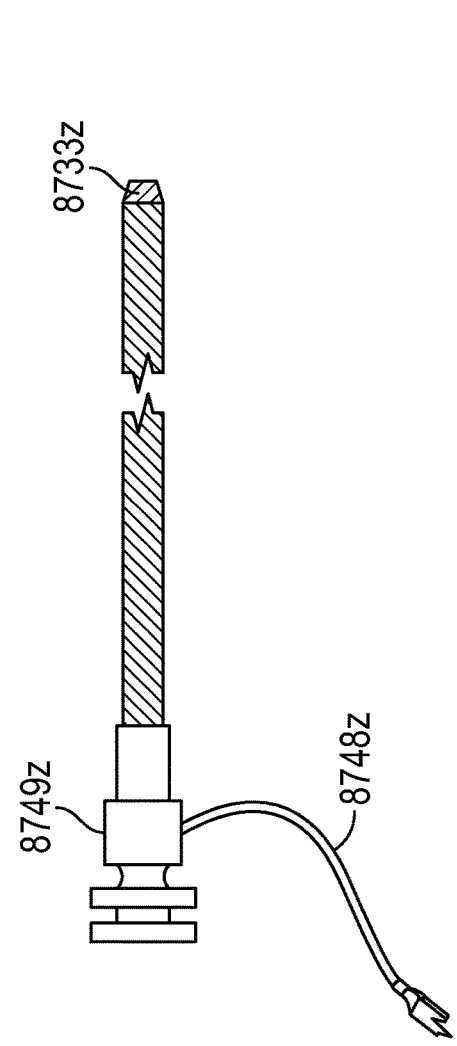
FIG. 60 shows a rigidizing introducer.

In some embodiments, the rigidizing devices described herein can be configured as an introducer (i.e., an instrument for introduction of a flexible device, such as an introducer sheath for interventional cardiology). For example, referring to FIG. 60, a rigidizing device 8700 can include a rigidizing elongate body 8703z with a tapered distal tip 8733z. The device 8700 can further include a hemostatic valve 8749z and/or a flush line 8748z.

The braid described herein can include or be replaced by a mesh, a woven material, a ribbon or a cloth. In some embodiments, the braid can be non-woven (i.e., fibers at different angles may not go over and under each other but instead be on separate layers that do not cross each other). Similarly, the braid can be replaced by a stent or a structure (e.g., metal structure) cut from a hypodermic tube.

Figure 61A:
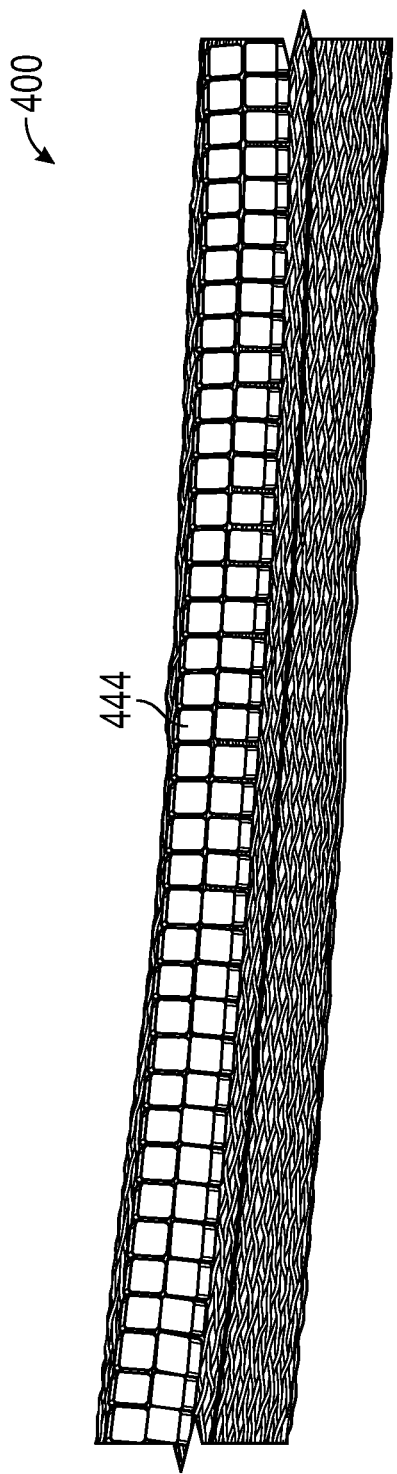
FIGS. 61A-61B show a rigidizing device with a side-access mechanism.
Figure 61B:
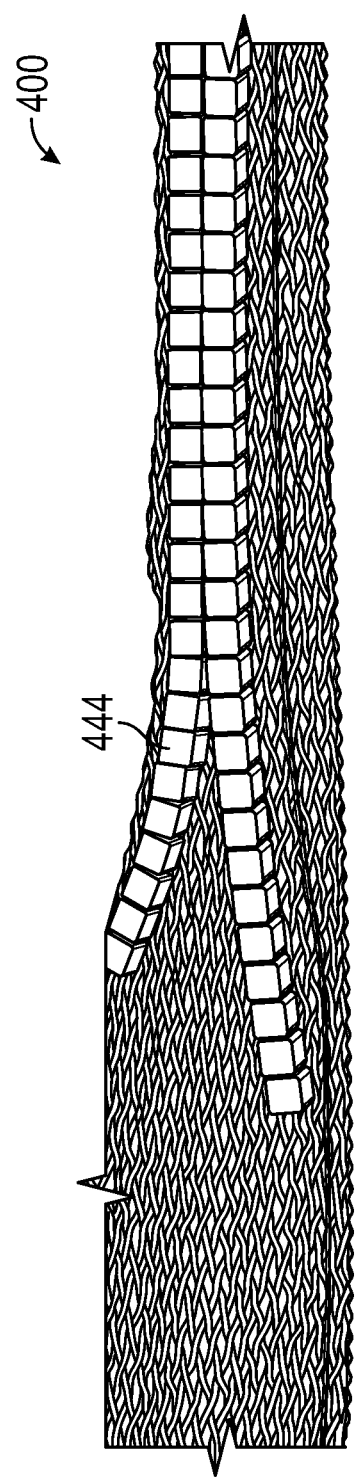

In some embodiments, the rigidizing devices described herein can be configured to be loaded over the side of the scope or other instrument (e.g., rather than requiring insertion of the scope/instrument into the proximal end of the rigidizing device). For example, as shown in FIGS. 61A-61B, the rigidizing device 400 can be split along the length thereof (i.e., split longitudinally through the wall from the proximal end to the distal end). Further, a connection feature 444 can connect the split wall together. In some embodiments, the connection feature 444 can be reusable. For example, the connection feature 444 can be a series of magnets that can engage (FIG. 61A) to hold the rigidizing device 400 together and disengage (FIG. 61B) to provide side access for the scope/instrument. Other exemplary reusable connection features include zippers, interlocking ziplock male and female configuration, or reusable tape. In some embodiments, the connection feature 444 can be permanent and not reusable, such as permanent tape or adhesive.

In some embodiments, the vacuum and pressure multi-layered systems described herein can be used to create stiffness for non-cylindrical or non-tubular structures. For example, the systems described herein could be used to create a balloon that assumes the desired shape when pressurized and/or rigidized. Such a structure can be a flexible structure that nevertheless contains elements that exhibit high hoop stiffness, such as wire (tension or compression) or thin fiber strands (tension).

In some embodiments, the rigidizing devices described herein can include proximal and distal seals within the innermost layer to create a space between the scope or instrument and the innermost layer to hold lubrication.

In some embodiments, the rigidizing devices described herein can be used in conjunction with other versions of the product. For example, an endoscope can include the rigidizing mechanisms described herein, and a rigidizing device can include the rigidizing mechanisms described herein. Used together, they can create a nested system that can advance, one after the other, allowing one of the elements to always remain stiffened, such that looping is reduced or eliminated (i.e., they can create a sequentially advancing nested system).

Figure 62:
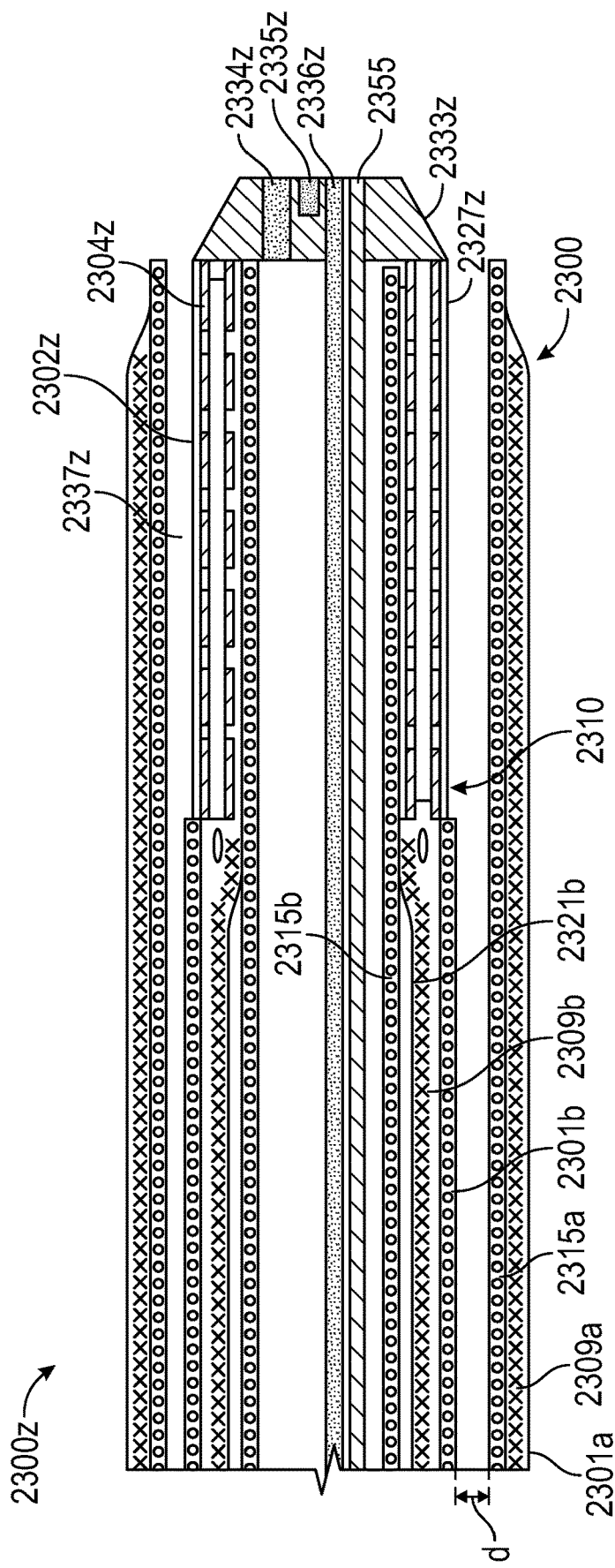
FIG. 62 shows a nested rigidizing system.

An exemplary nested system 2300z is shown in FIG. 62. The system 2300z can include an outer rigidizing device 2300 and an inner rigidizing device 2310 (here, configured as a rigidizing scope) that are axially movable with respect to one another either concentrically or non-concentrically. The outer rigidizing device 2300 and the inner rigidizing device 2310 can include any of the rigidizing features as described herein. For example, the outer rigidizing device 2300 can include an outermost layer 2301a, a braided layer 2309a, and an inner layer 2315a including a coil wound therethrough. The outer rigidizing device 2300 can be, for example, configured to receive vacuum between the outermost layer 2301a and the inner layer 2315a to provide rigidization. Similarly, the inner scope 2310 can include an outer layer 2301b (e.g., with a coil wound therethrough), a braid layer 2309b, a bladder layer 2321b, and an inner layer 2315b (e.g., with a coil wound therethrough). The inner scope 2310 can be, for example, configured to receive pressure between the bladder 2321b and the inner layer 2315b to provide rigidization. Further, an air/water channel 2336z and a working channel 2355 can extend through the inner rigidizing device 2310. Additionally, the inner rigidizing scope 2310 can include a distal section 2302z with a camera 2334z, lights 2335z, and steerable linkages 2304z. A cover 2327z can extend over the distal section 2302z. In another embodiment, the camera and/or lighting can be delivered in a separate assembly (e.g., the camera and lighting can be bundled together in a catheter and delivered down the working channel 2355 and/or an additional working channel to the distal-most end 2333z).

An interface 2337z can be positioned between the inner rigidizing device 2310 and the outer rigidizing device 2300. The interface 2337z can be a gap, for example, having a dimension d (see FIG. 62) of 0.001"-0.050", such as 0.0020", 0.005", or 0.020" thick. In some embodiments, the interface 2337z can be low friction and include, for example, powder, coatings, or laminations to reduce the friction. In some embodiments, there can be seals between the inner rigidizing device 2310 and outer rigidizing device 2300, and the intervening space can be pressurized, for example, with fluid or water, to create a hydrostatic bearing. In other embodiments, there can be seals between the inner rigidizing device 2310 and outer rigidizing device 2300, and the intervening space can be filled with small spheres to reduce friction.

The inner rigidizing device 2310 and outer rigidizing device 2300 can move relative to one another and alternately rigidize so as to transfer a bend or shape down the length of the nested system 2300z. For example, the inner device 2310 can be inserted into a lumen and bent or steered into the desired shape. Pressure can be applied to the inner rigidizing device 2310 to cause the braid elements to engage and lock the inner rigidizing device 2310 in the configuration. The rigidizing device (for instance, in a flexible state) 2300 can then be advanced over the rigid inner device 2310. When the outer rigidizing device 2300 reaches the tip of the inner device 2310, vacuum can be applied to the rigidizing device 2300 to cause the layers to engage and lock to fix the shape of the rigidizing device. The inner device 2310 can be transitioned to a flexible state, advanced, and the process repeated. Although the system 2300z is described as including a rigidizing device and an inner device configured as a scope, it should be understood that other configurations are possible. For example, the system might include two overtubes, two catheters, or a combination of overtube, catheter, and scope.

Figure 63:
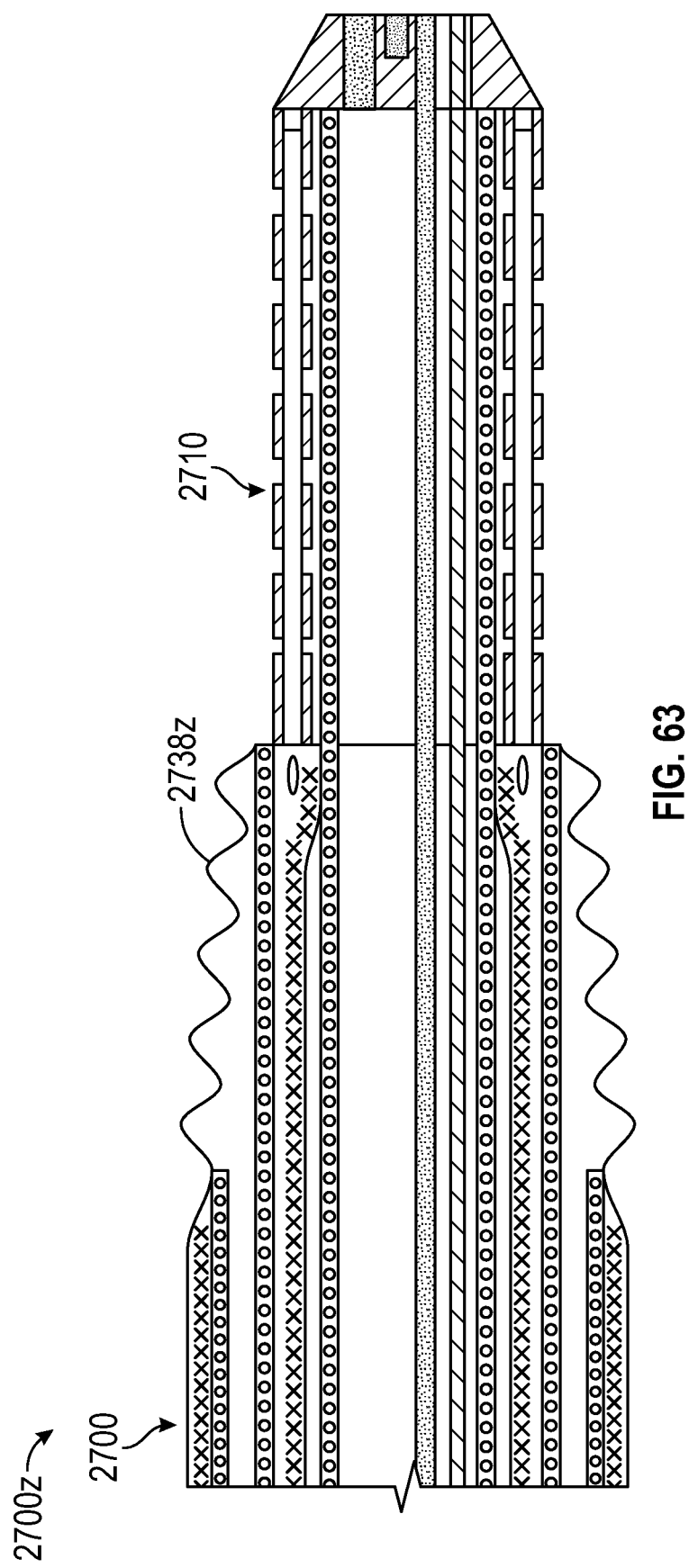
FIG. 63 shows a nested rigidizing system with a cover between the inner and outer rigidizing devices.

FIG. 63 shows another exemplary nested system 2700z. System 2700z is similar to system 2300z except that it includes a cover 2738z attached to both the inner and outer rigidizing device 2710, 2700. The cover 2738z may be, for example, low-durometer and thin-walled to allow elasticity and stretching. The cover 2738z may be a rubber, such as urethane, latex, or silicone. The cover 2738z may protect the interface/radial gap between the inner and outer devices 2710, 2700. The cover 2738z may prevent contamination from entering the space between the inner and outer tubes. The cover 2738z may further prevent tissue and other substances from becoming trapped in the space between the inner and outer tubes. The cover 2738z may stretch to allow the inner device 2710 and outer device 2700 to travel independently of one another within the elastic limits of the material. The cover 2738z may be bonded or attached to the rigidizing devices 2710, 2700 in such a way that the cover 2738z is always at a minimum slightly stretched. This embodiment may be wiped down externally for cleaning. In some embodiments, the cover 2738z can be configured as a "rolling" seal, such as disclosed in U.S. Pat. No. 6,447,491, the entire disclosure of which is incorporated by reference herein.

Figure 64A:
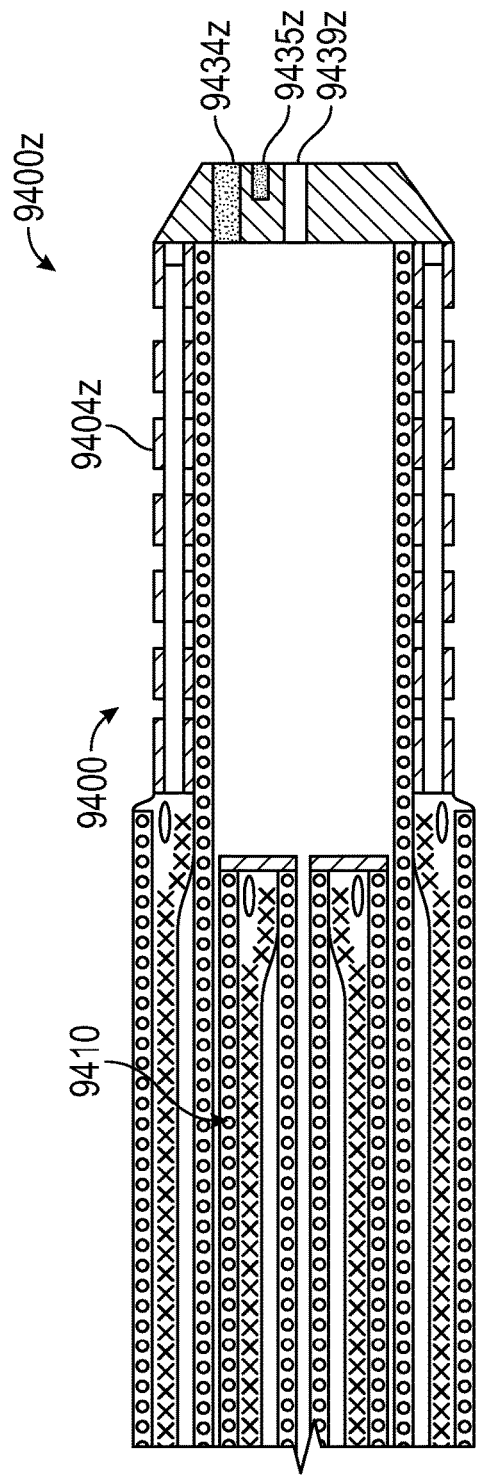
FIGS. 64A-64B show a nested rigidizing system where the outer rigidizing device includes steering and imaging.
Figure 64B:
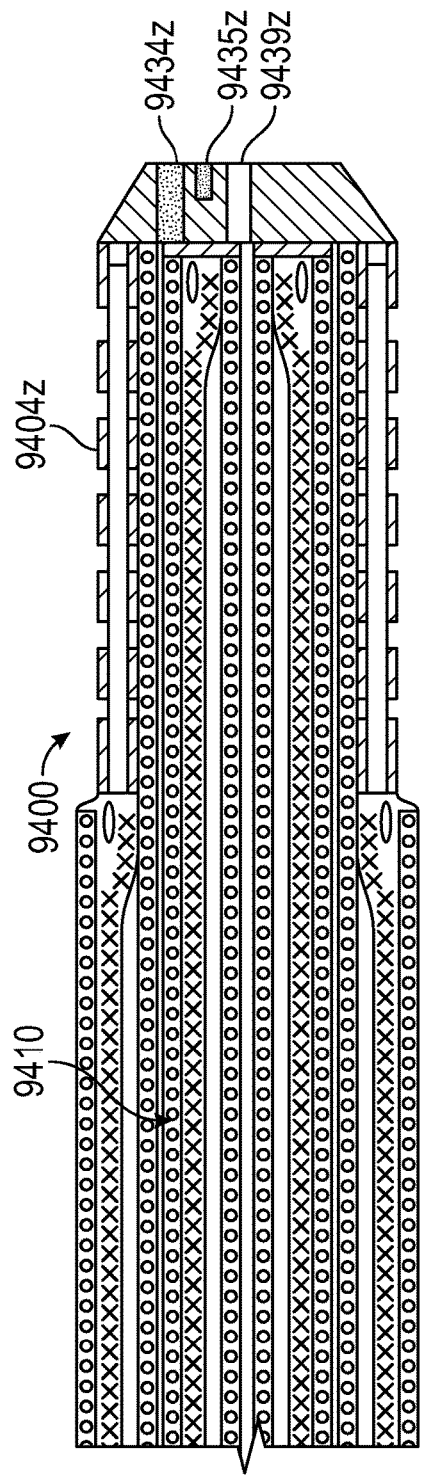

FIGS. 64A-64B show another exemplary nested system 9400z. In this system 9400z, the outer rigidizing device 9400 includes steering and imaging (e.g., similar to a scope) while the inner device includes only rigidization (though it could include additional steering elements as described elsewhere herein). Thus, outer device 9400 includes linkages or other steering means disclosed herein 9404z, camera 9434z, and lighting 9435z. The outer device 9400 can further include a central passageway 9439z for access to the inner device 9410 (e.g., lumens such as working channels therein). In some embodiments, bellows or a loop of tubing can connect the passageway 9439z to lumens of the inner device 9410. Similar to the other nested systems, at least one of the devices 9410, 9400 can be rigidized at a time while the other can conform to the rigidization and/or move through the anatomy. Here, the outer device 9400 can lead the inner device 9410 (the inner device 9410 is shown retracted relative to the outer device 9400 in FIG. 64A and extended substantially even with the outer device 9400 in FIG. 64B). Advantageously, system 9400z can provide a smooth exterior surface to avoid pinching the anatomy and/or entrance of fluid between the inner and outer devices 9410, 9400. Having the steering on the outer device 9400 can also provide additional leverage for steering the tip. Also, the outer device can facilitate better imaging capabilities due to the larger diameter of the outer device 9400 and its ability to accommodate a larger camera.

Figure 65A:
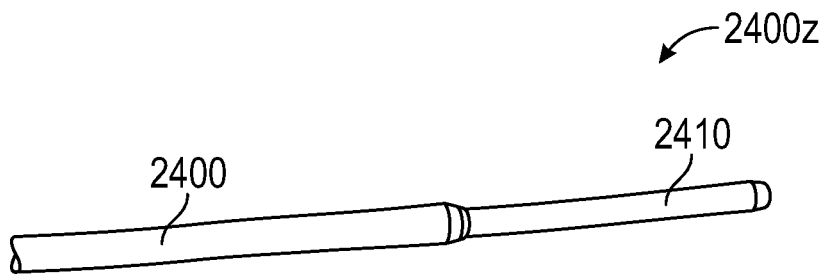
FIGS. 65A-65H show exemplary use of a nested rigidizing system.
Figure 65B:
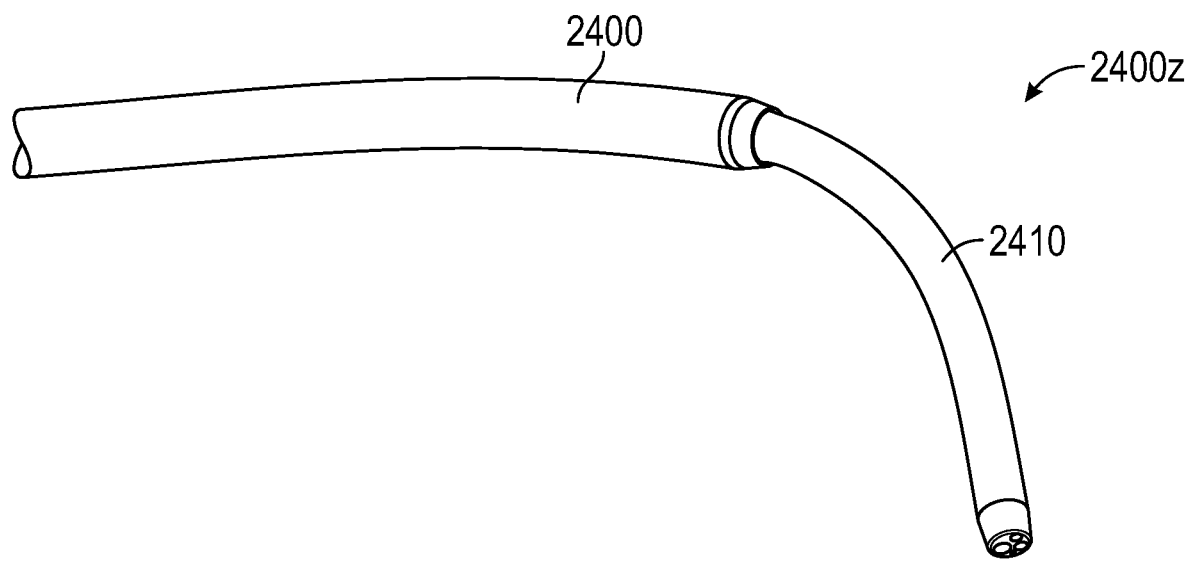
Figure 65C:
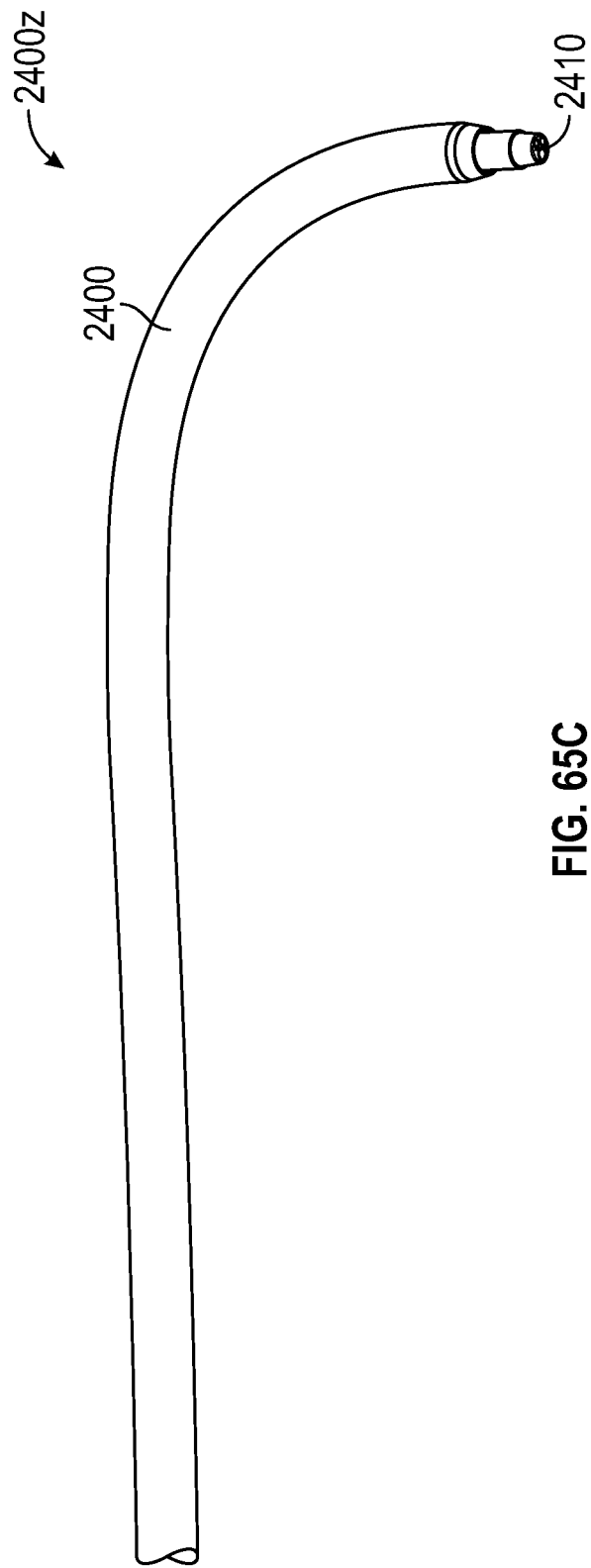
Figure 65D:
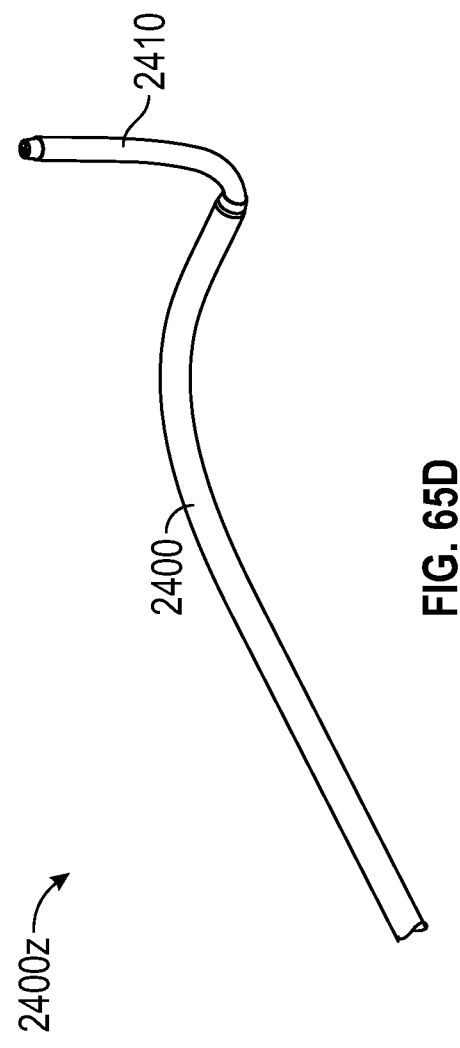
Figure 65E:
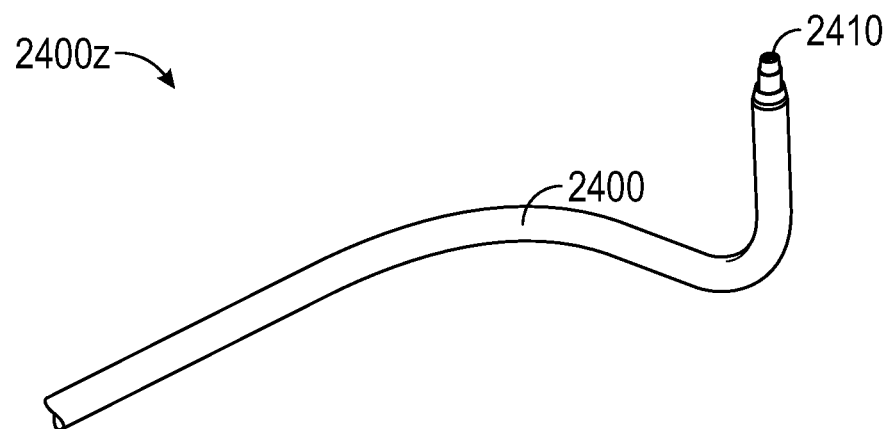
Figure 65F:
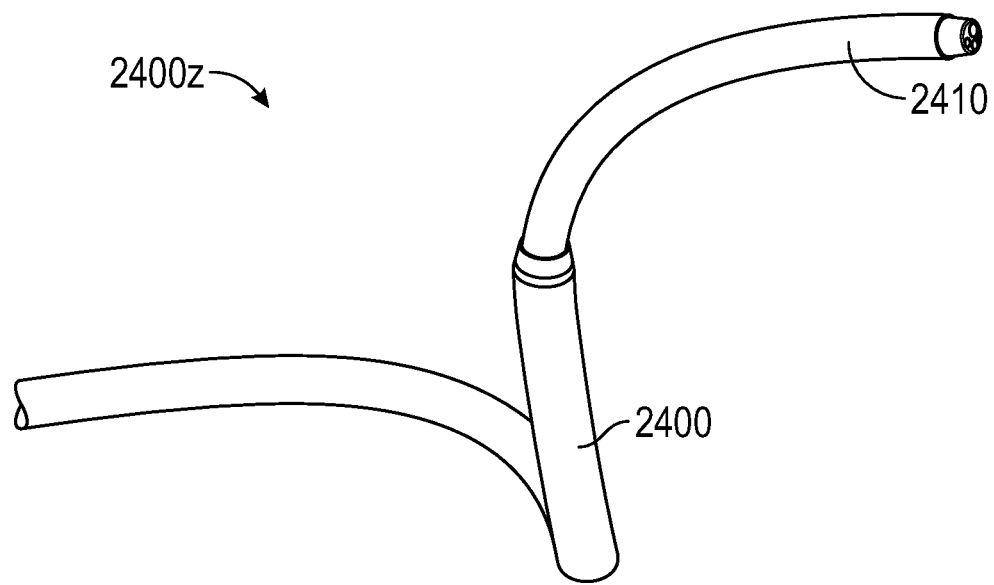
Figure 65G:
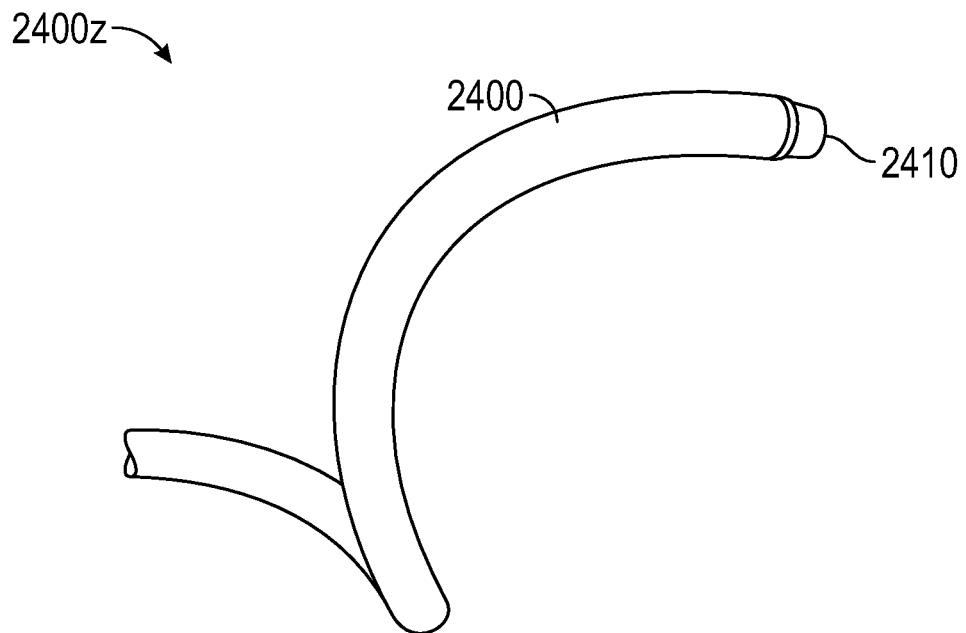
Figure 65H:
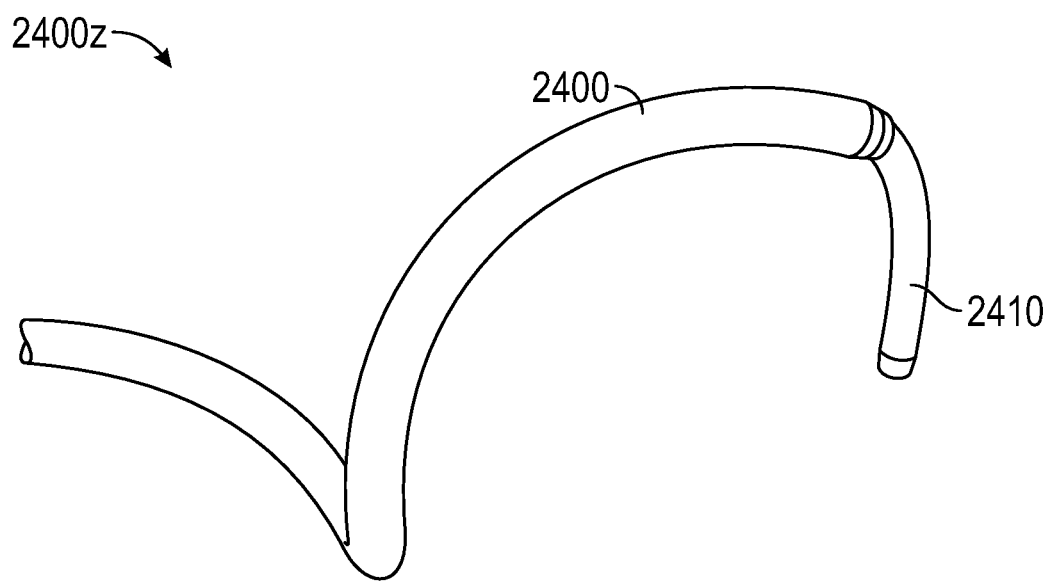

FIGS. 65A-65H show the exemplary use of a nested system 2400z as described herein. At FIG. 65A, the inner rigidizing device 2410 is positioned within the outer rigidizing device 2400 such that the distal end of the inner rigidizing device 2410 extends outside of the outer rigidizing device 2400. At FIG. 65B, the distal end of the inner rigidizing device 2410 is bent in the desired direction/orientation and then rigidized (e.g., using vacuum or pressure as described herein). At FIG. 65C, the outer rigidizing device 2400 (in the flexible configuration) is advanced over the rigidized inner rigidizing device 2410 (including over the bending distal section). Once the distal end of the outer rigidizing device 2400 is sufficiently advanced over the distal end of the inner rigidizing device 2410, then the outer rigidizing device 2400 can be rigidized (e.g., using vacuum or pressure as described herein). At FIG. 65D, the inner rigidizing device 2410 can then be transitioned to the flexible state (e.g., by removing the vacuum or pressure as described herein and by allowing the steering cables to go slack such that tip can move easily) and can be advanced and directed/oriented/steered as desired. Alternately, in FIG. 65D, the inner rigidizing device 2410 can be actively steered (either manually or via computational control) as it emerges such that is minimizes the load on the rigidized outer tube. Minimizing the load on the outer rigidizing device 2400 makes it easier for this tube to hold the rigidized shape. Once the inner rigidizing device 2410 is rigidized, the outer rigidizing device 2400 can be transitioned to the flexible state and advanced thereover (as shown in FIG. 65E). The process can then be repeated as shown in FIGS. 65F-H.

In some embodiments, at the completion of the sequence shown in FIGS. 65A-H, a third rigidizing device can be slid over the first two rigidizing devices (2400, 2410) and rigidized. Rigidizing devices 2400 and 2410 can then be withdrawn. Finally, a fourth rigidizing device can be inserted through the inner lumen of the third tube. This fourth rigidizing device may have a larger diameter and more features than rigidizing device 2410. For instance, it may have a larger working channel, more working channels, a better camera, or combinations thereof. This technique can allow two smaller tubes, which tend to be more flexible and maneuverable, to reach deep into the body while still ultimately deliver a larger tube for therapeutic purposes. Alternately, in the example above, the fourth rigidizing device can be a regular endoscope as is known in the art.

In some embodiments, at the completion of the sequence shown in FIGS. 65A-H, outer rigidizing device 2400 may be rigidized and then the inner rigidizing device 2410 may be removed. For example, the rigidizing device 2410 may be a "navigation" device comprising a camera, lighting and a distal steering section. The "navigation" device 2410 may be well sealed such that it is easy to clean between procedures. A second inner device may then be placed inside the rigidized outer device 2400 and advanced past the distal end of the outer device 2400. The second inner device may be a "therapeutic" tube comprising such elements as a camera, lights, water, suction and various tools. The "therapeutic" device may not have a steering section or the ability to rigidize, thereby giving additional room in the body of the therapeutic tube for the inclusion of other features, for example, tools for performing therapies. Once in place, the tools on the "therapeutic" tube may be used to perform a therapy in the body, such as, for example, a mucosal resection or dissection in the human GI tract.

In another embodiment, after or during the completion of the sequence shown in FIGS. 65A-H, a third device may be inserted inside inner tube 2410. The third device may be rigidizing and/or an endoscope.

Although the outer rigidizing device for the nested systems described herein is often referred to as rigidizing via vacuum and the inner scope rigidizing device as rigidizing via pressure, the opposite can be true (i.e., the outer rigidizing device can rigidize via pressure and the inner rigidizing device via vacuum) and/or both can have the same rigidizing source (pressure and/or vacuum).

Although the inner and outer elements of the nested systems are generally described as including integrated rigidizing elements, the rigidizing elements can be separate (e.g., so as to allow relative sliding between the imaging scope elements and the rigidizing elements).

The rigidizing devices of the nested systems described herein can be designed such that inner rigidizing device can't rotate substantially within outer rigidizing device when they are assembled. For instance, the outer surface of the inner rigidizing device can have longitudinal ridges and grooves that form a spline. The inner surface of the outer rigidizing device can have corresponding ridges and grooves that mate with the same features in the outer rigidizing device.

Either or both of the rigidizing devices of the nested systems described herein can be steerable. If both rigidizing devices are steerable, an algorithm can be implemented that steers whichever rigidizing device is flexible and moving longitudinally. The algorithm can steer the flexible rigidizing device to anticipate the shape of the rigidized device thus minimizing the tendency for the moving, flexible rigidizing device to straighten the rigid device.

If one rigidizing device of the nested systems described herein requires vacuum and the other rigidizing device requires pressure, user controls can be constructed in which moving one vs. the other (outer and inner) involves flipping a switch, with the switch toggling between a first condition in which, for example, one is pressurized for rigidity when the other is vented for flexibility and a second condition in which one is vented for flexibility and the other is vacuumed for stiffness. This, for example, could be a foot pedal or a hand switch.

In some embodiments, the alternate movement of the nested systems described herein can be controlled manually. In other embodiments, the alternate movement can be controlled automatically, via a computer and/or with a motorized motion control system.

The nested systems described herein can advantageously be of similar stiffness. This can ensure that the total stiffnesses of the nested system is relatively continuous. The nested systems described herein can be small so as to fit in a variety of different anatomies. For example, for neurology applications, the outside diameter of the system can be between 0.05"-0.15", such as approximately 0.1". For cardiology applications, the outside diameter of the system can be between 0.1"-0.3", such as approximately 0.2". For gastrointestinal applications, the outside diameter of the system can be between 0.3"-1.0", such as 0.8". Further, the nested systems described herein can maintain high stiffness even at a small profile. For example, the change in relative stiffness from the flexible configuration to the rigid configuration can be multiples of 10×, 20×, 30×, and even larger. Additionally, the nested systems described herein can advantageously move smoothly relative to one another.

The nested systems described herein can advantageously navigate an arbitrary path, or an open, complex, or tortuous space, and create a range of free-standing complex shapes. The nested systems can further advantageously provide shape propagation, allowing for shape memory to be imparted from one element to another. In some embodiments, periodically, both tubes can be placed in a partially or fully flexible state such that, for instance, the radii or curvature of the system increases, and the surrounding anatomy provides support to the system. The pressure or vacuum being used to rigidize the tubes can be reduced or stopped to place the tubes in a partially or fully flexible state. This momentary relaxation (for instance, for 1-10 seconds) may allow the system to find a shape that more closely matches the anatomy it is travelling through. For instance, in the colon, this relaxation may gently open tight turns in the anatomy.

In some embodiments, the stiffness capabilities of the inner or outer rigidizing devices may be designed such that tight turns formed by the inner rigidizing device at its tip, when copied by the outer rigidizing device, are gradually opened up (made to have a larger radius) as the shape propagates proximally down the outer tube. For instance, the outer rigidizing device may be designed to have a higher minimum radius of curvature when rigidized.

The nested systems are continuous (i.e., non-segmented) and therefor provide smooth and continuous movement through the body (e.g., the intestines). The nested systems can be disposable and low-cost.

In some embodiments, the outer rigidizing device can be a dynamically rigidizing overtube (e.g., as described in PCT/US18/42946, the entirety of which is incorporated by reference herein). In some embodiments, the inner rigidizing device can be a rigidizing system or a commercially available scope, for example a 5 mm diameter nasal scope. Utilizing rigidization and a nested system enables the utilization of a smaller scope that delivers, compared to a duodenoscope, more flexibility if desired, more stiffness if desired, enhanced maneuverability, and the ability to articulate at a much smaller radius of curvature.

In some embodiments, upon reaching the target destination, the inner rigidizing device of a nested system can be withdrawn. The outer rigidizing device can remain rigidized and contrast can be injected through the inner element's space to fluoroscopically image.

RF coils can be used in any of the nested systems described herein to provide a 3-D representation of whatever shape the nested system takes. That representation can be used to re-create a shape or return to a given point (e.g., for reexamination by the doctor after an automated colonoscopy).

In some embodiments, the nested systems described herein can be useful as a complete endoscope, with the internal structure carrying the payload of working channels, pressurization lines, vacuum lines, tip wash, and electronics for lighting and imaging (vision systems, ultrasound, x-ray, MRI).

The nested systems described herein can be used, for example, for colonoscopy. Such a colonoscopy nested system can reduce or eliminate looping. It could eliminate the need for endoscopic reduction. Without looping, the procedure can combine the speed and low cost of a sigmoidoscopy with the efficacy of a colonoscopy. Additionally, colonoscopy nested systems can eliminate conscious sedation and its associated costs, time, risks, and facility requirements. Further, procedural skill can be markedly reduced for such colonoscopy procedures by using the nested systems described herein. Further, in some embodiments, the nested systems described herein can provide automated colonoscopy, wherein a vision system automatically drives the nested system down the center of the colon while looking for polyps. Such an automated system would advantageously not require sedation nor a doctor for the basic exam while allowing the doctor to follow up for further examination if required.

Figure 66:
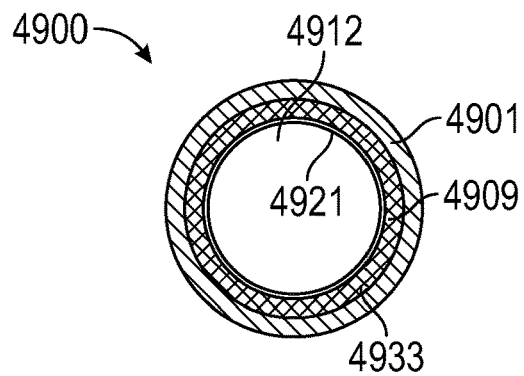
FIG. 66 shows a rigidizing rod.

In some embodiments, a rigidizing device as described herein can be configured as a rigidizing rod. Referring to FIG. 66, the rod 4900 can include an outer layer 4901, a braid layer 4909, and an inner bladder layer 4921. Further, the gap 4912 within the bladder layer can be sealed and filled, for example, with air or water (e.g., to push the bladder layer 4921 radially outwards). The outer layer 4901 can be a wire-reinforced layer, such as a coil reinforced urethane tube. The braid layer 4901 can include braided strands 4933 and can include any of the features of other braid layers described herein. The inner bladder layer 4921 can be made of a low durometer elastomer. The rod 4900 can further include an atraumatic tip that is soft and/or tapered.

In some embodiments, the distal end of the inner bladder layer 4921 can be sealed to the outer layer 4901, and the rod 4900 can include an inlet between the outer layer 4901 and the inner bladder layer 4921 to provide vacuum for rigidization. In other embodiments, the distal end of the inner bladder layer 4921 can be sealed to itself or to the atraumatic distal tip and the proximal end can be configured to have an inlet to the inside of the inner bladder layer 4921 (i.e., radially inward of the inner bladder layer 4921) to provide pressure rigidization. When pressure rigidization is used, the rod 4900 can further include a vent on the distal and/or proximal end to allow venting of air from between the inner bladder layer 4921 and outer layer 4901 (thereby allowing the bladder 4921 to fully push the braid layer 4909 against the outer layer 4901).

In some embodiments, the outer surface of the outer layer 4901 can be coated to provide a low friction surface including a hydrophilic coating. In some embodiments, the outer diameter of the rod 4900 can be less than 5 mm, less than 4 mm, or less than 3 mm. For example, the outer diameter can be between 2 mm and 5 mm, such as between 2.5 mm and 3 mm, such as approximately 2.8 mm. In some embodiments, an angle of the braid of the braid layer 4909 can be less than 25 degrees relative to a longitudinal axis of the tube, such as approximately 5-15 degrees. In some embodiments, there can be between 10 and 50 strands, such as 20-40 strands, extending within the braid layer 4909.

Figure 67:
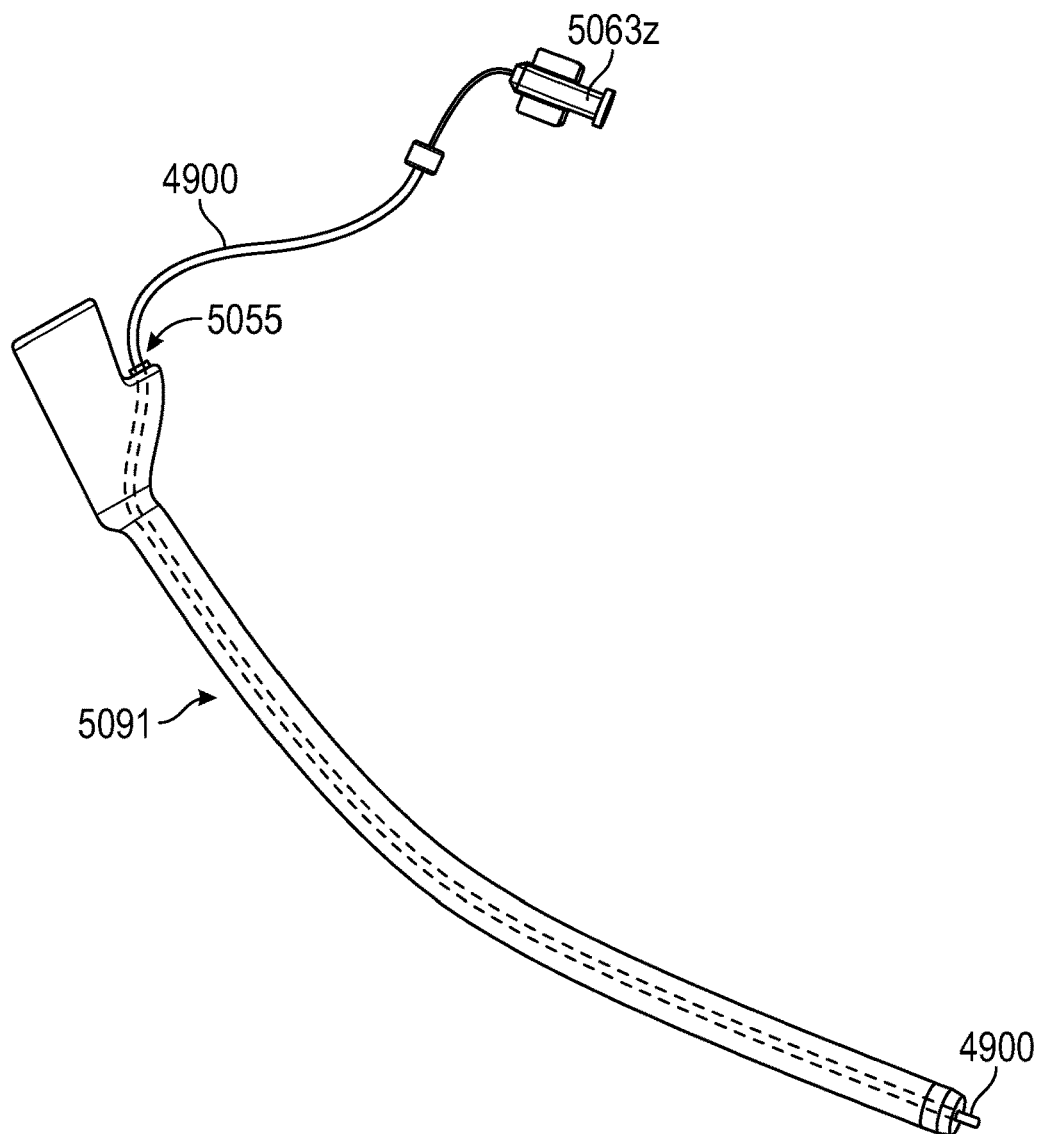
FIG. 67 shows a rigidizing rod in use with a colonoscope.

Referring to FIG. 67, the rod 4900 can be used, for example, as a stiffening wire for colonoscopy. In use as such, the colonoscope 5091 can be inserted into the patient's colon. If looping occurs (thereby hindering advancement of the colonoscope), the scope 5091 can be left in place, the working channel 5055 of the scope 5091 can be flushed, water can be applied to the outer surface of the rod 4900 to activate the hydrophilic coating, and the rod 4900 can be inserted in the flexible state (i.e., un-rigidized) through the working channel 5055. Once the rod 4900 is fully inserted into the endoscope such that the distal end of the rod 4900 is flush with the distal end of the colonoscope 5091 vacuum or pressure can be applied to the rod 4900 (e.g., via pressure inlet and/or connector 5063*z*), thereby rigidizing the rod. In some embodiments, the pressure or vacuum can be supplied to the rod 4900 through a syringe or locking insufflator The colonoscope 5091 can be advanced over the rod 4900 and relative to the patient while holding the rod 4900 stationary relative to the patient. The vacuum or pressure can be removed to advance or remove the rigidizing rod 4900.

Advantageously, the rod 4900 can thus be inserted into the scope 5091 in a flexible configuration so as to navigate around turns easily relative to a standard stiffening wire (i.e., relative to a stiffening wire of fixed rigidity). Further, the rod 4900 can conform to the shape of the looped colon in the flexible configuration while providing a rigid track for the scope to ride along in the rigid configuration. Dynamic transitions of the rod 4900 between flexible and stiff configurations can prevent unwanted straightening of the scope 5091 (which can otherwise occur with standard stiffening wires). Further, the atraumatic tip of the rod 4900 can prevent damaging of the working channel 5055. The rigidizing rod 4900 can further be relatively long (e.g., longer than the scope) without prohibiting navigation of the scope because the scope moves over and along the rigidizing rod 4900, and thus the rod 4900 can work with a variety of scopes regardless of length of the scope. Similarly, the rod 4900 can have a diameter of 3.2 mm or less and can thus work with a variety of endoscopes regardless of diameter (as most endoscopes have a working channel that is 3.2 mm or larger).

The rigidizing systems and devices described herein can be used to treat or access a number of different anatomical locations.

In one method of use, during a surgical procedure, a rigidizing device as described herein can be introduced to the patient in the flexible configuration. Once the distal end of the rigidizing device is positioned past the challenging anatomy (e.g., a portion of the anatomy that would cause looping or is otherwise difficult to pass with a standard instrument), the rigidizing device can be transitioned to the rigid configuration. An instrument (e.g., a scope) can then be passed over or through the rigid device.

For example, the devices described herein can be used to navigate the gastrointestinal tract, to reach anatomical locations in the stomach, for abdominal access to anatomical locations otherwise blocked by other organs, for interventional endoscopic procedures (including ESD (Endoscopic Submucosal Dissection) and EMR (Endoscopic Mucosal Resection)), for direct cholangioscopy, for endoscopic retrograde cholangiopancreatography, for cardiac applications, for resection or snaring of a lesion in the gastrointestinal tract, for enteroscopy, for EUS, to access the lungs, to access the kidneys, for neuro applications, for treatment of chronic total occlusions, for laparoscopic manual tools, for contralateral leg access, for ear nose and throat applications, during esophagogastroduodenoscopy, for transoral robotic surgery, for flexible robotic endoscopy, for natural orifice transluminal endoscopic surgery, or for altered anatomy cases. Specific examples are further described below.

Further, the rigidizing devices described herein can have different dimensions depending upon the desired application. For example, a rigidizing device can have an inner diameter of approximately 0.3"-0.8" (e.g., 0.5"), an outer diameter of 0.4"-1.0" (e.g., 0.6"), and a length of 50-200 cm, such as 75-150 cm, when designed, for example, for use in the gastrointestinal tract. The rigidizing device can have an inner diameter of, for example, 0.04"-0.3" (e.g., 0.2"), an outer diameter of 0.06"-0.4", and a length of 30-130 cm when designed, for example, for use in the cardiac vessels.

The rigidizing devices described herein can be used as overtubes for scopes in at least three different manners: (I) placement of the overtube after the scope has reached the destination; (II) overtube follows the scope closely, but remains proximal to the tip of the scope until the scope has reached its destination; or (III) the point and shoot method. An exemplary rigidizing device 2000 and scope 2091 is shown in FIGS. 68A-68B

For method I, the scope 2091 can be placed in the body at the desired location using standard technique, and then the rigidizing device 2000 can be advanced from the proximal end until the rigidizing device 2000 is sufficiently supporting the scope 2091. For instance, in order to perform a resection in the colon, a doctor may advance a colonoscope to the target site and then advance a rigidizing device almost or completely to the tip of the endoscope. The rigidizing device 2000 may then be rigidized. The rigidized device 2000 can, for example, advantageously enhance control during resection of a colon by providing a stable surgical platform. The rigidized device 2000 can also advantageously facilitate a good connection between the doctor's hand motion of the shaft of the scope 2091 external to the patient and motion of the tip of the scope 2091 (so called "1 to 1" motion).

For method II, the scope 2091 may lead the rigidizing device 2000 (for example, the distal end of the scope 2091 and the distal end of the rigidizing device 2000 may never approximately align) with the rigidizing device repeatedly being switched between a flexible and rigid state to aid advancement of the scope. For example, when advancing the scope 2091, the rigidizing device 2000 may be rigid, helping to prevent scope looping and aiding in scope force transmission. Once the scope 2091 has been advanced, the rigidizing device may be made flexible again and advanced distally on the scope. The process may be repeated.

Method III may include the following steps: (1) rigidizing device 2000 can be in a flexible state with the distal end of the rigidizing device 2000 approximately aligned with the distal end of the scope 2091; (2) scope 2091 can be steered with the distal end of the rigidizing device 2000 positioned thereover and therefore being steered by the scope 2091; (3) rigidizing device 2000 can be placed in a rigid state that mirrors the steering position of the scope 2091; (4) the distal end of scope 2091 can be advanced. This point and shoot method can advantageously allow the scope 2091 to be advanced in the direction to which the tip of the scope 2091 is pointing. In some embodiments, the steps can be repeated to advance the rigidizing device 2000 and scope 2091 within a body cavity or lumen.

It should be understood that methods I-III can be used in combination with one another. Further, in some embodiments, the rigidizing device can be steerable to further provide direction for the scope.

Figure 69A:
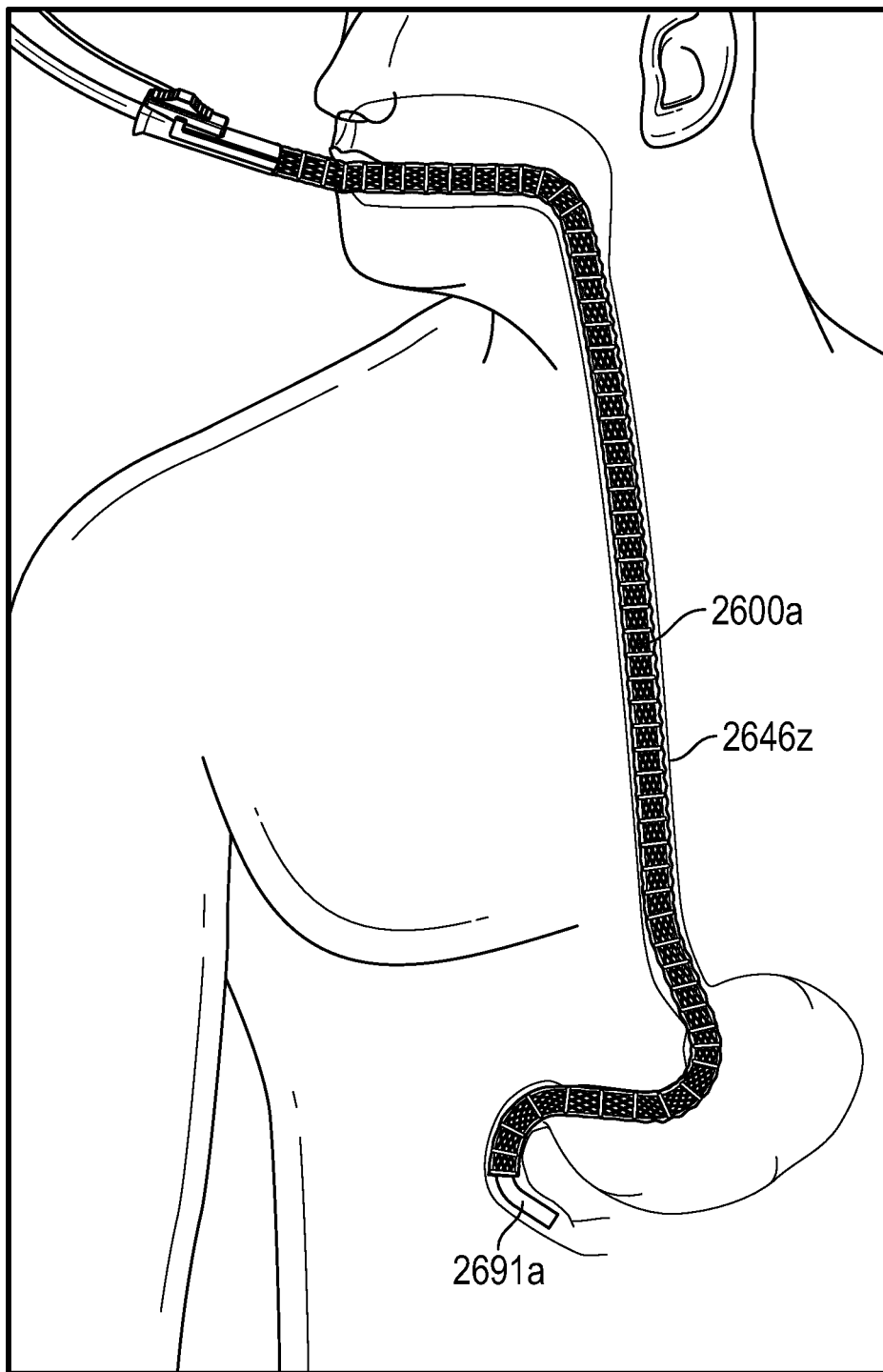
FIGS. 69A-69B show use of a rigidizing device in the gastrointestinal tract.
Figure 69B:
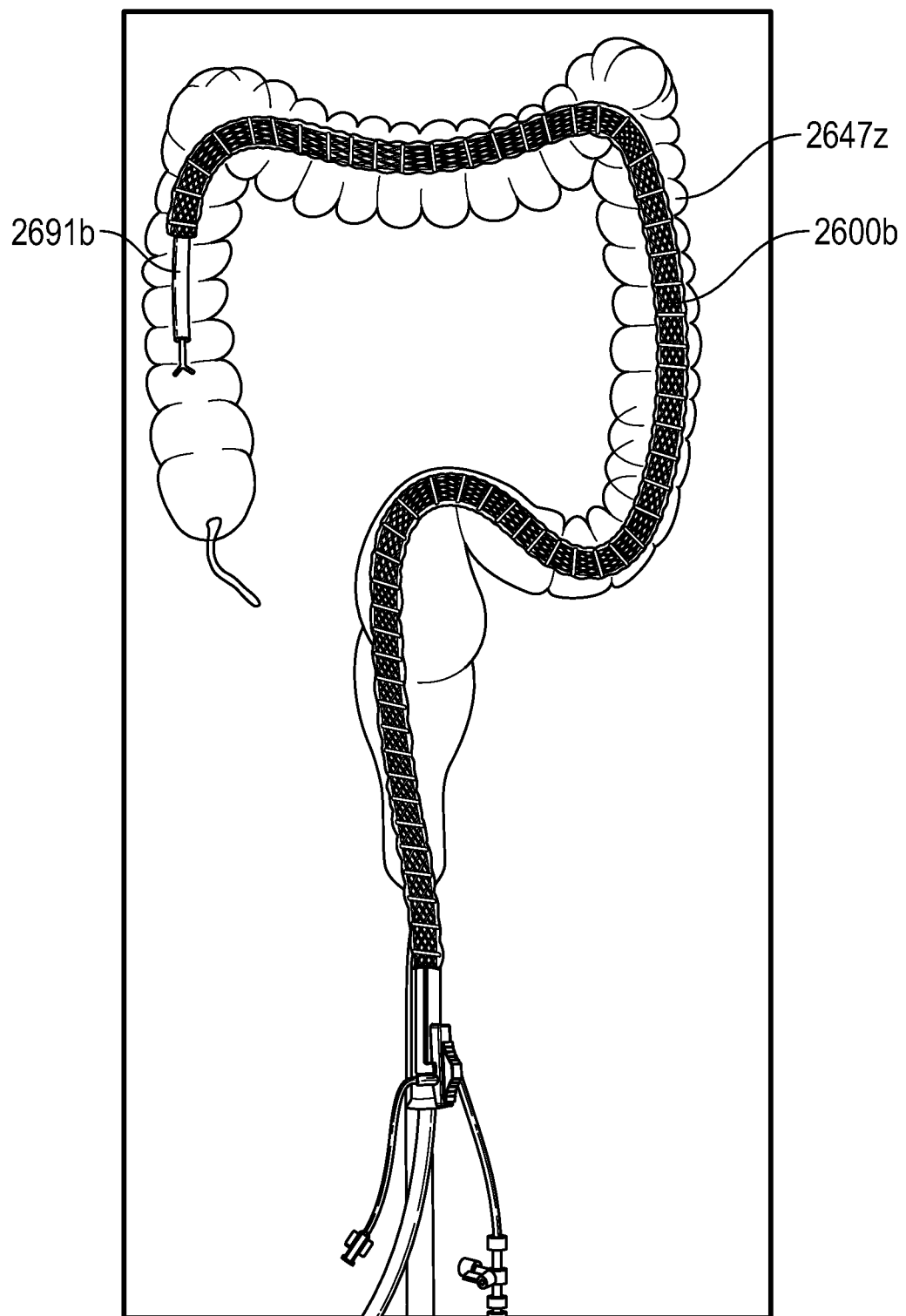

The three different manners of control can be used in the digestive tract. For example, these techniques may allow an endoscope 2691*a* to be positioned in the upper digestive tract 2646*z* with a rigidizing device 2600*a* as shown in FIG. 69A. As another example, a rigidizing device 2600*b* may be used to position an endoscope 2691*b* in the lower digestive tract 2647*z* as shown in FIG. 69B. The described manners of control may make the positioning shown in FIGS. 69A and 69B easier and faster to achieve, while minimizing risk of complications (such as GI tract perforation) and reducing or eliminating patient discomfort form endoscopic looping.

The rigidizing devices and systems described herein can be used for endoscopic retrograde cholangiopancreatography (ERCP) and/or direct cholangioscopy (DC). The goal of endoscopic retrograde cholangiopancreatography is to diagnose and treat disease in the bile and pancreatic ducts. This is most commonly performed with a side viewing duodenoscope by navigating a guidewire into the bile and pancreatic ducts, injecting contrast into the ducts, viewing under fluoroscopy, and passing various tools through the ducts over the wire. It is desirable to directly visualize the ducts with a camera rather than using radiation and contrast injections. By passing a small endoscope into the bile ducts, one can directly visualize the ducts without radiation. However, it is very difficult to navigate such a small endoscope through the stomach and into the bile duct as the scope will tend to loop.

Cannulation of the bile or pancreatic duct is made difficult due to two reasons. First, the endoscope must be small in order to fit inside the small ducts which means it is very flexible and buckles inside the stomach when trying to exit the stomach. Second, the duct entrance (papilla) is on the side of the duodenum wall which means the endoscope must bend and advance at an angle relative to the long axis of the endoscope which cannot be done without a surface to deflect against. The rigidizing devices described herein can be used to create more optimal access and stabilization during ERCP and DC, including the kinematically and clinically challenging tasks of cannulating the papilla. For example, the devices described herein can be used both for getting to the papilla (which is typically performed with a duodenoscope) and to cannulate the biliary and pancreatic trees.

Figure 70A:
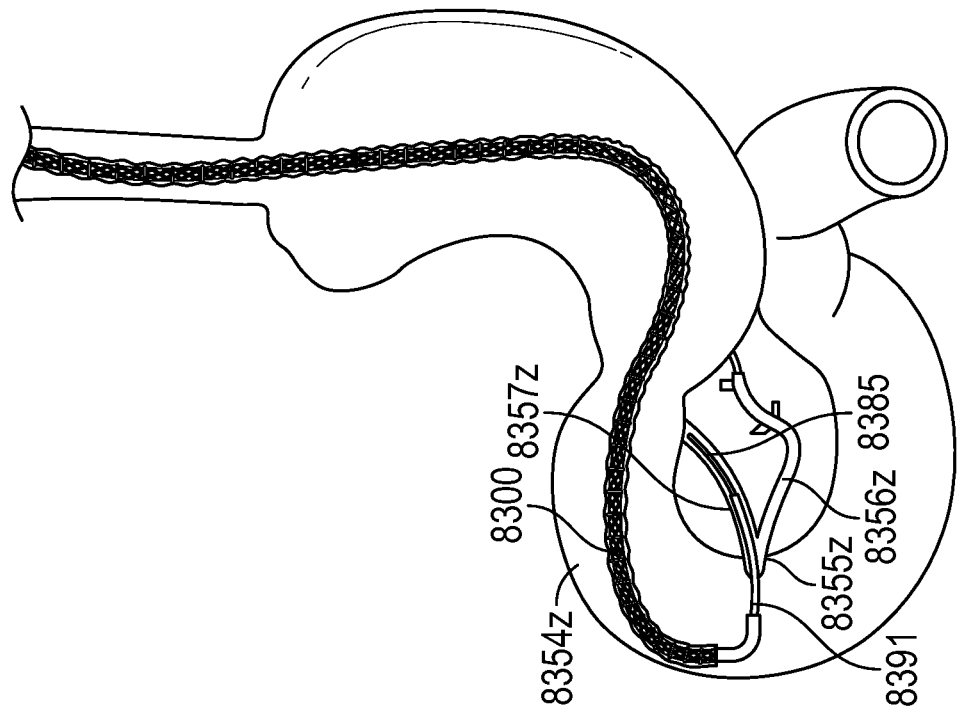
FIGS. 70A-70B show a method of use of a rigidizing device for ERCP.
Figure 70B:
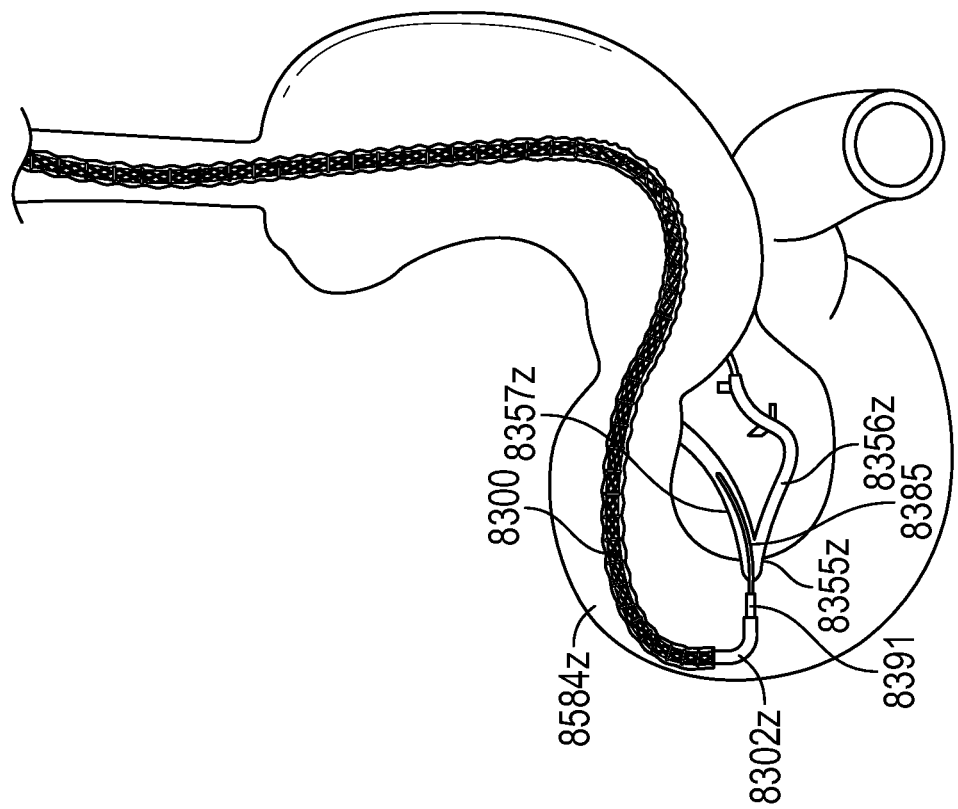

Referring to FIGS. 70A-72D, the rigidizing devices described herein can be used for ERCP and direct visualization of the pancreatic or bile duct (cholangioscopy) in a variety of ways. For example, as shown in FIGS. 70A-70B, a rigidizing device 8300 (which can be similar to the rigidizing device of FIG. 25) with a steerable distal end 8302*z* may be used over a cholangioscope 8391. The cholangioscope 8391 can be a flexible endoscope with a camera, lighting, and optionally a tool channel designed to achieve the bend radius and diameter necessary to navigate into the bile ducts. The bend radius of the cholangioscope 8391 can be 0.5" with a distal tip and insertion tube diameter of 2 mm-6 mm. The cholangioscope 8391 can be placed inside the rigidizing device 8300, and the rigidizing device 8300 can begin in the flexible condition. The two devices 8300, 8391 may be navigated together through the upper gastrointestinal tract to the duodenum 8354*z* (or the cholangioscope 8391 may be advanced ahead of the rigidizing device 8300 with the rigidizing device 8300 following it when deemed necessary by the operator). Once in the duodenum 8354*z*, the rigidizing device 8300 can be rigidized and steered to angle the cholangioscope 8391 towards the entrance to the ducts (papilla 8355*z*). The rigidizing device 8300 steering can be locked in place and the cholangioscope 8391 can be advanced towards the papilla 8355*z*. A guidewire 8385 can be pushed through the cholangioscope 8391 and aimed at the entrance to the papilla 8355*z* and pushed through into the bile duct 8357*z* or the pancreatic duct 8356*z* (positioning in the bile duct 8355*z* is shown in FIG. 70A). As shown in FIG. 70B, the cholangioscope 8391 can be advanced into the bile duct 8357*z* over the wire 8385 to achieve direct cannulation. This rigidizing device 8300 in this method can advantageously support the small cholangioscope 8391 to keep it from buckling in the stomach, and the steering section 8302*z* of the rigidizing device 8300 can advantageously deflect the cholangioscope 8391 and direct it towards the papilla. As a result, direct visualization can be achieved, reducing the amount of radiation required during ERCP.

Figure 71B:
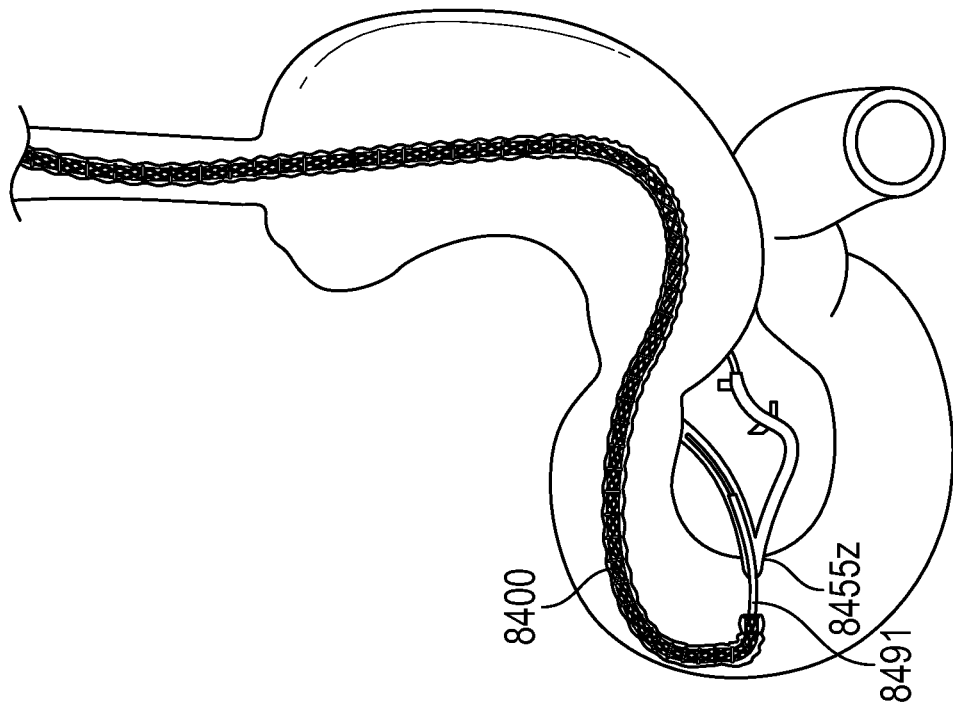
FIGS. 71A-71B show a method of use of a rigidizing device for ERCP.
Figure 71A:
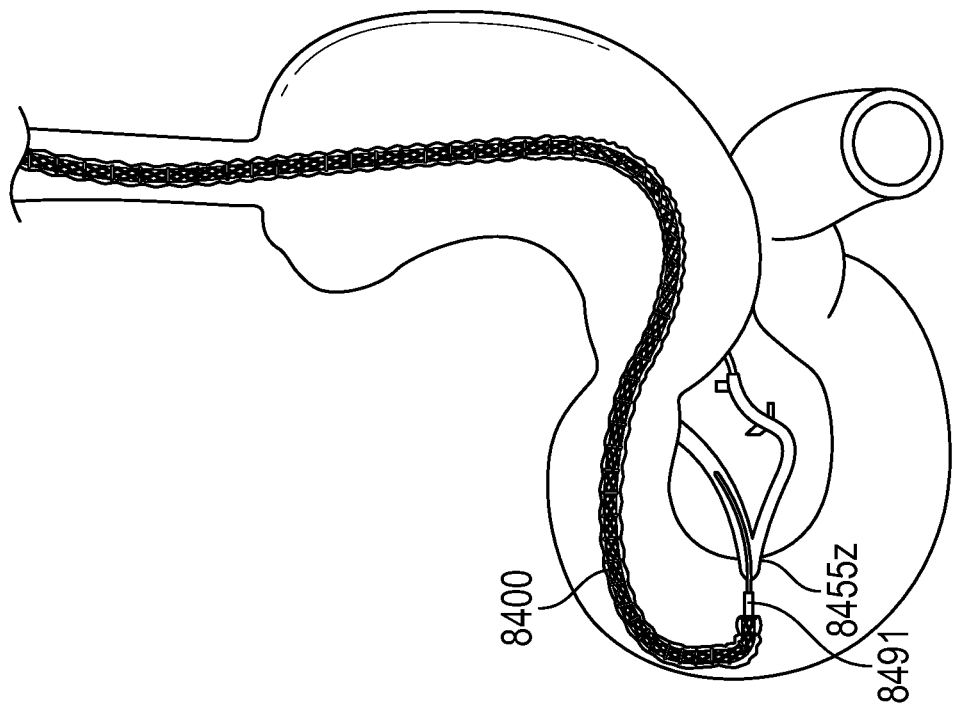

Another exemplary ERCP method is shown in FIGS. 71A-71B. In this embodiment, a rigidizing device 8400 without a steerable distal end can be used. The cholangioscope 8491 can be used to steer the rigidizing device 8400 while in the flexible configuration to point the rigidizing device 8400 towards the papilla 8455*z*. Once pointed in the correct direction, the rigidizing device 8400 can be rigidized. The cholangioscope 8491 can then be advanced in the same manner as described above with respect to FIGS. 70A-70B. This method can be referred to as the "point and shoot" method of direct cholangioscopy.

Figure 72B:
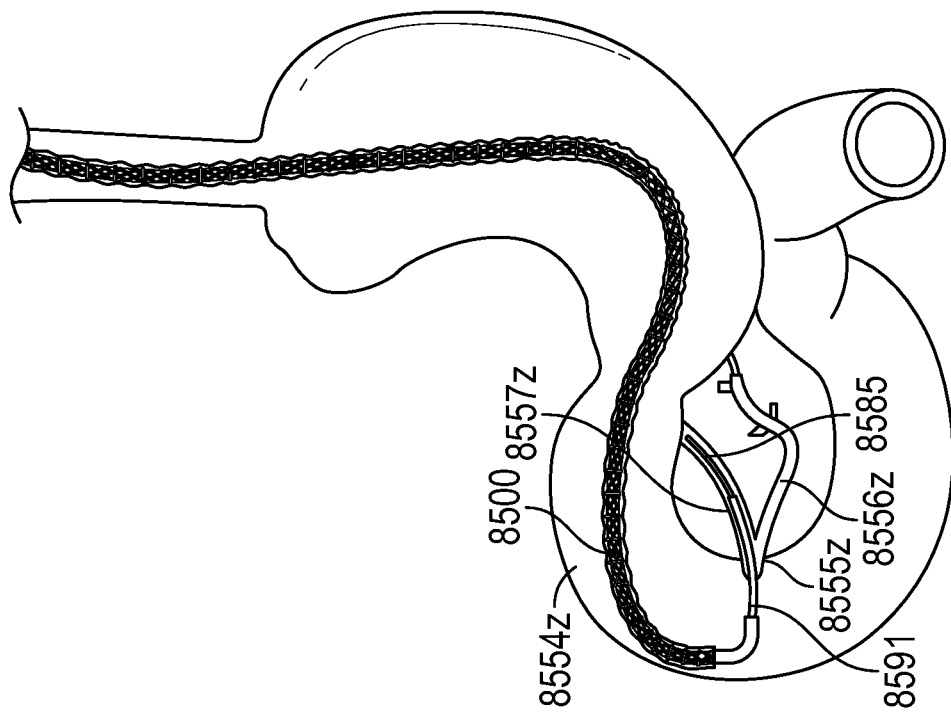
FIGS. 72A-72D show a method of use of a rigidizing device for ERCP.
Figure 72A:
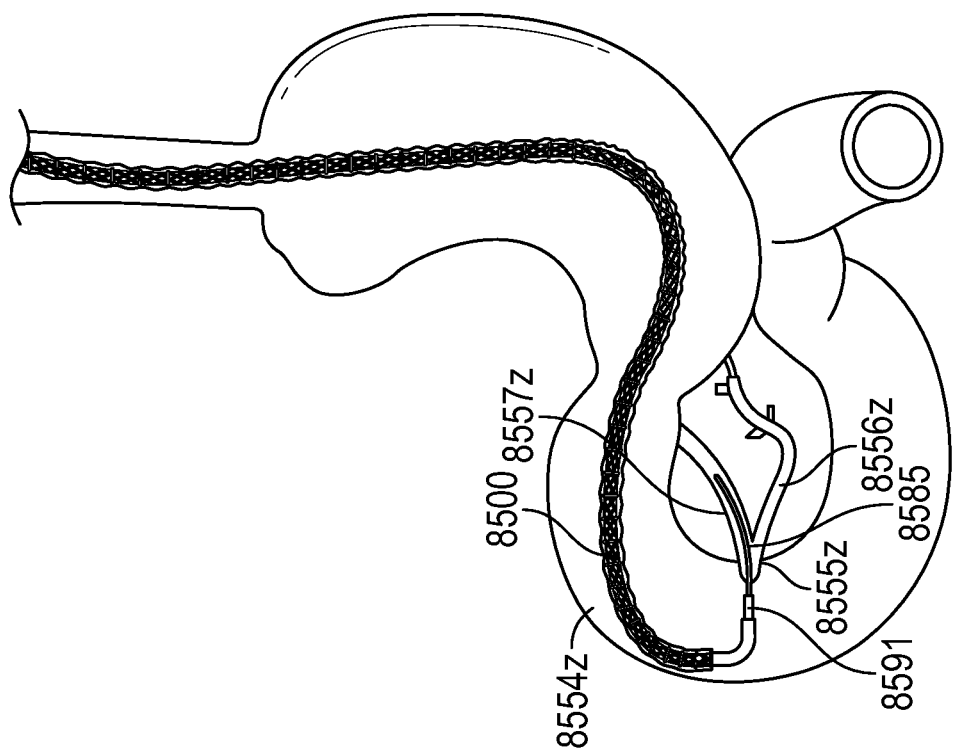
Figure 72D:
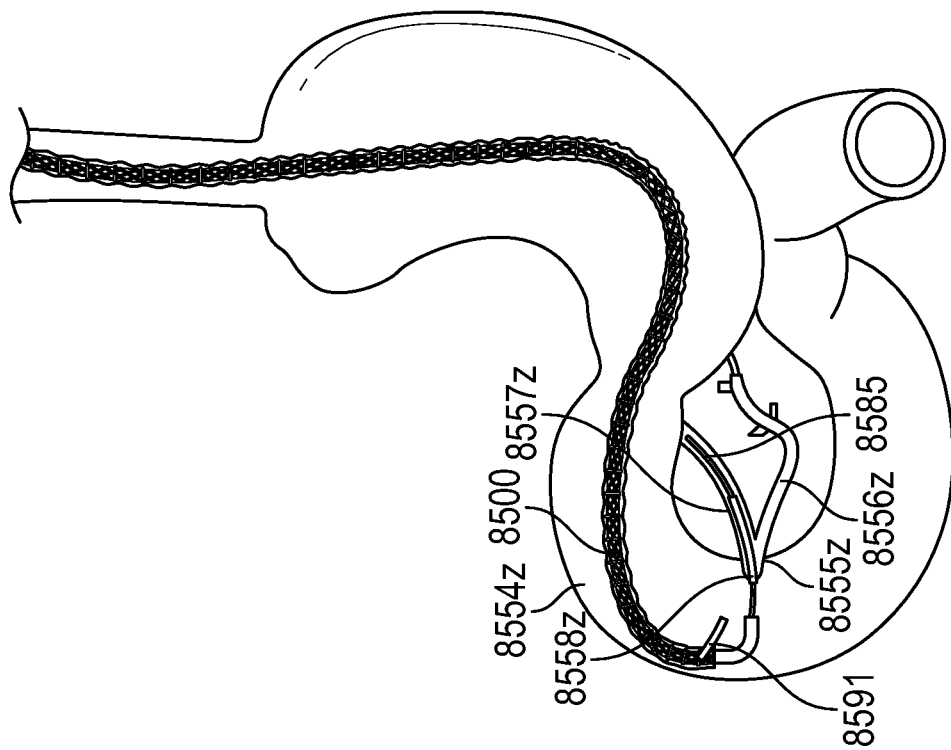
Figure 72C:
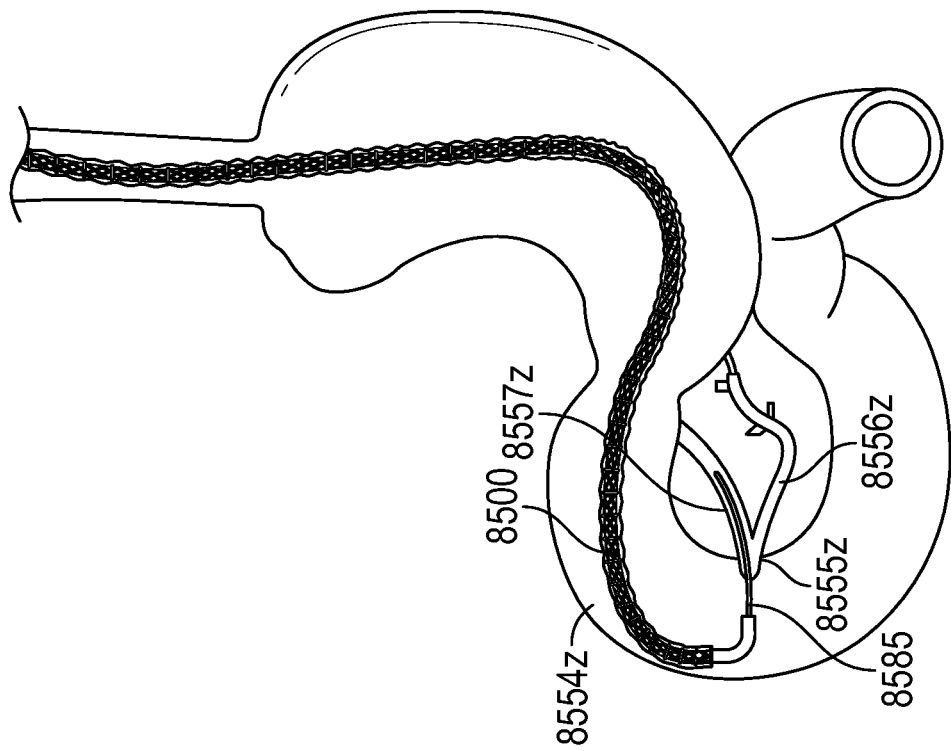

Another exemplary ERCP method is shown in FIGS. 72A-72D. In this embodiment, the rigidizing device 8500 includes at least two working channels therein (e.g., similar to the device of FIGS. 20A-20B and 21A-21B). The cholangioscope 8591 is placed down the first tool channel initially for navigation and cannulation of the papilla 8555*z*. Once the guidewire 8585 has been crossed into the bile duct 8557*z* (as shown in FIG. 72B) or pancreatic duct (8556*z*), the cholangioscope 8591 can be removed from the first tool channel with the wire 8585 remaining in place inside the duct 8557*z* (as shown in FIG. 72C). The cholangioscope 8591 can then be placed into the second tool channel (e.g., which may extend sideways out of the wall of the device 8500 as shown in FIG. 81) such that the duodenal side of the papilla 8555z can be seen (as shown in FIG. 72D). The first tool channel can be used to place larger instruments therethrough, such as a stent 8558z to be placed into the duct 8557z. In some embodiments, it may be useful to have to have exterior (duodenal) visualization of the papilla 8555z during stent placement since the stent 8558z takes up most of the diameter of the duct 8557z and a portion of the stent 8558z remains inside the duodenum 8554z.

In another exemplary ERCP method, a rigidizing device similar to the device of FIG. 59 includes a single tool channel running the entire length of the device. The rigidizing device includes a camera attached to the outside of the rigidizing device just proximal to the steering section. Cannulation, ERCP, and direct cholangioscopy can be performed similar to the methods described above. When a stent or larger tools are to be used, the cholangioscope can be removed from the tool channel and the rigidizing device camera can be used to view the exterior of the papilla while larger instruments or stents are used.

In another exemplary ERCP method, the rigidizing device includes a suction tip on the distal end thereof as described in FIGS. 46A-46B. The suction tip can surround the papilla, and suction can be applied at the tip. This action can stabilize the papilla and make it easier for the cholangioscope to aim to the appropriate location to cross the wire. Holding the surrounding tissue of the papilla can also provide some counter-tension when pushing on the papilla with the wire or cholangioscope. Providing counter tension to the compression force of the cholangioscope or other tools could decrease the number of sphincterotomies (cutting open the papilla) required.

Advantageously, the rigidizing devices used for ERCP as described herein can be disposable and sterile, reducing risk of infection or cross-patient contamination. The methods further result in less radiation and easy of navigation to the papilla with steering capabilities on the rigidizing device and/or the scope.

The rigidizing devices and systems described herein can be used for cardiology and cardiac surgery, including in the aortic and mitral valves.

Typically, in transcatheter, percutaneous procedures, the clinician affects motion from the access site (e.g., an artery or vein in the groin, arm, etc.) using some sort of flexible rod or shaft that has adequate stiffness to advance the catheter to the treatment site but is flexible enough to conform to the anatomy. This means that all the force or leverage is developed at the remote access site and may be reflected off of more local anatomy to: (a) bend the flexible rod or shaft to navigate to the procedure site; and to (b) provide localized forces (linear and torque) at the procedure site. In contrast, a dynamically rigidizing device as described herein effectively moves the access site to the treatment site by providing a means to both navigate through tortuous anatomy to the treatment site and to rigidize and form a stable port at the treatment site independent of anatomical reflections.

One of the advantages of the rigidizing devices described herein is the ability to conform to surrounding anatomy (e.g., the vasculature). Devices such as guide catheters need to provide a certain amount of stiffness to be advanced through the anatomy (e.g. vasculature) and perform the functions required. Stiff systems, however, can prevent the device from being advanced to the target anatomy due, at least in part, to highly tortuous paths, forcing the anatomy to conform to the device, which can lead to trauma to surrounding tissues and vessels. In contrast, the rigidizing devices described herein can be flexible enough to be moved through the vasculature, conforming to the vasculature instead of remodeling the vasculature. The inch-worming allowed by a rigidizing device or nested system as described herein allows for this flexible forward movement. Once the device has advanced to a target site, the rigidization allows for preservation and utilization of the created path through the vasculature. The rigidizing devices described herein, for example, can be 1/10 as stiff as a typical guide catheter when in a flexible state and 5 times stiffer than a typical guide catheter when in a rigid state.

In some embodiments, a rigidizing device as described herein can be used during percutaneous procedures in the heart or vasculature. The rigidizing device can both conform to the cardiac anatomy and provide a local distal fulcrum for instrument manipulation. Currently, when performing a percutaneous procedure, the mechanical fixation and stabilization occurs at the access site (e.g., femoral vein, radial artery, iliac vein, etc.). As described above, this fixation point creates a long moment arm extending from the access site to the procedure site. Further, as described in further detail below, the mechanical linkage created by typical stiff catheter systems between the access site and target anatomy relies on anatomical reflections to direct the catheter tip and transmit force to the tools being used. Stiff catheter systems create potential energy along the access route when they are bent to conform to the anatomy. This energy can be released when there is voluntary or involuntary patient movement or unintentional movement by the operator at the access site. In contrast, the rigidizing devices described herein conform to the anatomical pathway prior to rigidization, eliminating stored energy associated with stiff catheter systems. Once rigidized, the mechanical fixation is achieved independently of anatomical reflections, greatly reducing the moment arm and increasing a physician's control over the procedure tools leading to more predictable results. In some embodiments, the rigidizing device can comprise an integrated hemostasis valve, obviating the need for a separate access sheath.

In some embodiments, the rigidizing devices described herein can be used to stiffen a guide sheath in interventional cardiology or structural heart cases. For example, the rigidizing devices can be used to provide a "rail" for the transcatheter aortic valve replacement (TAVR) device, thereby keeping the tip of the TAVR catheter from scraping and skiving the top of the aortic arch where there is often thrombus burden (current systems tend to ride the outside of the arch, rubbing against plaques, creating embolic debris). The rigidizing devices can help enable superior alignment and placement as well as lower paravalvular leakage and optimal placement relative to pacing nodes.

In some embodiments, the rigidizing devices described herein can be used as a delivery system that may be passed from the venous circulation through the right atrium and atrial septum into the left atrium through the mitral valve and antegrade into the left ventricular outflow tract and aortic valve. In this manner, a transcatheter aortic valve implantation (TAVI) may be facilitated avoiding contact with the aortic arch and ascending aorta typical with retrograde deployment In some embodiments, the rigidizing devices described herein can be used to deliver a mitral valve replacement. That is, crossing the septal wall during mitral valve replacement can be particularly difficult, as it involves multiple curves, a beating heart, and the need for precisely aligned entry and stabilization before delivery of the implant. Current valve delivery platforms can be quite rigid, which can be dangerous for anatomy that it straightens (such as the femoral artery, which can be highly calcified and friable). The rigidizing devices described herein can advantageously create a conduit that goes in flexibly, then rigidizes in whatever shape the particular person's anatomy provided, such that the rigidizing device conforms to the entire anatomical track. As a result, the rigidizing devices described herein can allow the clinician to create a stable mechanical lumen leading directly to the anatomy, to locate it without significant local anatomical load, then to stabilize rigidly in that shape as a device is delivered through it.

Figures 73A, 73B:
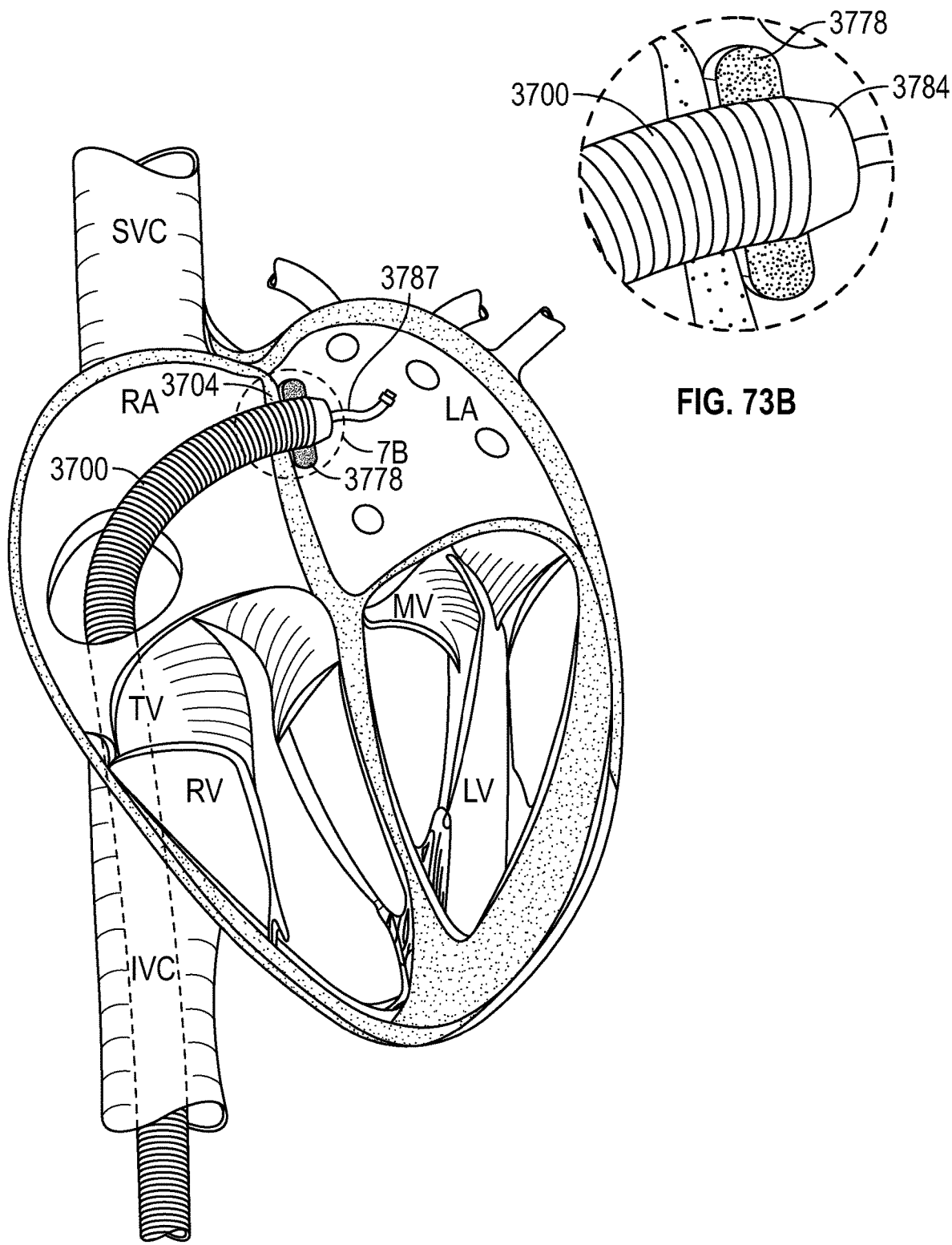
FIGS. 73A-73B show a method of use of a rigidizing device in the heart to create access to the left atrium.

FIG. 73A depicts an embodiment of a rigidizing device 3700 advanced through the right atrium RA to the left atrium of the heart. A guidewire or other piercing member and dilator can be used to puncture the atrial septum 3704 to create access to the left atrium LA. The rigidizing device 3700 can be advanced to the treatment site using the methods described herein. A cardiac tool 3787 (which may or may not be rigidizing) can be advanced within with the rigidizing device 3700. For example, the cardiac tool 3787 and rigidizing device 3700 can be advanced as described with respect to the nested system shown herein, such as in FIGS. 65A-H. The dynamic nature of the rigidization allows the device 3700 and tool 3787 to be advanced through tortuous anatomy. The rigidizing device 3700 can be rigidized once at the treatment site to provide a stable base for the treatment. Optionally, the rigidizing device 3700 may comprise an anchoring balloon 3778 near its distal tip to anchor the rigidizing device 3700 to chambers in the heart, e.g., to the atrial septum 3704 to maintain the tip of the tube 3700 in the left atrium LA. The detailed view of FIG. 73B shows the balloon 3778. The balloon 3778 can be positioned at any location around a circumference of the tube 3700. In some embodiments, the balloon is annular and surrounds a circumference of the tube 3700. The rigidizing device 3700 may include an echogenic tip. Other tips allowing real time visualization are also possible (e.g., radiographic tip, a scope within a saline filled bag, etc.).

Figure 74A:
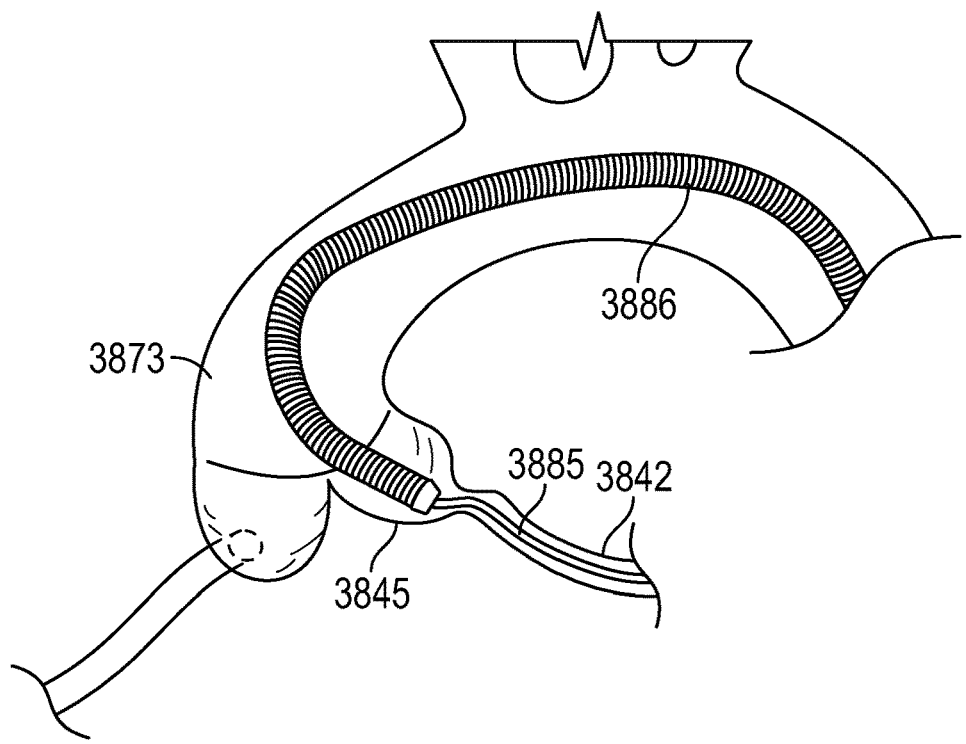
FIGS. 74A-74B show a method of use of a rigidizing device in the heart to perform treatment of a branching vessel.
Figure 74B:
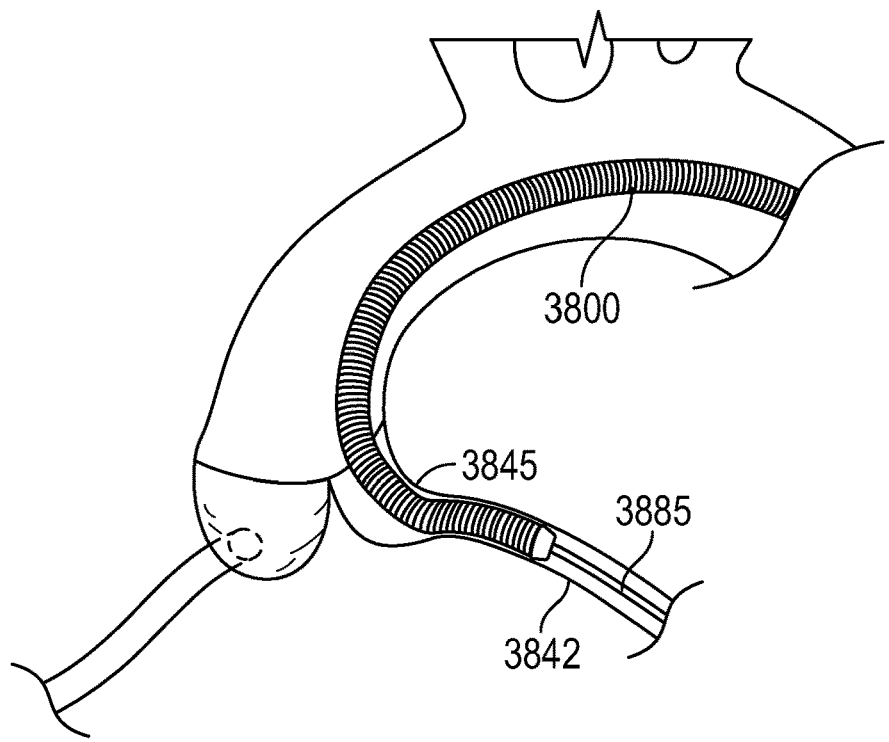

FIGS. 74A-74B show an exemplary method for use of a dynamically rigidizing device in performing treatment of a in a small branching vessel, such as the coronary arteries. When navigating to these smaller vessels, oftentimes, applying force in these areas can cause the guide catheter or other advanced devices to be pushed out of the area. Sometimes, access sheaths are used in such situations to provide a bit of mechanical advantage. Still, using such an access sheath, when applying force, for example, to push through an occlusion, the whole device can be pushed out of the area. FIG. 74A-74B compare the use of a standard guide catheter to a rigidizing device as described herein. In FIG. 74A, a standard guide catheter 3886 is used to navigate to the ostium 3845 of one of the main coronary arteries 3842. A guidewire 3885 extends from the tip of the guide catheter 3886 and can be used to perform a procedure (e.g., placing a stent). The guide catheter 3886 can, in some embodiments, reflect off of adjacent anatomy 3873 to achieve mechanical advantage, prevent catheter push back, and/or provide more local force. In contrast, FIG. 74B show a rigidizing device 3800 as described herein advanced through the ostium 3845 and into the coronary artery 3842. Because of the rigidization capability of the device 3800, it does not need to reflect off local anatomy and can instead provide inherent stabilization at the treatment site. Additionally, because of the dynamic rigidization capabilities of the rigidizing device, it can be advanced past the ostium 3845 and into the coronary artery 3842.

Figure 75A:
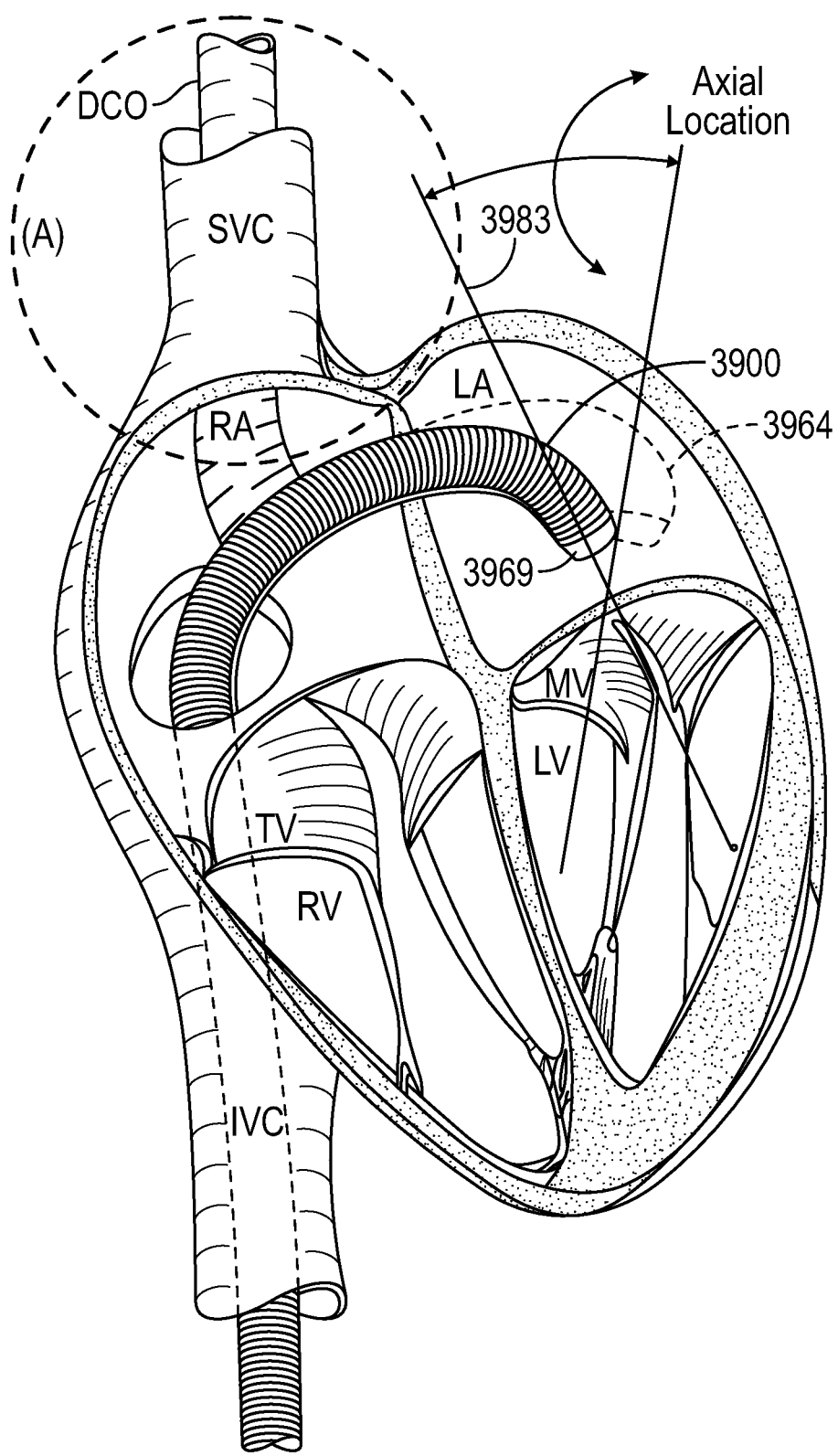
FIGS. 75A-75C show a method of use of a rigidizing device in the heart for mitral valve repair.

FIG. 75A shows an exemplary method of using a dynamically rigidizing overtube system for performing a mitral valve repair. This method illustrates how the rigidizing device 3900 can be positioned in the left atrium LA such that it independently maintains axial alignment with the treatment site, in this example, the mitral valve. As shown in FIG. 75A, the rigidizing device 3900 is advanced through the vasculature to the right atrium RA, through the atrial septum, and into the left atrium LA. The end of the rigidizing device can be steered such that a longitudinal axis 3983 extending through the end 3969 of the tube aligns with the desired treatment area (e.g., portion of the valve). The steering, dynamically rigidizing, and tip visualization capabilities can allow for precise positioning of the rigidizing device. For example, the axis 3983 extends through the mitral valve MV into the left ventricle LV. Another position 3964 of the rigidizing device 3900 is shown in phantom with the axis extending through a leaflet of the mitral valve MV. Current methods of mitral valve repair utilize a guide catheter to navigate to the left atrium LA, and often reliable axial alignment is not possible. The presently disclosed method of using the rigidizing device 3900 to achieve axial alignment in a flexible state prior to rigidization provides a significant benefit over currently used methods of positioning during procedures such as mitral valve repair. This sort of precise alignment can be beneficial in other areas of the anatomy as well (e.g., across other valves, in transseptal access sites, within a vessel lumen, etc.), including the ability to place sutures, clips and other devices within the heart with equivalent precision normally reserved for open heart surgery.

Figure 75B:
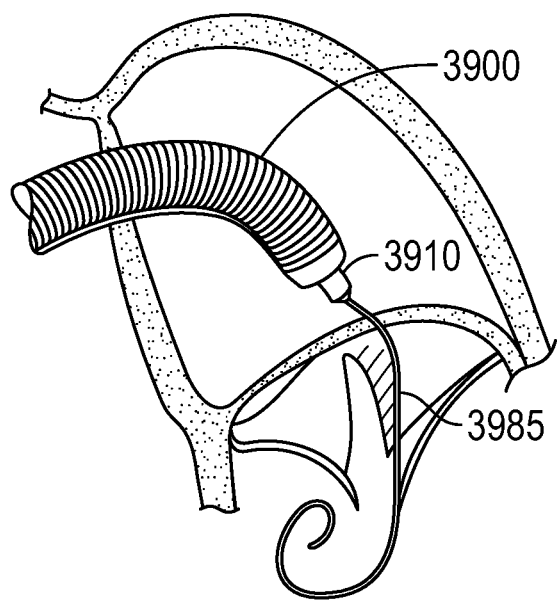

Referring to FIG. 75B, the rigidizing device 3900 used in a procedure such as that shown in FIG. 75A can comprise various configurations. In some embodiments, the rigidizing device 3900 can be steered and positioned using a guidewire 3985. In some embodiments, the rigidizing device 3900 can comprise a nested system comprising an inner rigidizing device 3910.

Figure 75C:
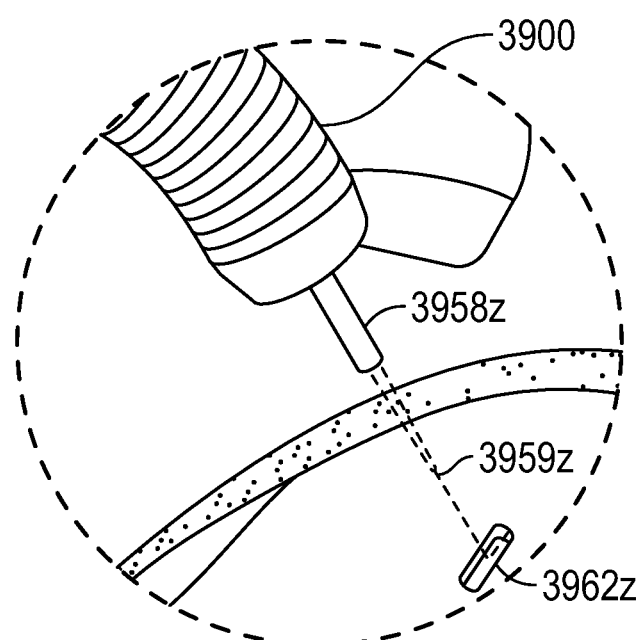

As shown in FIG. 75C, in one embodiment, at needle-tipped catheter 3958z can be advanced through the rigidizing device 3900 and positioned within the cardiac anatomy, such as above a mitral valve leaflet. In some embodiments, the needle-tipped catheter 3958z can contain an anchoring device 3962z (pledget, stainless steel pledget, etc.) attached to a length of suture 3959z that can be passed through the tissue creating an anchor for the suture. Suture and anchors delivered through the rigidizing device can be used to sew tissue structures together, such as leaflet plication for mitral valve repair.

It will be appreciated that a system comprising one or more rigidizing devices as described herein can be used in heart procedures other than mitral valve repair. For example, the system may be used in complex mitral valve procedures where the goal may be to effect leaflet repair and mitral annuloplasty during the same procedure. The system can be used to perform transseptal delivery of an aortic prosthesis (e.g., TAVI). In some embodiments, the system is used to perform aortic valve repair via transseptal access. A combination of dynamically rigidizing overtubes can used in synchrony to pass suture or other instruments from one heart chamber to another. In any of these procedures, the dynamically rigidizing systems described herein can advantageously provide a cannula or access sheath providing universal access to the various chambers of the heart.

Figure 76A:
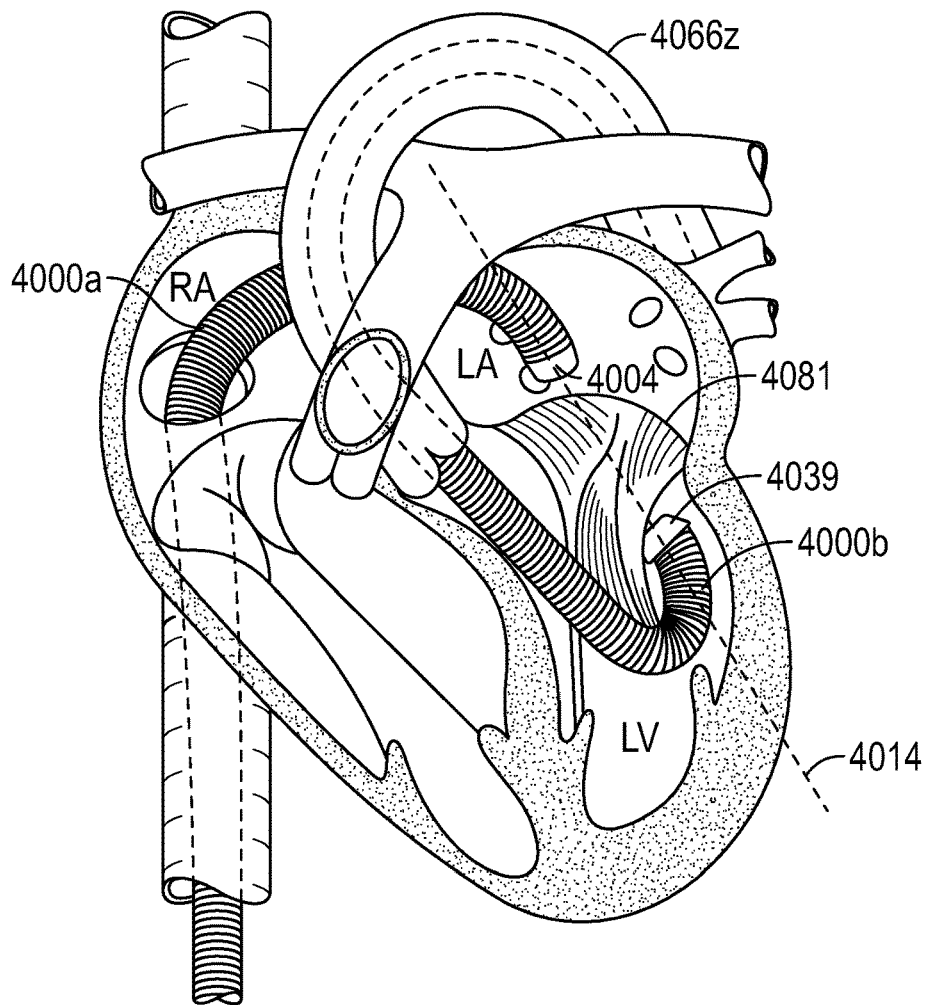
FIGS. 76A-76B show a method of use of a dual rigidizing device in the heart.

FIG. 76A shows an exemplary dual rigidizing cannula system that can be simultaneously placed in multiple chambers of the heart. The two rigidizing cannulas 4000a, 4000b can be axially aligned and provide the capability for clinicians to pass instruments from one cannula to the other. In use, the first rigidizing cannula 4000a can be navigated through the right atrium RA to the left atrium LA with the tip 4004 of the cannula facing towards the mitral valve 4081. The rigidizing cannula 4000a can be rigidized in this position. The cannula 4004a may comprise a bending section near the tip 4004 to properly position the tip and steer the device. The second cannula 4000b can be navigated retrograde through the aorta 4066z into the left ventricle LV. The cannula 4000b can be steered and positioned such that a tip 4039 is positioned below the mitral valve and facing the tip 40004 of the first cannula 4000a. The cannula 4000b can be rigidized in this position. The axis 4014 extending between the tip 4004 of the first cannula and the tip 4039 of the second cannula can be aligned with the area to be treated. This dual access can allow, for example, a suture to be passed from one cannula to the other and/or to allow tools to be passed therebetween. Using two cannulas can also allow the procedure to be performed with a greater degree of precision and accuracy (for example, the treatment site can be approached from the top, or bottom, or both). Examples of procedures that can be performed with two such rigidizing cannulas 4000a, 400b include leaflet plication with standard suture techniques and annuloplasty with conventional rings. Each cannula 4000a, 4000b can include multiple working channels and provide fixed access sites within the heart. The provision of these dual fixation sites can allow for replication of standard open heart surgical procedures through far less invasive percutaneous access.

Figure 76B:
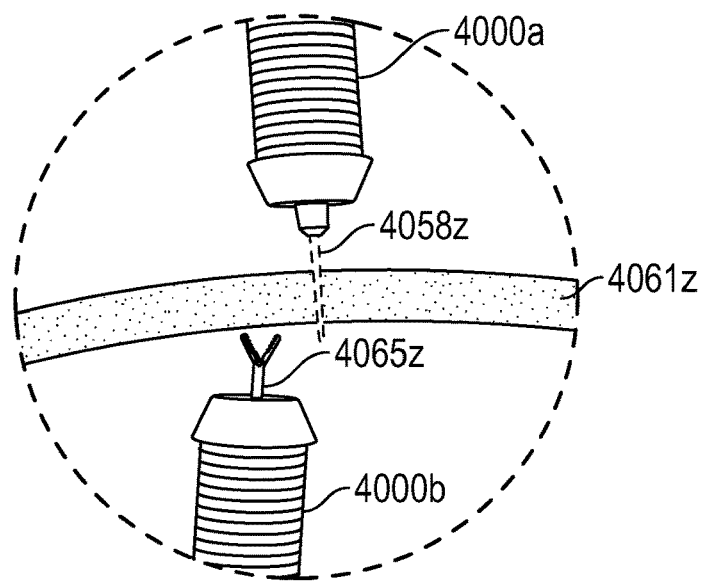

FIG. 76B shows the dual rigidizing cannula system of FIG. 76A being used to pass suture through a tissue. The first rigidizing device 4000a is positioned on a first side of tissue 4061z to be sutured. The second rigidizing device 4000b is positioned on an opposite side of the tissue 4061z. A needle catheter 4058z positioned by the first device 4000a can be used in combination with a tool 4065z such as a grasper, snare, or the like positioned by the second device 4000b to pass suture through the tissue 4061z.

Figure 77:
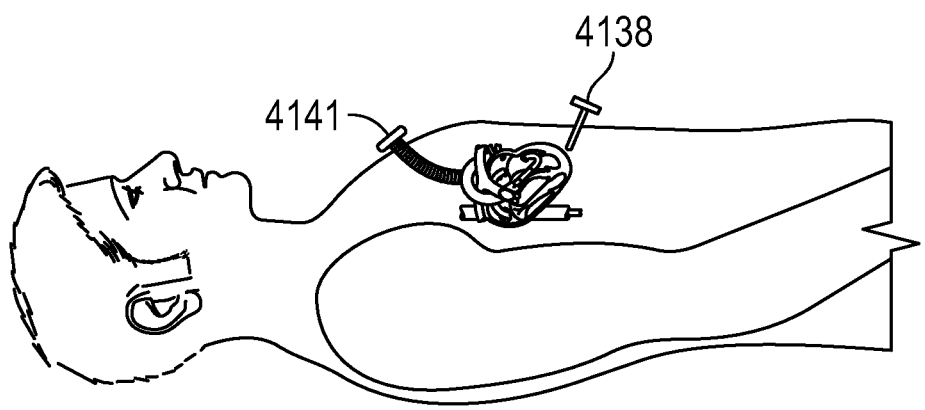
FIG. 77 shows a rigidizing device used as a trocar.

Referring to FIG. 77, in some embodiments, a rigidizing device as described herein can be used as a trocar during endoscopic procedures. FIG. 77 shows a dynamically rigidizing trocar 4141 and a standard trocar 4138. Typically, when using a standard trocar 4138, the initial placement of the trocar 4138 can be incorrect, requiring removal and repositioning. In contrast, the dynamically rigidizing trocar 4141 can allow for minor adjustments during or after placement of the trocar. The dynamically rigidizing trocar 4141 can have steering capability, as described with respect to other dynamically rigidizing devices disclosed herein. Using this capability, the trocar 4141 can be bent or deflected in a desired direction and then rigidized, allowing far greater control than standard trocars. The dynamically rigidizing trocar 4141 can be used in cardiac applications and/or elsewhere in the body. Additionally, the trocar 4141 can be provided in different sizes or shapes depending on the application.

Figure 78:
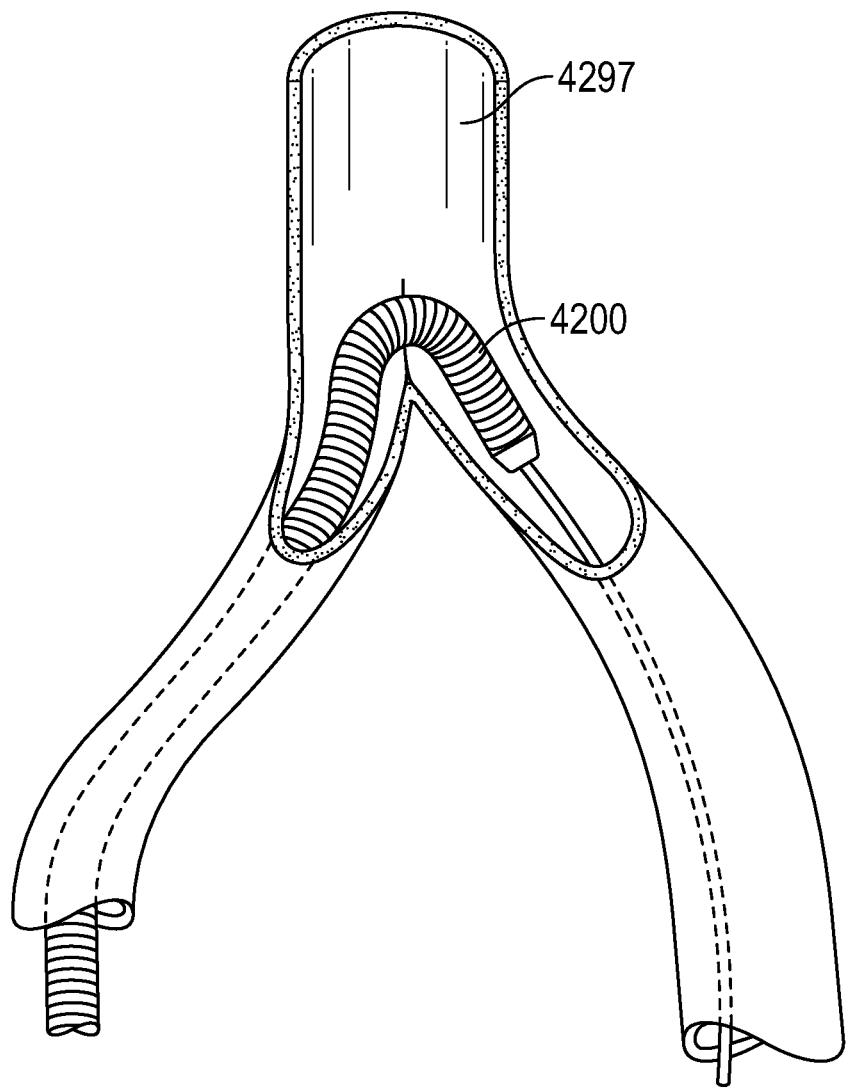
FIG. 78 shows a rigidizing device in use at the aortic bifurcation.

Referring to FIG. 78, a dynamically rigidizing device 4200 can be used at the aortic bifurcation 4297. This area of the vasculature can commonly become diseased and require complex repair based on the extreme tortuous anatomy at this site. Currently, many catheters or other delivery devices used to treat this area travel up to the apex of the bifurcation and then deploy tools down from there. As shown in FIG. 78, a dynamically rigidizing device 4200 can use a combination of steering and dynamic (e.g., periodic) rigidization to navigate around the bifurcation 4297 and be able to reach any treatment site in the area. For example, the system shown in FIG. 78 can be used to treat a CTO (chronic total occlusion) in one leg by making percutaneous access in the other leg.

Figure 79:
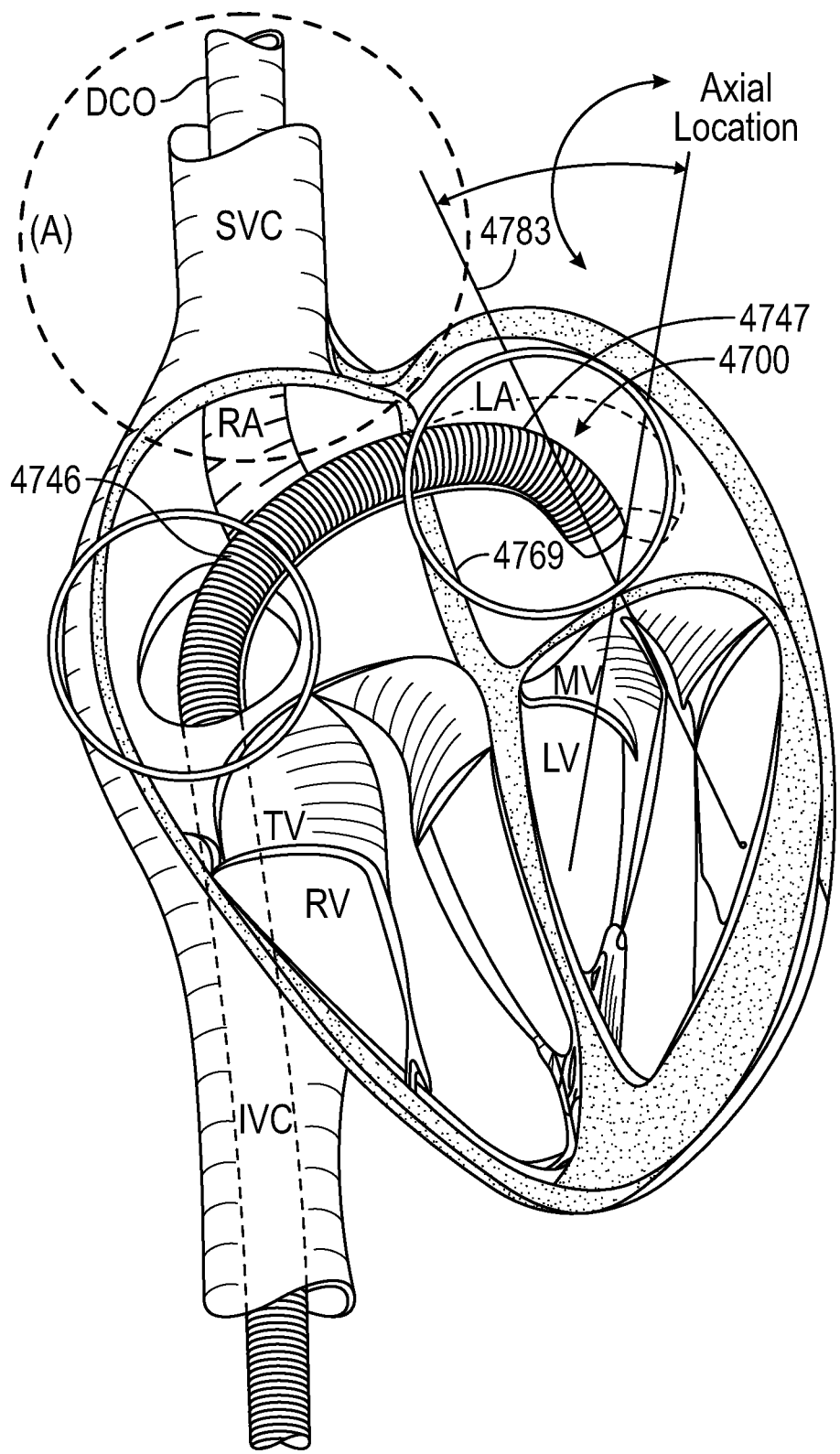
FIG. 79 shows a rigidizing device for mitral valve repair.

Referring to FIG. 79, a rigidizing device 4700 with an active deflection segment 4746 and a steerable distal section 4747 can be used in the heart to perform mitral valve repair. The rigidizing device 4700 can be positioned in the left atrium LA such that it independently maintains axial alignment with the treatment site, in this example, the mitral valve MV. The rigidizing device 4700 can thus be advanced through the vasculature to the right atrium RA, through the atrial septum, and into the left atrium LA. The end of the rigidizing device can be steered such that a longitudinal axis 4783 extending through the end 4769 of the tube aligns with the desired treatment area (e.g., portion of the valve). To achieve the desired positioning, the active deflection segment 4746 can be bent in the relatively unconstrained space between the IVC and the atrial septum while the distal steerable section 4747 can be positioned within the left atrium LA and steered or oriented towards the mitral valve MV. In such a position, the rigidizing device 4700 can have a bend with an arc radius of approximately 4-6 cm, such as 5 cm, at an angle of 90 degrees or more.

Figure 80:
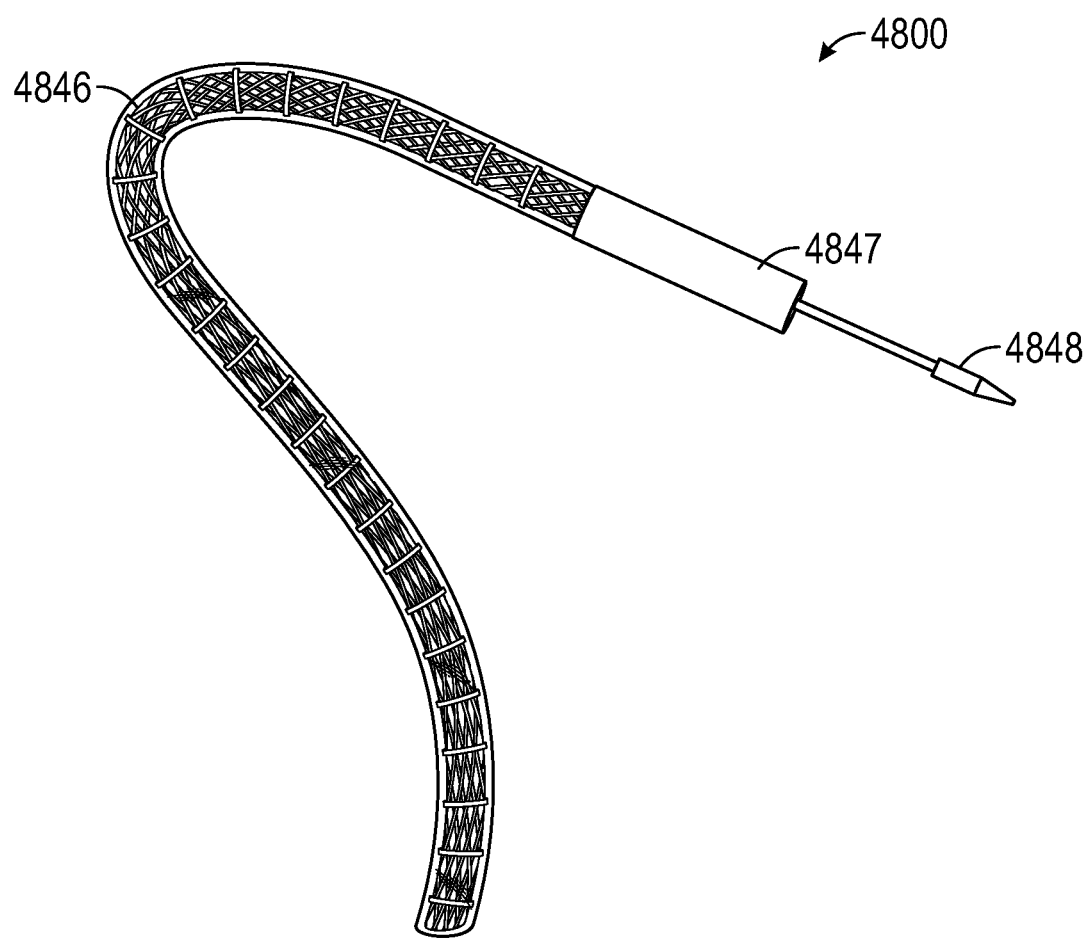
FIG. 80 shows a rigidizing device with a distal payload for mitral valve repair.

Referring to FIG. 80, a rigidizing device 4800 for use in mitral valve repair (with active deflection segment 4846 and steerable distal section 4847) can include a distal payload 4848 (e.g., a mitral clip, mitral valve replacement, or annuloplasty ring) attached thereto. Having the distal payload 4848 attached thereto while still incorporating the active deflection segment 4846 and steerable distal section 4847 can advantageously reduce or eliminate the need for an outer large-bore guide catheter during such procedures. The catheter 4800 (or 4700) for use in mitral valve procedures can, for example, be 14-40Fr with a length of 80-120 cm.

A method of using the rigidizing device 4700 or 4800 can include: (1) introducing the device into the distal circulation; (2) advancing the device to the target anatomy (e.g. heart valve); (3) making a first bend with the active deflection segment (e.g., negotiating the bend between the IVC and septal wall, which is approximately 90°); (4) locking the active deflection segment in the bent configuration using pressure or vacuum; and (5) using the steerable distal section to get to the mitral plane and mitral valve; and (6) delivering a therapy or payload.

A rigidizing device with an active deflection section and a steerable distal section as described herein can also be used, for example, for placement of fenestrated grafts for thoracic artery or for abdominal aneurysm repair that involves critical branch vessels that require treatment.

The rigidizing devices and systems described herein can be used for resection or snaring of a lesion in the gastrointestinal tract.

Figure 81A:
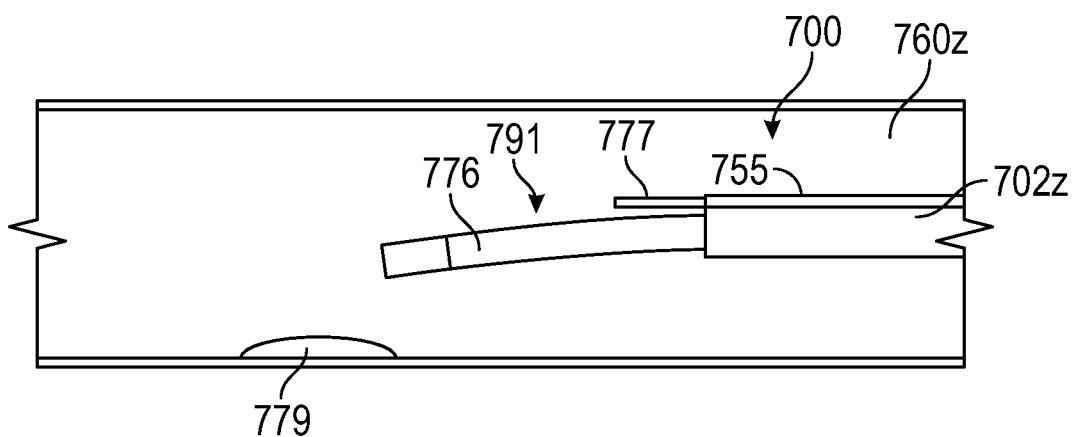
FIGS. 81A-81F show a method of using a rigidizing device to control a working tool.
Figure 81B:
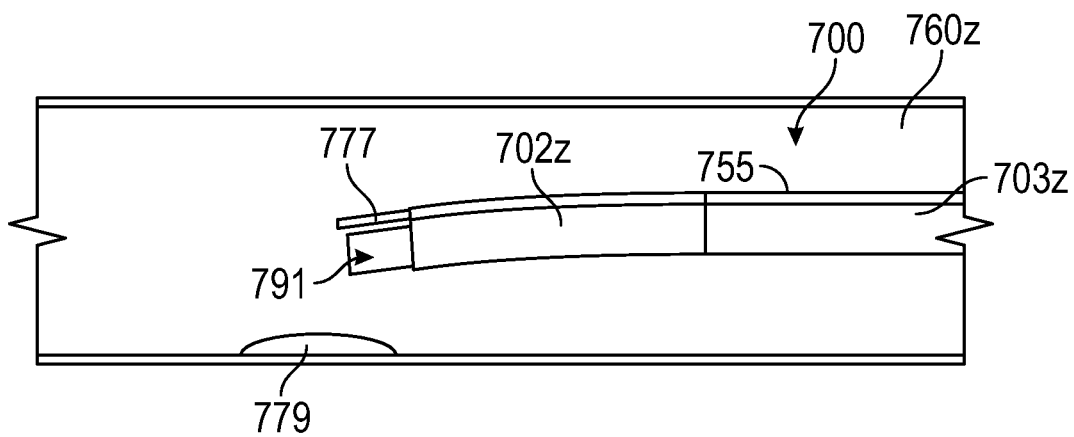
Figure 81C:
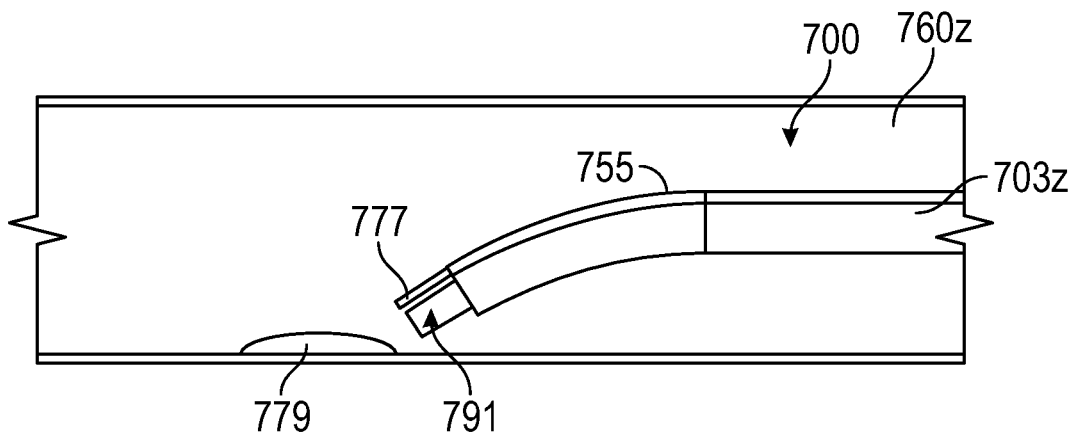
Figure 81D:
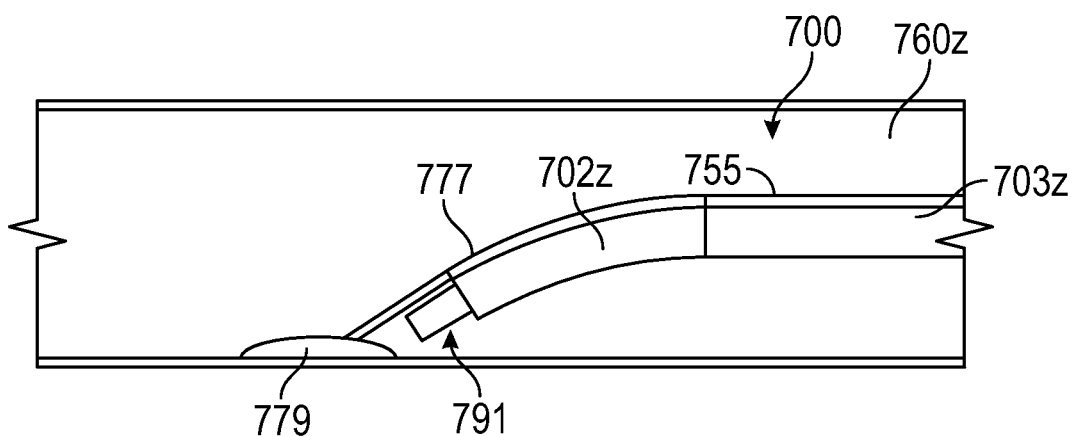

Referring to FIGS. 81A-81F, in some embodiments, the rigidizing device 700 can be configured so as to control the directionality of a working tool 777 that extends through the working channel 755. For example, the rigidizing device 700 can include a flexible distal section 702z that is highly flexible relative to the proximal rigidizing elongate body 703z (which can include rigidizing features as described herein) extending proximally thereof. Referring to FIG. 81A, the endoscope 791 with a scope steering section 776 can be placed within the rigidizing device 700 in vessel 760z. Referring to FIG. 81B, the rigidizing device 700 can be moved distally such that the flexible distal section 702z is positioned over the steering section 776 of the endoscope 791. As shown in FIG. 81C, as the steering section 776 bends, the flexible distal section 702z and the connected working channel 755 can bend with it, thereby providing steering of the tool 777 in the working channel 755 (e.g., towards the lesion 779 in the vessel 736). As shown in FIG.

Figure 81E:
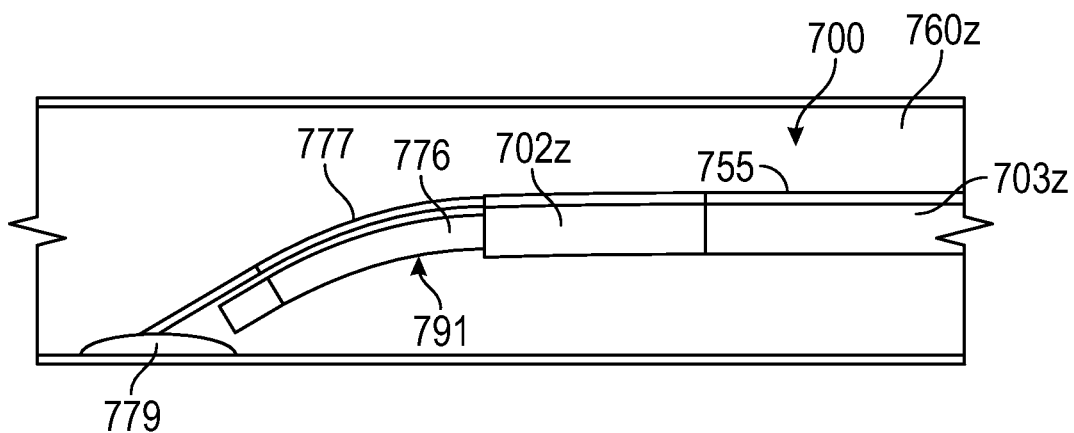
Figure 81F:
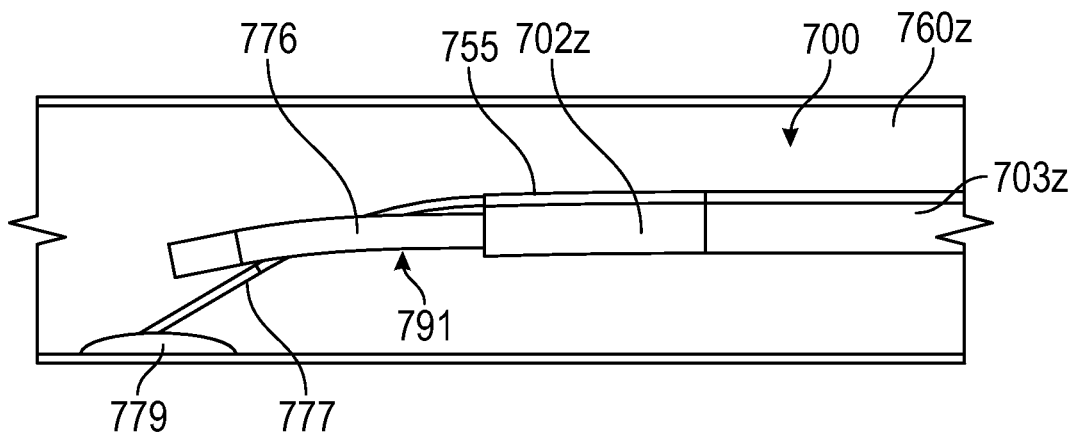

81D, the tool 777 can then be advanced out of the working channel 755 to the desired location (e.g., the lesion 779). Referring to FIG. 81E, the rigidizing device 700 can then be pulled proximally to move the flexible distal portion 702z off of the steerable section 776 and to move the working channel 755 further proximally as well. As shown in FIG. 81F, this can allow the scope 791 to be steered (with the steerable section 776) without disturbing the placement or direction of the working tool 777.

The rigidizing devices and systems described herein can be used for enteroscopy to navigate substantially all of the small intestine to diagnose and/or treat disease.

Enteroscopy is kinematically challenging for several reasons, including because the scopes are relatively small diameter (9 mm), they are very long (2 meters), and they frequently loop as they navigate the gastrointestinal tract to get to the beginning or end of the small intestine (the pylorus or the ileocecal valve, respectively).

The rigidizing devices and systems described herein can be used for IEUS.

The rigidizing devices and systems described herein can be used to access the lungs. For example, a rigidizing device 2100 and a scope 2191 can be assembled concentrically (the scope inside the rigidizing device) and then placed through the mouth down the trachea to the carina. As detailed herein, a "Point and Shoot" method may be employed at the carina to advance the scope into the left main or right main bronchus. The "Point and Shoot" method may be repeatedly used to select additional, deeper branches in the lungs.

The rigidizing devices and systems described herein can be used to access the kidneys. For example, a rigidizing device 2100 and a scope 2191 can be assembled concentrically (the scope inside the rigidizing device) and then placed through the urethra into the bladder. As detailed herein, a "Point and Shoot" method may be employed in the bladder to advance the scope into the left or right ureter. The "Point and Shoot" method may be repeatedly used to help the scope reach the kidneys The rigidizing devices and systems described herein can be used to navigate through neurological anatomy.

Systems described herein may be used to access the carotid arteries or the distal vessels leading to or in the brain.

For example, a guidewire may be placed into the carotid artery. A rigidizing device or sheath may be placed over the guidewire and directed into the carotid artery. Once the overtube or sheath is placed at the target site, it may be rigidized to decrease the likelihood of the catheter or guidewire prolapsing into the aortic arch during the procedure.

The rigidizing devices and systems described herein can be used for access and/or treatment of chronic total occlusions (CTO).

Thus, in some embodiments, the rigidizing devices can be incorporated into catheters for interventional cardiology, such that they track very easily (flexible), then can be rigidized for instances when the device is used to push through locally anatomy, such as for instance when treating a CTO.

The rigidizing devices and systems described herein can be used with laparoscopic manual tools.

The rigidizing devices and systems described herein can be used for contralateral leg access.

The rigidizing devices and systems described herein can be used for ear, nose, and throat (ENT) applications.

The rigidizing devices and systems described herein can be used to perform therapies during esophagogastroduodenoscopy (EGD), for example, on the roof of the stomach.

The rigidizing devices and systems described herein can be used for TORS (transoral robotic surgery).

The rigidizing devices and systems described herein can be used for NOTES (Natural Orifice Transluminal Endoscopic Surgery).

The rigidizing devices and systems described herein can be used for altered anatomy cases, including Roux-en-Y.

It should be understood that any feature described herein with respect to one embodiment can be combined with or substituted for any feature described herein with respect to another embodiment. For example, the various layers and/or features of the rigidizing devices described herein can be combined, substituted, and/or rearranged relative to other layers.

Additional details pertinent to the present invention, including materials and manufacturing techniques, may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are a plurality of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

What is claimed is:

1. A rigidizing device comprising:
an elongate flexible tube;
a variable stiffness layer comprising a plurality of strand lengths that cross each other;
an inlet configured to attach to a source of pressure; and
a bladder layer configured to push against the variable stiffness layer when pressure is applied through the inlet,
wherein the rigidizing device is configured to change between a flexible configuration in which the plurality of strand lengths are configured to move relative to each other and a rigid configuration in which the bladder layer limits the plurality of strand lengths from moving relative to each other when pressure is applied through the inlet.

2. The rigidizing device of claim 1, wherein the variable stiffness layer provides a coverage of 30%-70% relative to the elongate flexible tube.

3. The rigidizing device of claim 1, wherein the variable stiffness layer comprises a braid.

4. The rigidizing device of claim 1, wherein the variable stiffness layer comprises a mesh or a weave.

5. The rigidizing device of claim 1, wherein the elongate flexible tube comprises a coil-reinforced element.

6. The rigidizing device of claim 1, further comprising an outer layer over the elongate flexible tube and the variable stiffness layer.

7. The rigidizing device of claim 1, wherein the bladder layer comprises an elastomeric layer.

8. The rigidizing device of claim 1, wherein the bladder layer comprises a plastic layer.

9. The rigidizing device of claim 1, wherein the inlet is configured to attach to a source of positive pressure.

10. The rigidizing device of claim 1, wherein the inlet is configured to attach to a source of negative pressure.

11. The rigidizing device of claim 1, wherein a ratio of stiffness of the rigidizing device in the rigid configuration to stiffness of the rigidizing device in the flexible configuration is greater than 5.

12. A rigidizing device comprising:
an elongate flexible tube;
a variable stiffness layer comprising a plurality of strand lengths that cross each other;
an inlet configured to attach to a source of pressure;
a bladder layer configured to push against the variable stiffness layer when pressure is applied through the inlet; and
an outer layer over the elongate flexible tube and the variable stiffness layer the outer layer having a smooth surface,
wherein the rigidizing device is configured to change between a flexible configuration in which the plurality of strand lengths are configured to move relative to each other and a rigid configuration in which the bladder layer limits the plurality of strand lengths from moving relative to each other when pressure is applied through the inlet.

13. The rigidizing device of claim 12, wherein the variable stiffness layer provides a coverage of 30%-70% relative to the elongate flexible tube.

14. The rigidizing device of claim 12, wherein the variable stiffness layer comprises a braid.

15. The rigidizing device of claim 12, wherein the variable stiffness layer comprises a mesh or a weave.

16. The rigidizing device of claim 12, wherein the elongate flexible tube comprises a coil-reinforced element.

17. The rigidizing device of claim 12, wherein the bladder layer comprises an elastomeric layer.

18. The rigidizing device of claim 12, wherein the bladder layer comprises a plastic layer.

19. The rigidizing device of claim 12, wherein the inlet is configured to attach to a source of positive pressure.

20. The rigidizing device of claim 12, wherein the inlet is configured to attach to a source of negative pressure.

21. The rigidizing device of claim 12, wherein a ratio of stiffness of the rigidizing device in the rigid configuration to stiffness of the rigidizing device in the flexible configuration is greater than 5.

22. A rigidizing device comprising:
an elongate flexible tube having a continuous and smooth surface;

a variable stiffness layer comprising a plurality of strand lengths that cross each other;

an inlet configured to attach to a source of pressure; and a bladder layer configured to push the variable stiffness layer against the elongate flexible tube when pressure is applied through the inlet, wherein the rigidizing device is configured to change between a flexible configuration in which the plurality of strand lengths are configured to move relative to each other and a rigid configuration in which the bladder layer limits the plurality of strand lengths from moving relative to each other when pressure is applied through the inlet.

\* \* \* \* \*